United States Patent
Sharp et al.

(10) Patent No.: US 10,047,396 B2
(45) Date of Patent: Aug. 14, 2018

(54) BIOMARKERS FOR DIAGNOSIS OF TRANSIENT ISCHEMIC ATTACKS

(71) Applicant: The Regents of the University of California, Oakland, CA (US)

(72) Inventors: Frank Sharp, Davis, CA (US); Xinhua Zhan, Vacaville, CA (US); Glen C. Jickling, Sacramento, CA (US); S. Claiborne Johnston, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 108 days.

(21) Appl. No.: 15/043,577

(22) Filed: Feb. 14, 2016

(65) Prior Publication Data

US 2016/0237501 A1    Aug. 18, 2016

Related U.S. Application Data

(62) Division of application No. 13/182,630, filed on Jul. 14, 2011.

(60) Provisional application No. 61/364,334, filed on Jul. 14, 2010.

(51) Int. Cl.
| | | |
|---|---|---|
| *C12Q 1/68* | (2018.01) | |
| *C12Q 1/6883* | (2018.01) | |
| *A61K 31/37* | (2006.01) | |
| *A61K 31/4365* | (2006.01) | |
| *A61K 31/4439* | (2006.01) | |
| *A61K 31/616* | (2006.01) | |
| *A61K 31/727* | (2006.01) | |
| *G01N 33/68* | (2006.01) | |

(52) U.S. Cl.
CPC ............ *C12Q 1/6883* (2013.01); *A61K 31/37* (2013.01); *A61K 31/4365* (2013.01); *A61K 31/4439* (2013.01); *A61K 31/616* (2013.01); *A61K 31/727* (2013.01); *G01N 33/6893* (2013.01); *C12Q 2600/118* (2013.01); *C12Q 2600/158* (2013.01); *G01N 2800/2871* (2013.01)

(58) Field of Classification Search
None
See application file for complete search history.

(56) References Cited

U.S. PATENT DOCUMENTS

| | | |
|---|---|---|
| 9,057,109 B2 | 6/2015 | Chang |
| 9,200,322 B2 | 12/2015 | Barr et al. |
| 9,410,204 B2 | 8/2016 | Sharp et al. |
| 9,803,243 B2 | 10/2017 | Sharp et al. |
| 2001/0053519 A1 | 12/2001 | Fodor et al. |
| 2002/0115120 A1 | 8/2002 | Kapeller-Libermann et al. |
| 2003/0119064 A1 | 6/2003 | Valkirs et al. |
| 2003/0199000 A1 | 10/2003 | Valkirs et al. |
| 2004/0191783 A1 | 9/2004 | Leclercq et al. |
| 2004/0203083 A1 | 10/2004 | Buechler et al. |
| 2006/0046259 A1 | 3/2006 | Baird et al. |
| 2006/0078882 A1 | 4/2006 | Zetter et al. |
| 2007/0042425 A1 | 2/2007 | Hochstrasser et al. |
| 2007/0050146 A1 | 3/2007 | Bentwich et al. |
| 2007/0280917 A1 | 12/2007 | Helgadottir |
| 2009/0148933 A1 | 6/2009 | Battrell et al. |
| 2009/0197774 A1 | 8/2009 | Kozian et al. |
| 2010/0105046 A1 | 4/2010 | Epstein et al. |
| 2010/0197518 A1 | 8/2010 | Xu et al. |
| 2010/0216115 A1 | 8/2010 | Yan et al. |
| 2012/0015904 A1 | 1/2012 | Sharp et al. |
| 2012/0065087 A1 | 3/2012 | Sharp et al. |
| 2012/0316076 A1 | 12/2012 | Sharp et al. |
| 2015/0018234 A1* | 1/2015 | Sharp ............... C12Q 1/6883 506/9 |
| 2016/0222455 A1 | 8/2016 | Xu et al. |
| 2016/0265059 A1 | 9/2016 | Sharp et al. |
| 2016/0289765 A1 | 10/2016 | Sharp et al. |
| 2017/0029891 A1 | 2/2017 | Sharp et al. |

FOREIGN PATENT DOCUMENTS

| | | |
|---|---|---|
| WO | WO 02/12892 | 2/2002 |
| WO | WO 03/016910 | 2/2003 |
| WO | WO 2005/116268 | 12/2005 |
| WO | WO 2006/036220 | 4/2006 |
| WO | WO 2008/137465 | 11/2008 |
| WO | WO 2010/012834 | 2/2010 |
| WO | WO 2012/009547 | 1/2012 |
| WO | WO 2012/009567 | 1/2012 |
| WO | WO 2012/121978 | 9/2012 |
| WO | WO 2013/103781 | 7/2013 |

OTHER PUBLICATIONS

Indian First Examination Report dated Dec. 13, 2016 issued in Application No. In 3762/KOLNP/2009.
"*Homo sapiens* disabled homolog 2, mitogen-responsive phosphoprotein (*Drosophila*), mRNA (cDNA clone MGC:1764 Image:3504380)," Accession:BC003064.2, GI: 33870637, complete cds [Downloaded on Feb. 21, 2017 at https://www.ncbi.nim.nih.gov/nuccore/BC003064.2?report-girevhist], 1 page.
BETSI Project, Biotechnology Education & Training Sequence Investment, (2008) "Preparation of Human Chromosome Spreads," pp. 1-6; Southwestern College, 900 Otay Lakes Road, Chula Vista, 91910, www.swccd.edu/-betsi.
Jakobsen et al. (1990) "Purification of mRNA directly from crude plant tissues in 15 minutes using magnetic oligo dT microspheres," *Nucleic Acids Research*, 18(12):3669.
Shendure et al. (Oct. 2008) "Next-generation DNA sequencing," *Nature Biotechnology*, 26(10): 1135-1145.
U.S. Appl. No. 15/068,600, filed Mar. 13, 2016, Sharp et al.
U.S. Appl. No. 15/091,181, filed Apr. 5, 2016, Sharp et al.
U.S. Appl. No. 15/092,599, filed Apr. 6, 2016, Xu et al.
PCT International Search Report and Written Opinion dated Jul. 25, 2008 issued in PCT/US2008/062064 [P028WO].
PCT International Preliminary Report on Patentability dated Nov. 3, 2009 issued in PCT/US2008/062064 [P028WO].

(Continued)

*Primary Examiner* — Juliet C Switzer
(74) *Attorney, Agent, or Firm* — Weaver Austin Villeneuve & Sampson LLP

(57) ABSTRACT

The present invention provides methods and compositions for diagnosing and predicting the risk and cause of transient ischemic attacks (TIA).

19 Claims, 4 Drawing Sheets

(56) References Cited

OTHER PUBLICATIONS

PCT International Search Report and Written Opinion dated Mar. 28, 2012 issued in PCT/US2011/044062 [P038WO].
PCT International Preliminary Report on Patentability dated Jan. 15, 2013 issued in PCT/US2011/044062 [P038WO].
PCT International Search Report and Written Opinion dated Mar. 28, 2012 issued in PCT/US2011/044023 [P039WO].
PCT International Preliminary Report on Patentability dated Jan. 15, 2013 issued in PCT/US2011/044023 [P039WO].
PCT International Search Report and Written Opinion dated Oct. 24, 2012 issued in PCT/US2012/027316 [P057WO].
PCT International Preliminary Report on Patentability dated Sep. 10, 2013 issued in PCT/US2012/027316 [P057WO].
PCT International Search Report and Written Opinion dated Apr. 12, 2013 issued in PCT/US2013/020240 [P078WO].
PCT International Preliminary Report on Patentability dated Jul. 8, 2014 issued in PCT/US2013/020240 [P078WO].
European Extended Search Report dated Mar. 16, 2011 issued in EP10014221.5 [P028EPD1].
European Extended Search Report dated Nov. 12, 2013 issued in EP11807532.4 [P038EP].
European Extended Search Report dated Apr. 11, 2014 issued in EP11807519.1 [P039EP].
"Affymetrix GeneChip Human Genome U133 Array Set HG-U133B," *GEO Accession viewer* (Mar. 11, 2002), XP002427171 pp. 1-4.
"Affymetrix Genechip Human Genome U133 plus 2.0 Array," *GEO Accession viewer 7* (Nov. 7, 2003), XP002343693 pp. 1-3.
Barr et al. (2010) "Genomic biomarkers and cellular pathways of ischemic stroke by RNA gene expression profiling," *Neurology*, 75:1009-1014.
Benner et al. (2001) "Evolution, language and analogy in functional genomics," *Trends in Genetics*, 17(7):414-418.
Cheung et al. (2003) "Natural variation in human gene expression assessed in lymphoblastoid cells," *Nature Genetics*, 33:422-425.
Cobb et al. (2002) "Sepsis gene expression profiling: Murine splenic compared with hepatic responses determined by using complementary DNA microarrays," *Crit Care Med*, 30(12):2711-2721.
Crawford et al., (2007) "The biological importance of measuring individual variation," *J. Exp. Biol.*, 210:1613-1621.
Davi et al. (2009) "CD40 ligand and MCP-1 as predictors of cardiovascular events in diabetic patients with stroke," *J. Atheroscler. Thromb.* 16:707-713.
Ferronato et al. (2010) "Upregulated Expression of Toll-like Receptor 4 in Peripheral Blood of Ischaemic Stroke Patients Correlates with Cyclooxygenase 2 Expression," *European Journal of Vascular and Endovascular Surgery*, 41(3): 358-363.
Fung et al. (2008) "A biomarker panel for peripheral arterial disease," *Vasc. Med.*, 13:217-224.
Greenbaum et al. (2003) "Comparing protein abundance and mRNA expression levels on a genomic scale," *Genome Biology*, 4:117(1-8).
Haller et al. (2004) "Equivalence test in quantitative reverse transcription polymerase chain reaction: confirmation of reference genes suitable for normalization," *Anal. Biochem,*. 335:1-9.
Hassan et al. (2003) "Marker of endothelial dysfunction in lacunar infarction and ischaemic leukoaraiosis," *Brain*, 126:424-432.
Hou et al. (2003) "High-density DNA Microarray Analysis of Gene Expression Following Transient Focal Cerebral Ischemia in Mouse," *International Congress Series*, 1252:45-56.
Jensen et al. (2008) "The promise and potential pitfalls of serum biomarkers for ischemic stroke and transient ischemic attack," *Neurologist* 14(4):243-246.
Jensen et al. (2009) "Potential biomarkers for the diagnosis of stroke," *Expert Review of Cardiovascular Therapy*, 7(4):389-93.
Jickling et al. (2010) "Biomarkers of ischemic stroke," *US Neurology*, 5(2):52-54.
Jickling et al. (Nov. 2010) "Signatures of cardioembolic and large vessel ischemic stroke," *Ann Neurol.*, 68(5):681-692.
Jickling et al. (2011) "Profiles of lacunar and non-lacunar stroke," *Ann Neurol.*, 70(3):477-485.
Jickling et al. (2012) "Prediction of cardioembolic, arterial and lacunar causes of cryptogenic stroke by gene expression and infarct location," *Stroke*, 43(8): 2036-2041 [doi:10.1161/STROKEAHA.111.648725 pp. 1-12].
Karl-Olof Lövblad et al. (2006) "Actual diagnostic approach to the acute stroke patient," *Neuro Eur Radiol*, 16:1253-1269.
Laskowitz et al. (2005) "Panel of Biomarkers Predicts Stroke," *Ann. N.Y. Acad. Sci.*, 1053:30.
Leypoldt et al. (2009) "Dimethylarginine Dimethylaminohydrolase-1 Transgenic Mice are not Protected from Ischemic Stroke," *PlosOne*, 4(10):e7337(1-4).
Li et al. (Oct. 2013) "Transcriptome Analysis Reveals Distinct Patterns of Long Noncoding RNAs in Heart and Plasma of Mice with Heart Failure," *PLOS One*, 8(10):e77938, 10 pp.
Lim et al. (2010) "MicroRNA in Cerebral Ischemia," *Translational Stroke Research*, 1:287-303.
Lynch et al. (2004) "Novel diagnostic test for acute stroke," *Stroke*, 35(1):57-63.
May et al. (1988) "How many species are there on Earth," *Science*241:1441-1449.
Montaner et al. (2008) "Etiologic diagnosis of ischemic stroke subtypes with plasma biomarkers," *Stroke*, 39(8):2280-7.
Moore et al. (2005) "Using peripheral blood mononuclear cells to determine a gene expression profile of acute ischemic stroke: a pilot investigation," *Circulation*, 111(2):212-21.
Patel et al. (Dec. 12, 2001) "Lack of Clinical Significance of Early Ischemic Changes on Computed Tomography in Acute Stroke," *Jama*, 286(22):2830-2838.
Pradervand et al. (2008) "Affymetrix Whole-Transcript Human Gene 1.0 ST array is highly concordant with standard 3'expression arrays," *BioTechniques*, 44(6):759-762.
Read et al. (2001) "Stroke Genomics: Approaches to Identify, Validate, and Understand Ischemic Stroke Gene Expression," *J. Cereb. Blood Flow Metab.*, 21:755-778.
Reynolds et al. (2003) "Early Biomarkers of Stroke," *Clin. Chem.*, 49:1733-1739.
Rothwell et al. (2007) "Effect of urgent treatment of transient ischaemic attack and minor stroke on early recurrent stroke (Express study): a prospective population-based sequential comparison," *Lancet*, 370:1432-42.
Sendera et al. (2002) "Expression Profiling with Oligonucleotide Arrays: Technologies and Applications for Neurobiology," *Neurochemical Research*, 27:1005-1026.
Sharp et al. (2007) "Genomic Profiles of Stroke in Blood," *Stroke*, 28:691-693.
Slogoff et al. (1985) "Does Perioperative Myocardial Ischemia Lead to Postoperative Myocardial Infarction?" *Anesthesiology*, 62:107-114.
Stamova et al. (2009) "Identification and validation of suitable endogenous reference genes for gene expression studies in human peripheral blood," *BMC Medical Genomics* 2:49 pp. 1-13.
Stamova et al. (2010) "Gene Expression Profiling of Blood for the Prediction of Ischemic Stroke," *Stroke*, 41:2171-2177.
Stapleton et al. (Mar. 1999) "Prospective Comparison of Whole-Blood- and Plasma-Based Hepatitis C Virus RNA Detection Systems: Improved Detection Using Whole Blood as the Source of Viral RNA," *Journal of Clinical Microbiology*, 37(3):484-489.
Swarup et al. (2007) "Circulating (cell-free) nucleic acids—A promising, non-invasive tool for early detection of several human diseases," *FEBS Letters*, 581:795-799.
Tang et al. (2005) "Blood Gene Expression Profiling of Neurologic Diseases: A Pilot Microarray Study," *Arch Neurol.*, 62:210-215.
Tang et al. (2006) "Gene expression in blood changes rapidly in neutrophils and monocytes after ischemic stroke in humans: a microarray study," *Journal of Cerebral Blood Flow and Metabolism*, 26(8):1089-1102.
Thellin et al. (1999) "Housekeeping genes as internal standards: use and limits," *J. Biotechnol.*, 75:291-295.

(56) References Cited

OTHER PUBLICATIONS

Tombul et al. (2005) "Hemostatic markers and platelet aggregation factors as predictive markers for type of stroke and neurological disability following cerebral infarction," *Journal of Clinical Neuroscience*, 12(4): 429-434.

Veltkamp et al. (2002) "Transient focal ischemia increases endothelial nitric oxide synthase in cerebral blood vessels," *Stroke*, 33(11):2704-2710.

Viswanathan et al. (2006) "Cerebral Microhemorrhage," *Stroke, Journal of the American Heart Association*, 37:550-555.

Whiteley et al. (2008) "Blood Biomarkers in the Diagnosis of Ischemic Stroke: A Systematic Review," *Stroke*, 39(10):2902-2909.

Whiteley et al. (2009) "Blood Markers for the Prognosis of Ischemic Stroke: A Systematic Review," *Stroke*, 40:e380-e389, 27pp.

Xu et al. (2008) "Gene expression in peripheral blood differs after cardioembolic compared with large-vessel atherosclerotic stroke: biomarkers for the etiology of ischemic stroke," *J Cereb Blood Flow Metab.*, 28(7):1320-1328 [Epub Apr. 2, 2008].

Zhan et al. (2011) "Transient ischemic attacks characterized by RNA profiles in blood," *Neurology*, 77(19):1718-1724.

Zhan et al. (2010) "Brief focal cerebral ischemia that simulates transient ischemic attacks in humans regulates gene expression in rat peripheral blood" *J Cereb Blood Flow Metab.*, 30(1):110-118 DOI: 10.1038/jcbfm.2009.189.

Ziegler et al. (2007) "TLR2 has a Detrimental role in Mouse Transient Focal Cerebral Ischemia," *Biochemical and Biophsucal Research Communication*, 359:574-579.

\* cited by examiner

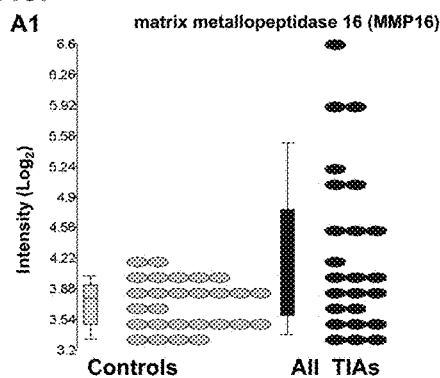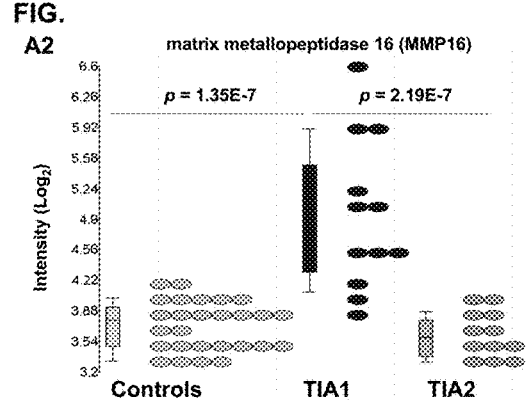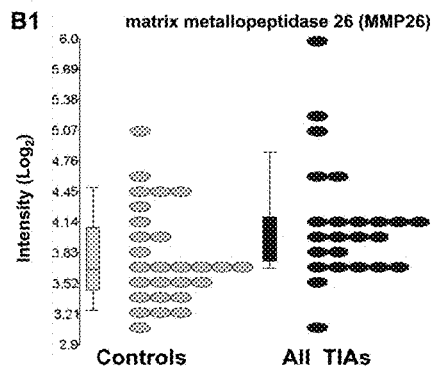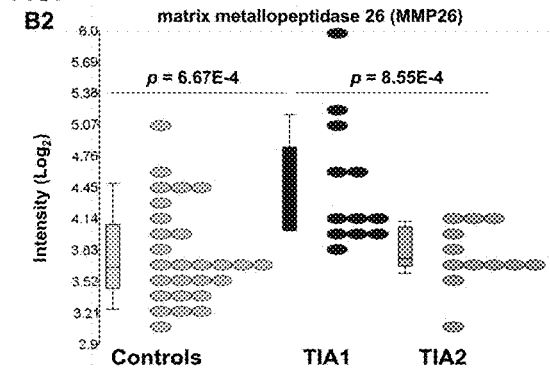
*Figure 4A-B*

BIOMARKERS FOR DIAGNOSIS OF TRANSIENT ISCHEMIC ATTACKS

CROSS-REFERENCE TO RELATED APPLICATIONS

This application is a divisional of U.S. application Ser. No. 13/182,630, filed on Jul. 14, 2011, which claims the benefit of U.S. Provisional Application No. 61/364,334, filed on Jul. 14, 2010, the entire disclosure of which is hereby incorporated herein by reference for all purposes.

STATEMENT AS TO RIGHTS TO INVENTIONS MADE UNDER FEDERALLY SPONSORED RESEARCH AND DEVELOPMENT

This invention was made with Government support under Grant No. NS056302, awarded by the National Institutes of Health. The government has certain rights in this invention.

FIELD OF THE INVENTION

The present invention provides methods and compositions for diagnosing and predicting the risk and cause of transient ischemic attacks (TIA).

BACKGROUND OF THE INVENTION

Transient ischemic attacks (TIAs) are common, affecting over 300,000 persons per year in the United States alone. Though TIA symptoms resolve by definition, TIAs are far from benign. As many as 25% of TIA patients have recurrent ischemic vascular events that occur within days to weeks following a TIA (1-3). Despite the high incidence and clinical importance, the development of therapies specifically targeted toward TIA has been limited by the paucity of knowledge regarding the underlying biology. Furthermore, the clinical diagnosis of TIA is imperfect and extensive evaluation in those incorrectly diagnosed with TIA is costly (4).

We have previously demonstrated that blood gene expression profiles in rats change following experimental ischemic strokes and TIAs (5). Very brief focal ischemia in rats, simulating human TIA, elicits a dramatic change in brain tissue characterized by increased Heat Shock Protein (HSP70) expression, microglial activation and macrophage infiltration (6). This change in brain cellular function and inflammation alters blood immune cells, a process that can be detected using whole genome expression analysis (5). Furthermore, the genes and associated functional pathways differ markedly between very brief focal ischemia and ischemic stroke (5).

Human TIAs have also been associated with alterations in systemic inflammation. TIA patients tend to have elevated C-reactive protein (CRP) (7), IL-6, VCAM-1 and cytokine levels, as well as elevated leukocyte counts (8-10). Lp-PLA2, a marker of unstable atherosclerotic plaque, is also associated with TIA (11-12) as are fibrinogen (13-14) and D-Dimer (15). Whether such biological differences represent a cause or consequence of TIA remains unclear. However, better understanding of the pathophysiology represented by such differences will facilitate development of treatments targeted to TIA.

Gene expression has been useful for identifying differences between patients with ischemic stroke and controls (16-18), but such studies have not been applied to TIA. The present invention is based, in part, on gene expression profiles that provide insight into the immunological differences that exist in patients with TIAs.

BRIEF SUMMARY OF THE INVENTION

The present invention provides compositions and methods for determining the occurrence, predicting the risk of occurrence and predicting the cause of transient ischemic attacks.

Accordingly, in one aspect, the invention provides methods for diagnosing a transient ischemic attack (TIA) or a predisposition for experiencing TIA, the method comprising: determining a level of expression of a plurality of TIA-associated biomarkers in a biological sample from a patient, wherein an increase or decrease of the level of expression compared to a control indicates that the patient has suffered or is at risk of experiencing TIA, wherein the plurality of TIA-associated biomarkers is selected from the biomarkers set forth in Tables 1, 2, 5A, 5B, 5C, 5D, 7, 8 and 9.

In some embodiments, the methods further comprise obtaining a biological sample from the patient. In some embodiments, the biological sample is blood, serum or plasma.

In some embodiments, the determining step is performed at 3 or fewer hours after a suspected ischemic event. In some embodiments, the determining step is performed at 3 or more hours after a suspected ischemic event, for example, at about 6, 12, 24, 36, 48 or more hours after a suspected ischemic event. In some embodiments, the determining step is performed at least 24 hours after a suspected ischemic event.

In some embodiments, an increased expression level of one or more or all TIA-associated biomarkers selected from the group consisting of DKFZP434B061, FAM55D, FLJ30375, IGFBP5, LTBR and SCN2A indicates that the patient has suffered or is at risk of experiencing TIA. In some embodiments, an increased expression level of one or more or all TIA-associated biomarkers selected from the group consisting of GABRB2, ELAVL3, TWIST1, DPPA4, DKFZP434P211, DLX6, ZNF479, ASTN2, SNX31, ALS2CR11, LOC440345 indicates that the patient has suffered or is at risk of experiencing TIA.

In some embodiments, an increased expression level of one or more or all TIA-associated biomarkers selected from the group consisting of GABRB2, ELAVL3, COL1A1, SHOX2, GABRB2, TWIST1, DPPA4, DKFZP434P211, WIT1, SOX9, DLX6, ANXA3, EPHA3, SOX11, SLC26A8, CCRL1, FREM2, STOX2, ZNF479, LOC338862, ASTN2, FOLH1, SNX31, KREMEN1, ZNF479, ALS2CR11, FIGN, RORB, LOC732096, GYPA, ALPL, LHX2, GALNT5, SRD5A2L2, GALNT14, OVOL2, BMPR1B, UNC5B, ODZ2, ALPL, RASAL2, SHOX, C19orf59, ZNF114, SRGAP1, ELAVL2, NCRNA00032, LOC440345, FLJ30375, TFPI, PTGR1, ROBO1, NR2F2, GRM5, LUM, FLJ39051, COL1A2, CASP5, OPCML, TTC6, TFAP2B, CRISP2, SOX11, ANKRD30B, FLJ39051, SCN2A, MYNN, FOXA2, DKFZP434B061, LOC645323, SNIP, LOC645323, LOC374491, ADAM30, SIX3, FLJ36144, CARD8, KREMEN1, RP1-127L4.6, FAM149A, B3GAT2, SPOCK3, G30, ITGBL1, IQGAP3, C7orf45, ZNF608, LOC375010, LRP2, TGFB2, SHOX2, HOXC4///HOXC6, ELTD1, FAM182B///RP13-401N8.2, PRO0478, LIFR, FOLH1, EHF, NDST3, BRUNOL5, LOC728460, PDE1A, POU2AF1, FAT1, PCDH11X///PCDH11Y, FLJ37786, SLC22A4, DHRS13, EHF, MEG3, PIWIL1, LOC203274, LOC100133920///LOC286297, DMRT1, ADM, VWA3B, GAFA3, HESX1, ADAMDEC1, CAV1, LAMB4, TPTE, PPP1R1C, HPSE, AIM2, RUNDC3B, CARD16, FAM124A, MGC39584, OSM, RFX2, MYBPC1, LTBR, C18orf2, SNRPN, FLJ36031, IL1B, TRPM1, OSTCL, MAPK14, KCNJ15///LOC100131955, FIGN, HNT, S100A12, CHIT1, C7orf53, FAM13A1, GNAO1, MAPK14, FAM55D, PRKD2, LIMK2, C18orf54, IGFBP5, EVI1, PLSCR1, FOXC1, LOC646627, ZNF462, CNTLN, ZNF438, DEFB105A///DEFB105B, LOC340017, C1orf67, ACSL1, ADH1B, SLC2A14///SLC2A3, IL1B, ST3GAL4, UBE2J1, PNPLA3 and PAPPA indicates that the patient has suffered or is at risk of experiencing TIA.

In some embodiments, a decreased expression level of one or more or all TIA-associated biomarkers selected from the group consisting of ATG9B, DIP2C, EDAR, GSTM1, GUSBL2, SMURF2, ZNF512B indicates that the patient has suffered or is at risk of experiencing TIA.

In some embodiments, a decreased expression level of one or more or all TIA-associated biomarkers selected from the group consisting of NBPF10///RP11-94I2.2, SFXN1, SPIN3, UNC84A, OLFM2, PPM1K, P2RY10, ZNF512B, MORF4L2, GIGYF2, ERAP2, SLFN13, LOC401431, MED6, BAIAP2L1///LOC100128461, LNPEP, MBNL1, NOS3, MCF2L, KIAA1659, SCAMP5, LOC648921, ANAPC5, SPON1, FUS, GPR22, GAL3ST4, METTL3, LOC100131096, FAAH2, SMURF2, SNRPN, FBLN7, GLS, G3BP1, RCAN3, EPHX2, DIP2C, CCDC141, CLTC, FOSB, CACNA1I, UNQ6228, ATG9B, AK5, SPIN3, RBM14, SNRPN, MAN1C1, HELLS, EDAR, SLC3A1, ZNF519, LOC100130070///LOC100130775///LOC100131787///LOC100131905///LOC100132291///LOC100132488///RPS27, ZC3H12B, IQGAP2, SOX8, WHDC1L2, TNPO1, TNFRSF21, TSHZ2, DMRTC1///DMRTC1B, GSTM1, GSTM2, PNMA6A, CAND1, CCND3, GSTM1, GUSBL2 indicates that the patient has suffered or is at risk of experiencing TIA.

In some embodiments, an increased expression level of 2, 3, 4, 5, 6, 7, or more or all, TIA-associated biomarkers selected from the group consisting of FLJ30375, SCN2A, DKFZP434B061, LTBR, FAM55D, and IGFBP5 and a decreased expression level of 2, 3, 4, 5, 6, 7, or more or all, TIA-associated biomarkers selected from the group consisting of GUSBL2, GSTM1, EDAR, ATG9B, DIP2C, SMURF2, and ZNF512B indicates that the patient has suffered or is at risk of experiencing TIA.

In some embodiments, the methods further comprise determining the level of expression of one or biomarkers selected from the group consisting of CNTN4, TLR5, GPR84, BCL6, NELL2, APBA2 and MLL. In some embodiments, detection of an increased level of expression of a biomarker selected from CNTN4, TLR5, GPR84 and BCL6 indicates that the patient has suffered or is at risk of experiencing TIA. In some embodiments, detection of a decreased level of expression of a biomarker selected from NELL2, APBA2 and MLL indicates that the patient suffered or is at risk of experiencing TIA.

In some embodiments, the methods further comprises the step of determining the cause of stroke. In some embodiments, the patient overexpresses a plurality of genes listed in Table 7, indicative of a chronic inflammatory state. In some embodiments, the level of expression of one or more or all genes selected from the group consisting of MMP16, MMP19, MMP26, COL1A1, COL1A2, COL3A1, COL10A1, COL11A1, COL25A1, COL27A1, FGFs and EGFR is increased in comparison to the control, and the patient is determined to have atherosclerosis.

In some embodiments, the patient is exhibiting symptoms of TIA. In some embodiments, the patient is asymptomatic.

In some embodiments, the methods further comprise the step of providing an appropriate treatment or prevention regime for TIA to the patient.

In some embodiments, the level of expression of the biomarker is determined at the transcriptional level. For example, RNA levels of the biomarker can be determined. The RNA can be mRNA, rRNA, tRNA or microRNA (miRNA). In some embodiments, the level of RNA expression is determined using a microarray.

In some embodiments, the level of expression is determined by detecting hybridization of an TIA-associated gene probe to gene transcripts of the biomarkers in the biological sample.

In some embodiments, the hybridization step is performed on a nucleic acid microarray chip. In some embodiments, the hybridization step is performed in a microfluidics assay plate.

In some embodiments, the level of expression is determined by amplification of gene transcripts of the biomarkers. In some embodiments, the amplification reaction is a polymerase chain reaction (PCR).

In some embodiments, the level of expression of the biomarker is determined at the protein level.

In some embodiments, the level of expression of at least 15 biomarkers is determined. In some embodiments, the level of expression of about 15-85, 20-70, 30-60 or 40-50 biomarkers are determined. In some embodiments, about 15, 20, 25, 30, 35, 40, 45, 50, 55, 60, 65, 70, 75, 80, 85, 90, 95, 100, or more, biomarkers are determined. The levels of expression of the plurality of biomarkers can be concurrently or sequentially determined.

In some embodiments, the control is the expression level of a plurality of expressed endogenous reference biomarkers. In some embodiments, the one or more or all endogenous reference biomarkers are listed in Table 3. In some embodiments, the TIA-associated biomarkers are overexpressed or underexpressed at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression levels of a plurality of stably expressed endogenous reference biomarkers, e.g., those listed in Table 3. In some embodiments, the expression levels of 2, 3, 4, 5, 6, 7, 8, 9, 10, 15, 20, 25, 30, 35, or all, the endogenous reference biomarkers selected from the group consisting of USP7, MAPRE2, CSNK1G2, SAFB2, PRKAR2A, PI4KB, CRTC1, HADHA, MAP1LC3B, KAT5, CDC2L1///CDC2L2, GTSE1, CDC2L1///CDC2L2, TCF25, CHP, LRRC40, hCG_2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445///LOC115110, PEX16 are determined as a control.

In some embodiments, the control is the expression level of the same biomarker in a healthy individual. In some embodiments, the control is the expression level of the same biomarker in an individual who has not experienced a vascular event (e.g., TIA, ischemic stroke, myocardial infarction, peripheral vascular disease, or venous thromboembolism). In some embodiments, the control is a threshold level of expression, e.g., of the same TIA-associated biomarker, optionally normalized to the expression level of a stably expressed endogenous reference biomarker, representative of a population of healthy individuals.

In a related aspect, the invention provides a solid support comprising a plurality of nucleic acids that hybridize to a plurality of the genes set forth in Tables 1, 2, 5A, 5B, 5C, 5D, 7, 8 and/or 9, wherein the nucleic acids are attached to the solid support. In some embodiments, the solid support comprises a plurality of nucleic acids that hybridize to a plurality of the genes set forth in Tables 1 and 2. The solid support can further comprise a plurality of nucleic acids that hybridize to a plurality of the genes set forth in Table 3. The solid support can be attached to at least about 15, 20, 25, 30, 35, 40, 45, 50, 55, 60, 75, 80, 85, 90, 95 or 100, or more, genes set forth in Tables 1, 2, 5A, 5B, 5C, 5D, 7, 8, 9 and/or 3. The solid support can be a microarray.

In one embodiment, the solid support comprises 2, 3, 4, 5, 6, 7, 8, 9, 10, 11, 12, 13, 14, or more or all, nucleic acids that hybridize to a plurality of the genes selected from the group consisting of GUSBL2, GSTM1, FLJ30375, SCN2A, DKFZP434B061, EDAR, ATG9B, DIP2C, LTBR, SMURF2, FAM55D, IGFBP5, and ZNF512B.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 3rd ed. (2001) Cold Spring Harbor Laboratory Press, Cold Spring Harbor, N.Y. and Ausubel, et al., CURRENT PROTOCOLS IN MOLECULAR BIOLOGY, 1990-2008, Wiley Interscience), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

"Ischemia" or "ischemic event" as used herein refers to diseases and disorders characterized by inadequate blood supply (i.e., circulation) to a local area due to blockage of the blood vessels to the area. Ischemia includes for example, strokes and transient ischemic attacks. Strokes include, e.g., ischemic stroke (including, but not limited to, cardioembolic strokes, atheroembolic or atherothrombotic strokes, i.e., strokes caused by atherosclerosis in the carotid, aorta, heart, and brain, small vessel strokes (i.e., lacunar strokes), strokes caused by diseases of the vessel wall, i.e., vasculitis, strokes caused by infection, strokes caused by hematological disorders, strokes caused by migraines, and strokes caused by medications such as hormone therapy), hemorrhagic ischemic stroke, intracerebral hemorrhage, and subarachnoid hemorrhage.

The term "transient ischemic attack," "TIA," or "mini-stroke" interchangeably refer to a change in the blood supply to a particular area of the brain, resulting in brief neurologic dysfunction that persists, by definition, for less than 24 hours. By definition, a TIA resolves within 24 hours, but most TIA symptoms resolve within a few minutes. If symptoms persist longer, then it is categorized as a stroke. Symptoms include temporary loss of vision (typically amaurosis fugax); difficulty speaking (aphasia); weakness on one side of the body (hemiparesis); numbness or tingling (paresthesia), usually on one side of the body, and dizziness, lack of coordination or poor balance. The symptoms of a TIA usually last a few seconds to a few minutes and most symptoms disappear within 60 minutes.

"TIA reference expression profile" refers to the pattern of expression of a set of genes (e.g., a plurality of the genes set forth in Tables 1, 2, 5A, 5B, 5C, 5D, 7, 8 and/or 9 differentially expressed (i.e., overexpressed or underexpressed) in an individual who has suffered or is at risk of experiencing TIA relative to the expression in a control (e.g., the expression level in an individual free of an ischemic event or the expression level of a stably expressed endogenous reference biomarker). A gene from Tables 1, 5B, 5C, 5D, 7, 8 and/or 9 that is expressed at a level that is at least about 1.5-, 1.6-, 1.7-, 1.8-, 1.9-, 2.0-, 2.1-, 2.2-, 2.3-, 2.4-, 2.5-, 2.6-, 2.7-, 2.8-, 2.9-, 3.0-, 3.1-, 3.2-, 3.3-, 3.4- or 3.5-fold higher than the level in a control is a gene overexpressed in TIA and a gene from Tables 2, 5A, 5C, 5D, 7, 8 and/or 9 that is expressed at a level that is at least about 1.5-, 1.6-, 1.7-, 1.8-, 1.9-, 2.0-, 2.1-, 2.2-, 2.3-, 2.4-, 2.5-, 2.6-, 2.7-, 2.8-, 2.9-, 3.0-, 3.1-, 3.2-, 3.3-, 3.4- or 3.5-fold lower than the level in a control is a gene underexpressed in TIA. Alternately, genes that are expressed at a level that is at least about 10%, 20%, 30%, 40%, 50%, 60%, 70%, 80%, 90%, or 100% higher than the level in a control is a gene overexpressed in TIA and a gene that is expressed at a level that is at least about 10%, 20%, 30%, 40%, 50%, 60%, 70%, 80%, 90%, or 100% lower than the level in a control is a gene underexpressed in TIA.

A "plurality" refers to two or more, for example, 2, 3, 4, 5, 6, 7, 8, 9, 10, 11, 12, 13, 14, 15, 16, 17, 18, 19, 20, 21, 22, 23 or more (e.g., genes). In some embodiments, a plurality refers to concurrent determination of expression levels about 15-85, 20-60 or 40-50 genes, for example, about 15, 20, 25, 30, 35, 40, 45, 50, 55, 60, 65, 70, 75, 80, 85, 90, 95, 100, or more, genes. In some embodiments, "plurality" refers to all genes listed in one or more or all tables, e.g., all genes listed in Tables 1, 2, 5A, 5B, 5C, 5D, 7, 8 and/or 9.

The terms "patient," "subject" or "individual" interchangeably refers to a mammal, for example, a human or a non-human mammal, including primates (e.g., macaque, pan troglodyte, pongo), a domesticated mammal (e.g., felines, canines), an agricultural mammal (e.g., bovine, ovine, porcine, equine) and a laboratory mammal or rodent (e.g., rattus, murine, lagomorpha, hamster, guinea pig).

"Sample" or "biological sample" includes sections of tissues such as biopsy and autopsy samples, and frozen sections taken for histologic purposes. Such samples include blood, sputum, tissue, lysed cells, brain biopsy, cultured cells, e.g., primary cultures, explants, and transformed cells, stool, urine, etc. A biological sample is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish.

"Array" as used herein refers to a solid support comprising attached nucleic acid or peptide probes. Arrays typically comprise a plurality of different nucleic acid or peptide probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., *Science,* 251:767-777 (1991). These arrays may generally be produced using mechanical synthesis methods or light directed synthesis methods which incorporate a combination of photolithographic methods and solid phase synthesis methods. Techniques for the synthesis of these arrays using mechanical synthesis methods are described in, e.g., U.S. Pat. No. 5,384,261. Arrays may comprise a planar surface or may be nucleic acids or peptides on beads, gels, polymeric surfaces, fibers such as fiber optics, glass or any other appropriate substrate as described in, e.g., U.S. Pat. Nos. 5,770,358, 5,789,162, 5,708,153, 6,040,193 and 5,800, 992. Arrays may be packaged in such a manner as to allow for diagnostics or other manipulation of an all inclusive device, as described in, e.g., U.S. Pat. Nos. 5,856,174 and 5,922,591.

The term "gene" means the segment of DNA involved in producing a polypeptide chain; it includes regions preceding and following the coding region (leader and trailer) as well as intervening sequences (introns) between individual coding segments (exons).

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The phrase "stringent hybridization conditions" refers to conditions under which a probe will hybridize to its target subsequence, typically in a complex mixture of nucleic acid, but to no other sequences. Stringent hybridization conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent hybridization conditions are selected to be about 5-10° C. lower than the thermal melting point for the specific sequence at a defined ionic strength Ph. The $T_m$ is the temperature (under defined ionic strength, Ph, and nucleic concentration) at which 50% of the probes complementary to the target hybridize to the target sequence at equilibrium (as the target sequences are present in excess, at $T_m$, 50% of the probes are occupied at equilibrium). Stringent hybridization conditions will be those in which the salt concentration is less than about 1.0 M sodium ion, typically about 0.01 to 1.0 M sodium ion concentration (or other salts) at Ph 7.0 to 8.3 and the temperature is at least about 30° C. for short probes (e.g., 10 to 50 nucleotides) and at least about 60° C. for long probes (e.g., greater than 50 nucleotides). Stringent hybridization conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent hybridization conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. "Amino acid analogs" refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine I, Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region of a TIA-associated gene (e.g., a gene set forth in Tables 1, 2, 5A, 5B, 5C, 5D, 7, 8 and/or 9), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to TIA-associated nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention.

Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

By "host cell" is meant a cell that contains an expression vector and supports the replication or expression of the expression vector. Host cells may be, for example, prokaryotic cells such as *E. coli* or eukaryotic cells such as yeast cells or mammalian cells such as CHO cells.

"Inhibitors," "activators," and "modulators" of expression or of activity are used to refer to inhibitory, activating, or modulating molecules, respectively, identified using in vitro and in vivo assays for expression or activity, e.g., ligands, agonists, antagonists, and their homologs and mimetics. The term "modulator" includes inhibitors and activators. Inhibitors are agents that, e.g., inhibit expression of a polypeptide or polynucleotide of the invention or bind to, partially or totally block stimulation or enzymatic activity, decrease, prevent, delay activation, inactivate, desensitize, or down regulate the activity of a polypeptide or polynucleotide of the invention, e.g., antagonists. Activators are agents that, e.g., induce or activate the expression of a polypeptide or polynucleotide of the invention or bind to, stimulate, increase, open, activate, facilitate, enhance activation or enzymatic activity, sensitize or up regulate the activity of a polypeptide or polynucleotide of the invention, e.g., agonists. Modulators include naturally occurring and synthetic ligands, antagonists, agonists, small chemical molecules and the like. Assays to identify inhibitors and activators include, e.g., applying putative modulator compounds to cells, in the presence or absence of a polypeptide or polynucleotide of the invention and then determining the functional effects on a polypeptide or polynucleotide of the invention activity. Samples or assays comprising a polypeptide or polynucleotide of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a polypeptide or polynucleotide of the invention relative to the control is about 80%, optionally 50% or 25-1%. Activation is achieved when the activity value of a polypeptide or polynucleotide of the invention relative to the control is 110%, optionally 150%, optionally 200-500%, or 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, RNAi, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, preferably less than about 2000 Daltons,

BRIEF DESCRIPTION OF THE DRAWINGS

FIGS. 4A-B. MMP16 (A) and MMP26 (B) transcript expression in TIA patients (blue) and control subjects (pink). A. MMP16. There was no difference in MMP16 expression for all control subjects compared to all TIA patients (A1). There was a significant increase in expression of MMP16 in the TIA1 patients compared to both control (p=1.35×10$^{-7}$) and TIA2 groups (p=2.19×10$^{-7}$) and no difference in MMP16 expression between control subjects and TIA2 patients (A2). B. MMP26. There was no difference in MMP26 expression for all control subjects compared to all TIA patients (B1). There was a significant increase in expression of MMP26 in the TIA1 group compared to both control (p=6.67×10$^{-4}$) and TIA2 groups (p=8.55×10$^{-4}$) and no difference in MMP26 expression between control subjects and TIA2 patients (B2). The X axis shows categories of subjects. The Y axis shows the log 2-intensity/RNA expression. Pink=controls. Dark blue=All TIA or TIA1. Light blue=TIA2.

DETAILED DESCRIPTION

1. Introduction

Figure 1:
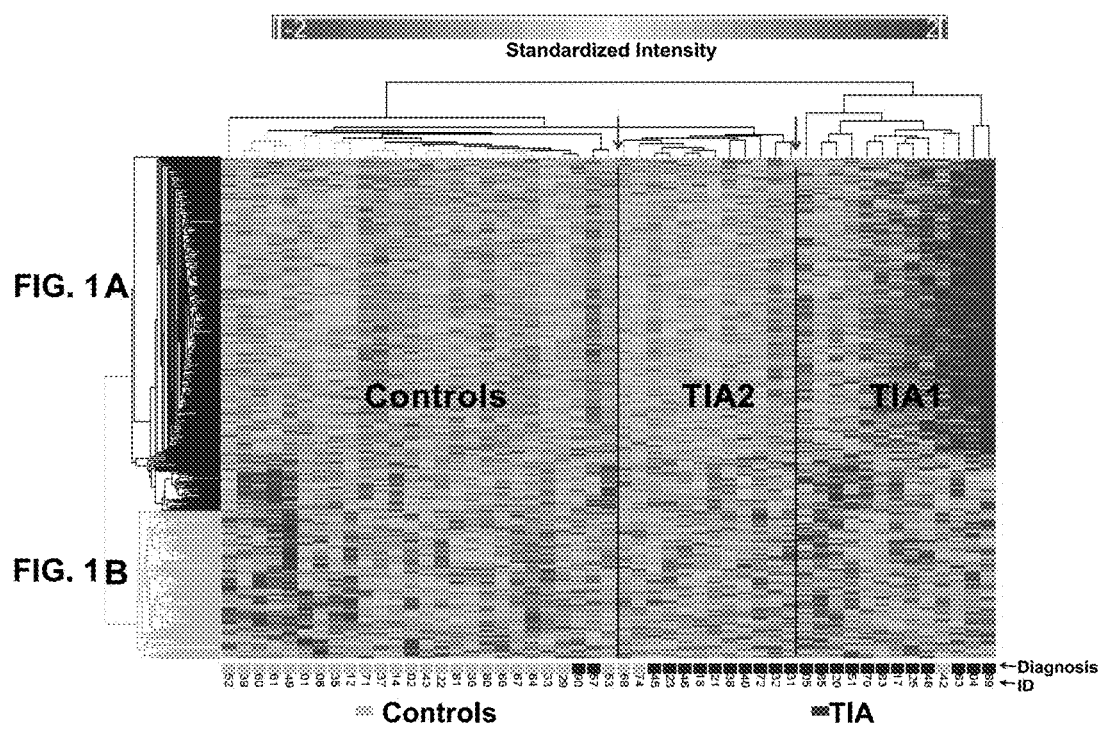
FIGS. 1A-B. Heat map of 460 genes/probes differentially expressed in blood between Transient Ischemic Attack (TIA) patients and controls (FDR≤0.05, absolute fold change>1.5). Each column on the X axis represents 1 patient, with 24 TIA patients (blue) and 27 controls (pink). Each row on the Y axis represents individual genes. TIAs cluster separately from controls as indicated by the green arrow (top). Within TIA subjects, at least two clusters are apparent as indicated by the red arrow. These two TIA clusters are labeled TIA1 and TIA2. Two TIA patients (ID: 57 and 90) clustered with controls. Three controls (ID: 42, 68, and 74) clustered with TIAs. Red=up regulation. Green=down regulation. ID=subjects ID. Diagnosis=blue (TIA) and pink (Controls).

Although transient ischemic attacks (TIAs) are common, the underlying biology remains poorly understood. The present invention is based, in part, on the discovery that TIAs differentially regulate gene expression in blood. The differentially regulated genes indicative of the occurrence or risk of occurrence of TIAs find use in the diagnosis, treatment and prevention of TIAs in patients. Patients with recent TIAs can be differentiated from controls without previous vascular events using gene expression profiles in blood. In addition, human patients appear to develop different immune response subtypes following transient ischemic attacks.

2. Individuals Who can Benefit from the Present Methods

Individuals who will benefit from the present methods may be exhibiting symptoms of TIA or stroke. Alternatively, the subject may be suspected of having experienced TIA. In some embodiments, the subject has not experienced and/or is not at risk of having an intracerebral hemorrhage. In some embodiments, the subject has not experienced and/or is not at risk of having an intracerebral hemorrhage or hemorrhagic stroke. In some embodiments, the subject has been diagnosed as having not experienced and/or not at risk of having an intracerebral hemorrhage or hemorrhagic stroke.

In some embodiments, the levels of expression of the panel of biomarkers is determined within 3 hours of a suspected ischemic event. In some embodiments, the levels of expression of the panel of biomarkers are determined at 3 or more hours after a suspected ischemic event. In some embodiments, the levels of expression of the panel of biomarkers are determined within 6, 12, 18, 24, 36, 48 hours of a suspected ischemic event.

In some cases, the subject is asymptomatic, but may have a risk or predisposition to experiencing TIA, e.g., based on genetics, a related disease condition, environment or lifestyle. For example, in some embodiments, the patient suffers from a chronic inflammatory condition, e.g., has an autoimmune disease (e.g., rheumatoid arthritis, Crohn's disease inflammatory bowel disease), atherosclerosis, hypertension, or diabetes. In some embodiments, the patient has high LDL-cholesterol levels or suffers from a cardiovascular disease (e.g., atherosclerosis, coronary artery disease). In some embodiments, the patient has an endocrine system disorder, a neurodegenerative disorder, a connective tissue disorder, or a skeletal and muscular disorder. Exemplary disorders associated with, related to, or causative of TIA are provided in Table 7.

In some embodiments, the patient may have a neurological disorder and have increased or decreased expression relative to a control level of expression of a plurality of biomarkers selected from the group consisting of ACSL1, ADH1B, AK5, ANXA3, APBA2, ASTN2 (includes EG:23245), BCL6, BMPR1B, CASP5, CAV1, CNTN4, DIP2C, ELAVL2, EPHX2, ERAP2, FAM124A, FAM13A, FAM149A, FAT1, FOLH1, FOXC1, GABRB2, GIGYF2, GNAO1, GRM5, GSTM1, HESX1, HOXC6, IGFBP5, IL1B, IQGAP2, ITGBL1, LAMB4, LIFR, LTBR, MECOM, NBPF10, NDST3, NELL2, NOS3, NTM, ODZ2, OLFM2, OPCML, PDE1A, RFX2, ROBO1, S100A12, SCN2A, SLC22A4 (includes EG:6583), SLC2A3, SLC3A1, SOX9, SPOCK3, SPON1, TGFB2, TLR5, TNFRSF21, TRPM1, TSHZ2, TTC6 (includes EG:115669), UNC5B, UNC84A and ZNF608.

In some embodiments, the patient may have a skeletal or muscular disorder and have increased or decreased expression relative to a control level of expression of a plurality of biomarkers selected from the group consisting of ACSL1, ADM, AK5, ASTN2 (includes EG:23245), BCL6, BMPR1B, CARD8, CASP5, CCND3, CLTC, CNTN4, COL1A1, COL1A2, DIP2C, DNAH14, EDAR, ELAVL2, EPHA3, EPHX2, FAM124A, FOSB, GABRB2, GIGYF2, GNAO1, HOXC6, IL1B, KCNJ15, LAMB4, LIFR, LTBR, LUM, MAPK14, MYBPC1, NOS3, ODZ2, OSM, PAPPA, PDE1A, ROBO1, RUNDC3B, S100A12, SCN2A, SHOX, SLC22A4 (includes EG:6583), SOX9, SPOCK3, TLR5, TNFRSF21, TNPO1, TSHZ2, TTC6 (includes EG:115669), TWIST1, UNC5B, VWA3B and ZNF438.

In some embodiments, the patient may have an inflammatory disorder and have increased or decreased expression relative to a control level of expression of a plurality of biomarkers selected from the group consisting of ACSL1, ADM, AK5, ANXA3, APBA2, ASTN2 (includes EG:23245), BCL6, CARD8, CASP5, CAV1, CCND3, CCRL1, CLTC, CNTN4, DIP2C, DNAH14, EDAR, EPHA3, EPHX2, ERAP2, FAM124A, FBLN7, FOSB, FREM2, GABRB2, GRM5, IL1B, KCNJ15, LAMB4, LHX2, LNPEP, LRP2, LTBR, LUM, MAPK14, MECOM, MYBPC1, NOS3, ODZ2, OPCML, OSM, PAPPA, PDE1A, PPP1R1C, ROBO1, RUNDC3B, S100A12, SCN2A, SFXN1, SLC22A4 (includes EG:6583), SLC26A8, SMURF2, SNRPN, SPON1, TGFB2, TLR5, TNFRSF21, TNPO1, TTC6 (includes EG:115669), TWIST1, UNC5B, VWA3B and ZNF438.

In some embodiments, the patient may have a cardiovascular disorder and have increased or decreased expression relative to a control level of expression of a plurality of biomarkers selected from the group consisting of ACSL1, ADM, AK5, ALPL, ASTN2 (includes EG:23245), BCL6, BMPR1B, C18ORF54, CACNA1I, CARD16, CAV1, CNTN4, DMRT1, DNAH14, EDAR, EPHX2, ERAP2, FAM13A, FOLH1, FOSB, FREM2, GABRB2, GRM5, GSTM1, IL1B, IQGAP2, LIFR, LTBR, MAN1C1, MAPK14, MBNL1, MCF2L, MECOM, MYBPC1, NOS3, NTM, ODZ2, OLFM2, OPCML, PAPPA, PDE1A, ROBO1, RORB, S100A12, SMURF2, SNRPN, SOX9, SPOCK3, SPON1, TFPI, TRPM1, UNC84A and VWA3B.

In some embodiments, the patient may have an immunological disorder and have increased or decreased expression relative to a control level of expression of a plurality of biomarkers selected from the group consisting of ACSL1, ADM, AK5, ANXA3, ASTN2 (includes EG:23245), BCL6, CARD8, CASP5, CCND3, CCRL1, CLTC, CNTN4, COL1A2, DIP2C, DNAH14, EDAR, EPHA3, EPHX2, FAM124A, FAT1, FOSB, GABRB2, GOLGA6L2, GSTM1, GUSBL2, IL1B, IQGAP2, KCNJ15, LAMB4, LTBR, MAPK14, MYBPC1, NELL2, NOS3, NTM, ODZ2, OPCML, OSM, PAPPA, PDE1A, ROBO1, RUNDC3B, S100A12, SLC22A4 (includes EG:6583), SNRPN, SPON1, TLR5, TNFRSF21, TNPO1, TSHZ2, TTC6 (includes EG:115669), VWA3B and ZNF438.

In some embodiments, the patient may have a metabolic disorder and have increased or decreased expression relative to a control level of expression of a plurality of biomarkers selected from the group consisting of ACSL1, ADAM30, AK5, ALPL, ALS2CR11, ASTN2 (includes EG:23245), BCL6, CARD8, CASP5, CCRL1, CNTLN, CNTN4, COL1A2, DIP2C, DMRT1, DNAH14, EPHA3, EPHX2, FAT1, FOXA2, GABRB2, GUSBL2, IGFBP5, IL1B, IQGAP2, ITGBL1, LRP2, LTBR, MAPK14, MBNL1, NELL2, NOS3, NTM, ODZ2, OPCML, PAPPA, PLSCR1, ROBO1, SLC22A4 (includes EG:6583), SLC2A3, SLC3A1, SMURF2, SNRPN, SPON1, SRGAP1, TLR5, TSHZ2, UNC84A and VWA3B.

In some embodiments, the patient may have an endocrine system disorder and have increased or decreased expression relative to a control level of expression of a plurality of biomarkers selected from the group consisting of ACSL1, ADAM30, AK5, ALPL, ALS2CR11, ASTN2 (includes EG:23245), BCL6, CARD8, CASP5, CCRL1, CNTLN, CNTN4, COL1A2, DIP2C, DMRT1, DNAH14, EPHA3, FAT1, FOXA2, GABRB2, GUSBL2, IL1B, IQGAP2, ITGBL1, LRP2, LTBR, MAPK14, MBNL1, NELL2, NOS3, NTM, ODZ2, OPCML, PAPPA, PLSCR1, ROBO1, SHOX, SLC22A4 (includes EG:6583), SLC2A3, SMURF2, SNRPN, SPON1, SRGAP1, TLR5, TSHZ2, UNC84A and VWA3B.

In some embodiments, the patient may have an autoimmune disease and have increased or decreased expression relative to a control level of expression of a plurality of biomarkers selected from the group consisting of ACSL1, ADM, AK5, ASTN2 (includes EG:23245), BCL6, CARD8, CASP5, CCND3, CLTC, CNTN4, COL1A2, DIP2C, DNAH14, EDAR, EPHA3, EPHX2, FAM124A, FOSB, GABRB2, GUSBL2, IL1B, IQGAP2, KCNJ15, LAMB4, LTBR, MAPK14, MYBPC1, NELL2, ODZ2, OPCML, OSM, PAPPA, PDE1A, ROBO1, RUNDC3B, S100A12, SLC22A4 (includes EG:6583), SNRPN, SPON1, TLR5, TNFRSF21, TNPO1, TSHZ2, TTC6 (includes EG:115669), VWA3B and ZNF438.

In some embodiments, the patient may have diabetes and have increased or decreased expression relative to a control level of expression of a plurality of biomarkers selected from the group consisting of ACSL1, ADAM30, AK5, ALPL, ALS2CR11, ASTN2 (includes EG:23245), BCL6, CARD8, CASP5, CCRL1, CNTLN, CNTN4, COL1A2, DIP2C, DMRT1, DNAH14, EPHA3, FAT1, FOXA2, GABRB2, GUSBL2, IL1B, IQGAP2, ITGBL1, LTBR, MAPK14, MBNL1, NELL2, NOS3, NTM, ODZ2, OPCML, PAPPA, PLSCR1, ROBO1, SLC22A4 (includes EG:6583), SLC2A3, SMURF2, SNRPN, SPON1, SRGAP1, TLR5, TSHZ2, UNC84A and VWA3B.

In some embodiments, the patient may have a connective tissue disorder and have increased or decreased expression relative to a control level of expression of a plurality of biomarkers selected from the group consisting of ACSL1, ADM, ASTN2 (includes EG:23245), BCL6, CARD8, CASP5, CCND3, CLTC, CNTN4, COL1A1, COL1A2, DIP2C, DNAH14, EDAR, EPHA3, EPHX2, FAM124A, FOSB, GABRB2, IL1B, KCNJ15, LAMB4, LTBR, LUM, MAPK14, ODZ2, OSM, PAPPA, PDE1A, ROBO1, RUNDC3B, S100A12, SHOX, SLC22A4 (includes EG:6583), TLR5, TNFRSF21, TNPO1, TTC6 (includes EG:115669), VWA3B and ZNF438.

In some embodiments, the patient may have rheumatic disease and have increased or decreased expression relative to a control level of expression of a plurality of biomarkers selected from the group consisting of ACSL1, ADM, ASTN2 (includes EG:23245), BCL6, CARD8, CASP5, CCND3, CLTC, CNTN4, DIP2C, DNAH14, EDAR, EPHA3, EPHX2, FAM124A, FOSB, GABRB2, IL1B, KCNJ15, LAMB4, LTBR, LUM, MAPK14, ODZ2, OSM, PAPPA, PDE1A, ROBO1, RUNDC3B, S100A12, SLC22A4 (includes EG:6583), TLR5, TNFRSF21, TNPO1, TTC6 (includes EG:115669), VWA3B and ZNF438.

In some embodiments, the patient may have arthritis and have increased or decreased expression relative to a control level of expression of a plurality of biomarkers selected from the group consisting of ACSL1, ADM, ASTN2 (includes EG:23245), BCL6, CARD8, CASP5, CCND3, CLTC, CNTN4, DIP2C, DNAH14, EDAR, EPHA3, EPHX2, FAM124A, FOSB, GABRB2, IL1B, KCNJ15, LAMB4, LTBR, LUM, MAPK14, ODZ2, OSM, PAPPA, PDE1A, ROBO1, RUNDC3B, S100A12, SLC22A4 (includes EG:6583), TNFRSF21, TNPO1, TTC6 (includes EG:115669), VWA3B, ZNF438.

In some embodiments, the patient may have atherosclerosis and have increased or decreased expression relative to a control level of expression of a plurality of biomarkers selected from the group consisting of ACSL1, AK5, ASTN2 (includes EG:23245), BMPR1B, CARD16, CNTN4, DMRT1, DNAH14, ERAP2, FOSB, FREM2, GRM5, IL1B, IQGAP2, LIFR, MAN1C1, MBNL1, MCF2L, MECOM, NOS3, NTM, ODZ2, OLFM2, PDE1A, ROBO1, RORB, SNRPN, SPOCK3, SPON1, TRPM1, UNC84A and VWA3B.

In some embodiments, the patient may have inflammatory bowel disease and have increased or decreased expression relative to a control level of expression of a plurality of biomarkers selected from the group consisting of ACSL1, AK5, APBA2, ASTN2 (includes EG:23245), CARD8, DIP2C, DNAH14, ERAP2, FBLN7, FREM2, GRM5, IL1B, LHX2, LNPEP, LTBR, MECOM, NOS3, ODZ2, OPCML, PAPPA, PDE1A, PPP1R1C, ROBO1, SFXN1, SLC22A4 (includes EG:6583), SLC26A8, SNRPN, SPON1, TGFB2, TLR5, VWA3B and ZNF438.

In some embodiments, the patient may have non-insulin-dependent diabetes mellitus and have increased or decreased expression relative to a control level of expression of a plurality of biomarkers selected from the group consisting of ADAM30, AK5, ALPL, ALS2CR11, ASTN2 (includes EG:23245), CARD8, CCRL1, CNTLN, CNTN4, COL1A2, DIP2C, DMRT1, EPHA3, FAT1, FOXA2, GABRB2, IL1B, IQGAP2, ITGBL1, MBNL1, NOS3, NTM, ODZ2, PLSCR1, ROBO1, SLC22A4 (includes EG:6583), SLC2A3, SPON1, SRGAP1, TLR5, UNC84A and VWA3B.

In some embodiments, the patient may have rheumatoid arthritis and have increased or decreased expression relative to a control level of expression of a plurality of biomarkers selected from the group consisting of ACSL1, ADM, ASTN2 (includes EG:23245), BCL6, CARD8, CLTC, CNTN4, DIP2C, DNAH14, EDAR, EPHA3, EPHX2, FAM124A, FOSB, GABRB2, IL1B, KCNJ15, LAMB4, MAPK14, ODZ2, OSM, PAPPA, PDE1A, ROBO1, RUNDC3B, S100A12, SLC22A4 (includes EG:6583), TNFRSF21, TNPO1, TTC6 (includes EG:115669), VWA3B and ZNF438.

In some embodiments, the patient may have coronary artery disease and have increased or decreased expression relative to a control level of expression of a plurality of biomarkers selected from the group consisting of ACSL1, AK5, ASTN2 (includes EG:23245), BMPR1B, CARD16, CNTN4, DMRT1, DNAH14, ERAP2, FREM2, GRM5, IL1B, IQGAP2, LIFR, MAN1C1, MBNL1, MCF2L, MECOM, NOS3, NTM, ODZ2, OLFM2, PDE1A, ROBO1, RORB, SNRPN, SPOCK3, SPON1, TRPM1, UNC84A and VWA3B.

In some embodiments, the patient may have Crohn's disease and have increased or decreased expression relative to a control level of expression of a plurality of biomarkers selected from the group consisting of ACSL1, AK5, APBA2, ASTN2 (includes EG:23245), CARD8, DIP2C, DNAH14, ERAP2, FBLN7, FREM2, GRM5, LHX2, LNPEP, MECOM, ODZ2, OPCML, PAPPA, PDE1A, PPP1R1C, ROBO1, SFXN1, SLC22A4 (includes EG:6583), SLC26A8, SNRPN, SPON1, TGFB2, TLR5, VWA3B and ZNF438.

In some embodiments, the patient may have a neurodegenerative disorder and have increased or decreased expression relative to a control level of expression of a plurality of biomarkers selected from the group consisting of ASTN2 (includes EG:23245), CASP5, CNTN4, FAM124A, FOLH1, GABRB2, GRM5, IL1B, MECOM, NDST3, NOS3, OPCML, RFX2, SCN2A, SLC22A4 (includes EG:6583), SLC2A3, SLC3A1, SPON1, TSHZ2 and ZNF608.

In some embodiments, the patient may have Alzheimer's disease and have increased or decreased expression relative to a control level of expression of a plurality of biomarkers selected from the group consisting of ASTN2 (includes EG:23245), CASP5, CNTN4, FAM124A, FOLH1, GABRB2, GRM5, IL1B, MECOM, NDST3, NOS3, OPCML, RFX2, SLC22A4 (includes EG:6583), SLC2A3, SLC3A1, SPON1, TSHZ2 and ZNF608.

3. Biomarkers Indicative of the Occurrence or Risk of TIA

Overexpressed biomarkers indicative of the occurrence of TIA or useful to predict the risk of experiencing TIA are listed in Table 1. In practicing the present methods, the expression levels of a plurality of biomarkers from Table 1 are determined, optionally in combination with other TIA-associated biomarkers described herein (e.g., in Tables 2, 5A, 5B, 5C, 5D, 7, 8 and/or 9) and known in the art.

Preferably, the expression levels of a plurality in the range of about 15-85 total biomarkers are determined, for example, about 20-70, 30-60 or 40-50 biomarkers. The expression levels of the biomarkers can be concurrently or sequentially determined. In some embodiments, the expression levels of at least about 2, 3, 4, 5, 6, 7, 8, 9, 10, 15, 20, 30, 45, 50, 60, 65, 70, 75, 80, 85, 90, 95, 100, or more, biomarkers listed in Table 1 are determined, optionally in combination with other TIA-associated biomarkers described herein (e.g., in Tables 2, 5A, 5B, 5C, 5D, 7, 8 and/or 9) and known in the art.

In patients who have experienced TIA or who are at risk of developing TIA, the biomarkers of Table 1 are overexpressed in comparison to a control level of expression. A control level of expression can refer to the level of expression of the same biomarker in an individual who has not had and is not at risk for a vascular event or the level of expression of a stably expressed endogenous control gene. In patients who have experienced TIA or who are at risk of developing TIA, the biomarkers of Table 1 are overexpressed at least 1.5-fold, e.g., at least 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to a control level of expression.

TABLE 1

TIA-associated biomarkers that are upregulated

| Probeset ID | Gene Symbol | Gene Title | RefSeq Transcript ID | Fold-Change (TIA vs. Control) | Fold-Change (TIA vs. Control) (Description) |
|---|---|---|---|---|---|
| 1557122_s_at | GABRB2 | gamma-aminobutyric acid (GABA) A receptor, beta 2 | NM_000813 /// NM_021911 | 3.49668 | TIA up vs Control |
| 227612_at | ELAVL3 | ELAV (embryonic lethal, abnormal vision, *Drosophila*)-like 3 (Hu antigen C) | NM_001420 /// NM_032281 | 3.23425 | TIA up vs Control |
| 1556499_s_at | COL1A1 | collagen, type I, alpha 1 | NM_000088 | 2.87107 | TIA up vs Control |
| 210135_s_at | SHOX2 | short stature homeobox 2 | NM_003030 /// NM_006884 | 2.86893 | TIA up vs Control |
| 242344_at | GABRB2 | gamma-aminobutyric acid (GABA) A receptor, beta 2 | NM_000813 /// NM_021911 | 2.72458 | TIA up vs Control |
| 213943_at | TWIST1 | twist homolog 1 (*Drosophila*) | NM_000474 | 2.72279 | TIA up vs Control |
| 241199_x_at | DPPA4 | developmental pluripotency associated 4 | NM_018189 | 2.68174 | TIA up vs Control |
| 222253_s_at | DKFZP434P211 | POM121 membrane glycoprotein-like 1 pseudogene | NR_003714 | 2.61011 | TIA up vs Control |
| 206954_at | WIT1 | Wilms tumor upstream neighbor 1 | NM_015855 /// NR_023920 | 2.58643 | TIA up vs Control |
| 202935_s_at | SOX9 | SRY (sex determining region Y)-box 9 | NM_000346 | 2.45928 | TIA up vs Control |
| 239309_at | DLX6 | distal-less homeobox 6 | NM_005222 | 2.4523 | TIA up vs Control |
| 209369_at | ANXA3 | annexin A3 | NM_005139 | 2.41095 | TIA up vs Control |
| 211164_at | EPHA3 | EPH receptor A3 | NM_005233 /// NM_182644 | 2.39314 | TIA up vs Control |
| 204913_s_at | SOX11 | SRY (sex determining region Y)-box 11 | NM_003108 | 2.34727 | TIA up vs Control |
| 237340_at | SLC26A8 | solute carrier family 26, member 8 | NM_052961 /// NM_138718 | 2.32491 | TIA up vs Control |
| 220351_at | CCRL1 | chemokine (C-C motif) receptor-like 1 | NM_016557 /// NM_178445 | 2.32444 | TIA up vs Control |
| 230964_at | FREM2 | FRAS1 related extracellular matrix protein 2 | NM_207361 | 2.30984 | TIA up vs Control |
| 231969_at | STOX2 | storkhead box 2 | NM_020225 | 2.2552 | TIA up vs Control |
| 1555367_at | ZNF479 | zinc finger protein 479 | NM_033273 /// XM_001714591 /// XM_001719979 | 2.25193 | TIA up vs Control |
| 1557717_at | LOC338862 | hypothetical protein LOC338862 | — | 2.22946 | TIA up vs Control |
| 1554816_at | ASTN2 | astrotactin 2 | NM_014010 /// NM_198186 /// NM_198187 /// NM_198188 | 2.22748 | TIA up vs Control |
| 217487_x_at | FOLH1 | folate hydrolase (prostate-specific membrane antigen) 1 | NM_001014986 /// NM_004476 | 2.19987 | TIA up vs Control |
| 241987_x_at | SNX31 | sorting nexin 31 | NM_152628 | 2.19167 | TIA up vs Control |
| 227250_at | KREMEN1 | kringle containing transmembrane protein 1 | NM_001039570 /// NM_001039571 | 2.16406 | TIA up vs Control |
| 1555368_x_at | ZNF479 | zinc finger protein 479 | NM_033273 /// XM_001714591 /// XM_001719979 | 2.16203 | TIA up vs Control |
| 1563673_a_at | ALS2CR11 | amyotrophic lateral sclerosis 2 (juvenile) chromosome region, candidate 11 | NM_152525 | 2.15177 | TIA up vs Control |
| 239710_at | FIGN | fidgetin | NM_018086 | 2.14096 | TIA up vs Control |
| 242385_at | RORB | RAR-related orphan receptor B | NM_006914 | 2.14023 | TIA up vs Control |
| 1570009_at | LOC732096 | similar to hCG2040240 | XM_001720784 /// XM_001725388 /// XR_016064 | 2.13184 | TIA up vs Control |
| 1559520_at | GYPA | Glycophorin A | NM_002099 | 2.12904 | TIA up vs Control |
| 215783_s_at | ALPL | alkaline phosphatase, liver/bone/kidney | NM_000478 /// NM_001127501 | 2.1006 | TIA up vs Control |
| 206140_at | LHX2 | LIM homeobox 2 | NM_004789 | 2.0959 | TIA up vs Control |
| 240390_at | GALNT5 | UDP-N-acetyl-alpha-D-galactosamine:polypeptide N-acetylgalactosaminyltransferase | NM_014568 | 2.09257 | TIA up vs Control |

TABLE 1-continued

TIA-associated biomarkers that are upregulated

| Probeset ID | Gene Symbol | Gene Title | RefSeq Transcript ID | Fold-Change (TIA vs. Control) | Fold-Change (TIA vs. Control) (Description) |
|---|---|---|---|---|---|
| 241961_at | SRD5A2L2 | steroid 5 alpha-reductase 2-like 2 | NM_001010874 | 2.08494 | TIA up vs Control |
| 219271_at | GALNT14 | UDP-N-acetyl-alpha-D-galactosamine:polypeptide N-acetylgalactosaminyltransferase | NM_024572 | 2.07605 | TIA up vs Control |
| 206048_at | OVOL2 | ovo-like 2 (*Drosophila*) | NM_021220 | 2.06333 | TIA up vs Control |
| 242579_at | BMPR1B | bone morphogenetic protein receptor, type IB | NM_001203 | 2.05687 | TIA up vs Control |
| 226899_at | UNC5B | unc-5 homolog B (*C. elegans*) | NM_170744 | 2.04351 | TIA up vs Control |
| 231867_at | ODZ2 | odz, odd Oz/ten-m homolog 2 (*Drosophila*) | NM_001080428 /// NM_001122679 | 2.03143 | TIA up vs Control |
| 1557924_s_at | ALPL | alkaline phosphatase, liver/bone/kidney | NM_000478 /// NM_001127501 | 2.02022 | TIA up vs Control |
| 217194_at | RASAL2 | RAS protein activator like 2 | NM_004841 /// NM_170692 | 2.00632 | TIA up vs Control |
| 207570_at | SHOX | short stature homeobox | NM_000451 /// NM_006883 | 2.00103 | TIA up vs Control |
| 235568_at | C19orf59 | chromosome 19 open reading frame 59 | NM_174918 | 1.99789 | TIA up vs Control |
| 1552946_at | ZNF114 | zinc finger protein 114 | NM_153608 | 1.99445 | TIA up vs Control |
| 1554473_at | SRGAP1 | SLIT-ROBO Rho GTPase activating protein 1 | NM_020762 | 1.99203 | TIA up vs Control |
| 228260_at | ELAVL2 | ELAV (embryonic lethal, abnormal vision, *Drosophila*)-like 2 (Hu antigen B) | NM_004432 | 1.9905 | TIA up vs Control |
| 1559292_s_at | NCRNA00032 | Clone IMAGE: 2275835 C9orf14 mRNA, partial sequence; alternatively spliced | XM_376821 /// XM_938938 | 1.98554 | TIA up vs Control |
| 214984_at | LOC440345 | hypothetical protein LOC440345 | XR_015786 | 1.98536 | TIA up vs Control |
| 1557155_a_at | FLJ30375 | CDNA clone IMAGE: 5301781 | XM_001724993 /// XM_001725199 /// XM_001725628 | 1.97451 | TIA up vs Control |
| 215447_at | TFPI | Tissue factor pathway inhibitor (lipoprotein-associated coagulation inhibitor), | NM_001032281 /// NM_006287 | 1.96509 | TIA up vs Control |
| 228825_at | PTGR1 | prostaglandin reductase 1 | NM_012212 | 1.95262 | TIA up vs Control |
| 213194_at | ROBO1 | roundabout, axon guidance receptor, homolog 1 (*Drosophila*) | NM_002941 /// NM_133631 | 1.95207 | TIA up vs Control |
| 209119_x_at | NR2F2 | nuclear receptor subfamily 2, group F, member 2 | NM_021005 | 1.94377 | TIA up vs Control |
| 206819_at | DKFZP434P211 | POM121 membrane glycoprotein-like 1 pseudogene | NR_003714 | 1.93567 | TIA up vs Control |
| 207235_s_at | GRM5 | glutamate receptor, metabotropic 5 | NM_000842 /// NM_001143831 | 1.93451 | TIA up vs Control |
| 201744_s_at | LUM | lumican | NM_002345 | 1.93131 | TIA up vs Control |
| 230999_at | FLJ39051 | CDNA FLJ39051 fis, clone NT2RP7011452 | — | 1.92605 | TIA up vs Control |
| 229218_at | COL1A2 | collagen, type I, alpha 2 | NM_000089 | 1.92067 | TIA up vs Control |
| 207500_at | CASP5 | caspase 5, apoptosis-related cysteine peptidase | NM_001136109 /// NM_001136110 /// NM_001136111 /// NM_001136112 /// NM_004347 // | 1.91798 | TIA up vs Control |
| 214111_at | OPCML | opioid binding protein/cell adhesion molecule-like | NM_001012393 /// NM_002545 | 1.91158 | TIA up vs Control |
| 1556666_a_at | TTC6 | tetratricopeptide repeat domain 6 | NM_001007795 | 1.91015 | TIA up vs Control |
| 214451_at | TFAP2B | transcription factor AP-2 beta (activating enhancer binding protein 2 beta) | NM_003221 | 1.89347 | TIA up vs Control |
| 210262_at | CRISP2 | cysteine-rich secretory protein 2 | NM_001142407 /// NM_001142408 /// NM_001142417 /// NM_001142435 /// NM_003296 | 1.88349 | TIA up vs Control |

TABLE 1-continued

TIA-associated biomarkers that are upregulated

| Probeset ID | Gene Symbol | Gene Title | RefSeq Transcript ID | Fold-Change (TIA vs. Control) | Fold-Change (TIA vs. Control) (Description) |
|---|---|---|---|---|---|
| 204914_s_at | SOX11 | SRY (sex determining region Y)-box 11 | NM_003108 | 1.88201 | TIA up vs Control |
| 1562292_at | ANKRD30B | ankyrin repeat domain 30B | XM_001716904 /// XM_001717561 /// XM_001717810 | 1.86641 | TIA up vs Control |
| 227925_at | FLJ39051 | CDNA FLJ39051 fis, clone NT2RP7011452 | — | 1.86433 | TIA up vs Control |
| 229057_at | SCN2A | sodium channel, voltage-gated, type II, alpha subunit | NM_001040142 /// NM_001040143 /// NM_021007 | 1.85129 | TIA up vs Control |
| 237510_at | MYNN | Myoneurin, mRNA (cDNA clone IMAGE: 4721583) | NM_018657 | 1.85041 | TIA up vs Control |
| 40284_at | FOXA2 | forkhead box A2 | NM_021784 /// NM_153675 | 1.8498 | TIA up vs Control |
| 233092_s_at | DKFZP434B061 | DKFZP434B061 protein | XR_015528 /// XR_040812 | 1.84946 | TIA up vs Control |
| 230902_at | LOC645323 | CDNA clone IMAGE: 5260726 | NR_015436 /// NR_024383 /// NR_024384 /// XR_041118 /// XR_041119 /// XR_041120 | 1.84336 | TIA up vs Control |
| 232547_at | SNIP | SNAP25-interacting protein | NM_025248 | 1.83841 | TIA up vs Control |
| 238850_at | LOC645323 | hypothetical LOC645323 | NR_015436 /// NR_024383 /// NR_024384 /// XR_041118 /// XR_041119 /// XR_041120 | 1.81503 | TIA up vs Control |
| 233879_at | LOC374491 | TPTE and PTEN homologous inositol lipid phosphatase pseudogene | NR_002815 | 1.81019 | TIA up vs Control |
| 243520_x_at | ADAM30 | ADAM metallopeptidase domain 30 | NM_021794 | 1.80193 | TIA up vs Control |
| 206634_at | SIX3 | SIX homeobox 3 | NM_005413 | 1.78989 | TIA up vs Control |
| 1560790_at | FLJ36144 | hypothetical protein FLJ36144 | XR_040632 /// XR_040633 /// XR_040634 | 1.78391 | TIA up vs Control |
| 232969_at | CARD8 | caspase recruitment domain family, member 8 | NM_014959 | 1.78265 | TIA up vs Control |
| 235370_at | KREMEN1 | kringle containing transmembrane protein 1 | NM_001039570 /// NM_001039571 | 1.77475 | TIA up vs Control |
| 1555990_at | RP1-127L4.6 | hypothetical protein LOC150297 | NM_001010859 | 1.76603 | TIA up vs Control |
| 222291_at | FAM149A | family with sequence similarity 149, member A | NM_001006655 /// NM_015398 | 1.75785 | TIA up vs Control |
| 239144_at | B3GAT2 | beta-1,3-glucuronyltransferase 2 (glucuronosyltransferase S) | NM_080742 | 1.75721 | TIA up vs Control |
| 235342_at | SPOCK3 | sparc/osteonectin, cwcv and kazal-like domains proteoglycan (testican) 3 | NM_001040159 /// NM_016950 | 1.75314 | TIA up vs Control |
| 1553024_at | G30 | protein LG30-like | — | 1.75094 | TIA up vs Control |
| 214927_at | ITGBL1 | integrin, beta-like 1 (with EGF-like repeat domains) | NM_004791 | 1.73813 | TIA up vs Control |
| 229538_s_at | IQGAP3 | IQ motif containing GTPase activating protein 3 | NM_178229 | 1.73797 | TIA up vs Control |
| 1553329_at | C7orf45 | chromosome 7 open reading frame 45 | NM_145268 | 1.72974 | TIA up vs Control |
| 232303_at | ZNF608 | zinc finger protein 608 | NM_020747 | 1.72629 | TIA up vs Control |
| 1558982_at | LOC375010 | hypothetical LOC375010 | XR_041271 | 1.72485 | TIA up vs Control |
| 230863_at | LRP2 | low density lipoprotein-related protein 2 | NM_004525 | 1.71146 | TIA up vs Control |
| 228121_at | TGFB2 | transforming growth factor, beta 2 | NM_001135599 /// NM_003238 | 1.70904 | TIA up vs Control |
| 208443_x_at | SHOX2 | short stature homeobox 2 | NM_003030 /// NM_006884 | 1.70616 | TIA up vs Control |

TABLE 1-continued

TIA-associated biomarkers that are upregulated

| Probeset ID | Gene Symbol | Gene Title | RefSeq Transcript ID | Fold-Change (TIA vs. Control) | Fold-Change (TIA vs. Control) (Description) |
|---|---|---|---|---|---|
| 206858_s_at | HOXC4 /// HOXC6 | homeobox C4 /// homeobox C6 | NM_004503 /// NM_014620 /// NM_153633 /// NM_153693 | 1.70414 | TIA up vs Control |
| 219134_at | ELTD1 | EGF, latrophilin and seven transmembrane domain containing 1 | NM_022159 | 1.70282 | TIA up vs Control |
| 222205_x_at | FAM182B /// RP13-401N8.2 | family with sequence similarity 182, member B /// hypothetical gene supported by | XM_001132551 /// XM_001133521 /// XM_001718365 /// XM_933752 | 1.70042 | TIA up vs Control |
| 220696_at | PRO0478 | PRO0478 protein | — | 1.69169 | TIA up vs Control |
| 225571_at | LIFR | leukemia inhibitory factor receptor alpha | NM_001127671 /// NM_002310 | 1.69168 | TIA up vs Control |
| 217483_at | FOLH1 | folate hydrolase (prostate-specific membrane antigen) 1 | NM_001014986 /// NM_004476 | 1.68955 | TIA up vs Control |
| 232360_at | EHF | ets homologous factor | NM_012153 | 1.68951 | TIA up vs Control |
| 220429_at | NDST3 | N-deacetylase/N-sulfotransferase (heparan glucosaminyl) 3 | NM_004784 | 1.68889 | TIA up vs Control |
| 232416_at | BRUNOL5 | bruno-like 5, RNA binding protein (Drosophila) | NM_021938 | 1.68747 | TIA up vs Control |
| 231434_at | LOC728460 | similar to FLJ32921 protein | XM_001128581 /// XM_001129498 /// XM_001723364 | 1.68733 | TIA up vs Control |
| 208396_s_at | PDE1A | phosphodiesterase 1A, calmodulin-dependent | NM_001003683 /// NM_005019 | 1.68453 | TIA up vs Control |
| 1569675_at | POU2AF1 | POU class 2 associating factor 1, mRNA (cDNA clone MGC: 45211 IMAGE: 5554134) | NM_006235 | 1.67876 | TIA up vs Control |
| 201579_at | FAT1 | FAT tumor suppressor homolog 1 (Drosophila) | NM_005245 | 1.67288 | TIA up vs Control |
| 210292_s_at | PCDH11X /// PCDH11Y | protocadherin 11 X-linked /// protocadherin 11 Y-linked | NM_014522 /// NM_032967 /// NM_032968 /// NM_032969 /// NM_032971 /// NM_032972 | 1.6605 | TIA up vs Control |
| 1558579_at | FLJ37786 | hypothetical LOC642691 | XR_041472 /// XR_041473 | 1.66029 | TIA up vs Control |
| 205896_at | SLC22A4 | solute carrier family 22 (organic cation/ergothioneine transporter), member 4 | NM_003059 | 1.65918 | TIA up vs Control |
| 226121_at | DHRS13 | dehydrogenase/reductase (SDR family) member 13 | NM_144683 | 1.65414 | TIA up vs Control |
| 219850_s_at | EHF | ets homologous factor | NM_012153 | 1.64412 | TIA up vs Control |
| 235077_at | MEG3 | maternally expressed 3 (non-protein coding) | NR_002766 /// NR_003530 /// NR_003531 | 1.6384 | TIA up vs Control |
| 214868_at | PIWIL1 | piwi-like 1 (Drosophila) | NM_004764 | 1.63171 | TIA up vs Control |
| 232034_at | LOC203274 | CDNA FLJ31544 fis, clone NT2RI2000865 | — | 1.63147 | TIA up vs Control |
| 1556704_s_at | LOC100133920 /// LOC286297 | hypothetical protein LOC100133920 /// hypothetical protein LOC286297 | NR_024443 /// XM_001714612 /// XM_372109 /// XM_933054 /// XM_933058 | 1.63034 | TIA up vs Control |
| 220493_at | DMRT1 | doublesex and mab-3 related transcription factor 1 | NM_021951 | 1.61917 | TIA up vs Control |
| 202912_at | ADM | adrenomedullin | NM_001124 | 1.61874 | TIA up vs Control |
| 1561200_at | VWA3B | von Willebrand factor A domain containing 3B | NM_144992 | 1.61802 | TIA up vs Control |
| 1555726_at | GAFA3 | FGF-2 activity-associated protein 3 | XM_001715321 /// XM_001722922 /// XM_001723636 | 1.61768 | TIA up vs Control |
| 211267_at | HESX1 | HESX homeobox 1 | NM_003865 | 1.61355 | TIA up vs Control |
| 206134_at | ADAMDEC1 | ADAM-like, decysin 1 | NM_014479 | 1.61274 | TIA up vs Control |
| 203065_s_at | CAV1 | caveolin 1, caveolae protein, 22 kDa | NM_001753 | 1.60773 | TIA up vs Control |

TABLE 1-continued

TIA-associated biomarkers that are upregulated

| Probeset ID | Gene Symbol | Gene Title | RefSeq Transcript ID | Fold-Change (TIA vs. Control) | Fold-Change (TIA vs. Control) (Description) |
|---|---|---|---|---|---|
| 215516_at | LAMB4 | laminin, beta 4 | NM_007356 | 1.60646 | TIA up vs Control |
| 220205_at | TPTE | transmembrane phosphatase with tensin homology | NM_199259 /// NM_199260 /// NM_199261 | 1.60547 | TIA up vs Control |
| 1555462_at | PPP1R1C | protein phosphatase 1, regulatory (inhibitor) subunit 1C | NM_001080545 | 1.60542 | TIA up vs Control |
| 219403_s_at | HPSE | heparanase | NM_001098540 /// NM_006665 | 1.60481 | TIA up vs Control |
| 206513_at | AIM2 | absent in melanoma 2 | NM_004833 | 1.60396 | TIA up vs Control |
| 215321_at | RUNDC3B | RUN domain containing 3B | NM_001134405 /// NM_001134406 /// NM_138290 | 1.60322 | TIA up vs Control |
| 1552701_a_at | CARD16 | caspase recruitment domain family, member 16 | NM_001017534 /// NM_052889 | 1.59587 | TIA up vs Control |
| 230519_at | FAM124A | family with sequence similarity 124A | NM_145019 | 1.59499 | TIA up vs Control |
| 240814_at | MGC39584 | hypothetical gene supported by BC029568 | XR_017735 /// XR_017787 /// XR_041937 | 1.59341 | TIA up vs Control |
| 230170_at | OSM | oncostatin M | NM_020530 | 1.58899 | TIA up vs Control |
| 226872_at | RFX2 | regulatory factor X, 2 (influences HLA class II expression) | NM_000635 /// NM_134433 | 1.58786 | TIA up vs Control |
| 214087_s_at | MYBPC1 | myosin binding protein C, slow type | NM_002465 /// NM_206819 /// NM_206820 /// NM_206821 | 1.58609 | TIA up vs Control |
| 203005_at | LTBR | lymphotoxin beta receptor (TNFR superfamily, member 3) | NM_002342 | 1.58399 | TIA up vs Control |
| 223977_s_at | C18orf2 | chromosome 18 open reading frame 2 | NM_031416 /// NR_023925 /// NR_023926 /// NR_023927 /// NR_023928 | 1.58384 | TIA up vs Control |
| 240204_at | SNRPN | small nuclear ribonucleoprotein polypeptide N | NM_003097 /// NM_022805 /// NM_022806 /// NM_022807 /// NM_022808 /// NR_001289 | 1.58295 | TIA up vs Control |
| 229521_at | FLJ36031 | hypothetical protein FLJ36031 | NM_175884 | 1.58141 | TIA up vs Control |
| 205067_at | IL1B | interleukin 1, beta | NM_000576 | 1.57884 | TIA up vs Control |
| 206479_at | TRPM1 | transient receptor potential cation channel, subfamily M, member 1 | NM_002420 | 1.57541 | TIA up vs Control |
| 1553931_at | OSTCL | oligosaccharyltransferase complex subunit-like | NM_145303 | 1.57501 | TIA up vs Control |
| 210449_x_at | MAPK14 | mitogen-activated protein kinase 14 | NM_001315 /// NM_139012 /// NM_139013 /// NM_139014 | 1.57327 | TIA up vs Control |
| 238428_at | KCNJ15 /// LOC100131955 | potassium inwardly-rectifying channel, subfamily J, member 15 /// similar to pot | NM_002243 /// NM_170736 /// NM_170737 /// XM_001713900 /// XM_001715532 /// XM_0 | 1.56965 | TIA up vs Control |
| 238964_at | FIGN | fidgetin | NM_018086 | 1.56796 | TIA up vs Control |
| 227566_at | HNT | neurotrimin | NM_001048209 /// NM_016522 | 1.56554 | TIA up vs Control |
| 205863_at | S100A12 | S100 calcium binding protein A12 | NM_005621 | 1.5633 | TIA up vs Control |
| 208168_s_at | CHIT1 | chitinase 1 (chitotriosidase) | NM_003465 | 1.56138 | TIA up vs Control |
| 239203_at | C7orf53 | chromosome 7 open reading frame 53 | NM_001134468 /// NM_182597 | 1.55912 | TIA up vs Control |
| 1569025_s_at | FAM13A1 | family with sequence similarity 13, member A1 | NM_001015045 /// NM_014883 | 1.55876 | TIA up vs Control |

TABLE 1-continued

TIA-associated biomarkers that are upregulated

| Probeset ID | Gene Symbol | Gene Title | RefSeq Transcript ID | Fold-Change (TIA vs. Control) | Fold-Change (TIA vs. Control) (Description) |
|---|---|---|---|---|---|
| 204763_s_at | GNAO1 | guanine nucleotide binding protein (G protein), alpha activating activity polype | NM_020988 /// NM_138736 | 1.5542 | TIA up vs Control |
| 211561_x_at | MAPK14 | mitogen-activated protein kinase 14 | NM_001315 /// NM_139012 /// NM_139013 /// NM_139014 | 1.55337 | TIA up vs Control |
| 220645_at | FAM55D | family with sequence similarity 55, member D | NM_001077639 /// NM_017678 | 1.55166 | TIA up vs Control |
| 241669_x_at | PRKD2 | protein kinase D2 | NM_001079880 /// NM_001079881 /// NM_001079882 /// NM_016457 | 1.55139 | TIA up vs Control |
| 210582_s_at | LIMK2 | LIM domain kinase 2 | NM_001031801 /// NM_005569 /// NM_016733 | 1.5485 | TIA up vs Control |
| 1553652_a_at | C18orf54 | chromosome 18 open reading frame 54 | NM_173529 | 1.54796 | TIA up vs Control |
| 211959_at | IGFBP5 | insulin-like growth factor binding protein 5 | NM_000599 | 1.54545 | TIA up vs Control |
| 243277_x_at | EVI1 | ecotropic viral integration site 1 | NM_001105077 /// NM_001105078 /// NM_005241 | 1.5445 | TIA up vs Control |
| 202446_s_at | PLSCR1 | phospholipid scramblase 1 | NM_021105 | 1.54059 | TIA up vs Control |
| 1553613_s_at | FOXC1 | forkhead box C1 | NM_001453 | 1.53964 | TIA up vs Control |
| 1568933_at | LOC646627 | phospholipase inhibitor | NM_001085474 | 1.53874 | TIA up vs Control |
| 244007_at | ZNF462 | zinc finger protein 462 | NM_021224 | 1.53545 | TIA up vs Control |
| 239989_at | CNTLN | centlein, centrosomal protein | NM_001114395 /// NM_017738 | 1.53478 | TIA up vs Control |
| 229743_at | ZNF438 | zinc finger protein 438 | NM_001143766 /// NM_001143767 /// NM_001143768 /// NM_001143769 /// NM_001143770 | 1.53049 | TIA up vs Control |
| 1553002_at | DEFB105A /// DEFB105B | defensin, beta 105A /// defensin, beta 105B | NM_001040703 /// NM_152250 | 1.52948 | TIA up vs Control |
| 1560823_at | LOC340017 | hypothetical protein LOC340017 | — | 1.51946 | TIA up vs Control |
| 1554540_at | C1orf67 | chromosome 1 open reading frame 67 | NM_144989 | 1.51941 | TIA up vs Control |
| 207275_s_at | ACSL1 | acyl-CoA synthetase long-chain family member 1 | NM_001995 | 1.51866 | TIA up vs Control |
| 209614_at | ADH1B | alcohol dehydrogenase 1B (class I), beta polypeptide | NM_000668 | 1.51397 | TIA up vs Control |
| 216236_s_at | SLC2A14 /// SLC2A3 | solute carrier family 2 (facilitated glucose transporter), member 14 /// solute | NM_006931 /// NM_153449 | 1.51356 | TIA up vs Control |
| 39402_at | IL1B | interleukin 1, beta | NM_000576 | 1.51316 | TIA up vs Control |
| 203759_at | ST3GAL4 | ST3 beta-galactoside alpha-2,3-sialyltransferase 4 | NM_006278 /// XM_001714343 /// XM_001726541 /// XM_001726562 | 1.51002 | TIA up vs Control |
| 222435_s_at | UBE2J1 | ubiquitin-conjugating enzyme E2, J1 (UBC6 homolog, yeast) | NM_016021 | 1.50758 | TIA up vs Control |
| 233030_at | PNPLA3 | patatin-like phospholipase domain containing 3 | NM_025225 | 1.50269 | TIA up vs Control |
| 1559400_s_at | PAPPA | pregnancy-associated plasma protein A, pappalysin 1 | NM_002581 | 1.50009 | TIA up vs Control |

Underexpressed biomarkers indicative of the occurrence of TIA or useful to predict the risk of experiencing TIA are listed in Table 2. In practicing the present methods, the expression levels of a plurality of biomarkers from Table 2 are determined, optionally in combination with other TIA-associated biomarkers described herein (e.g., in Tables 1, 5A, 5B, 5C, 5D, 7, 8 and/or 9) and known in the art. In some embodiments, the expression levels of at least about 2, 3, 4, 5, 6, 7, 8, 9, 10, 15, 20, 30, 45, 50, 60, 65, 70, 75, 80, 85, 90, 95, 100, or more, biomarkers listed in Table 2 are determined, optionally in combination with other TIA-associated biomarkers described herein (e.g., in Tables 1, 5A, 5B, 5C, 5D, 7, 8 and/or 9) and known in the art.

In patients who have experienced TIA or who are at risk of developing TIA, the biomarkers of Table 2 are underexpressed in comparison to a control level of expression. A control level of expression can refer to the level of expression of the same biomarker in an individual who has not had and is not at risk for a vascular event or the level of expression of a stably expressed endogenous control gene. In patients who have experienced TIA or who are at risk of developing TIA, the biomarkers of Table 2 are underexpressed at least 1.5-fold, e.g., at least 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to a control level of expression.

TABLE 2

TIA-associated biomarkers that are downregulated

| Probeset ID | Gene Symbol | Gene Title | RefSeq Transcript ID | Fold-Change (TIA vs. Control) | Fold-Change (TIA vs. Control) (Description) |
|---|---|---|---|---|---|
| 242191_at | NBPF10 /// RP11-94I2.2 | neuroblastoma breakpoint family, member 10 /// hypothetical protein LOC200030 | NM_001039703 /// NM_183372 /// XM_001722184 | −1.50043 | TIA down vs Control |
| 232055_at | SFXN1 | sideroflexin 1 | NM_022754 | −1.50117 | TIA down vs Control |
| 1555883_s_at | SPIN3 | spindlin family, member 3 | NM_001010862 | −1.50348 | TIA down vs Control |
| 206487_at | UNC84A | unc-84 homolog A (*C. elegans*) | NM_001130965 /// NM_025154 | −1.50376 | TIA down vs Control |
| 223601_at | OLFM2 | olfactomedin 2 | NM_058164 | −1.5119 | TIA down vs Control |
| 244011_at | PPM1K | protein phosphatase 1K (PP2C domain containing) | NM_152542 | −1.51501 | TIA down vs Control |
| 214615_at | P2RY10 | purinergic receptor P2Y, G-protein coupled, 10 | NM_014499 /// NM_198333 | −1.51779 | TIA down vs Control |
| 55872_at | ZNF512B | zinc finger protein 512B | NM_020713 | −1.52158 | TIA down vs Control |
| 243857_at | MORF4L2 | Mrgx mRNA for MRGX | NM_001142418 /// NM_001142419 /// NM_001142420 /// NM_001142421 /// NM_001142422 | −1.52328 | TIA down vs Control |
| 1560133_at | GIGYF2 | GRB10 interacting GYF protein 2 | NM_001103146 /// NM_001103147 /// NM_001103148 /// NM_015575 | −1.52626 | TIA down vs Control |
| 1554273_a_at | ERAP2 | endoplasmic reticulum aminopeptidase 2 | NM_001130140 /// NM_022350 | −1.52883 | TIA down vs Control |
| 1553423_a_at | SLFN13 | schlafen family member 13 | NM_144682 | −1.53028 | TIA down vs Control |
| 229094_at | LOC401431 | hypothetical gene LOC401431 | XR_040272 /// XR_040273 /// XR_040274 /// XR_040275 | −1.53069 | TIA down vs Control |
| 207078_at | MED6 | mediator complex subunit 6 | NM_005466 | −1.53192 | TIA down vs Control |
| 227372_s_at | BAIAP2L1 /// LOC100128461 | BAI1-associated protein 2-like 1 /// hypothetical protein LOC100128461 | NM_018842 /// XM_001722656 /// XM_001724217 /// XM_001724858 | −1.53271 | TIA down vs Control |
| 236728_at | LNPEP | leucyl/cystinyl aminopeptidase | NM_005575 /// NM_175920 | −1.53387 | TIA down vs Control |
| 215663_at | MBNL1 | muscleblind-like (*Drosophila*) | NM_021038 /// NM_207292 /// NM_207293 /// NM_207294 /// NM_207295 /// NM_207296 | −1.53726 | TIA down vs Control |
| 229093_at | NOS3 | nitric oxide synthase 3 (endothelial cell) | NM_000603 | −1.53818 | TIA down vs Control |
| 212935_at | MCF2L | MCF.2 cell line derived transforming sequence-like | NM_001112732 /// NM_024979 | −1.53863 | TIA down vs Control |

TABLE 2-continued

TIA-associated biomarkers that are downregulated

| Probeset ID | Gene Symbol | Gene Title | RefSeq Transcript ID | Fold-Change (TIA vs. Control) | Fold-Change(TIA vs. Control) (Description) |
|---|---|---|---|---|---|
| 215750_at | KIAA1659 | KIAA1659 protein | XM_001723799 /// XM_001725435 /// XM_001726785 | −1.54646 | TIA down vs Control |
| 212699_at | SCAMP5 | secretory carrier membrane protein 5 | NM_138967 | −1.54948 | TIA down vs Control |
| 1565911_at | LOC648921 | MRNA full length insert cDNA clone EUROIMAGE 209544 | XM_001715629 /// XM_001720571 /// XR_018520 | −1.54981 | TIA down vs Control |
| 239651_at | ANAPC5 | anaphase promoting complex subunit 5 | NM_001137559 /// NM_016237 | −1.55844 | TIA down vs Control |
| 213993_at | SPON1 | spondin 1, extracellular matrix protein | NM_006108 | −1.55928 | TIA down vs Control |
| 231108_at | FUS | fusion (involved in t(12; 16) in malignant liposarcoma) | NM_004960 | −1.56277 | TIA down vs Control |
| 221288_at | GPR22 | G protein-coupled receptor 22 | NM_005295 | −1.56303 | TIA down vs Control |
| 219815_at | GAL3ST4 | galactose-3-O-sulfotransferase 4 | NM_024637 | −1.5674 | TIA down vs Control |
| 242111_at | METTL3 | methyltransferase like 3 | NM_019852 | −1.56742 | TIA down vs Control |
| 239062_at | LOC100131096 | hypothetical LOC100131096 | XM_001720907 /// XM_001726205 /// XM_001726705 | −1.57675 | TIA down vs Control |
| 230792_at | FAAH2 | fatty acid amide hydrolase 2 | NM_174912 | −1.57807 | TIA down vs Control |
| 232020_at | SMURF2 | SMAD specific E3 ubiquitin protein ligase 2 | NM_022739 | −1.57992 | TIA down vs Control |
| 226587_at | SNRPN | small nuclear ribonucleoprotein polypeptide N | NM_003097 /// NM_022805 /// NM_022806 /// NM_022807 /// NM_022808 /// NR_001289 | −1.58006 | TIA down vs Control |
| 229247_at | FBLN7 | fibulin 7 | NM_001128165 /// NM_153214 | −1.58734 | TIA down vs Control |
| 223080_at | GLS | Glutaminase, mRNA (cDNA clone MGC: 33744 IMAGE: 5263220) | NM_014905 | −1.59404 | TIA down vs Control |
| 1557350_at | G3BP1 | GTPase activating protein (SH3 domain) binding protein 1 | NM_005754 /// NM_198395 | −1.6194 | TIA down vs Control |
| 219864_s_at | RCAN3 | RCAN family member 3 | NM_013441 | −1.61977 | TIA down vs Control |
| 209368_at | EPHX2 | epoxide hydrolase 2, cytoplasmic | NM_001979 | −1.62474 | TIA down vs Control |
| 212504_at | DIP2C | DIP2 disco-interacting protein 2 homolog C (*Drosophila*) | NM_014974 | −1.62614 | TIA down vs Control |
| 1553645_at | CCDC141 | coiled-coil domain containing 141 | NM_173648 | −1.62867 | TIA down vs Control |
| 239871_at | CLTC | Clathrin, heavy chain (Hc), mRNA (cDNA clone IMAGE: 4812912) | NM_004859 | −1.63031 | TIA down vs Control |
| 202768_at | FOSB | FBJ murine osteosarcoma viral oncogene homolog B | NM_001114171 /// NM_006732 | −1.63049 | TIA down vs Control |
| 221631_at | CACNA1I | calcium channel, voltage-dependent, T type, alpha 1I subunit | NM_001003406 /// NM_021096 | −1.63297 | TIA down vs Control |
| 1558569_at | UNQ6228 | MRNA; cDNA DKFZp667K1619 (from clone DKFZp667K1619) | XM_001725293 /// XM_001725359 /// XM_001726164 | −1.63796 | TIA down vs Control |
| 229252_at | ATG9B | ATG9 autophagy related 9 homolog B (*S. cerevisiae*) | NM_173681 | −1.64694 | TIA down vs Control |
| 222862_s_at | AK5 | adenylate kinase 5 | NM_012093 /// NM_174858 | −1.64741 | TIA down vs Control |
| 1555882_at | SPIN3 | spindlin family, member 3 | NM_001010862 | −1.65127 | TIA down vs Control |
| 239635_at | RBM14 | RNA binding motif protein 14 | NM_006328 | −1.65349 | TIA down vs Control |
| 1560741_at | SNRPN | small nuclear ribonucleoprotein polypeptide N | NM_003097 /// NM_022805 /// NM_022806 /// | −1.65945 | TIA down vs Control |

TABLE 2-continued

TIA-associated biomarkers that are downregulated

| Probeset ID | Gene Symbol | Gene Title | RefSeq Transcript ID | Fold-Change (TIA vs. Control) | Fold-Change(TIA vs. Control) (Description) |
|---|---|---|---|---|---|
| | | | NM_022807 /// NM_022808 /// NR_001289 | | |
| 214180_at | MAN1C1 | mannosidase, alpha, class 1C, member 1 | NM_020379 | −1.66631 | TIA down vs Control |
| 220085_at | HELLS | helicase, lymphoid-specific | NM_018063 | −1.67692 | TIA down vs Control |
| 220048_at | EDAR | ectodysplasin A receptor | NM_022336 | −1.69385 | TIA down vs Control |
| 239667_at | SLC3A1 | solute carrier family 3 (cystine, dibasic and neutral amino acid transporters, a | NM_000341 | −1.69708 | TIA down vs Control |
| 1568873_at | ZNF519 | zinc finger protein 519 | NM_145287 | −1.70283 | TIA down vs Control |
| 236621_at | LOC100130070 /// LOC100130775 /// LOC100131787 /// LOC100131905 /// LOC100132291 /// LOC100132488 /// RPS27 | similar to metallopanstimulin /// similar to rCG63653 /// similar to metallopans | NM_001030 /// XM_001721002 /// XM_001722161 /// XM_001722965 /// XM_001723889 // | −1.70558 | TIA down vs Control |
| 229234_at | ZC3H12B | zinc finger CCCH-type containing 12B | NM_001010888 | −1.72127 | TIA down vs Control |
| 241723_at | IQGAP2 | IQ motif containing GTPase activating protein 2 | NM_006633 | −1.73571 | TIA down vs Control |
| 226913_s_at | SOX8 | SRY (sex determining region Y)-box 8 | NM_014587 | −1.73755 | TIA down vs Control |
| 1557450_s_at | WHDC1L2 | WAS protein homology region 2 domain containing 1-like 2 | XM_926785 | −1.75555 | TIA down vs Control |
| 1556116_s_at | TNPO1 | Transportin 1, mRNA (cDNA clone MGC: 17116 IMAGE: 4178989) | NM_002270 /// NM_153188 | −1.7577 | TIA down vs Control |
| 218856_at | TNFRSF21 | tumor necrosis factor receptor superfamily, member 21 | NM_014452 | −1.77712 | TIA down vs Control |
| 244521_at | TSHZ2 | Cell growth-inhibiting protein 7 | NM_173485 | −1.86192 | TIA down vs Control |
| 1553998_at | DMRTC1 /// DMRTC1B | DMRT-like family C1 /// DMRT-like family C1B | NM_001080851 /// NM_033053 | −1.86704 | TIA down vs Control |
| 204550_x_at | GSTM1 | glutathione S-transferase mu 1 | NM_000561 /// NM_146421 | −1.95136 | TIA down vs Control |
| 219308_s_at | AK5 | adenylate kinase 5 | NM_012093 /// NM_174858 | −1.95614 | TIA down vs Control |
| 204418_x_at | GSTM2 | glutathione S-transferase mu 2 (muscle) | NM_000848 /// NM_001142368 | −1.95729 | TIA down vs Control |
| 235758_at | PNMA6A | paraneoplastic antigen like 6A | NM_032882 | −1.95731 | TIA down vs Control |
| 239771_at | CAND1 | cullin-associated and neddylation-dissociated 1 | NM_018448 | −1.97531 | TIA down vs Control |
| 1562028_at | CCND3 | Cyclin D3 (CCND3), transcript variant 3, mRNA | NM_001136017 /// NM_001136125 /// NM_001136126 /// NM_001760 | −2.00377 | TIA down vs Control |
| 215333_x_at | GSTM1 | glutathione S-transferase mu 1 | NM_000561 /// NM_146421 | −2.03103 | TIA down vs Control |
| 232207_at | GUSBL2 | glucuronidase, beta-like 2 | NR_003660 /// XR_042150 /// XR_042151 | −2.10621 | TIA down vs Control |

4. Comparison to a Control Level of Expression

The expression of the TIA-associated biomarkers are compared to a control level of expression. As appropriate, the control level of expression can be the expression level of the same TIA-associated biomarker in an otherwise healthy individual (e.g., in an individual who has not experienced and/or is not at risk of experiencing TIA). In some embodiments, the control level of expression is the expression level of a plurality of stably expressed endogenous reference biomarkers, as described herein or known in the art. In some embodiments, the control level of expression is a predetermined threshold level of expression of the same TIA-associated biomarker, e.g., based on the expression level of the biomarker in a population of otherwise healthy individuals. In some embodiments, the expression level of the TIA-associated biomarker and the TIA-associated biomarker in an otherwise healthy individual are normalized to (i.e., divided by), e.g., the expression levels of a plurality of stably expressed endogenous reference biomarkers.

In some embodiments, the overexpression or underexpression of a TIA-associated biomarker is determined with reference to the expression of the same TIA-associated biomarker in an otherwise healthy individual. For example, a healthy or normal control individual has not experienced and/or is not at risk of experiencing TIA. The healthy or normal control individual generally has not experienced a vascular event (e.g., TIA, ischemic stroke, myocardial infarction, peripheral vascular disease, or venous thromboembolism). The healthy or normal control individual generally does not have one or more vascular risk factors (e.g., hypertension, diabetes mellitus, hyperlipidemia, or tobacco smoking). As appropriate, the expression levels of the target TIA-associated biomarker in the healthy or normal control individual can be normalized (i.e., divided by) the expression levels of a plurality of stably expressed endogenous reference biomarkers.

In some embodiments, the overexpression or underexpression of a TIA-associated biomarker is determined with reference to one or more stably expressed endogenous reference biomarkers. Internal control biomarkers or endogenous reference biomarkers are expressed at the same or nearly the same expression levels in the blood of patients with stroke or TIAs as compared to control patients. Target biomarkers are expressed at higher or lower levels in the blood of the stroke or TIA patients. The expression levels of the target biomarker to the reference biomarker are normalized by dividing the expression level of the target biomarker to the expression levels of a plurality of endogenous reference biomarkers. The normalized expression level of a target biomarker can be used to predict the occurrence or lack thereof of stroke or TIA, and/or the cause of stroke or TIA.

In some embodiments, the expression level of the TIA-associated biomarker from a patient suspected of having or experiencing TIA and from a control patient are normalized with respect to the expression levels of a plurality of stably expressed endogenous. The expression levels of the normalized expression of the TIA-associated biomarker is compared to the expression levels of the normalized expression of the same TIA-associated biomarker in a control patient. The determined fold change in expression=normalized expression of target biomarker in TIA patient/normalized expression of target biomarker in control patient. Overexpression or underexpression of the normalized TIA-associated biomarker in the TIA patient by at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression levels of the normalized TIA-associated biomarker in a healthy control patient indicates that the TIA patient has experienced or is at risk of experiencing TIA.

In some embodiments, the control level of expression is a predetermined threshold level. The threshold level can correspond to the level of expression of the same TIA-associated biomarker in an otherwise healthy individual or a population of otherwise healthy individuals, optionally normalized to the expression levels of a plurality of endogenous reference biomarkers. After expression levels and normalized expression levels of the TIA-associated biomarkers are determined in a representative number of otherwise healthy individuals and individuals predisposed to experiencing TIA, normal and TIA expression levels of the TIA-associated biomarkers can be maintained in a database, allowing for determination of threshold expression levels indicative of the presence or absence of risk to experience TIA or the occurrence of TIA. If the predetermined threshold level of expression is with respect to a population of normal control patients, then overexpression or underexpression of the TIA-associated biomarker (usually normalized) in the TIA patient by at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the threshold level indicates that the TIA patient has experienced or is at risk of experiencing TIA. If the predetermined threshold level of expression is with respect to a population of patients known to have experienced TIA or known to be at risk for experiencing TIA, then an expression level in the patient suspected of experiencing TIA that is approximately equal to the threshold level (or overexpressed or underexpressed greater than the threshold level of expression), indicates that the TIA patient has experienced or is at risk of experiencing TIA.

With respect to the endogenous reference biomarkers used for comparison, preferably, the endogenous reference biomarkers are stably expressed in blood. Exemplary endogenous reference biomarkers that find use are listed in Table 3, below. Further suitable endogenous reference biomarkers are published, e.g., in Stamova, et al., *BMC Medical Genomics* (2009) 2:49. In some embodiments, the expression levels of a plurality of endogenous reference biomarkers are determined as a control. In some embodiments, the expression levels of at least about 2, 3, 4, 5, 6, 7, 8, 9, 10, 15, 20, 25, 30, 35, or more, endogenous reference biomarkers, e.g., as listed in Table 3 or known in the art, are determined as a control.

In some embodiments, the expression levels of the endogenous reference biomarkers GAPDH, ACTB, B2M, HMBS and PPIB are determined as a control. In some embodiments, the expression levels of 2, 3, 4, 5, 6, 7, 8, 9, 10, 15, 20, 25, or more, endogenous reference biomarkers selected from the group consisting of USP7, MAPRE2, CSNK1G2, SAFB2, PRKAR2A, PI4KB, CRTC1, HADHA, MAP1LC3B, KAT5, CDC2L1///CDC2L2, GTSE1, CDC2L1///CDC2L2, TCF25, CHP, LRRC40, hCG_2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445///LOC115110, PEX16 are determined as a control.

TABLE 3

The 38 endogenous reference biomarkers stably expressed in blood for use in
normalization and as control levels.
Table 3 - Stably Expressed Endogenous Reference Biomarkers

| Probe Set ID | Gene Symbol | Gene Title | GenBank ID | UniGene ID | RefSeq Transcript ID | RefSeq Protein ID |
|---|---|---|---|---|---|---|
| 201499_s_at | USP7 | ubiquitin specific peptidase 7 (herpes virus-associated) | NM_003470.1 | Hs.706830 | NM_003470 | NP_003461 |
| 202501_at | MAPRE2 | microtubule-associated protein, RP/EB family, member 2 | NM_014268.1 | Hs.532824 | NM_001143826 /// NM_001143827 /// NM_014268 /// NR_026570 | NP_001137298 /// NP_001137299 /// NP_055083 |
| 202573_at | CSNK1G2 | casein kinase 1, gamma 2 | AL530441 | Hs.651905 | NM_001319 | NP_001310 |
| 203280_at | SAFB2 | scaffold attachment factor B2 | NM_014649.1 | Hs.655392 | NM_014649 | NP_055464 |
| 204842_x_at | PRKAR2A | protein kinase, cAMP-dependent, regulatory, type II, alpha | BC002763.1 | Hs.631923 | NM_004157 | NP_004148 |
| 206138_s_at | PI4KB | phosphatidylinositol 4-kinase, catalytic, beta | NM_002651.1 | Hs.632465 | NM_002651 | NP_002642 |
| 207159_x_at | CRTC1 | CREB regulated transcription coactivator 1 | NM_025021.1 | Hs.371096 | NM_001098482 /// NM_015321 | NP_001091952 /// NP_056136 |
| 208630_at | HADHA | hydroxyacyl-Coenzyme A dehydrogenase/3-ketoacyl-Coenzyme A thiolase/enoyl-Coenzyme A hydratase (trifunctional protein), alpha subunit | AI972144 | Hs.516032 | NM_000182 | NP_000173 |
| 208786_s_at | MAP1LC3B | microtubule-associated protein 1 light chain 3 beta | AF183417.1 | Hs.356061 | NM_022818 | NP_073729 |
| 209192_x_at | KAT5 | K(lysine) acetyltransferase 5 | BC000166.2 | Hs.397010 | NM_006388 /// NM_182709 /// NM_182710 | NP_006379 /// NP_874368 /// NP_874369 |
| 210474_s_at | CDC2L1 /// CDC2L2 | cell division cycle 2-like 1 (PITSLRE proteins) /// cell division cycle 2-like 2 (PITSLRE proteins) | U04819.1 | Hs.651228 | NM_024011 /// NM_033486 /// NM_033487 /// NM_033488 /// NM_033489 /// NM_033492 /// NM_033493 /// NM_033529 | NP_076916 /// NP_277021 /// NP_277022 /// NP_277023 /// NP_277024 /// NP_277027 /// NP_277028 /// NP_277071 |
| 211040_x_at | GTSE1 | G-2 and S-phase expressed 1 | BC006325.1 | Hs.386189 | NM_016426 | NP_057510 |
| 211289_x_at | CDC2L1 /// CDC2L2 | cell division cycle 2-like 1 (PITSLRE proteins) /// cell division cycle 2-like 2 (PITSLRE proteins) | AF067524.1 | Hs.651228 | NM_024011 /// NM_033486 /// NM_033487 /// NM_033488 /// NM_033489 /// NM_033492 /// NM_033493 /// NM_033529 | NP_076916 /// NP_277021 /// NP_277022 /// NP_277023 /// NP_277024 /// NP_277027 /// NP_277028 /// NP_277071 |
| 213311_s_at | TCF25 | transcription factor 25 (basic helix-loop-helix) | BF000251 | Hs.415342 | NM_014972 | NP_055787 |
| 214665_s_at | CHP | calcium binding protein P22 | AK000095.1 | Hs.406234 | NM_007236 | NP_009167 |
| 215063_x_at | LRRC40 | leucine rich repeat containing 40 | AL390149.1 | Hs.147836 | NM_017768 | NP_060238 |
| 215200_x_at | — | — | AK022362.1 | Hs.663419 | — | — |
| 215568_x_at | hCG_2003956 /// LYPLA2 /// LYPLA2P1 | hCG2003956 /// lysophospholipase II /// lysophospholipase II pseudogene 1 | AL031295 | Hs.533479 | NM_007260 /// NR_001444 | NP_009191 |
| 216038_x_at | DAXX | death-domain associated protein | BE965715 | Hs.336916 | NM_001141969 /// NM_001141970 /// NM_001350 /// NR_024517 | NP_001135441 /// NP_001135442 /// NP_001341 |
| 217393_x_at | UBE2NL | ubiquitin-conjugating enzyme E2N-like | AL109622 | Hs.585177 | NM_001012989 | NP_001013007 |
| 217549_at | — | — | AW574933 | Hs.527860 | — | — |
| 217672_x_at | EIF1 | eukaryotic translation initiation factor 1 | BF114906 | Hs.150580 | NM_005801 | NP_005792 |
| 217938_s_at | KCMF1 | potassium channel modulatory factor 1 | NM_020122.1 | Hs.654968 | NM_020122 | NP_064507 |
| 218378_s_at | PRKRIP1 | PRKR interacting protein 1 (IL11 inducible) | NM_024653.1 | Hs.406395 | NM_024653 | NP_078929 |
| 218571_s_at | CHMP4A | chromatin modifying protein 4A | NM_014169.1 | Hs.279761 | NM_014169 | NP_054888 |

TABLE 3-continued

The 38 endogenous reference biomarkers stably expressed in blood for use in normalization and as control levels.
Table 3 - Stably Expressed Endogenous Reference Biomarkers

| Probe Set ID | Gene Symbol | Gene Title | GenBank ID | UniGene ID | RefSeq Transcript ID | RefSeq Protein ID |
|---|---|---|---|---|---|---|
| 219074_at | TMEM184C | transmembrane protein 184C | NM_018241.1 | Hs.203896 | NM_018241 | NP_060711 |
| 220052_s_at | TINF2 | TERF1 (TRF1)-interacting nuclear factor 2 | NM_012461.1 | Hs.496191 | NM_001099274 /// NM_012461 | NP_001092744 /// NP_036593 |
| 220411_x_at | PODNL1 | podocan-like 1 | NM_024825.1 | Hs.448497 | NM_001146254 /// NM_001146255 /// NM_024825 | NP_001139726 /// NP_001139727 /// NP_079101 |
| 221813_at | FBXO42 | F-box protein 42 | AI129395 | Hs.522384 | NM_018994 | NP_061867 |
| 222207_x_at | LOC441258 | Williams Beuren syndrome chromosome region 19 pseudogene | AK024602.1 | Hs.711232 | — | — |
| 222733_x_at | RRP1 | ribosomal RNA processing 1 homolog (*S. cerevisiae*) | BC000380.1 | Hs.110757 | NM_003683 | NP_003674 |
| 224667_x_at | C10orf104 | chromosome 10 open reading frame 104 | AK023981.1 | Hs.426296 | NM_173473 | NP_775744 |
| 224858_at | ZDHHC5 | zinc finger, DHHC-type containing 5 | AK023130.1 | Hs.27239 | NM_015457 | NP_056272 |
| 225403_at | C9orf23 | chromosome 9 open reading frame 23 | AL528391 | Hs.15961 | NM_148178 /// NM_148179 | NP_680544 /// NP_680545 |
| 226253_at | LRRC45 | leucine rich repeat containing 45 | BE965418 | Hs.143774 | NM_144999 | NP_659436 |
| 227651_at | NACC1 | nucleus accumbens associated 1, BEN and BTB (POZ) domain containing | AI498126 | Hs.531614 | NM_052876 | NP_443108 |
| 232190_x_at | LOC100133445 /// LOC115110 | hypothetical LOC100133445 /// hypothetical protein LOC115110 | AI393958 | Hs.132272 | NR_026927 /// XR_036887 /// XR_038144 | — |
| 49878_at | PEX16 | peroxisomal biogenesis factor 16 | AA523441 | Hs.100915 | NM_004813 /// NM_057174 | NP_004804 /// NP_476515 |

5. Methods of Determining the Cause of TIA

Subsets of the TIA-associated biomarkers described herein further find use in predicting or determining the cause of TIA.

For example, patients that overexpress genes involved in extracellular matrix remodeling including one or more or all genes selected from MMP16, MMP19, MMP26, COL1A1, COL1A2, COL3A1, COL10A1, COL11A1, COL25A1, COL27A1, FGFs and EGFR may have atherosclerosis.

Individuals can have a risk or predisposition to experiencing TIA, e.g., based on genetics, a related disease condition, environment or lifestyle. For example, in some embodiments, the patient suffers from a chronic inflammatory condition, e.g., has an autoimmune disease (e.g., rheumatoid arthritis, Crohn's disease inflammatory bowel disease), atherosclerosis, hypertension, or diabetes. In some embodiments, the patient has high LDL-cholesterol levels or suffers from a cardiovascular disease (e.g., atherosclerosis, coronary artery disease). In some embodiments, the patient has an endocrine system disorder, a neurodegenerative disorder, a connective tissue disorder, or a skeletal and muscular disorder. Exemplary disorders associated with, related to, or causative of TIA are provided in Table 7.

In some embodiments, the patient may have a neurological disorder and have increased or decreased expression relative to a control level of expression of a plurality of biomarkers selected from the group consisting of ACSL1, ADH1B, AK5, ANXA3, APBA2, ASTN2 (includes EG:23245), BCL6, BMPR1B, CASP5, CAV1, CNTN4, DIP2C, ELAVL2, EPHX2, ERAP2, FAM124A, FAM13A, FAM149A, FAT1, FOLH1, FOXC1, GABRB2, GIGYF2, GNAO1, GRM5, GSTM1, HESX1, HOXC6, IGFBP5, IL1B, IQGAP2, ITGBL1, LAMB4, LIFR, LTBR, MECOM, NBPF10, NDST3, NELL2, NOS3, NTM, ODZ2, OLFM2, OPCML, PDE1A, RFX2, ROBO1, S100A12, SCN2A, SLC22A4 (includes EG:6583), SLC2A3, SLC3A1, SOX9, SPOCK3, SPON1, TGFB2, TLR5, TNFRSF21, TRPM1, TSHZ2, TTC6 (includes EG:115669), UNC5B, UNC84A and ZNF608.

In some embodiments, the patient may have a skeletal or muscular disorder and have increased or decreased expression relative to a control level of expression of a plurality of biomarkers selected from the group consisting of ACSL1, ADM, AK5, ASTN2 (includes EG:23245), BCL6, BMPR1B, CARD8, CASP5, CCND3, CLTC, CNTN4, COL1A1, COL1A2, DIP2C, DNAH14, EDAR, ELAVL2, EPHA3, EPHX2, FAM124A, FOSB, GABRB2, GIGYF2, GNAO1, HOXC6, IL1B, KCNJ15, LAMB4, LIFR, LTBR, LUM, MAPK14, MYBPC1, NOS3, ODZ2, OSM, PAPPA, PDE1A, ROBO1, RUNDC3B, S100A12, SCN2A, SHOX, SLC22A4 (includes EG:6583), SOX9, SPOCK3, TLR5, TNFRSF21, TNPO1, TSHZ2, TTC6 (includes EG:115669), TWIST1, UNC5B, VWA3B and ZNF438.

In some embodiments, the patient may have an inflammatory disorder and have increased or decreased expression relative to a control level of expression of a plurality of biomarkers selected from the group consisting of ACSL1, ADM, AK5, ANXA3, APBA2, ASTN2 (includes EG:23245), BCL6, CARD8, CASP5, CAV1, CCND3, CCRL1, CLTC, CNTN4, DIP2C, DNAH14, EDAR, EPHA3, EPHX2, ERAP2, FAM124A, FBLN7, FOSB, FREM2, GABRB2, GRM5, IL1B, KCNJ15, LAMB4, LHX2, LNPEP, LRP2, LTBR, LUM, MAPK14, MECOM, MYBPC1, NOS3, ODZ2, OPCML, OSM, PAPPA, PDE1A, PPP1R1C, ROBO1, RUNDC3B, S100A12, SCN2A, SFXN1, SLC22A4 (includes EG:6583), SLC26A8, SMURF2, SNRPN, SPON1, TGFB2, TLR5, TNFRSF21, TNPO1, TTC6 (includes EG:115669), TWIST1, UNC5B, VWA3B and ZNF438.

In some embodiments, the patient may have a cardiovascular disorder and have increased or decreased expression relative to a control level of expression of a plurality of biomarkers selected from the group consisting of ACSL1, ADM, AK5, ALPL, ASTN2 (includes EG:23245), BCL6, BMPR1B, C18ORF54, CACNA1I, CARD16, CAV1, CNTN4, DMRT1, DNAH14, EDAR, EPHX2, ERAP2, FAM13A, FOLH1, FOSB, FREM2, GABRB2, GRM5, GSTM1, IL1B, IQGAP2, LIFR, LTBR, MAN1C1, MAPK14, MBNL1, MCF2L, MECOM, MYBPC1, NOS3, NTM, ODZ2, OLFM2, OPCML, PAPPA, PDE1A, ROBO1, RORB, S100A12, SMURF2, SNRPN, SOX9, SPOCK3, SPON1, TFPI, TRPM1, UNC84A and VWA3B.

In some embodiments, the patient may have an immunological disorder and have increased or decreased expression relative to a control level of expression of a plurality of biomarkers selected from the group consisting of ACSL1, ADM, AK5, ANXA3, ASTN2 (includes EG:23245), BCL6, CARD8, CASP5, CCND3, CCRL1, CLTC, CNTN4, COL1A2, DIP2C, DNAH14, EDAR, EPHA3, EPHX2, FAM124A, FAT1, FOSB, GABRB2, GOLGA6L2, GSTM1, GUSBL2, IL1B, IQGAP2, KCNJ15, LAMB4, LTBR, MAPK14, MYBPC1, NELL2, NOS3, NTM, ODZ2, OPCML, OSM, PAPPA, PDE1A, ROBO1, RUNDC3B, S100A12, SLC22A4 (includes EG:6583), SNRPN, SPON1, TLR5, TNFRSF21, TNPO1, TSHZ2, TTC6 (includes EG:115669), VWA3B and ZNF438.

In some embodiments, the patient may have a metabolic disorder and have increased or decreased expression relative to a control level of expression of a plurality of biomarkers selected from the group consisting of ACSL1, ADAM30, AK5, ALPL, ALS2CR11, ASTN2 (includes EG:23245), BCL6, CARD8, CASP5, CCRL1, CNTLN, CNTN4, COL1A2, DIP2C, DMRT1, DNAH14, EPHA3, EPHX2, FAT1, FOXA2, GABRB2, GUSBL2, IGFBP5, IL1B, IQGAP2, ITGBL1, LRP2, LTBR, MAPK14, MBNL1, NELL2, NOS3, NTM, ODZ2, OPCML, PAPPA, PLSCR1, ROBO1, SLC22A4 (includes EG:6583), SLC2A3, SLC3A1, SMURF2, SNRPN, SPON1, SRGAP1, TLR5, TSHZ2, UNC84A and VWA3B.

In some embodiments, the patient may have an endocrine system disorder and have increased or decreased expression relative to a control level of expression of a plurality of biomarkers selected from the group consisting of ACSL1, ADAM30, AK5, ALPL, ALS2CR11, ASTN2 (includes EG:23245), BCL6, CARD8, CASP5, CCRL1, CNTLN, CNTN4, COL1A2, DIP2C, DMRT1, DNAH14, EPHA3, FAT1, FOXA2, GABRB2, GUSBL2, IL1B, IQGAP2, ITGBL1, LRP2, LTBR, MAPK14, MBNL1, NELL2, NOS3, NTM, ODZ2, OPCML, PAPPA, PLSCR1, ROBO1, SHOX, SLC22A4 (includes EG:6583), SLC2A3, SMURF2, SNRPN, SPON1, SRGAP1, TLR5, TSHZ2, UNC84A and VWA3B.

In some embodiments, the patient may have an autoimmune disease and have increased or decreased expression relative to a control level of expression of a plurality of biomarkers selected from the group consisting of ACSL1, ADM, AK5, ASTN2 (includes EG:23245), BCL6, CARD8, CASP5, CCND3, CLTC, CNTN4, COL1A2, DIP2C, DNAH14, EDAR, EPHA3, EPHX2, FAM124A, FOSB, GABRB2, GUSBL2, IL1B, IQGAP2, KCNJ15, LAMB4, LTBR, MAPK14, MYBPC1, NELL2, ODZ2, OPCML, OSM, PAPPA, PDE1A, ROBO1, RUNDC3B, S100A12, SLC22A4 (includes EG:6583), SNRPN, SPON1, TLR5, TNFRSF21, TNPO1, TSHZ2, TTC6 (includes EG:115669), VWA3B and ZNF438.

In some embodiments, the patient may have diabetes and have increased or decreased expression relative to a control level of expression of a plurality of biomarkers selected from the group consisting of ACSL1, ADAM30, AK5, ALPL, ALS2CR11, ASTN2 (includes EG:23245), BCL6, CARD8, CASP5, CCRL1, CNTLN, CNTN4, COL1A2, DIP2C, DMRT1, DNAH14, EPHA3, FAT1, FOXA2, GABRB2, GUSBL2, IL1B, IQGAP2, ITGBL1, LTBR, MAPK14, MBNL1, NELL2, NOS3, NTM, ODZ2, OPCML, PAPPA, PLSCR1, ROBO1, SLC22A4 (includes EG:6583), SLC2A3, SMURF2, SNRPN, SPON1, SRGAP1, TLR5, TSHZ2, UNC84A and VWA3B.

In some embodiments, the patient may have a connective tissue disorder and have increased or decreased expression relative to a control level of expression of a plurality of biomarkers selected from the group consisting of ACSL1, ADM, ASTN2 (includes EG:23245), BCL6, CARD8, CASP5, CCND3, CLTC, CNTN4, COL1A1, COL1A2, DIP2C, DNAH14, EDAR, EPHA3, EPHX2, FAM124A, FOSB, GABRB2, IL1B, KCNJ15, LAMB4, LTBR, LUM, MAPK14, ODZ2, OSM, PAPPA, PDE1A, ROBO1, RUNDC3B, S100A12, SHOX, SLC22A4 (includes EG:6583), TLR5, TNFRSF21, TNPO1, TTC6 (includes EG:115669), VWA3B and ZNF438.

In some embodiments, the patient may have rheumatic disease and have increased or decreased expression relative to a control level of expression of a plurality of biomarkers selected from the group consisting of ACSL1, ADM, ASTN2 (includes EG:23245), BCL6, CARD8, CASP5, CCND3, CLTC, CNTN4, DIP2C, DNAH14, EDAR, EPHA3, EPHX2, FAM124A, FOSB, GABRB2, IL1B, KCNJ15, LAMB4, LTBR, LUM, MAPK14, ODZ2, OSM, PAPPA, PDE1A, ROBO1, RUNDC3B, S100A12, SLC22A4 (includes EG:6583), TLR5, TNFRSF21, TNPO1, TTC6 (includes EG:115669), VWA3B and ZNF438.

In some embodiments, the patient may have arthritis and have increased or decreased expression relative to a control level of expression of a plurality of biomarkers selected from the group consisting of ACSL1, ADM, ASTN2 (includes EG:23245), BCL6, CARD8, CASP5, CCND3, CLTC, CNTN4, DIP2C, DNAH14, EDAR, EPHA3, EPHX2, FAM124A, FOSB, GABRB2, IL1B, KCNJ15, LAMB4, LTBR, LUM, MAPK14, ODZ2, OSM, PAPPA, PDE1A, ROBO1, RUNDC3B, S100A12, SLC22A4 (includes EG:6583), TNFRSF21, TNPO1, TTC6 (includes EG:115669), VWA3B, ZNF438.

In some embodiments, the patient may have atherosclerosis and have increased or decreased expression relative to a control level of expression of a plurality of biomarkers selected from the group consisting of ACSL1, AK5, ASTN2 (includes EG:23245), BMPR1B, CARD16, CNTN4, DMRT1, DNAH14, ERAP2, FOSB, FREM2, GRM5, IL1B, IQGAP2, LIFR, MAN1C1, MBNL1, MCF2L, MECOM, NOS3, NTM, ODZ2, OLFM2, PDE1A, ROBO1, RORB, SNRPN, SPOCK3, SPON1, TRPM1, UNC84A and VWA3B.

In some embodiments, the patient may have inflammatory bowel disease and have increased or decreased expression relative to a control level of expression of a plurality of biomarkers selected from the group consisting of ACSL1, AK5, APBA2, ASTN2 (includes EG:23245), CARD8, DIP2C, DNAH14, ERAP2, FBLN7, FREM2, GRM5, IL1B, LHX2, LNPEP, LTBR, MECOM, NOS3, ODZ2, OPCML, PAPPA, PDE1A, PPP1R1C, ROBO1, SFXN1, SLC22A4 (includes EG:6583), SLC26A8, SNRPN, SPON1, TGFB2, TLR5, VWA3B and ZNF438.

In some embodiments, the patient may have non-insulin-dependent diabetes mellitus and have increased or decreased expression relative to a control level of expression of a plurality of biomarkers selected from the group consisting of ADAM30, AK5, ALPL, ALS2CR11, ASTN2 (includes EG:23245), CARD8, CCRL1, CNTLN, CNTN4, COL1A2, DIP2C, DMRT1, EPHA3, FAT1, FOXA2, GABRB2, IL1B, IQGAP2, ITGBL1, MBNL1, NOS3, NTM, ODZ2, PLSCR1, ROBO1, SLC22A4 (includes EG:6583), SLC2A3, SPON1, SRGAP1, TLR5, UNC84A and VWA3B.

In some embodiments, the patient may have rheumatoid arthritis and have increased or decreased expression relative to a control level of expression of a plurality of biomarkers selected from the group consisting of ACSL1, ADM, ASTN2 (includes EG:23245), BCL6, CARD8, CLTC, CNTN4, DIP2C, DNAH14, EDAR, EPHA3, EPHX2, FAM124A, FOSB, GABRB2, IL1B, KCNJ15, LAMB4, MAPK14, ODZ2, OSM, PAPPA, PDE1A, ROBO1, RUNDC3B, S100A12, SLC22A4 (includes EG:6583), TNFRSF21, TNPO1, TTC6 (includes EG:115669), VWA3B and ZNF438.

In some embodiments, the patient may have coronary artery disease and have increased or decreased expression relative to a control level of expression of a plurality of biomarkers selected from the group consisting of ACSL1, AK5, ASTN2 (includes EG:23245), BMPR1B, CARD16, CNTN4, DMRT1, DNAH14, ERAP2, FREM2, GRM5, IL1B, IQGAP2, LIFR, MAN1C1, MBNL1, MCF2L, MECOM, NOS3, NTM, ODZ2, OLFM2, PDE1A, ROBO1, RORB, SNRPN, SPOCK3, SPON1, TRPM1, UNC84A and VWA3B.

In some embodiments, the patient may have Crohn's disease and have increased or decreased expression relative to a control level of expression of a plurality of biomarkers selected from the group consisting of ACSL1, AK5, APBA2, ASTN2 (includes EG:23245), CARD8, DIP2C, DNAH14, ERAP2, FBLN7, FREM2, GRM5, LHX2, LNPEP, MECOM, ODZ2, OPCML, PAPPA, PDE1A, PPP1R1C, ROBO1, SFXN1, SLC22A4 (includes EG:6583), SLC26A8, SNRPN, SPON1, TGFB2, TLR5, VWA3B and ZNF438.

In some embodiments, the patient may have a neurodegenerative disorder and have increased or decreased expression relative to a control level of expression of a plurality of biomarkers selected from the group consisting of ASTN2 (includes EG:23245), CASP5, CNTN4, FAM124A, FOLH1, GABRB2, GRM5, IL1B, MECOM, NDST3, NOS3, OPCML, RFX2, SCN2A, SLC22A4 (includes EG:6583), SLC2A3, SLC3A1, SPON1, TSHZ2 and ZNF608.

In some embodiments, the patient may have Alzheimer's disease and have increased or decreased expression relative to a control level of expression of a plurality of biomarkers selected from the group consisting of ASTN2 (includes EG:23245), CASP5, CNTN4, FAM124A, FOLH1, GABRB2, GRM5, IL1B, MECOM, NDST3, NOS3, OPCML, RFX2, SLC22A4 (includes EG:6583), SLC2A3, SLC3A1, SPON1, TSHZ2 and ZNF608.

6. Methods of Detecting Biomarkers Associated with TIA

Gene expression may be measured using any method known in the art. One of skill in the art will appreciate that the means of measuring gene expression is not a critical aspect of the invention. The expression levels of the biomarkers can be detected at the transcriptional or translational (i.e., protein) level.

In some embodiments, the expression levels of the biomarkers are detected at the transcriptional level. A variety of methods of specific DNA and RNA measurement using nucleic acid hybridization techniques are known to those of skill in the art (see, Sambrook, supra and Ausubel, supra) and may be used to detect the expression of the genes set forth in Tables 1, 2, 5A, 5B, 5C, 5D, 7, 8 and/or 9. Some methods involve an electrophoretic separation (e.g., Southern blot for detecting DNA, Northern blot for detecting RNA, RNAse protection assays), but measurement of DNA and RNA can also be carried out in the absence of electrophoretic separation (e.g., by dot blot). Southern blot of genomic DNA (e.g., from a human) can be used for screening for restriction fragment length polymorphism (RFLP) to detect the presence of a genetic disorder affecting a polypeptide of the invention. All forms of RNA can be detected, including, e.g., message RNA (mRNA), microRNA (miRNA), ribosomal RNA (rRNA) and transfer RNA (tRNA).

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins *Nucleic Acid Hybridization, A Practical Approach*, IRL Press (1985); Gall and Pardue, *Proc. Natl. Acad. Sci. U.S.A.*, 63:378-383 (1969); and John et al. *Nature*, 223:582-587 (1969).

Detection of a hybridization complex may require the binding of a signal-generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tijssen, *"Practice and Theory of Enzyme Immunoassays,"* Laboratory Techniques in Biochemistry and Molecular Biology, Burdon and van Knippenberg Eds., Elsevier (1985), pp. 9-20).

The probes are typically labeled either directly, as with isotopes, chromophores, lumiphores, chromogens, or indirectly, such as with biotin, to which a streptavidin complex may later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like.

Other labels include, e.g., ligands that bind to labeled antibodies, fluorophores, chemiluminescent agents, enzymes, and antibodies which can serve as specific binding pair members for a labeled ligand. An introduction to labels, labeling procedures and detection of labels is found in Polak and Van Noorden *Introduction to Immunocytochemistry*, 2nd ed., Springer Verlag, NY (1997); and in Haugland *Handbook of Fluorescent Probes and Research Chemicals*, a combined handbook and catalogue Published by Molecular Probes, Inc. (1996).

In general, a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill in the art. Commonly, an optical image of a substrate comprising bound labeling moieties is digitized for subsequent computer analysis.

Most typically, the amount of RNA is measured by quantifying the amount of label fixed to the solid support by binding of the detection reagent. Typically, the presence of a modulator during incubation will increase or decrease the amount of label fixed to the solid support relative to a control incubation which does not comprise the modulator, or as compared to a baseline established for a particular reaction type. Means of detecting and quantifying labels are well known to those of skill in the art.

In preferred embodiments, the target nucleic acid or the probe is immobilized on a solid support. Solid supports suitable for use in the assays of the invention are known to those of skill in the art. As used herein, a solid support is a matrix of material in a substantially fixed arrangement.

For example, in one embodiment of the invention, microarrays are used to detect the pattern of gene expression. Microarrays provide one method for the simultaneous measurement of the expression levels of large numbers of genes. Each array consists of a reproducible pattern of a plurality of nucleic acids (e.g., a plurality of nucleic acids that hybridize to a plurality of the genes set forth in Tables 1, 2, 5A, 5B, 5C, 5D, 7, 8 and/or 9) attached to a solid support. Labeled RNA or DNA is hybridized to complementary probes on the array and then detected by laser scanning. Hybridization intensities for each probe on the array are determined and converted to a quantitative read-out of relative gene expression levels in transient ischemic attacks.

In some embodiments, a sample is obtained from a subject, total mRNA is isolated from the sample and is converted to labeled cRNA and then hybridized to an array. Relative transcript levels are calculated by reference to appropriate controls present on the array and in the sample. See, Mahadevappa and Warrington, *Nat. Biotechnol.* 17, 1134-1136 (1999).

A variety of automated solid-phase assay techniques are also appropriate. For instance, very large scale immobilized polymer arrays (VLSIPS™), available from Affymetrix, Inc. (Santa Clara, Calif.) can be used to detect changes in expression levels of a plurality of genes involved in the same regulatory pathways simultaneously. See, Tijssen, supra., Fodor et al. (1991) *Science*, 251: 767-777; Sheldon et al. (1993) *Clinical Chemistry* 39(4): 718-719, and Kozal et al. (1996) *Nature Medicine* 2(7): 753-759. Integrated microfluidic systems and other point-of-care diagnostic devices available in the art also find use. See, e.g., Liu and Mathies, *Trends Biotechnol.* (2009) 27(10):572-81 and Tothill, *Semin Cell Dev Biol* (2009) 20(1):55-62. Microfluidics systems for use in detecting levels of expression of a plurality of nucleic acids are available, e.g., from NanoString Technologies, on the internet at nanostring.com.

Detection can be accomplished, for example, by using a labeled detection moiety that binds specifically to duplex nucleic acids (e.g., an antibody that is specific for RNA-DNA duplexes). One preferred example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Coutlee et al. (1989) *Analytical Biochemistry* 181: 153-162; Bogulayski (1986) et al. *J. Immunol. Methods* 89:123-130; Prooijen-Knegt (1982) *Exp. Cell Res.* 141:397-407; Rudkin (1976) *Nature* 265:472-473, Stollar (1970) *Proc. Nat'l Acad. Sci. USA* 65:993-1000; Ballard (1982) *Mol. Immunol.* 19:793-799; Pisetsky and Caster (1982) *Mol. Immunol.* 19:645-650; Viscidi et al. (1988) *J. Clin. Microbial.* 41:199-209; and Kiney et al. (1989) *J. Clin. Microbiol.* 27:6-12 describe antibodies to RNA duplexes, including homo and heteroduplexes. Kits comprising antibodies specific for DNA:RNA hybrids are available, e.g., from Digene Diagnostics, Inc. (Beltsville, Md.).

In addition to available antibodies, one of skill in the art can easily make antibodies specific for nucleic acid duplexes using existing techniques, or modify those antibodies that are commercially or publicly available. In addition to the art referenced above, general methods for producing polyclonal and monoclonal antibodies are known to those of skill in the art (see, e.g., Paul (3rd ed.) *Fundamental Immunology* Raven Press, Ltd., NY (1993); Coligan, et al., *Current Protocols in Immunology*, Wiley Interscience (1991-2008); Harlow and Lane, *Antibodies: A Laboratory Manual* Cold Spring Harbor Press, NY (1988); Harlow and Lane, *Using Antibodies*, Cold Spring Harbor Press, NY (1999); Stites et al. (eds.) *Basic and Clinical Immunology* (4th ed.) Lange Medical Publications, Los Altos, Calif., and references cited therein; Goding *Monoclonal Antibodies: Principles and Practice* (2d ed.) Academic Press, New York, N.Y., (1986); and Kohler and Milstein *Nature* 256: 495-497 (1975)). Other suitable techniques for antibody preparation include selection of libraries of recombinant antibodies in phage or similar vectors (see, Huse et al. *Science* 246:1275-1281 (1989); and Ward et al. *Nature* 341:544-546 (1989)). Specific monoclonal and polyclonal antibodies and antisera will usually bind with a $K_D$ of at least about 0.1 µM, preferably at least about 0.01 µM or better, and most typically and preferably, 0.001 µM or better.

The nucleic acids used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may serve as a negative probe in an assay sample where only the nucleotide sequence of interest is present.

The sensitivity of the hybridization assays may be enhanced through use of a nucleic acid amplification system that multiplies the target nucleic acid being detected. Examples of such systems include the polymerase chain reaction (PCR) system, in particular RT-PCR, multiplex PCR, quantitative PCR or real time PCR, and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. High throughput multiplex nucleic acid sequencing or "deep sequencing" to detect captured expressed biomarker genes also finds use. High throughput sequencing techniques are known in the art (e.g., 454 Sequencing on the internet at 454.com).

An alternative means for determining the level of expression of the nucleic acids of the present invention is in situ hybridization. In situ hybridization assays are well known and are generally described in Angerer et al., *Methods Enzymol.* 152:649-660 (1987). In an in situ hybridization assay, cells, preferentially human cells, e.g., blood cells, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

In other embodiments, quantitative RT-PCR is used to detect the expression of a plurality of the genes set forth in Tables 1, 2, 5A, 5B, 5C, 5D, 7, 8 and/or 9. A general overview of the applicable technology can be found, for example, in *A-Z of Quantitative PCR*, Bustin, ed., 2004, International University Line; *Quantitative PCR Protocols*, Kochanowski and Reischl, eds., 1999, Humana Press; *Clinical Applications of PCR*, Lo, ed., 2006, Humana Press; *PCR Protocols: A Guide to Methods and Applications* (Innis et al. eds. (1990)) and *PCR Technology: Principles and Applications for DNA Amplification* (Erlich, ed. (1992)). In addition, amplification technology is described in U.S. Pat. Nos. 4,683,195 and 4,683,202. Methods for multiplex PCR, known in the art, are applicable to the present invention.

Accordingly, in one embodiment of the invention provides a reaction mixture comprising a plurality of polynucleotides which specifically hybridize (e.g., primers) to a plurality of nucleic acid sequences of the genes set forth in Tables 1, 2, 5A, 5B, 5C, 5D, 7, 8 and/or 9. In some embodiments, the reaction mixture is a PCR mixture, for example, a multiplex PCR mixture.

This invention relies on routine techniques in the field of recombinant genetics. Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-2008, Wiley Interscience)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, Tetrahedron Letts. 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

In some embodiments, the expression level of the biomarkers described herein are detected at the translational or protein level. Detection of proteins is well known in the art, and methods for protein detection known in the art find use. Exemplary assays for determining the expression levels of a plurality of proteins include, e.g., ELISA, flow cytometry, mass spectrometry (e.g., MALDI or SELDI), surface plasmon resonance (e.g., BiaCore), microfluidics and other biosensor technologies. See, e.g., Tothill, *Semin Cell Dev Biol* (2009) 20(1):55-62.

7. TIA Reference Profiles

The invention also provides ischemia reference profiles. The TIA reference profiles comprise information correlating the expression levels of a plurality of TIA-associated genes (i.e., a plurality of the genes set forth in Tables 1, 2, 5A, 5B, 5C, 5D, 7, 8 and/or 9) to the occurrence or risk of TIA. The profiles can conveniently be used to diagnose, monitor and prognose ischemia.

The reference profiles can be entered into a database, e.g., a relational database comprising data fitted into predefined categories. Each table, or relation, contains one or more data categories in columns. Each row contains a unique instance of data for the categories defined by the columns. For example, a typical database for the invention would include a table that describes a sample with columns for age, gender, reproductive status, expression profile and so forth. Another table would describe a disease: symptoms, level, sample identification, expression profile and so forth. In one embodiment, the invention matches the experimental sample to a database of reference samples. The database is assembled with a plurality of different samples to be used as reference samples. An individual reference sample in one embodiment will be obtained from a patient during a visit to a medical professional. Information about the physiological, disease and/or pharmacological status of the sample will also be obtained through any method available. This may include, but is not limited to, expression profile analysis, clinical analysis, medical history and/or patient interview. For example, the patient could be interviewed to determine age, sex, ethnic origin, symptoms or past diagnosis of disease, and the identity of any therapies the patient is currently undergoing. A plurality of these reference samples will be taken. A single individual may contribute a single reference sample or more than one sample over time. One skilled in the art will recognize that confidence levels in predictions based on comparison to a database increase as the number of reference samples in the database increases.

The database is organized into groups of reference samples. Each reference sample contains information about physiological, pharmacological and/or disease status. In one aspect the database is a relational database with data organized in three data tables, one where the samples are grouped primarily by physiological status, one where the samples are grouped primarily by disease status and one where the samples are grouped primarily by pharmacological status. Within each table the samples can be further grouped according to the two remaining categories. For example the physiological status table could be further categorized according to disease and pharmacological status.

As will be appreciated by one of skill in the art, the present invention may be embodied as a method, data processing system or program products. Accordingly, the present invention may take the form of data analysis systems, methods, analysis software, etc. Software written according to the present invention is to be stored in some form of computer readable medium, such as memory, hard-drive, DVD ROM or CD ROM, or transmitted over a network, and executed by a processor. The present invention also provides a computer system for analyzing physiological states, levels of disease states and/or therapeutic efficacy. The computer system comprises a processor, and memory coupled to said processor which encodes one or more programs. The programs encoded in memory cause the processor to perform the steps of the above methods wherein the expression profiles and information about physiological, pharmacological and disease states are received by the computer system as input. Computer systems may be used to execute the software of an embodiment of the invention (see, e.g., U.S. Pat. No. 5,733,729).

8. Providing Appropriate Treatment and Prevention Regimes to Patient

In some embodiments, the methods further comprise the step of prescribing and providing appropriate treatment and/or prevention regimes to a patient diagnosed as having TIA or at risk of the occurrence of TIA or stroke. For example, medications and life-style adjustments (e.g., diet, exercise, stress) to minimize risk factors can be recommended, including reducing blood pressure and cholesterol levels, and controlling diabetes.

In additions, several medications to decrease the likelihood of a stroke after a transient ischemic attack. The medication selected will depend on the location, cause, severity and type of TIA, if TIA has occurred.

In some embodiments, the patient may be prescribed a regime of an anti-platelet drug. The most frequently used anti-platelet medication is aspirin. An alternative to aspirin is the anti-platelet drug clopidogrel (Plavix). Some studies indicate that aspirin is most effective in combination with another anti-platelet drug. In some embodiments, the patient is prescribed a combination of low-dose aspirin and the anti-platelet drug dipyridamole (Aggrenox), to reduce blood clotting. Ticlopidine (Ticlid) is another anti-platelet medication that finds use to prevent or reduce the risk of stroke in patients who have experienced TIA.

In some embodiments, the patient may be prescribed a regime of an anticoagulant. Exemplary anticoagulants include aspirin, heparin, warfarin, and dabigatran.

Patients having a moderately or severely narrowed neck (carotid) artery, may require or benefit from carotid endarterectomy. This preventive surgery clears carotid arteries of fatty deposits (atherosclerotic plaques) before another TIA or stroke can occur. In some embodiments, the patient may require or benefit from carotid angioplasty, or stenting. Carotid angioplasty involves using a balloon-like device to open a clogged artery and placing a small wire tube (stent) into the artery to keep it open.

9. Solid Supports and Kits

The invention further provides a solid supports comprising a plurality of nucleic acid probes that hybridize to a plurality (e.g., two or more, or all) of the genes set forth in Tables 1, 2, 5A, 5B, 5C, 5D, 7, 8 and/or 9, and optionally Table 3. For example, the solid support can be a microarray attached to a plurality of nucleic acid probes that hybridize to a plurality (e.g., two or more, or all) of the genes set forth in Table 1, and optionally Table 3. In various embodiments, the solid support can be a microarray attached to a plurality of nucleic acid probes that hybridize to a plurality (e.g., two or more, or all) of the genes set forth in Tables 5A, 5B, 5C, and 5D, and optionally Table 3. In various embodiments, the solid support can be a microarray attached to a plurality of nucleic acid probes that hybridize to a plurality (e.g., two or more, or all) of the genes set forth in Table 7, and optionally Table 3. In various, the solid support can be a microarray attached to a plurality of nucleic acid probes that hybridize to a plurality (e.g., two or more, or all) of the genes set forth in Table 8, and optionally Table 3. In various, the solid support can be a microarray attached to a plurality of nucleic acid probes that hybridize to a plurality (e.g., two or more, or all) of the genes set forth in Table 9, and optionally Table 3.

In various embodiments, the solid supports are configured to exclude genes not associated with or useful to the diagnosis, prediction or confirmation of a stroke or the causes of stroke. For example, genes which are overexpressed or underexpressed less than 1.5-fold in subjects having or suspected of having TIA, in comparison to a control level of expression can be excluded from the present solid supports. In some embodiments, genes that are overexpressed or underexpressed less than 1.2-fold in subjects with ischemic stroke, including cardioembolic stroke, atherothrombotic stroke, and stroke subsequent to atrial fibrillation, in comparison to a control level of expression can be excluded from the present solid supports. The solid support can comprise a plurality of nucleic acid probes that hybridize to a plurality (e.g., two or more, or all) of the genes useful for the diagnosis of ischemic stroke, cardioembolic stroke, carotid stenosis, and/or atrial fibrillation, as described herein. As appropriate, nucleic acid probes that hybridize to a plurality (e.g., two or more, or all) of the genes useful for the diagnosis of ischemic stroke, cardioembolic stroke, carotid stenosis, and/or atrial fibrillation can be arranged in a predetermined array on the solid support. In various embodiments, nucleic acids not specifically identified and/or not relating to the diagnosis of and/or not associated with the diagnosis of TIA are not attached to the solid support. In various embodiments, nucleic acids not specifically identified and/or not relating to the diagnosis of and/or not associated with the diagnosis of ischemic stroke, cardioembolic stroke, carotid stenosis, and/or atrial fibrillation are not attached to the solid support. The solid support may be a component in a kit.

The invention also provides kits for diagnosing TIA or a predisposition for developing TIA. For example, the invention provides kits that include one or more reaction vessels that have aliquots of some or all of the reaction components of the invention in them. Aliquots can be in liquid or dried form. Reaction vessels can include sample processing cartridges or other vessels that allow for the containment, processing and/or amplification of samples in the same vessel. The kits can comprise a plurality of nucleic acid probes that hybridize to a plurality the genes set forth in Tables 1, 2, 5A, 5B, 5C, 5D, 7, 8 and/or 9. The probes may be immobilized on a microarray as described herein.

In addition, the kit can comprise appropriate buffers, salts and other reagents to facilitate amplification and/or detection reactions (e.g., primers, labels) for determining the expression levels of a plurality of the biomarkers set forth in Tables 1, 2, 5A, 5B, 5C, 5D, 7, 8 and/or 9. The kits can also include written instructions for the use of the kit.

In one embodiment, the kits comprise a plurality of antibodies that bind to a plurality of the biomarkers set forth in Tables 1, 2, 5A, 5B, 5C, 5D, 7, 8 and/or 9. The antibodies may or may not be immobilized on a solid support, e.g., an ELISA plate.

EXAMPLES

The following examples are offered to illustrate, but not to limit the claimed invention.

Example 1

Materials and Methods
Subjects

TIA and control patients were recruited from the University of California Davis Medical Center, University of California San Francisco Medical Center and Wake Forest University Health Sciences. Institutional Review Boards at each institution approved the study, and written informed consent was obtained from all patients.

A total of 27 control patients were compared to 24 TIA patients studied within 3 to 69 hours (average=29.2 hours) of symptoms onset. The diagnosis of TIA was made by two independent board certified neurologists with access to all clinical data. TIA was defined as an acute loss of focal cerebral or ocular function lasting <12 hours with a presumed ischemic etiology. To be recruited into the study TIA patients were required to have an $ABCD^2$ score≥4 to further support the diagnosis of TIA. This ensured that TIA patients at higher risk for recurrent vascular events were studied (4, 19). The controls were recruited from the spouses or family members of TIA patients or people from the community. They were subjects free of vascular events such as TIA, ischemic stroke, myocardial infarction, peripheral vascular disease, or venous thromboembolism. Control subjects with hypertension and/or diabetes were also excluded in order to reduce the possibility of controls having silent TIA or other vascular events. Hypertension and diabetes both increase the probability of TIA, as shown by the $ABCD^2$ score (4, 20).

RNA Isolation

A venous blood sample was collected into PAXgene vacutainers (PreAnalytiX, Hilden, Germany). Total RNA was isolated according to the manufacturer's protocol.

Microarray Hybridization

Biotin-labeled cDNA was synthesized from 50 ng of total RNA using the Ovation Whole Blood Solution (Nugen) kit according to protocol. Each RNA sample was processed on Affymetrix Human Genome HG-U133-Plus-2.0 microarrays as previously described (18).

Statistical Analysis

Microarray probeset-level data were log transformed and normalized using Robust Multichip Average (RMA). Analysis of Covariance (ANCOVA) was conducted in Partek Genomics Suite 6.5 (Partek Inc., St. Louis, Mich., USA) to identify genes/probes significantly different between TIA and control subjects with adjustment for microarray batch effect and age. Genes/probes were considered significant with a p-value≤0.05 after Benjamini-Hochberg multiple-comparison correction, and an absolute fold change>1.5. To exclude genes associated with hypertension, a second comparison was performed for 33 controls with hypertension to controls without hypertension. The Identified "hypertension" genes that overlapped with the TIA gene lists were excluded from further analysis.

All data are presented as mean±SE. Differences in demographic data between groups were analyzed using Chi-square test or t-test as appropriate. Prediction analysis was performed using 10-fold leave-one-out cross-validation in Prediction Analysis of Microarrays (PAM). Functional and pathway analyses were performed using Ingenuity Pathways Analysis (IPA).

Results
Subjects

The demographic information for TIA and control subjects showed that age was significantly different between TIA and controls (Table 4). Thus, age was adjusted for in the ANCOVA model.

TABLE 4

Demographic summary of Transient Ischemic Attack (TIA) patients and control subjects

|  | Controls (n = 27) | TIA (n = 24) | p value |
|---|---|---|---|
| Age (yrs ± SE) | 55.7 ± 0.8 | 70.2 ± 2.5 | <0.001 |
| Gender Female: n (%) | 19 (70.4) | 14 (58.3) | 0.39 |
| Race |  |  |  |
| Caucasian: n (%) | 18 (66.6) | 16 (66.6) | 1.00 |
| Non-Caucasian: n (%) | 9 (33.3) | 8 (33.3) | 1.00 |

TIA Genomic Profiles

A total of 460 genes were differentially expressed between TIA patients and controls (FDR≤0.05; fold change≥1.5) (Tables 5A-D). 135 genes were down-regulated (Table 2 and Table 5A) and 325 were up-regulated (Table 1 and Table 5B) in TIA compared to controls. A Hierarchical cluster analysis of the 460 genes showed that they separated TIAs from controls (FIG. 1) except that two TIA patients (ID numbers: 57 and 90) clustered in the control group, and three control patients (ID numbers: 42, 68 and 74) clustered in the TIA group (FIG. 1). The hierarchical cluster analysis also suggested the presence of two distinct TIA groups. Most of the up-regulated genes in the TIA1 group separated it from the TIA2 group and from controls (FIG. 1).

Prediction Analysis

Figure 2:
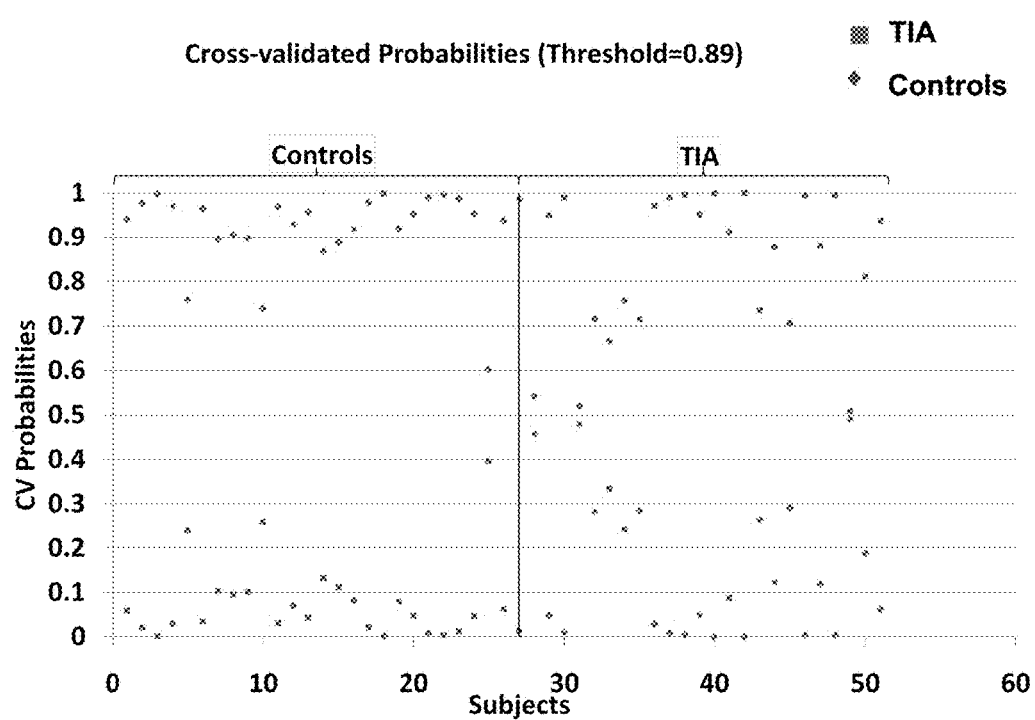
FIG. 2. Cross-validation results for the 34 out of 460 TIA regulated genes that distinguish TIA patients from control subjects. The probability of predicted diagnosis is shown on the Y axis, and subjects are shown on the X axis. TIA patients are shown on the right, and Control subjects on the left. The predicted probability of TIA is shown in red, and the predicted probability of being control is shown in blue. TIA patients were distinguished from controls with 87.5% sensitivity and 96.3% specificity using a 10-fold cross-validation.

Cross-correlation performed with PAM using the 34 (Table 5C) out of 460 TIA associated genes distinguished TIA patients from controls with 87.5% sensitivity (21 out of 24 TIAs correctly classified) and 96.3% specificity (26 out of 27 controls correctly classified) (FIG. 2).

TIA Specific Up-Regulated Genes

Figure 3:
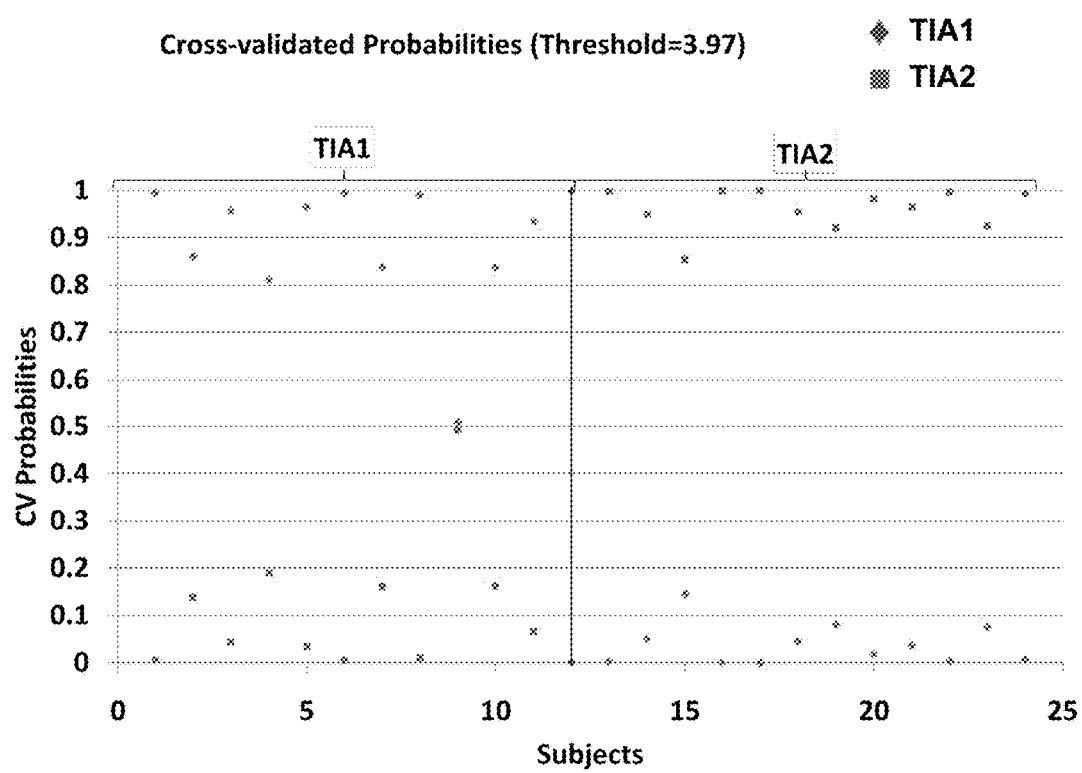
FIG. 3. Cross-validation results for the 26 up-regulated genes identified by PAM to distinguish the TIA1 from TIA2 groups. The probability of the predicted diagnosis is shown on the Y axis, and subjects are shown on the X axis. TIA1 subjects are shown on the left, and TIA2 subjects on the right. The predicted probability of TIA2 is shown in red, and the predicted probability of TIA1 is shown in blue. TIA1 could be distinguished from TIA2 patients with 100% sensitivity and 100% specificity.

The 325 up-regulated genes that distinguished TIA1 from TIA2 patients were input into PAM to derive the minimum number (n=26) of genes that differentiated the two groups. The 26 genes (Table 5D) distinguished TIA1 from TIA2 patients with 100% sensitivity and specificity (FIG. 3). No clinical factors were identified that were significantly different between TIA1 and TIA2 including age, time after TIA, hypertension, diabetes, $ABCD^2$ score (Table 6) and medications. Notably, Metalloproteinase 16 and Metalloproteinase 26 were up-regulated in the TIA1 group but not in the TIA2 group (FIG. 4).

TABLE 6

Demographic Summary of TIA subgroups

|  | TIA1 (n = 12) | TIA2 (n = 12) | P value |
|---|---|---|---|
| Age (yrs ± SE) | 64.8 ± 3.7 | 63.7 ± 8.8 | 0.91 |
| Gender Female (%) | 5 (42) | 5 (42) | 1.00 |
| Race |  |  |  |
| Caucasian n (%) | 7 (58) | 9 (75) | 0.18 |
| Non-Caucasian n (%) | 5 (42) | 3 (25) | 0.18 |
| Vascular risk factor |  |  |  |
| Hypertension n (%) | 10 (83) | 10 (83) | 1.00 |
| Diabetes n (%) | 4 (33) | 4 (33) | 1.00 |
| Hyperlipidemia n (%) | 6 (50) | 7 (58) | 0.56 |
| Smoke n (%) | 6 (50) | 4 (33) | 0.22 |
| Hours since TIA (±SE) | 28.7 ± 4.4 | 29.7 ± 4.3 | 0.87 |
| History of stroke n (%) | 3 (25) | 4 (33) | 0.54 |
| CVD n (%) | 3 (25) | 4 (33) | 0.54 |
| AF n (%) | 1 (8) | 2 (16) | 0.43 |
| LVD n (%) | 1 (8) | 2 (16) | 0.43 |
| ABCD$^2$ score (±SE) | 5.42 ± 0.29 | 5.25 ± 0.28 | 0.68 |

CVD: Cardiovascular Disorder; AF: Atrial Fibrillation; LVD: Large Vessel Disease.

There was no any significant difference among two groups analyzed using t-test or Chi-square test.

The factors contributed to the differences in RNA expression between TIA1 and TIA2 remained unclear.

Function Analysis of TIA Specific Genes

Functional analysis of the TIA specific genes (460 genes derived from TIA vs control) using IPA demonstrated that they were significantly associated with immune functions. Amongst the TIA specific genes, a number have been associated with autoimmune disease, diabetes, arthritis, rheumatoid arthritis, atherosclerosis, coronary artery disease and Crohn's disease (Table 7). The significantly regulated genes for the TIA1 group compared to the TIA2 group (FDR≤0.05; fold change≥1.5) are shown in Table 8 along with the most significant pathways (Table 9; see discussion below).

TABLE 7

TIA specific gene-functions

| Category | Function | p-value | Molecules |
|---|---|---|---|
| Genetic Disorder | genetic disorder | 2.29E−03 | ACSL1, ADAM30, ADAMDEC1, ADH1B, AK5, ALPL, ALS2CR11, ANXA3, APBA2, ASTN2 (includes EG:23245), BCL6, BMPR1B, CACNA1I, CARD8, CARD16, CASP5, CAV1, CCND3, CCRL1, CHIT1, CLTC, CNTLN, CNTN4, COL1A1, COL1A2, DIP2C, DMRT1, DNAH14, EDAR, ELAVL2, EPHA3, EPHX2, ERAP2, FAM124A, FAM13A, FAM149A, FAT1, FBLN7, FOLH1, FOXA2, FOXC1, FREM2, GABRB2, GIGYF2, GNAO1, GRM5, GSTM1, GYPA, HESX1, HOXC6, IGFBP5, IL1B, IQGAP2, ITGBL1, LAMB4, LHX2, LIFR, LNPEP, LRP2, LTBR, MAN1C1, MBNL1, MCF2L, MECOM, MLL, NBPF10, NDST3, NELL2, NOS3, NTM, ODZ2, OLFM2, OPCML, OSM, PAPPA, PDE1A, PLSCR1, PPP1R1C, RFX2, ROBO1, RORB, S100A12, SCN2A, SFXN1, SHOX, SIX3, SLC22A4 (includes EG:6583), SLC26A8, SLC2A3, SLC3A1, SMURF2, SNRPN, SOX9, SPOCK3, SPON1, SRGAP1, TFAP2B, TGFB2, TLR5, TRPM1, TSHZ2, TTC6 (includes EG:115669), TWIST1, UNC5B, UNC84A, VWA3B, ZNF438, ZNF608 |
| Neurological Disease | neurological disorder | 1.99E−02 | ACSL1, ADH1B, AK5, ANXA3, APBA2, ASTN2 (includes EG:23245), BCL6, BMPR1B, CASP5, CAV1, CNTN4, DIP2C, ELAVL2, EPHX2, ERAP2, FAM124A, FAM13A, FAM149A, FAT1, FOLH1, FOXC1, GABRB2, GIGYF2, GNAO1, GRM5, GSTM1, HESX1, HOXC6, IGFBP5, IL1B, IQGAP2, ITGBL1, LAMB4, LIFR, LTBR, MECOM, NBPF10, NDST3, NELL2, NOS3, NTM, ODZ2, OLFM2, OPCML, PDE1A, RFX2, ROBO1, S100A12, SCN2A, SLC22A4 (includes EG:6583), SLC2A3, SLC3A1, SOX9, SPOCK3, SPON1, TGFB2, TLR5, TNFRSF21, TRPM1, TSHZ2, TTC6 (includes EG:115669), UNC5B, UNC84A, ZNF608 |
| Inflammatory Disease | inflammatory disorder | 8.17E−06 | ACSL1, ADM, AK5, ANXA3, APBA2, ASTN2 (includes EG:23245), BCL6, CARD8, CASP5, CAV1, CCND3, CCRL1, CLTC, CNTN4, DIP2C, DNAH14, EDAR, EPHA3, EPHX2, ERAP2, FAM124A, FBLN7, FOSB, FREM2, GABRB2, GRM5, IL1B, KCNJ15, LAMB4, LHX2, LNPEP, LRP2, LTBR, LUM, MAPK14, MECOM, MYBPC1, NOS3, ODZ2, OPCML, OSM, PAPPA, PDE1A, PPP1R1C, ROBO1, RUNDC3B, S100A12, SCN2A, SFXN1, SLC22A4 (includes EG:6583), SLC26A8, SMURF2, SNRPN, SPON1, TGFB2, TLR5, TNFRSF21, TNPO1, TTC6 (includes EG:115669), TWIST1, UNC5B, VWA3B, ZNF438 |
| Skeletal and Muscular Disorders | skeletal and muscular disorder | 2.32E−03 | ACSL1, ADM, AK5, ASTN2 (includes EG:23245), BCL6, BMPR1B, CARD8, CASP5, CCND3, CLTC, CNTN4, COL1A1, COL1A2, DIP2C, DNAH14, EDAR, ELAVL2, EPHA3, EPHX2, FAM124A, FOSB, GABRB2, GIGYF2, GNAO1, HOXC6, IL1B, KCNJ15, LAMB4, LIFR, LTBR, LUM, MAPK14, MYBPC1, NOS3, ODZ2, OSM, PAPPA, PDE1A, ROBO1, RUNDC3B, S100A12, SCN2A, SHOX, SLC22A4 (includes EG:6583), SOX9, SPOCK3, TLR5, TNFRSF21, TNPO1, TSHZ2, TTC6 (includes EG:115669), TWIST1, UNC5B, VWA3B, ZNF438 |
| Cardiovascular Disease | cardiovascular disorder | 3.05E−05 | ACSL1, ADM, AK5, ALPL, ASTN2 (includes EG:23245), BCL6, BMPR1B, C18ORF54, CACNA1I, CARD16, CAV1, CNTN4, DMRT1, DNAH14, EDAR, EPHX2, ERAP2, FAM13A, FOLH1, FOSB, FREM2, GABRB2, GSTM1, IL1B, IQGAP2, LIFR, LTBR, MAN1C1, MAPK14, MBNL1, MCF2L, MECOM, MYBPC1, NOS3, NTM, ODZ2, OLFM2, OPCML, PAPPA, PDE1A, ROBO1, RORB, S100A12, SMURF2, SNRPN, SOX9, SPOCK3, SPON1, TFPI, TRPM1, UNC84A, VWA3B |
| Immunological Disease | immunological disorder | 2.11E−04 | ACSL1, ADM, AK5, ANXA3, ASTN2 (includes EG:23245), BCL6, CARD8, CASP5, CCND3, CCRL1, CLTC, CNTN4, COL1A2, DIP2C, DNAH14, EDAR, EPHA3, EPHX2, FAM124A, FAT1, FOSB, GABRB2, GOLGA6L2, GSTM1, GUSBL2, IL1B, IQGAP2, KCNJ15, LAMB4, LTBR, MAPK14, MYBPC1, NELL2, NOS3, NTM, ODZ2, OPCML, OSM, PAPPA, PDE1A, ROBO1, RUNDC3B, |

TABLE 7-continued

TIA specific gene-functions

| Category | Function | p-value | Molecules |
|---|---|---|---|
| | | | S100A12, SLC22A4 (includes EG:6583), SNRPN, SPON1, TLR5, TNFRSF21, TNPO1, TSHZ2, TTC6 (includes EG:115669), VWA3B, ZNF438 |
| Metabolic Disease | metabolic disorder | 1.03E-02 | ACSL1, ADAM30, AK5, ALPL, ALS2CR11, ASTN2 (includes EG:23245), BCL6, CARD8, CASP5, CCRL1, CNTLN, CNTN4, COL1A2, DIP2C, DMRT1, DNAH14, EPHA3, EPHX2, FAT1, FOXA2, GABRB2, GUSBL2, IGFBP5, IL1B, IQGAP2, ITGBL1, LRP2, LTBR, MAPK14, MBNL1, NELL2, NOS3, NTM, ODZ2, OPCML, PAPPA, PLSCR1, ROBO1, SLC22A4 (includes EG:6583), SLC2A3, SLC3A1, SMURF2, SNRPN, SPON1, SRGAP1, TLR5, TSHZ2, UNC84A, VWA3B |
| Endocrine System Disorders | endocrine system disorder | 3.00E-03 | ACSL1, ADAM30, AK5, ALPL, ALS2CR11, ASTN2 (includes EG:23245), BCL6, CARD8, CASP5, CCRL1, CNTLN, CNTN4, COL1A2, DIP2C, DMRT1, DNAH14, EPHA3, FAT1, FOXA2, GABRB2, GUSBL2, IL1B, IQGAP2, ITGBL1, LRP2, LTBR, MAPK14, MBNL1, NELL2, NOS3, NTM, ODZ2, OPCML, PAPPA, PLSCR1, ROBO1, SHOX, SLC22A4 (includes EG:6583), SLC2A3, SMURF2, SNRPN, SPON1, SRGAP1, TLR5, TSHZ2, UNC84A, VWA3B |
| Immunological Disease | autoimmune disease | 3.60E-04 | ACSL1, ADM, AK5, ASTN2 (includes EG:23245), BCL6, CARD8, CASP5, CCND3, CLTC, CNTN4, COL1A2, DIP2C, DNAH14, EDAR, EPHA3, EPHX2, FAM124A, FOSB, GABRB2, GUSBL2, IL1B, IQGAP2, KCNJ15, LAMB4, LTBR, MAPK14, MYBPC1, NELL2, ODZ2, OPCML, OSM, PAPPA, PDE1A, ROBO1, RUNDC3B, S100A12, SLC22A4 (includes EG:6583), SNRPN, SPON1, TLR5, TNFRSF21, TNPO1, TSHZ2, TTC6 (includes EG:115669), VWA3B, ZNF438 |
| Endocrine System Disorders | diabetes | 2.09E-03 | ACSL1, ADAM30, AK5, ALPL, ALS2CR11, ASTN2 (includes EG:23245), BCL6, CARD8, CASP5, CCRL1, CNTLN, CNTN4, COL1A2, DIP2C, DMRT1, DNAH14, EPHA3, FAT1, FOXA2, GABRB2, GUSBL2, IL1B, IQGAP2, ITGBL1, LTBR, MAPK14, MBNL1, NELL2, NOS3, NTM, ODZ2, OPCML, PAPPA, PLSCR1, ROBO1, SLC22A4 (includes EG:6583), SLC2A3, SMURF2, SNRPN, SPON1, SRGAP1, TLR5, TSHZ2, UNC84A, VWA3B |
| Connective Tissue Disorders | connective tissue disorder | 2.72E-04 | ACSL1, ADM, ASTN2 (includes EG:23245), BCL6, CARD8, CASP5, CCND3, CLTC, CNTN4, COL1A1, COL1A2, DIP2C, DNAH14, EDAR, EPHA3, EPHX2, FAM124A, FOSB, GABRB2, IL1B, KCNJ15, LAMB4, LTBR, LUM, MAPK14, ODZ2, OSM, PAPPA, PDE1A, ROBO1, RUNDC3B, S100A12, SHOX, SLC22A4 (includes EG:6583), TLR5, TNFRSF21, TNPO1, TTC6 (includes EG:115669), VWA3B, ZNF438 |
| Cell Death | apoptosis | 1.65E-02 | ADM, AIM2, BCL6, BMPR1B, CARD8, CASP5, CAV1, CCND3, EDAR, FOSB, FOXA2, FUS, GALNT5, GNAO1, GRM5, HOXC6, IGFBP5, IL1B, IQGAP2, LTBR, MAPK14, MCF2L, MECOM, MLL, NOS3, OSM, PIWIL1, PLSCR1, POU2AF1, SCN2A, SHOX, SLC2A3, SOX9, TFAP2B, TGFB2, TNFRSF21, TWIST1, UNC5B |
| Gene Expression | transcription | 4.26E-04 | BCL6, BMPR1B, CAV1, CCND3, EHF, ELAVL2, FOSB, FOXA2, FOXC1, FUS, GRM5, HELLS, HOXC6, IL1B, LTBR, MAPK14, MECOM, MED6, MEG3 (includes EG:55384), MLL, NR2F2, OSM, OVOL2, POU2AF1, RBM14, RORB, SHOX, SHOX2, SIX3, SLC3A1, SMURF2, SOX8, SOX9, SOX11, TFAP2B, TGFB2, TWIST1, ZNF462 |
| Inflammatory Disease | rheumatic disease | 8.49E-04 | ACSL1, ADM, ASTN2 (includes EG:23245), BCL6, CARD8, CASP5, CCND3, CLTC, CNTN4, DIP2C, DNAH14, EDAR, EPHA3, EPHX2, FAM124A, FOSB, GABRB2, IL1B, KCNJ15, LAMB4, LTBR, LUM, MAPK14, ODZ2, OSM, PAPPA, PDE1A, ROBO1, RUNDC3B, S100A12, SLC22A4 (includes EG:6583), TLR5, TNFRSF21, TNPO1, TTC6 (includes EG:115669), VWA3B, ZNF438 |
| Inflammatory Disease | arthritis | 7.29E-04 | ACSL1, ADM, ASTN2 (includes EG:23245), BCL6, CARD8, CASP5, CCND3, CLTC, CNTN4, DIP2C, DNAH14, EDAR, EPHA3, EPHX2, FAM124A, FOSB, GABRB2, IL1B, KCNJ15, LAMB4, LTBR, LUM, MAPK14, ODZ2, OSM, PAPPA, PDE1A, ROBO1, RUNDC3B, S100A12, SLC22A4 (includes EG:6583), TLR5, TNFRSF21, TNPO1, TTC6 (includes EG:115669), VWA3B, ZNF438 |
| Cellular Growth and Proliferation | proliferation | 5.91E-03 | ADM, AIM2, BCL6, BMPR1B, CAV1, CCND3, CLTC, COL1A1, DLX6, DPPA4, FOSB, FOXA2, FUS, GRM5, GSTM1, HOXC6, IGFBP5, IL1B, LIFR, MAPK14, MECOM, MEG3 (includes EG:55384), MLL, NOS3, OSM, PAPPA, PIWIL1, PLSCR1, SHOX2, SOX9, TFPI, TGFB2, TLR5, TNFRSF21 |
| Cardiovascular Disease | atherosclerosis | 1.22E-04 | ACSL1, AK5, ASTN2 (includes EG:23245), BMPR1B, CARD16, CNTN4, DMRT1, DNAH14, ERAP2, FOSB, FREM2, GRM5, IL1B, IQGAP2, LIFR, MAN1C1, MBNL1, MCF2L, MECOM, NOS3, NTM, ODZ2, OLFM2, PDE1A, ROBO1, RORB, SNRPN, SPOCK3, SPON1, TRPM1, UNC84A, VWA3B |
| Inflammatory Disease | inflammatory bowel disease | 5.07E-05 | ACSL1, AK5, APBA2, ASTN2 (includes EG:23245), CARD8, DIP2C, DNAH14, ERAP2, FBLN7, FREM2, GRM5, IL1B, LHX2, LNPEP, LTBR, MECOM, NOS3, ODZ2, OPCML, PAPPA, PDE1A, PPP1R1C, ROBO1, SFXN1, SLC22A4 (includes EG:6583), SLC26A8, SNRPN, SPON1, TGFB2, TLR5, VWA3B, ZNF438 |
| Endocrine System Disorders | non-insulin-dependent diabetes mellitus | 4.48E-04 | ADAM30, AK5, ALPL, ALS2CR11, ASTN2 (includes EG:23245), CARD8, CCRL1, CNTLN, CNTN4, COL1A2, DIP2C, DMRT1, EPHA3, FAT1, FOXA2, GABRB2, IL1B, IQGAP2, ITGBL1, MBNL1, NOS3, NTM, ODZ2, PLSCR1, ROBO1, SLC22A4 (includes EG:6583), SLC2A3, SPON1, SRGAP1, TLR5, UNC84A, VWA3B |
| Inflammatory Disease | rheumatoid arthritis | 1.54E-03 | ACSL1, ADM, ASTN2 (includes EG:23245), BCL6, CARD8, CLTC, CNTN4, DIP2C, DNAH14, EDAR, EPHA3, EPHX2, FAM124A, FOSB, GABRB2, IL1B, KCNJ15, LAMB4, MAPK14, ODZ2, OSM, PAPPA, PDE1A, ROBO1, RUNDC3B, S100A12, SLC22A4 (includes EG:6583), TNFRSF21, TNPO1, TTC6 (includes EG:115669), VWA3B, ZNF438 |
| Cardiovascular Disease | coronary artery disease | 6.94E-05 | ACSL1, AK5, ASTN2 (includes EG:23245), BMPR1B, CARD16, CNTN4, DMRT1, DNAH14, ERAP2, FREM2, GRM5, IL1B, IQGAP2, LIFR, MAN1C1, MBNL1, MCF2L, MECOM, NOS3, NTM, ODZ2, OLFM2, PDE1A, ROBO1, RORB, SNRPN, SPOCK3, SPON1, TRPM1, UNC84A, VWA3B |
| Cell Death | cell death | 7.84E-03 | ADM, AIM2, BCL6, CARD8, CAV1, CCND3, DPPA4, FOSB, FOXA2, FUS, GALNT5, GNAO1, GSTM1, HOXC6, IGFBP5, IL1B, LTBR, MAPK14, MLL, NOS3, PIWIL1, PLSCR1, SHOX, SOX9, TFAP2B, TGFB2, TNFRSF21, TWIST1, UNC5B |
| Inflammatory Disease | Crohn's disease | 2.08E-04 | ACSL1, AK5, APBA2, ASTN2 (includes EG:23245), CARD8, DIP2C, DNAH14, ERAP2, FBLN7, FREM2, GRM5, LHX2, LNPEP, MECOM, ODZ2, OPCML, PAPPA, PDE1A, PPP1R1C, ROBO1, SFXN1, SLC22A4 (includes EG:6583), SLC26A8, SNRPN, SPON1, TGFB2, TLR5, VWA3B, ZNF438 |
| Neurological Disease | neurodegenerative disorder | 1.57E-62 | ASTN2 (includes EG:23245), CASP5, CNTN4, FAM124A, FOLH1, GABRB2, GRM5, IL1B, MECOM, NDST3, NOS3, OPCML, RFX2, SCN2A, SLC22A4 (includes EG:6583), SLC2A3, SLC3A1, SPON1, TSHZ2, ZNF608 |

TABLE 7-continued

TIA specific gene-functions

| Category | Function | p-value | Molecules |
|---|---|---|---|
| Neurological Disease | Alzheimer's disease | 1.72E−02 | ASTN2 (includes EG:23245), CASP5, CNTN4, FAM124A, FOLH1, GABRB2, GRM5, IL1B, MECOM, NDST3, NOS3, OPCML, RFX2, SLC22A4 (includes EG:6583), SLC2A3, SLC3A1, SPON1, TSHZ2, ZNF608 |

Discussion

TIA is a harbinger of stroke and other vascular events. The present biomarker panels find use for intervention in TIA to prevent future vascular events. Prior to the present invention, there was limited knowledge regarding human TIA biology, and the development of specific TIA therapies has been limited. The present biomarker panels provide information to better understand the immune response in blood that occurs in patients with TIA. By examining the whole genome, unique TIA gene expression profiles showing two TIA subtypes were identified. These findings provide unique insight into TIA pathophysiology, and are consistent with the conclusion that there are specific immune responses that occur following transient focal cerebral ischemia in humans. They also suggest diagnostic tests to confirm a TIA diagnosis can be developed.

Systemic Inflammation and TIA

TIA patients appear to have unique patterns of inflammation associated with their vascular events. Indeed, compared to controls, TIA patients tend to have increased leukocyte activation and a systemic inflammatory response (8-9). Transient ischemic attacks have also been associated with a number of systemic inflammatory markers such as CRP (7), and inflammatory conditions such as inflammatory bowel disease (21-24). Alterations in immune function in TIAs are further implicated by an association between TIA and systemic infection, as well as TIA and periodontal disease (25-29). In this study, 63 genes involved in inflammation were differentially expressed in TIA compared to controls (Table 7). These genes show patterns of inflammation similar to that of inflammatory bowel disease (32 genes), rheumatoid arthritis (32 genes), and Crohn's disease (29 genes), suggesting that different, but related patterns of inflammation are associated with TIA. If the expression of these genes changed in a time-dependent manner after TIA onset, the inflammation could be a consequence of TIA. Otherwise, there might be some pre-existing inflammation that did not change with time that might promote the development of TIA. Therefore, a time-dependent analysis on the gene expression in the acute phase (blood draw within 24 h of TIA onset; n=11) and the sub acute phase (blood draw between 24 h to 72 h of TIA onset; n=13) of TIA was performed. The results showed that the large majority of the genes expressed in the acute phase were similar to those expressed in the sub acute phase (>90% similar). Thus, there may be a chronic inflammatory state prior to TIA and this could contribute to causing TIAs.

Anti-Oxidant Capacity

GSTM1 and GSTM2 encode cytosolic glutathione S-transferases (GSTs) that belong to the mu class. GST enzymes function in the detoxification of electrophilic compounds, such products of oxidative stress by conjugation with glutathione (30). GSTM1 and GSTM2 were both down-regulated in TIA patients, suggesting a decreased anti-oxidant capacity may exist in patients with TIAs. The resultant enhanced oxidative stress may in turn promote ischemic vascular disease such as TIA. This result is consistent with our previous animal study that showed a specific GST family member (GSTT1) regulated following 10 minutes of brief focal ischemia simulating human TIAs (5).

Extracellular Matrix Remodeling

Our data suggest the presence of two subgroups of TIA patients. No measured clinical factor was significantly different between each group. The notion of subtypes of TIA is not new. For example, TIA subtypes exist based on MRI DWI status, $ABCD^2$ score, or the presence of large vessel disease or atrial fibrillation. In our study, two molecular subtypes of TIA were evident based on gene expression profiles. Functional analysis of these two groups suggested over representation of genes involved in extracellular matrix remodeling in TIA1 compared to TIA2 including: MMP16, MMP19, MMP26, COL1A1, COL1A2, COL3A1, COL10A1, COL11A1, COL25A1, COL27A1, FGFs and EGFR. TIA1 patients may be more prone to extracellular matrix breakdown at the blood brain barrier and/or in atherosclerotic plaque.

Limitations of the Study

The sample size is small. A control group at very low risk of TIA and other vascular events was chosen so that the controls would be very unlikely to have silent ischemic events that would complicate comparison to TIA. By doing so, differences due to vascular risk factors are inevitably introduced. These factors were adjusted for by including age in the ANCOVA model, and excluding genes associated with hypertension and diabetes. The advantage of comparing TIA to the controls in this study, therefore, is that the gene expression differences between TIA and controls were maximized, and allowed for the search for TIA subgroups. However, future studies will need to compare TIA patients to other controls to identify "TIA specific gene markers". These controls should include patients with similar vascular risk factors and "TIA mimic" patients with migraine or seizures.

Group heterogeneity is another limitation in the study of TIA. Though stringent criteria were used to ensure subjects with TIA were indeed true transient ischemic events, it is possible that a few TIA patients were in fact TIA mimics. Similarly, though a comparison group at low risk for having silent ischemic vascular events was used, it is possible some patients in the control group had silent vascular events.

This is a discovery type study and thus there is no previous study to compare to. Though FDR correction was applied, the only way to account for multiple comparisons is to perform a future replication study. PCR verification was not performed since most changes on Affymetrix arrays have correlated extremely well with PCR in previous studies. In addition, PCR would only be needed once this study has been replicated and the PCR confirmed genes were to be used to develop clinical tests.

In summary, patients with recent TIAs can be differentiated from controls without previous vascular events using gene expression profiles in blood. In addition, there may be different immune response subtypes following transient ischemic attacks in humans.

TABLE 5

TIA associated gene lists (FDR ≤ 0.05, absolute fold change ≥ 1.5 compared with control).

| AFFY ID | Gene Symbol | Gene Title | Fold-Change |
|---|---|---|---|
| Table 5A. 135 Downregulated Genes | | | |
| TABLE 5A | | | |
| 233034_at | — | — | −2.44997 |
| 237597_at | — | — | −2.4398 |
| 1558409_at | — | — | −2.26242 |
| 1566485_at | — | — | −2.22393 |
| 1556932_at | — | — | −2.11785 |
| 242874_at | — | — | −2.03355 |
| 1561166_a_at | — | — | −1.9781 |
| 217671_at | — | — | −1.9453 |
| 1557733_a_at | — | — | −1.91008 |
| 1557580_at | — | — | −1.85725 |
| 1558410_s_at | — | — | −1.7902 |
| 242710_at | — | — | −1.76712 |
| 215314_at | — | — | −1.75283 |
| 229654_at | — | — | −1.74432 |
| 1560861_at | — | — | −1.74348 |
| 243512_x_at | — | — | −1.73922 |
| 238812_at | — | — | −1.70108 |
| 232943_at | — | — | −1.69925 |
| 233677_at | — | — | −1.68615 |
| 244226_s_at | — | — | −1.68579 |
| 233614_at | — | — | −1.68298 |
| 1557581_x_at | — | — | −1.67676 |
| 244860_at | — | — | −1.67397 |
| 239588_s_at | — | — | −1.667 |
| 244665_at | — | — | −1.65812 |
| 243107_at | — | — | −1.65279 |
| 1557519_at | — | — | −1.64084 |
| 242564_at | — | — | −1.63967 |
| 1557551_at | — | — | −1.63028 |
| 238281_at | — | — | −1.62416 |
| 1558710_at | — | — | −1.62037 |
| 239646_at | — | — | −1.60914 |
| 1568781_at | — | — | −1.60862 |
| 234148_at | — | — | −1.60079 |
| 233302_at | — | — | −1.59557 |
| 233862_at | — | — | −1.58604 |
| 1570329_at | — | — | −1.56927 |
| 241638_at | — | — | −1.56143 |
| 232834_at | — | — | −1.559 |
| 236524_at | — | — | −1.55759 |
| 1559723_s_at | — | — | −1.55744 |
| 1559401_a_at | — | — | −1.55691 |
| 236558_at | — | — | −1.55664 |
| 237803_x_at | — | — | −1.55619 |
| 231069_at | — | — | −1.5535 |
| 1557477_at | — | — | −1.54943 |
| 237953_at | — | — | −1.54815 |
| 243641_at | — | — | −1.547 |
| 1555194_at | — | — | −1.54304 |
| 217060_at | — | — | −1.54232 |
| 239449_at | — | — | −1.54082 |
| 237334_at | — | — | −1.53953 |
| 242074_at | — | — | −1.53917 |
| 1570106_at | — | — | −1.53564 |
| 244674_at | — | — | −1.53173 |
| 232372_at | — | — | −1.52446 |
| 238744_at | — | — | −1.52032 |
| 233127_at | — | — | −1.5089 |
| 243310_at | — | — | −1.50605 |
| 214309_s_at | — | — | −1.50383 |
| 244290_at | — | — | −1.50381 |
| 1562013_a_at | — | — | −1.50343 |
| 219308_s_at | AK5 | adenylate kinase 5 | −1.95614 |
| 222862_s_at | AK5 | adenylate kinase 5 | −1.64741 |
| 239651_at | ANAPC5 | anaphase promoting complex subunit 5 | −1.55844 |
| 209871_s_at | APBA2 | amyloid beta (A4) precursor protein-binding, family A, member 2 | −1.56895 |
| 229252_at | ATG9B | ATG9 autophagy related 9 homolog B (S. cerevisiae) | −1.64694 |
| 227372_s_at | BAIAP2L1 /// LOC100128461 | BAI1-associated protein 2-like 1 /// hypothetical protein LOC100128461 | −1.53271 |
| 221631_at | CACNA1I | calcium channel, voltage-dependent, T type, alpha 1I subunit | −1.63297 |

TABLE 5-continued

TIA associated gene lists (FDR ≤ 0.05, absolute fold change ≥ 1.5 compared with control).

| AFFY ID | Gene Symbol | Gene Title | Fold-Change |
| --- | --- | --- | --- |
| 239771_at | CAND1 | cullin-associated and neddylation-dissociated 1 | −1.97531 |
| 1553645_at | CCDC141 | coiled-coil domain containing 141 | −1.62867 |
| 1562028_at | CCND3 | Cyclin D3 (CCND3), transcript variant 3, mRNA | −2.00377 |
| 239871_at | CLTC | Clathrin, heavy chain (Hc), mRNA (cDNA clone IMAGE: 4812912) | −1.63031 |
| 212504_at | DIP2C | DIP2 disco-interacting protein 2 homolog C (Drosophila) | −1.62614 |
| 1553998_at | DMRTC1 /// DMRTC1B | DMRT-like family C1 /// DMRT-like family C1B | −1.86704 |
| 220048_at | EDAR | ectodysplasin A receptor | −1.69385 |
| 209368_at | EPHX2 | epoxide hydrolase 2, cytoplasmic | −1.62474 |
| 1554273_a_at | ERAP2 | endoplasmic reticulum aminopeptidase 2 | −1.52883 |
| 230792_at | FAAH2 | fatty acid amide hydrolase 2 | −1.57807 |
| 229247_at | FBLN7 | fibulin 7 | −1.58734 |
| 202768_at | FOSB | FBJ murine osteosarcoma viral oncogene homolog B | −1.63049 |
| 231108_at | FUS | fusion (involved in t(12; 16) in malignant liposarcoma) | −1.56277 |
| 1557350_at | G3BP1 | GTPase activating protein (SH3 domain) binding protein 1 | −1.6194 |
| 219815_at | GAL3ST4 | galactose-3-O-sulfotransferase 4 | −1.5674 |
| 1560133_at | GIGYF2 | GRB10 interacting GYF protein 2 | −1.52626 |
| 223080_at | GLS | Glutaminase, mRNA (cDNA clone MGC: 33744 IMAGE: 5263220) | −1.59404 |
| 221288_at | GPR22 | G protein-coupled receptor 22 | −1.56303 |
| 215333_x_at | GSTM1 | glutathione S-transferase mu 1 | −2.03103 |
| 204550_x_at | GSTM1 | glutathione S-transferase mu 1 | −1.95136 |
| 204418_x_at | GSTM2 | glutathione S-transferase mu 2 (muscle) | −1.95729 |
| 232207_at | GUSBL2 | glucuronidase, beta-like 2 | −2.10621 |
| 220085_at | HELLS | helicase, lymphoid-specific | −1.67692 |
| 241723_at | IQGAP2 | IQ motif containing GTPase activating protein 2 | −1.73571 |
| 215750_at | KIAA1659 | KIAA1659 protein | −1.54646 |
| 236728_at | LNPEP | leucyl/cystinyl aminopeptidase | −1.53387 |
| 236621_at | LOC100130070 /// LOC100130775 /// LOC100131787 /// LOC100131905 /// LOC100132291 /// LOC100132488 /// RPS27 | similar to metallopanstimulin /// similar to rCG63653 /// similar to metallopans | −1.70558 |
| 239062_at | LOC100131096 | hypothetical LOC100131096 | −1.57675 |
| 229094_at | LOC401431 | hypothetical gene LOC401431 | −1.53069 |
| 1565911_at | LOC648921 | MRNA full length insert cDNA clone EUROIMAGE 209544 | −1.54981 |
| 214180_at | MAN1C1 | mannosidase, alpha, class 1C, member 1 | −1.66631 |
| 215663_at | MBNL1 | muscleblind-like (Drosophila) | −1.53726 |
| 212935_at | MCF2L | MCF.2 cell line derived transforming sequence-like | −1.53863 |
| 207078_at | MED6 | mediator complex subunit 6 | −1.53192 |
| 242111_at | METTL3 | methyltransferase like 3 | −1.56742 |
| 1559856_s_at | MLL | myeloid/lymphoid or mixed-lineage leukemia (trithorax homolog, Drosophila) | −1.59219 |
| 243857_at | MORF4L2 | Mrgx mRNA for MRGX | −1.52328 |
| 242191_at | NBPF10 /// RP11-9412.2 | neuroblastoma breakpoint family, member 10 /// hypothetical protein LOC200030 | −1.50043 |
| 203413_at | NELL2 | NEL-like 2 (chicken) | −1.5281 |
| 229093_at | NOS3 | nitric oxide synthase 3 (endothelial cell) | −1.53818 |
| 223601_at | OLFM2 | olfactomedin 2 | −1.5119 |
| 214615_at | P2RY10 | purinergic receptor P2Y, G-protein coupled, 10 | −1.51779 |
| 235758_at | PNMA6A | paraneoplastic antigen like 6A | −1.95731 |
| 244011_at | PPM1K | protein phosphatase 1K (PP2C domain containing) | −1.51501 |
| 239635_at | RBM14 | RNA binding motif protein 14 | −1.65349 |
| 219864_s_at | RCAN3 | RCAN family member 3 | −1.61977 |
| 212699_at | SCAMP5 | secretory carrier membrane protein 5 | −1.54948 |
| 232055_at | SFXN1 | sideroflexin 1 | −1.50117 |
| 239667_at | SLC3A1 | solute carrier family 3 (cystine, dibasic and neutral amino acid transporters, a | −1.69708 |
| 1553423_a_at | SLFN13 | schlafen family member 13 | −1.53028 |
| 232020_at | SMURF2 | SMAD specific E3 ubiquitin protein ligase 2 | −1.57992 |
| 1560741_at | SNRPN | small nuclear ribonucleoprotein polypeptide N | −1.65945 |
| 226587_at | SNRPN | small nuclear ribonucleoprotein polypeptide N | −1.58006 |
| 226913_s_at | SOX8 | SRY (sex determining region Y)-box 8 | −1.73755 |
| 1555882_at | SPIN3 | spindlin family, member 3 | −1.65127 |
| 1555883_s_at | SPIN3 | spindlin family, member 3 | −1.50348 |
| 213993_at | SPON1 | spondin 1, extracellular matrix protein | −1.55928 |
| 218856_at | TNFRSF21 | tumor necrosis factor receptor superfamily, member 21 | −1.77712 |
| 1556116_s_at | TNPO1 | Transportin 1, mRNA (cDNA clone MGC: 17116 IMAGE: 4178989) | −1.7577 |
| 244521_at | TSHZ2 | Cell growth-inhibiting protein 7 | −1.86192 |
| 206487_at | UNC84A | unc-84 homolog A (C. elegans) | −1.50376 |

TABLE 5-continued

TIA associated gene lists (FDR ≤ 0.05, absolute fold change ≥ 1.5 compared with control).

| AFFY ID | Gene Symbol | Gene Title | Fold-Change |
|---|---|---|---|
| 1558569_at | UNQ6228 | MRNA; cDNA DKFZp667K1619 (from clone DKFZp667K1619) | −1.63796 |
| 1557450_s_at | WHDC1L2 | WAS protein homology region 2 domain containing 1-like 2 | −1.75555 |
| 229234_at | ZC3H12B | zinc finger CCCH-type containing 12B | −1.72127 |
| 55872_at | ZNF512B | zinc finger protein 512B | −1.52158 |
| 1568873_at | ZNF519 | zinc finger protein 519 | −1.70283 |

Table 5B. 325 Upregulated Genes
TABLE 5B

| AFFY ID | Gene Symbol | Gene Title | Fold-Change |
|---|---|---|---|
| 1563546_at | — | — | 3.50048 |
| 1559696_at | — | — | 3.23854 |
| 1563033_x_at | — | — | 3.16355 |
| 1563032_at | — | — | 2.97375 |
| 1558496_at | — | — | 2.87094 |
| 241566_at | — | — | 2.82164 |
| 1568589_at | — | — | 2.7205 |
| 215448_at | — | — | 2.69149 |
| 237479_at | — | — | 2.68144 |
| 234235_at | — | — | 2.64462 |
| 231074_at | — | — | 2.63519 |
| 1560905_at | — | — | 2.63286 |
| 237871_x_at | — | — | 2.55976 |
| 237937_x_at | — | — | 2.541 |
| 207731_at | — | — | 2.52426 |
| 240988_x_at | — | — | 2.46734 |
| 243398_at | — | — | 2.43872 |
| 241675_s_at | — | — | 2.39854 |
| 241674_s_at | — | — | 2.38362 |
| 228827_at | — | — | 2.3697 |
| 233944_at | — | — | 2.36679 |
| 227952_at | — | — | 2.31481 |
| 1554225_a_at | — | — | 2.30748 |
| 1560049_at | — | — | 2.29877 |
| 215962_at | — | — | 2.28524 |
| 1564306_at | — | — | 2.20443 |
| 1557762_at | — | — | 2.18276 |
| 231091_x_at | — | — | 2.17817 |
| 1566862_at | — | — | 2.1529 |
| 1560760_s_at | — | — | 2.1184 |
| 230959_at | — | — | 2.10492 |
| 238103_at | — | — | 2.08283 |
| 242802_x_at | — | — | 2.06924 |
| 234502_at | — | — | 2.05567 |
| 241636_x_at | — | — | 2.0384 |
| 236038_at | — | — | 2.0344 |
| 216406_at | — | — | 2.02612 |
| 1566805_at | — | — | 2.00292 |
| 239464_at | — | — | 2.00073 |
| 233875_at | — | — | 1.99361 |
| 1561713_at | — | — | 1.9693 |
| 1562480_at | — | — | 1.94431 |
| 1556983_a_at | — | — | 1.93605 |
| 1570191_at | — | — | 1.93494 |
| 243902_at | — | — | 1.93045 |
| 207744_at | — | — | 1.92381 |
| 237233_at | — | — | 1.90496 |
| 1561199_at | — | — | 1.89756 |
| 1561902_at | — | — | 1.89021 |
| 243273_at | — | — | 1.88315 |
| 238368_at | — | — | 1.88178 |
| 243666_at | — | — | 1.87601 |
| 1556989_at | — | — | 1.86984 |
| 238358_x_at | — | — | 1.86726 |
| 229635_at | — | — | 1.8637 |
| 238361_s_at | — | — | 1.84576 |
| 231503_at | — | — | 1.84378 |
| 229490_s_at | — | — | 1.84229 |
| 1569344_a_at | — | — | 1.83229 |
| 234083_at | — | — | 1.83201 |
| 243183_at | — | — | 1.83176 |
| 238405_at | — | — | 1.82494 |
| 1559336_at | — | — | 1.82388 |
| 1563568_at | — | — | 1.81339 |
| 237983_at | — | — | 1.81139 |

TABLE 5-continued

TIA associated gene lists (FDR ≤ 0.05, absolute fold change ≥ 1.5 compared with control).

| AFFY ID | Gene Symbol | Gene Title | Fold-Change |
|---|---|---|---|
| 1563881_at | — | — | 1.801 |
| 242198_at | — | — | 1.79799 |
| 1562613_at | — | — | 1.78841 |
| 1560086_at | — | — | 1.78528 |
| 237893_at | — | — | 1.77856 |
| 1562992_at | — | — | 1.75888 |
| 240112_at | — | — | 1.75583 |
| 1569810_at | — | — | 1.75522 |
| 1566609_at | — | — | 1.75501 |
| 243533_x_at | — | — | 1.74919 |
| 1570152_at | — | — | 1.74489 |
| 1561112_at | — | — | 1.74035 |
| 231040_at | — | — | 1.73604 |
| 1559695_a_at | — | — | 1.7325 |
| 1560296_at | — | — | 1.72689 |
| 1561473_at | — | — | 1.72375 |
| 241654_at | — | — | 1.71535 |
| 1557645_at | — | — | 1.70892 |
| 1566498_at | — | — | 1.70831 |
| 237399_at | — | — | 1.70373 |
| 1562811_at | — | — | 1.70357 |
| 1561448_at | — | — | 1.68957 |
| 237933_at | — | — | 1.68559 |
| 241457_at | — | — | 1.67974 |
| 242420_at | — | — | 1.67555 |
| 222342_at | — | — | 1.6753 |
| 1556021_at | — | — | 1.67385 |
| 239984_at | — | — | 1.67188 |
| 244216_at | — | — | 1.67082 |
| 234794_at | — | — | 1.66748 |
| 215290_at | — | — | 1.65929 |
| 243279_at | — | — | 1.65749 |
| 1570268_at | — | — | 1.65328 |
| 244384_at | — | — | 1.65237 |
| 238571_at | — | — | 1.64715 |
| 237552_at | — | — | 1.64653 |
| 241461_at | — | — | 1.63938 |
| 242718_at | — | — | 1.63417 |
| 238392_at | — | — | 1.62252 |
| 238354_x_at | — | — | 1.62228 |
| 1560453_at | — | — | 1.62059 |
| 215976_at | — | — | 1.62035 |
| 1564840_at | — | — | 1.6194 |
| 1561767_at | — | — | 1.61738 |
| 1553275_s_at | — | — | 1.61253 |
| 1563087_at | — | — | 1.61106 |
| 1566597_at | — | — | 1.59925 |
| 244668_at | — | — | 1.59371 |
| 216518_at | — | — | 1.5937 |
| 1563561_at | — | — | 1.59351 |
| 236571_at | — | — | 1.5893 |
| 216214_at | — | — | 1.58555 |
| 240904_at | — | — | 1.58293 |
| 235494_at | — | — | 1.57849 |
| 240067_at | — | — | 1.57319 |
| 237071_at | — | — | 1.57301 |
| 233306_at | — | — | 1.56521 |
| 216463_at | — | — | 1.56326 |
| 237192_at | — | — | 1.56114 |
| 1560517_s_at | — | — | 1.55983 |
| 1555263_at | — | — | 1.556 |
| 1566968_at | — | — | 1.55262 |
| 241173_at | — | — | 1.54723 |
| 1561351_at | — | — | 1.54685 |
| 1559629_at | — | — | 1.54679 |
| 238395_at | — | — | 1.54457 |
| 1563026_at | — | — | 1.54135 |
| 1562610_at | — | — | 1.53899 |
| 1570506_at | — | — | 1.53071 |
| 231546_at | — | — | 1.52352 |
| 240714_at | — | — | 1.52183 |
| 242495_at | — | — | 1.51926 |
| 1561642_at | — | — | 1.51919 |
| 234825_at | — | — | 1.51483 |
| 241247_at | — | — | 1.51115 |

TABLE 5-continued

TIA associated gene lists (FDR ≤ 0.05, absolute fold change ≥ 1.5 compared with control).

| AFFY ID | Gene Symbol | Gene Title | Fold-Change |
|---|---|---|---|
| 236276_at | — | — | 1.50976 |
| 238386_x_at | — | — | 1.50861 |
| 241569_at | — | — | 1.50674 |
| 1564851_at | — | — | 1.50551 |
| 1556185_a_at | — | — | 1.50406 |
| 243424_at | — | — | 1.50374 |
| 238274_at | — | — | 1.50237 |
| 207275_s_at | ACSL1 | acyl-CoA synthetase long-chain family member 1 | 1.51866 |
| 243520_x_at | ADAM30 | ADAM metallopeptidase domain 30 | 1.80193 |
| 206134_at | ADAMDEC1 | ADAM-like, decysin 1 | 1.61274 |
| 209614_at | ADH1B | alcohol dehydrogenase 1B (class I), beta polypeptide | 1.51397 |
| 202912_at | ADM | adrenomedullin | 1.61874 |
| 206513_at | AIM2 | absent in melanoma 2 | 1.60396 |
| 215783_s_at | ALPL | alkaline phosphatase, liver/bone/kidney | 2.1006 |
| 1557924_s_at | ALPL | alkaline phosphatase, liver/bone/kidney | 2.02022 |
| 1563673_a_at | ALS2CR11 | amyotrophic lateral sclerosis 2 (juvenile) chromosome region, candidate 11 | 2.15177 |
| 1562292_at | ANKRD30B | ankyrin repeat domain 30B | 1.86641 |
| 209369_at | ANXA3 | annexin A3 | 2.41095 |
| 1554816_at | ASTN2 | astrotactin 2 | 2.22748 |
| 239144_at | B3GAT2 | beta-1,3-glucuronyltransferase 2 (glucuronosyltransferase S) | 1.75721 |
| 228758_at | BCL6 | Zinc finger protein | 1.69127 |
| 215990_s_at | BCL6 | B-cell CLL/lymphoma 6 | 1.59315 |
| 242579_at | BMPR1B | bone morphogenetic protein receptor, type IB | 2.05687 |
| 232416_at | BRUNOL5 | bruno-like 5, RNA binding protein (*Drosophila*) | 1.68747 |
| 223977_s_at | C18orf2 | chromosome 18 open reading frame 2 | 1.58384 |
| 1553652_a_at | C18orf54 | chromosome 18 open reading frame 54 | 1.54796 |
| 235568_at | C19orf59 | chromosome 19 open reading frame 59 | 1.99789 |
| 1554540_at | C1orf67 | chromosome 1 open reading frame 67 | 1.51941 |
| 1553329_at | C7orf45 | chromosome 7 open reading frame 45 | 1.72974 |
| 239203_at | C7orf53 | chromosome 7 open reading frame 53 | 1.55912 |
| 1552701_a_at | CARD16 | caspase recruitment domain family, member 16 | 1.59587 |
| 232969_at | CARD8 | caspase recruitment domain family, member 8 | 1.78265 |
| 207500_at | CASP5 | caspase 5, apoptosis-related cysteine peptidase | 1.91798 |
| 203065_s_at | CAV1 | caveolin 1, caveolae protein, 22 kDa | 1.60773 |
| 220351_at | CCRL1 | chemokine (C-C motif) receptor-like 1 | 2.32444 |
| 208168_s_at | CHIT1 | chitinase 1 (chitotriosidase) | 1.56138 |
| 239989_at | CNTLN | centlein, centrosomal protein | 1.53478 |
| 229084_at | CNTN4 | contactin 4 | 1.7244 |
| 1556499_s_at | COL1A1 | collagen, type I, alpha 1 | 2.87107 |
| 229218_at | COL1A2 | collagen, type I, alpha 2 | 1.92067 |
| 210262_at | CRISP2 | cysteine-rich secretory protein 2 | 1.88349 |
| 1553002_at | DEFB105A /// DEFB105B | defensin, beta 105A /// defensin, beta 105B | 1.52948 |
| 226121_at | DHRS13 | dehydrogenase/reductase (SDR family) member 13 | 1.65414 |
| 233092_s_at | DKFZP434B061 | DKFZP434B061 protein | 1.84946 |
| 222253_s_at | DKFZP434P211 | POM121 membrane glycoprotein-like 1 pseudogene | 2.61011 |
| 206819_at | DKFZP434P211 | POM121 membrane glycoprotein-like 1 pseudogene | 1.93567 |
| 239309_at | DLX6 | distal-less homeobox 6 | 2.4523 |
| 220493_at | DMRT1 | doublesex and mab-3 related transcription factor 1 | 1.61917 |
| 241199_x_at | DPPA4 | developmental pluripotency associated 4 | 2.68174 |
| 232360_at | EHF | ets homologous factor | 1.68951 |
| 219850_s_at | EHF | ets homologous factor | 1.64412 |
| 228260_at | ELAVL2 | ELAV (embryonic lethal, abnormal vision, *Drosophila*)-like 2 (Hu antigen B) | 1.9905 |
| 227612_at | ELAVL3 | ELAV (embryonic lethal, abnormal vision, *Drosophila*)-like 3 (Hu antigen C) | 3.23425 |
| 219134_at | ELTD1 | EGF, latrophilin and seven transmembrane domain containing 1 | 1.70282 |
| 211164_at | EPHA3 | EPH receptor A3 | 2.39314 |
| 243277_x_at | EVI1 | ecotropic viral integration site 1 | 1.5445 |
| 230519_at | FAM124A | family with sequence similarity 124A | 1.59499 |
| 1569025_s_at | FAM13A1 | family with sequence similarity 13, member A1 | 1.55876 |
| 222291_at | FAM149A | family with sequence similarity 149, member A | 1.75785 |
| 222205_x_at | FAM182B /// RP13-401N8.2 | family with sequence similarity 182, member B /// hypothetical gene supported by | 1.70042 |
| 220645_at | FAM55D | family with sequence similarity 55, member D | 1.55166 |
| 201579_at | FAT1 | FAT tumor suppressor homolog 1 (*Drosophila*) | 1.67288 |
| 239710_at | FIGN | fidgetin | 2.14096 |
| 238964_at | FIGN | fidgetin | 1.56796 |
| 1557155_a_at | FLJ30375 | CDNA clone IMAGE: 5301781 | 1.97451 |
| 229521_at | FLJ36031 | hypothetical protein FLJ36031 | 1.58141 |
| 1560790_at | FLJ36144 | hypothetical protein FLJ36144 | 1.78391 |
| 1558579_at | FLJ37786 | hypothetical LOC642691 | 1.66029 |

TABLE 5-continued

TIA associated gene lists (FDR ≤ 0.05, absolute fold change ≥ 1.5 compared with control).

| AFFY ID | Gene Symbol | Gene Title | Fold-Change |
|---|---|---|---|
| 230999_at | FLJ39051 | CDNA FLJ39051 fis, clone NT2RP7011452 | 1.92605 |
| 227925_at | FLJ39051 | CDNA FLJ39051 fis, clone NT2RP7011452 | 1.86433 |
| 217487_x_at | FOLH1 | folate hydrolase (prostate-specific membrane antigen) 1 | 2.19987 |
| 217483_at | FOLH1 | folate hydrolase (prostate-specific membrane antigen) 1 | 1.68955 |
| 40284_at | FOXA2 | forkhead box A2 | 1.8498 |
| 1553613_s_at | FOXC1 | forkhead box C1 | 1.53964 |
| 230964_at | FREM2 | FRAS1 related extracellular matrix protein 2 | 2.30984 |
| 1553024_at | G30 | protein LG30-like | 1.75094 |
| 1557122_s_at | GABRB2 | gamma-aminobutyric acid (GABA) A receptor, beta 2 | 3.49668 |
| 242344_at | GABRB2 | gamma-aminobutyric acid (GABA) A receptor, beta 2 | 2.72458 |
| 1555726_at | GAFA3 | FGF-2 activity-associated protein 3 | 1.61768 |
| 219271_at | GALNT14 | UDP-N-acetyl-alpha-D-galactosamine: polypeptide N-acetylgalactosaminyltransferase | 2.07605 |
| 240390_at | GALNT5 | UDP-N-acetyl-alpha-D-galactosamine: polypeptide N-acetylgalactosaminyltransferase | 2.09257 |
| 204763_s_at | GNAO1 | guanine nucleotide binding protein (G protein), alpha activating activity polype | 1.5542 |
| 223767_at | GPR84 | G protein-coupled receptor 84 | 1.76044 |
| 207235_s_at | GRM5 | glutamate receptor, metabotropic 5 | 1.93451 |
| 1559520_at | GYPA | Glycophorin A | 2.12904 |
| 211267_at | HESX1 | HESX homeobox 1 | 1.61355 |
| 227566_at | HNT | neurotrimin | 1.56554 |
| 206858_s_at | HOXC4 /// HOXC6 | homeobox C4 /// homeobox C6 | 1.70414 |
| 219403_s_at | HPSE | heparanase | 1.60481 |
| 211959_at | IGFBP5 | insulin-like growth factor binding protein 5 | 1.54545 |
| 205067_at | IL1B | interleukin 1, beta | 1.57884 |
| 39402_at | IL1B | interleukin 1, beta | 1.51316 |
| 229538_s_at | IQGAP3 | IQ motif containing GTPase activating protein 3 | 1.73797 |
| 214927_at | ITGBL1 | integrin, beta-like 1 (with EGF-like repeat domains) | 1.73813 |
| 238428_at | KCNJ15 /// LOC100131955 | potassium inwardly-rectifying channel, subfamily J, member 15 /// similar to pot | 1.56965 |
| 227250_at | KREMEN1 | kringle containing transmembrane protein 1 | 2.16406 |
| 235370_at | KREMEN1 | kringle containing transmembrane protein 1 | 1.77475 |
| 215516_at | LAMB4 | laminin, beta 4 | 1.60646 |
| 206140_at | LHX2 | LIM homeobox 2 | 2.0959 |
| 225571_at | LIFR | leukemia inhibitory factor receptor alpha | 1.69168 |
| 210582_s_at | LIMK2 | LIM domain kinase 2 | 1.5485 |
| 1556704_s_at | LOC100133920 /// LOC286297 | hypothetical protein LOC100133920 /// hypothetical protein LOC286297 | 1.63034 |
| 232034_at | LOC203274 | CDNA FLJ31544 fis, clone NT2RI2000865 | 1.63147 |
| 1557717_at | LOC338862 | hypothetical protein LOC338862 | 2.22946 |
| 1560823_at | LOC340017 | hypothetical protein LOC340017 | 1.51946 |
| 233879_at | LOC374491 | TPTE and PTEN homologous inositol lipid phosphatase pseudogene | 1.81019 |
| 1558982_at | LOC375010 | hypothetical LOC375010 | 1.72485 |
| 214984_at | LOC440345 | hypothetical protein LOC440345 | 1.98536 |
| 230902_at | LOC645323 | CDNA clone IMAGE: 5260726 | 1.84336 |
| 238850_at | LOC645323 | hypothetical LOC645323 | 1.81503 |
| 1568933_at | LOC646627 | phospholipase inhibitor | 1.53874 |
| 231434_at | LOC728460 | similar to FLJ32921 protein | 1.68733 |
| 1570009_at | LOC732096 | similar to hCG2040240 | 2.13184 |
| 230863_at | LRP2 | low density lipoprotein-related protein 2 | 1.71146 |
| 203005_at | LTBR | lymphotoxin beta receptor (TNFR superfamily, member 3) | 1.58399 |
| 201744_s_at | LUM | lumican | 1.93131 |
| 210449_x_at | MAPK14 | mitogen-activated protein kinase 14 | 1.57327 |
| 211561_x_at | MAPK14 | mitogen-activated protein kinase 14 | 1.55337 |
| 235077_at | MEG3 | maternally expressed 3 (non-protein coding) | 1.6384 |
| 240814_at | MGC39584 | hypothetical gene supported by BC029568 | 1.59341 |
| 214087_s_at | MYBPC1 | myosin binding protein C, slow type | 1.58609 |
| 237510_at | MYNN | Myoneurin, mRNA (cDNA clone IMAGE: 4721583) | 1.85041 |
| 1559292_s_at | NCRNA00032 | Clone IMAGE: 2275835 C9orf14 mRNA, partial sequence; alternatively spliced | 1.98554 |
| 220429_at | NDST3 | N-deacetylase/N-sulfotransferase (heparan glucosaminyl) 3 | 1.68889 |
| 209119_x_at | NR2F2 | nuclear receptor subfamily 2, group F, member 2 | 1.94377 |
| 231867_at | ODZ2 | odz, odd Oz/ten-m homolog 2 (Drosophila) | 2.03143 |
| 214111_at | OPCML | opioid binding protein/cell adhesion molecule-like | 1.91158 |
| 230170_at | OSM | oncostatin M | 1.58899 |
| 1553931_at | OSTCL | oligosaccharyltransferase complex subunit-like | 1.57501 |
| 206048_at | OVOL2 | ovo-like 2 (Drosophila) | 2.06333 |
| 1559400_s_at | PAPPA | pregnancy-associated plasma protein A, pappalysin 1 | 1.50009 |
| 210292_s_at | PCDH11X /// PCDH11Y | protocadherin 11 X-linked /// protocadherin 11 Y-linked | 1.6605 |
| 208396_s_at | PDE1A | phosphodiesterase 1A, calmodulin-dependent | 1.68453 |
| 214868_at | PIWIL1 | piwi-like 1 (Drosophila) | 1.63171 |

TABLE 5-continued

TIA associated gene lists (FDR ≤ 0.05, absolute fold change ≥ 1.5 compared with control).

| AFFY ID | Gene Symbol | Gene Title | Fold-Change |
|---|---|---|---|
| 202446_s_at | PLSCR1 | phospholipid scramblase 1 | 1.54059 |
| 233030_at | PNPLA3 | patatin-like phospholipase domain containing 3 | 1.50269 |
| 1569675_at | POU2AF1 | POU class 2 associating factor 1, mRNA (cDNA clone MGC: 45211 IMAGE: 5554134) | 1.67876 |
| 1555462_at | PPP1R1C | protein phosphatase 1, regulatory (inhibitor) subunit 1C | 1.60542 |
| 241669_x_at | PRKD2 | protein kinase D2 | 1.55139 |
| 220696_at | PRO0478 | PRO0478 protein | 1.69169 |
| 228825_at | PTGR1 | prostaglandin reductase 1 | 1.95262 |
| 217194_at | RASAL2 | RAS protein activator like 2 | 2.00632 |
| 226872_at | RFX2 | regulatory factor X, 2 (influences HLA class II expression) | 1.58786 |
| 213194_at | ROBO1 | roundabout, axon guidance receptor, homolog 1 (Drosophila) | 1.95207 |
| 242385_at | RORB | RAR-related orphan receptor B | 2.14023 |
| 1555990_at | RP1-127L4.6 | hypothetical protein LOC150297 | 1.76603 |
| 215321_at | RUNDC3B | RUN domain containing 3B | 1.60322 |
| 205863_at | S100A12 | S100 calcium binding protein A12 | 1.5633 |
| 229057_at | SCN2A | sodium channel, voltage-gated, type II, alpha subunit | 1.85129 |
| 207570_at | SHOX | short stature homeobox | 2.00103 |
| 210135_s_at | SHOX2 | short stature homeobox 2 | 2.86893 |
| 208443_x_at | SHOX2 | short stature homeobox 2 | 1.70616 |
| 206634_at | SIX3 | SIX homeobox 3 | 1.78989 |
| 205896_at | SLC22A4 | solute carrier family 22 (organic cation/ergothioneine transporter), member 4 | 1.65918 |
| 237340_at | SLC26A8 | solute carrier family 26, member 8 | 2.32491 |
| 216236_s_at | SLC2A14 /// SLC2A3 | solute carrier family 2 (facilitated glucose transporter), member 14 /// solute | 1.51356 |
| 232547_at | SNIP | SNAP25-interacting protein | 1.83841 |
| 240204_at | SNRPN | small nuclear ribonucleoprotein polypeptide N | 1.58295 |
| 241987_x_at | SNX31 | sorting nexin 31 | 2.19167 |
| 204913_s_at | SOX11 | SRY (sex determining region Y)-box 11 | 2.34727 |
| 204914_s_at | SOX11 | SRY (sex determining region Y)-box 11 | 1.88201 |
| 202935_s_at | SOX9 | SRY (sex determining region Y)-box 9 | 2.45928 |
| 235342_at | SPOCK3 | sparc/osteonectin, cwcv and kazal-like domains proteoglycan (testican) 3 | 1.75314 |
| 241961_at | SRD5A2L2 | steroid 5 alpha-reductase 2-like 2 | 2.08494 |
| 1554831_at | SRGAP1 | SLIT-ROBO Rho GTPase activating protein 1 | 1.99203 |
| 203759_at | ST3GAL4 | ST3 beta-galactoside alpha-2,3-sialyltransferase 4 | 1.51002 |
| 231969_at | STOX2 | storkhead box 2 | 2.2552 |
| 214451_at | TFAP2B | transcription factor AP-2 beta (activating enhancer binding protein 2 beta) | 1.89347 |
| 215447_at | TFPI | Tissue factor pathway inhibitor (lipoprotein-associated coagulation inhibitor), | 1.96509 |
| 228121_at | TGFB2 | transforming growth factor, beta 2 | 1.70904 |
| 210166_at | TLR5 | toll-like receptor 5 | 1.9168 |
| 220205_at | TPTE | transmembrane phosphatase with tensin homology | 1.60547 |
| 206479_at | TRPM1 | transient receptor potential cation channel, subfamily M, member 1 | 1.57541 |
| 1556666_a_at | TTC6 | tetratricopeptide repeat domain 6 | 1.91015 |
| 213943_at | TWIST1 | twist homolog 1 (Drosophila) | 2.72279 |
| 222435_s_at | UBE2J1 | ubiquitin-conjugating enzyme E2, J1 (UBC6 homolog, yeast) | 1.50758 |
| 226899_at | UNC5B | unc-5 homolog B (C. elegans) | 2.04351 |
| 1561200_at | VWA3B | von Willebrand factor A domain containing 3B | 1.61802 |
| 206954_at | WIT1 | Wilms tumor upstream neighbor 1 | 2.58643 |
| 1552946_at | ZNF114 | zinc finger protein 114 | 1.99445 |
| 229743_at | ZNF438 | zinc finger protein 438 | 1.53049 |
| 244007_at | ZNF462 | zinc finger protein 462 | 1.53545 |
| 1555367_at | ZNF479 | zinc finger protein 479 | 2.25193 |
| 1555368_x_at | ZNF479 | zinc finger protein 479 | 2.16203 |
| 232303_at | ZNF608 | zinc finger protein 608 | 1.72629 |
| TABLE 5C. 34 Genes that differentiate TIA from Control ||||
| 1557580_at | — | — | −1.85725 |
| 1559695_a_at | — | — | 1.7325 |
| 1561767_at | — | — | 1.61738 |
| 1563026_at | — | — | 1.54135 |
| 1563568_at | — | — | 1.81339 |
| 1568589_at | — | — | 2.7205 |
| 1568781_at | — | — | −1.60862 |
| 216406_at | — | — | 2.02612 |
| 229654_at | — | — | −1.74432 |
| 231040_at | — | — | 1.73604 |
| 231069_at | — | — | −1.5535 |
| 231546_at | — | — | 1.52352 |

TABLE 5-continued

TIA associated gene lists (FDR ≤ 0.05, absolute fold change ≥ 1.5 compared with control).

| AFFY ID | Gene Symbol | Gene Title | Fold-Change |
|---|---|---|---|
| 233306_at | — | — | 1.56521 |
| 236571_at | — | — | 1.5893 |
| 237597_at | — | — | −2.4398 |
| 237953_at | — | — | −1.54815 |
| 242495_at | — | — | 1.51926 |
| 242564_at | — | — | −1.63967 |
| 242710_at | — | — | −1.76712 |
| 244226_s_at | — | — | −1.68579 |
| 244665_at | — | — | −1.65812 |
| 229252_at | ATG9B | ATG9 autophagy related 9 homolog B (*S. cerevisiae*) | −1.64694 |
| 212504_at | DIP2C | DIP2 disco-interacting protein 2 homolog C (*Drosophila*) | −1.62614 |
| 233092_s_at | DKFZP434B061 | DKFZP434B061 protein | 1.84946 |
| 220048_at | EDAR | ectodysplasin A receptor | −1.69385 |
| 220645_at | FAM55D | family with sequence similarity 55, member D | 1.55166 |
| 1557155_a_at | FLJ30375 | CDNA clone IMAGE: 5301781 | 1.97451 |
| 215333_x_at | GSTM1 | glutathione S-transferase mu 1 | −2.03103 |
| 232207_at | GUSBL2 | glucuronidase, beta-like 2 | −2.10621 |
| 211959_at | IGFBP5 | insulin-like growth factor binding protein 5 | 1.54545 |
| 203005_at | LTBR | lymphotoxin beta receptor (TNFR superfamily, member 3) | 1.58399 |
| 229057_at | SCN2A | sodium channel, voltage-gated, type II, alpha subunit | 1.85129 |
| 232020_at | SMURF2 | SMAD specific E3 ubiquitin protein ligase 2 | −1.57992 |
| 55872_at | ZNF512B | zinc finger protein 512B | −1.52158 |
| TABLE 5D. 26 Upregulated Genes that differentiate TIA1 from TIA2 | | | |
| 1557122_s_at | GABRB2 | gamma-aminobutyric acid (GABA) A receptor, beta 2 | 3.49668 |
| 1559696_at | — | — | 3.23854 |
| 227612_at | ELAVL3 | ELAV (embryonic lethal, abnormal vision, *Drosophila*)-like 3 (Hu antigen C) | 3.23425 |
| 1563032_at | — | — | 2.97375 |
| 1558496_at | — | — | 2.87094 |
| 241566_at | — | — | 2.82164 |
| 213943_at | TWIST1 | twist homolog 1 (*Drosophila*) | 2.72279 |
| 215448_at | — | — | 2.69149 |
| 241199_x_at | DPPA4 | developmental pluripotency associated 4 | 2.68174 |
| 237479_at | — | — | 2.68144 |
| 234235_at | — | — | 2.64462 |
| 1560905_at | — | — | 2.63286 |
| 222253_s_at | DKFZP434P211 | POM121 membrane glycoprotein-like 1 pseudogene | 2.61011 |
| 237937_x_at | — | — | 2.541 |
| 207731_at | — | — | 2.52426 |
| 239309_at | DLX6 | distal-less homeobox 6 | 2.4523 |
| 243398_at | — | — | 2.43872 |
| 241675_s_at | — | — | 2.39854 |
| 241674_s_at | — | — | 2.38362 |
| 1555367_at | ZNF479 | zinc finger protein 479 | 2.25193 |
| 1554816_at | ASTN2 | astrotactin 2 | 2.22748 |
| 241987_x_at | SNX31 | sorting nexin 31 | 2.19167 |
| 1557762_at | — | — | 2.18276 |
| 1563673_a_at | ALS2CR11 | amyotrophic lateral sclerosis 2 (juvenile) chromosome region, candidate 11 | 2.15177 |
| 214984_at | LOC440345 | hypothetical protein LOC440345 | 1.98536 |
| 1556983_a_at | — | — | 1.93605 |

TABLE 8

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 1553422_s_at | A2BP1 | ataxin 2-binding protein 1 | 1.72186 |
| 223593_at | AADAT | aminoadipate aminotransferase | 1.85564 |
| 214829_at | AASS | aminoadipate-semialdehyde synthase | 1.89032 |
| 1552582_at | ABCC13 | ATP-binding cassette, sub-family C (CFTR/MRP), member 13 | 2.62247 |
| 1557374_at | ABCC9 | ATP-binding cassette, sub-family C (CFTR/MRP), member 9 | 1.74138 |
| 208462_s_at | ABCC9 | ATP-binding cassette, sub-family C (CFTR/MRP), member 9 | 2.03195 |
| 220518_at | ABI3BP | ABI family, member 3 (NESH) binding protein | 1.81797 |
| 220061_at | ACSM5 | acyl-CoA synthetase medium-chain family member 5 | 1.74065 |
| 89977_at | ACSM5 | acyl-CoA synthetase medium-chain family member 5 | 2.18846 |
| 215613_at | ADAM12 | Meltrin-S (ADAM12) mRNA, complete cds, alternatively spliced | 1.79057 |
| 1568970_at | ADAM18 | ADAM metallopeptidase domain 18 | 2.48574 |
| 207664_at | ADAM2 | ADAM metallopeptidase domain 2 | 1.9154 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 243520_x_at | ADAM30 | ADAM metallopeptidase domain 30 | 2.74216 |
| 1552266_at | ADAM32 | ADAM metallopeptidase domain 32 | 1.65164 |
| 206134_at | ADAMDEC1 | ADAM-like, decysin 1 | 3.08521 |
| 230040_at | ADAMTS18 | ADAM metallopeptidase with thrombospondin type 1 motif, 18 | 1.68813 |
| 1553180_at | ADAMTS19 | ADAM metallopeptidase with thrombospondin type 1 motif, 19 | 2.44377 |
| 214913_at | ADAMTS3 | ADAM metallopeptidase with thrombospondin type 1 motif, 3 | 1.58473 |
| 220287_at | ADAMTS9 | ADAM metallopeptidase with thrombospondin type 1 motif, 9 | 1.97398 |
| 209614_at | ADH1B | alcohol dehydrogenase 1B (class I), beta polypeptide | 1.60016 |
| 231678_s_at | ADH4 | alcohol dehydrogenase 4 (class II), pi polypeptide | 1.66033 |
| 204120_s_at | ADK | adenosine kinase | −1.79666 |
| 211491_at | ADRA1A | adrenergic, alpha-1A-, receptor | 1.6033 |
| 204333_s_at | AGA | aspartylglucosaminidase | −1.54576 |
| 1553447_at | AGBL1 | ATP/GTP binding protein-like 1 | 1.51198 |
| 1554820_at | AGBL3 | ATP/GTP binding protein-like 3 | 1.79467 |
| 232007_at | AGPAT5 | 1-acylglycerol-3-phosphate O-acyltransferase 5 (lysophosphatidic acid acyltransf | −1.78587 |
| 205357_s_at | AGTR1 | angiotensin II receptor, type 1 | 1.51953 |
| 206957_at | AGXT | alanine-glyoxylate aminotransferase | 1.50599 |
| 230630_at | AK3L1 /// AK3L2 | adenylate kinase 3-like 1 /// adenylate kinase 3-like 2 | 1.52481 |
| 207870_at | AKAP9 | A kinase (PRKA) anchor protein (yotiao) 9 | 1.76652 |
| 244205_at | ALAS2 | aminolevulinate, delta-, synthase 2 | 1.67115 |
| 211617_at | ALDOAP2 | aldolase A, fructose-bisphosphate pseudogene 2 | 3.07845 |
| 211357_s_at | ALDOB | aldolase B, fructose-bisphosphate | 1.74204 |
| 1553261_x_at | ALS2CR11 | amyotrophic lateral sclerosis 2 (juvenile) chromosome region, candidate 11 | 2.08857 |
| 1553260_s_at | ALS2CR11 | amyotrophic lateral sclerosis 2 (juvenile) chromosome region, candidate 11 | 2.81678 |
| 1563673_a_at | ALS2CR11 | amyotrophic lateral sclerosis 2 (juvenile) chromosome region, candidate 11 | 3.60798 |
| 1553471_at | AMAC1 | acyl-malonyl condensing enzyme 1 | 1.53576 |
| 236760_at | AMMECR1 | Alport syndrome, mental retardation, midface hypoplasia and elliptocytosis chrom | −1.61791 |
| 203002_at | AMOTL2 | angiomotin like 2 | 1.52446 |
| 243799_x_at | ANGPTL3 | Angiopoietin-like 3, mRNA (cDNA clone IMAGE: 3934961) | 1.63129 |
| 232606_at | ANK2 | Ankyrin, Brank-1 protein | 1.69608 |
| 1553211_at | ANKFN1 | ankyrin-repeat and fibronectin type III domain containing 1 | 1.66982 |
| 1560370_x_at | ANKH | CDNA FLJ30404 fis, clone BRACE2008481 | 1.53577 |
| 243181_at | ANKIB1 | ankyrin repeat and IBR domain containing 1 | −1.59952 |
| 206029_at | ANKRD1 | ankyrin repeat domain 1 (cardiac muscle) | 1.58224 |
| 1559406_at | ANKRD18A | ankyrin repeat domain 18A | 1.76934 |
| 1570255_s_at | ANKRD20A1 /// ANKRD20A2 /// ANKRD20A3 /// ANKRD20A4 /// ANKRD20B /// LOC375010 /// LOC647595 /// LOC728371 | ankyrin repeat domain 20 family, member A1 /// ankyrin repeat domain 20 family, | 2.65731 |
| 205706_s_at | ANKRD26 | ankyrin repeat domain 26 | −1.69786 |
| 1561079_at | ANKRD28 | ankyrin repeat domain 28 | 1.96635 |
| 1562292_at | ANKRD30B | ankyrin repeat domain 30B | 2.5644 |
| 1562294_x_at | ANKRD30B | ankyrin repeat domain 30B | 3.18306 |
| 227034_at | ANKRD57 | ankyrin repeat domain 57 | −1.62847 |
| 213553_x_at | APOC1 | apolipoprotein C-I | 1.51627 |
| 215931_s_at | ARFGEF2 | ADP-ribosylation factor guanine nucleotide-exchange factor 2 (brefeldin A-inhibi | −1.50024 |
| 228368_at | ARHGAP20 | Rho GTPase activating protein 20 | 1.60285 |
| 1560318_at | ARHGAP29 | Rho GTPase activating protein 29 | 4.60468 |
| 235412_at | ARHGEF7 | Rho guanine nucleotide exchange factor (GEF) 7 (ARHGEF7), transcript variant 2, | 1.63916 |
| 242727_at | ARL5B | ADP-ribosylation factor-like 5B | −1.54355 |
| 219094_at | ARMC8 | armadillo repeat containing 8 | −1.57518 |
| 227444_at | ARMCX4 | Armadillo repeat containing, X-linked 4, mRNA (cDNA clone IMAGE: 5261888) | −1.81523 |
| 239147_at | ARSK | arylsulfatase family, member K | 1.97592 |
| 239002_at | ASPM | asp (abnormal spindle) homolog, microcephaly associated (*Drosophila*) | 2.35391 |
| 1554816_at | ASTN2 | astrotactin 2 | 4.64925 |
| 233536_at | ASXL3 | additional sex combs like 3 (*Drosophila*) | 2.11586 |
| 1569729_a_at | ASZ1 | ankyrin repeat, SAM and basic leucine zipper domain containing 1 | 1.59531 |
| 1559485_at | ATG2B | ATG2 autophagy related 2 homolog B (*S. cerevisiae*) | 1.71224 |
| 228190_at | ATG4C /// CTR9 | ATG4 autophagy related 4 homolog C (*S. cerevisiae*) /// Ctr9, Paf1/RNA polymerase | −1.50066 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 220920_at | ATP10B | ATPase, class V, type 10B | 1.91809 |
| 220556_at | ATP1B4 | ATPase, (Na+)/K+ transporting, beta 4 polypeptide | 1.63153 |
| 211137_s_at | ATP2C1 | ATPase, Ca++ transporting, type 2C, member 1 | −1.51541 |
| 214594_x_at | ATP8B1 | ATPase, class I, type 8B, member 1 | 1.78628 |
| 216129_at | ATP9A | ATPase, class II, type 9A | 1.98899 |
| 1560404_a_at | ATPBD4 | ATP binding domain 4 | 1.5843 |
| 1569796_s_at | ATRNL1 | attractin-like 1 | 2.48281 |
| 222969_at | B3GALT1 | UDP-Gal: betaGlcNAc beta 1,3-galactosyltransferase, polypeptide 1 | 1.97721 |
| 239144_at | B3GAT2 | beta-1,3-glucuronyltransferase 2 (glucuronosyltransferase S) | 2.24315 |
| 206233_at | B4GALT6 | UDP-Gal: betaGlcNAc beta 1,4-galactosyltransferase, polypeptide 6 | 1.51182 |
| 222446_s_at | BACE2 | beta-site APP-cleaving enzyme 2 | −1.70556 |
| 207712_at | BAGE | B melanoma antigen | 1.65959 |
| 1555605_x_at | BAGE | B melanoma antigen | 1.7285 |
| 1555369_at | BAGE | B melanoma antigen | 1.55591 |
| 1555603_at | BAGE | B melanoma antigen | 2.17743 |
| 211568_at | BAI3 | brain-specific angiogenesis inhibitor 3 | 1.99551 |
| 219688_at | BBS7 | Bardet-Biedl syndrome 7 | −1.8488 |
| 1555555_at | BBS9 | Bardet-Biedl syndrome 9 | 1.67715 |
| 233464_at | BCL2L14 | BCL2-like 14 (apoptosis facilitator) | 1.59747 |
| 1560683_at | BCL8 | B-cell CLL/lymphoma 8 | 1.76236 |
| 1560684_x_at | BCL8 | B-cell CLL/lymphoma 8 | 1.85157 |
| 239367_at | BDNF | brain-derived neurotrophic factor | 1.96176 |
| 232368_at | BET3L | BET3 like (*S. cerevisiae*) | 1.85928 |
| 1569674_at | BHLHB9 | Clone 23955 mRNA sequence | 1.73214 |
| 1569289_at | BIVM | Full length insert cDNA clone YB21E09 | 1.62223 |
| 205431_s_at | BMP5 | bone morphogenetic protein 5 | 2.03195 |
| 242579_at | BMPR1B | bone morphogenetic protein receptor, type IB | 3.69028 |
| 235723_at | BNC2 | basonuclin 2 | 1.76632 |
| 232103_at | BPNT1 | 3'(2'),5'-bisphosphate nucleotidase 1 | −1.52974 |
| 206044_s_at | BRAF /// KIAA1549 | v-raf murine sarcoma viral oncogene homolog B1 /// KIAA1549 | 1.58869 |
| 1569960_at | BRD7P3 | bromodomain containing 7 pseudogene 3 | 3.05416 |
| 206787_at | BRDT | bromodomain, testis-specific | 1.53605 |
| 207369_at | BRS3 | bombesin-like receptor 3 | 2.10739 |
| 238966_at | BRUNOL4 | bruno-like 4, RNA binding protein (*Drosophila*) | 1.59417 |
| 230497_at | BRUNOL5 | bruno-like 5, RNA binding protein (*Drosophila*) | 1.81119 |
| 232416_at | BRUNOL5 | bruno-like 5, RNA binding protein (*Drosophila*) | 2.98452 |
| 202946_s_at | BTBD3 | BTB (POZ) domain containing 3 | −1.51798 |
| 207326_at | BTC | betacellulin | 1.76063 |
| 234243_at | BXDC5 | brix domain containing 5 | 3.97286 |
| 224667_x_at | C10orf104 | chromosome 10 open reading frame 104 | 1.56473 |
| 1557548_at | C10orf108 | chromosome 10 open reading frame 108 | 4.2936 |
| 1560851_at | C10orf136 | chromosome 10 open reading frame 136 | 2.78294 |
| 244435_at | C10orf141 | chromosome 10 open reading frame 141 | 1.90679 |
| 1556648_a_at | C10orf40 | chromosome 10 open reading frame 40 | 2.61956 |
| 1557801_x_at | C11orf31 | chromosome 11 open reading frame 31 | −1.50635 |
| 1561985_at | C14orf39 | chromosome 14 open reading frame 39 | 2.08706 |
| 224213_at | C14orf91 | chromosome 14 open reading frame 91 | 1.51441 |
| 232507_at | C15orf41 | chromosome 15 open reading frame 41 | 1.77387 |
| 208109_s_at | C15orf5 | chromosome 15 open reading frame 5 | 1.62118 |
| 1560751_at | C18orf16 | chromosome 18 open reading frame 16 | 3.41883 |
| 223977_s_at | C18orf2 | chromosome 18 open reading frame 2 | 2.32467 |
| 244495_x_at | C18orf45 | chromosome 18 open reading frame 45 | 1.64232 |
| 1553652_a_at | C18orf54 | chromosome 18 open reading frame 54 | 1.96326 |
| 1556288_at | C18orf62 | chromosome 18 open reading frame 62 | 2.60662 |
| 1552908_at | C1orf150 | chromosome 1 open reading frame 150 | 2.85331 |
| 1554540_at | C1orf67 | chromosome 1 open reading frame 67 | 1.74707 |
| 233598_at | C20orf187 | chromosome 20 open reading frame 187 | 2.12033 |
| 1554657_a_at | C20orf26 | chromosome 20 open reading frame 26 | 1.7578 |
| 232953_at | C20orf69 /// DKFZP434B2016 /// LOC643670 /// LOC728105 /// LOC728323 /// PCMTD2 | chromosome 20 open reading frame 69 /// similar to hypothetical protein LOC28470 | 1.62957 |
| 234314_at | C20orf74 | chromosome 20 open reading frame 74 | 1.68 |
| 240068_at | C21orf130 | chromosome 21 open reading frame 130 | 2.30653 |
| 1557481_a_at | C21orf131 | chromosome 21 open reading frame 131 | 2.67119 |
| 239999_at | C21orf34 | CDNA FLJ38295 fis, clone FCBBF3012332 | 1.71918 |
| 240801_at | C21orf37 | chromosome 21 open reading frame 37 | 2.52149 |
| 1552876_at | C21orf89 | chromosome 21 open reading frame 89 | 1.74874 |
| 244467_at | C22:CTA-250D10.9 | transmembrane protein 46-like | −1.50447 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 1552979_at | C2orf52 | chromosome 2 open reading frame 52 | 1.5065 |
| 1558519_at | C2orf67 /// RPE | Chromosome 2 open reading frame 67, mRNA (cDNA clone MGC: 27010 IMAGE: 4829661) // | 1.54141 |
| 231081_at | C2orf73 | chromosome 2 open reading frame 73 | 1.83581 |
| 241998_at | C2orf80 | chromosome 2 open reading frame 80 | 2.15326 |
| 1554147_s_at | C3orf15 | chromosome 3 open reading frame 15 | 1.5927 |
| 1554528_at | C3orf15 | chromosome 3 open reading frame 15 | 2.15191 |
| 1555719_a_at | C3orf15 | chromosome 3 open reading frame 15 | 2.82189 |
| 223990_at | C4orf17 | chromosome 4 open reading frame 17 | 1.61603 |
| 231565_at | C4orf22 | chromosome 4 open reading frame 22 | 1.55741 |
| 231612_at | C4orf35 | chromosome 4 open reading frame 35 | 1.55132 |
| 1555096_at | C4orf37 | chromosome 4 open reading frame 37 | 1.87794 |
| 1553106_at | C5orf24 | chromosome 5 open reading frame 24 | −1.84772 |
| 234457_at | C6orf12 | chromosome 6 open reading frame 12 | 2.8135 |
| 1552575_a_at | C6orf141 | chromosome 6 open reading frame 141 | 1.70056 |
| 232152_at | C6orf182 /// C6orf182P | chromosome 6 open reading frame 182 /// chromosome 6 open reading frame 182 pseu | 2.19633 |
| 244829_at | C6orf218 | Chromosome 6 open reading frame 218 (C6orf218), mRNA | 2.4961 |
| 211351_at | C6orf54 | chromosome 6 open reading frame 54 | 2.04304 |
| 1566865_at | C7orf38 | chromosome 7 open reading frame 38 | 1.98885 |
| 209446_s_at | C7orf44 | chromosome 7 open reading frame 44 | −1.51989 |
| 1553329_at | C7orf45 | chromosome 7 open reading frame 45 | 2.3417 |
| 240626_at | C8orf15 | chromosome 8 open reading frame 15 | 1.70317 |
| 231380_at | C8orf34 | chromosome 8 open reading frame 34 | 1.78353 |
| 218541_s_at | C8orf4 | chromosome 8 open reading frame 4 | 1.99089 |
| 214796_at | C8orf79 | chromosome 8 open reading frame 79 | 1.71345 |
| 1560207_at | C8orf81 | chromosome 8 open reading frame 81 | 3.37061 |
| 206727_at | C9 | complement component 9 | 1.66942 |
| 230522_s_at | C9orf100 | chromosome 9 open reading frame 100 | −1.55527 |
| 1557541_at | C9orf122 | chromosome 9 open reading frame 122 | 1.55302 |
| 208077_at | C9orf38 | chromosome 9 open reading frame 38 | 2.77328 |
| 1558414_at | C9orf4 | chromosome 9 open reading frame 4 | 1.61823 |
| 1560558_at | C9orf80 | chromosome 9 open reading frame 80 | 3.13268 |
| 1556516_at | C9orf93 | CDNA clone IMAGE: 5312512 | 2.11837 |
| 1553433_at | C9orf93 | chromosome 9 open reading frame 93 | 2.37646 |
| 1557666_s_at | C9orf98 | chromosome 9 open reading frame 98 | 1.57862 |
| 230976_at | C9orf98 | chromosome 9 open reading frame 98 | −1.65509 |
| 238636_at | CACNA1C | calcium channel, voltage-dependent, L type, alpha 1C subunit | 1.73954 |
| 244256_at | CACNA1E | Voltage-operated calcium channel, alpha-1 subunit | 2.70154 |
| 239884_at | CADPS | Ca++-dependent secretion activator | 2.05688 |
| 219572_at | CADPS2 | Ca++-dependent secretion activator 2 | 1.64739 |
| 201617_x_at | CALD1 | caldesmon 1 | 2.15522 |
| 235834_at | CALD1 | Caldesmon, 3′ UTR | 1.76734 |
| 205525_at | CALD1 | caldesmon 1 | 2.04665 |
| 1552421_a_at | CALR3 | calreticulin 3 | 1.59981 |
| 212551_at | CAP2 | CAP, adenylate cyclase-associated protein, 2 (yeast) | 1.94441 |
| 1569450_at | CAPZA2 | capping protein (actin filament) muscle Z-line, alpha 2 | −1.55786 |
| 1553323_a_at | CATSPER2 | cation channel, sperm associated 2 | −1.76772 |
| 230981_at | CATSPER3 | cation channel, sperm associated 3 | −1.5308 |
| 1555920_at | CBX3 | Heterochromatin protein HP1Hs-gamma | −1.65486 |
| 1553886_at | CCDC108 | coiled-coil domain containing 108 | 2.91507 |
| 1561477_at | CCDC144A | coiled-coil domain containing 144A | 3.37527 |
| 1561271_at | CCDC144C | coiled-coil domain containing 144C | 3.46131 |
| 243565_at | CCDC150 | coiled-coil domain containing 150 | 1.71562 |
| 237475_x_at | CCDC152 | coiled-coil domain containing 152 | 1.54515 |
| 1553849_at | CCDC26 | coiled-coil domain containing 26 | 1.9386 |
| 1553666_at | CCDC34 | coiled-coil domain containing 34 | 1.8159 |
| 233259_at | CCDC48 | PREDICTED: Homo sapiens similar to hCG20004 (LOC729581), mRNA | 2.53391 |
| 1558893_a_at | CCDC67 | coiled-coil domain containing 67 | 1.69471 |
| 214710_s_at | CCNB1 | cyclin B1 | −1.54345 |
| 220351_at | CCRL1 | chemokine (C-C motif) receptor-like 1 | 3.68023 |
| 229900_at | CD109 | CD109 molecule | 1.62542 |
| 215784_at | CD1E | CD1e molecule | 2.06446 |
| 1552509_a_at | CD300LG | CD300 molecule-like family member g | 1.53768 |
| 1554519_at | CD80 | CD80 molecule | −1.71348 |
| 241120_s_at | CDC20B | Cell division cycle 20 homolog B (S. cerevisiae), mRNA (cDNA clone IMAGE: 5206729 | 1.50701 |
| 240161_s_at | CDC20B | Cell division cycle 20 homolog B (S. cerevisiae), mRNA (cDNA clone IMAGE: 5206729 | 2.04212 |
| 1555772_a_at | CDC25A | cell division cycle 25 homolog A (S. pombe) | 3.35221 |
| 232266_x_at | CDC2L5 | CDNA FLJ35215 fis, clone PROST2000079, highly similar to Homo sapiens mRNA for C | 1.52631 |
| 240735_at | CDC42BPA | Ser-thr protein kinase PK428 | 1.53612 |
| 220115_s_at | CDH10 | cadherin 10, type 2 (T2-cadherin) | 2.15879 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 236179_at | CDH11 | cadherin 11, type 2, OB-cadherin (osteoblast) | 1.70475 |
| 207149_at | CDH12 | cadherin 12, type 2 (N-cadherin 2) | 1.62637 |
| 206898_at | CDH19 | cadherin 19, type 2 | 1.56233 |
| 220679_s_at | CDH7 | cadherin 7, type 2 | 1.80801 |
| 241911_at | CDKL3 | cyclin-dependent kinase-like 3 | 1.65132 |
| 204159_at | CDKN2C | cyclin-dependent kinase inhibitor 2C (p18, inhibits CDK4) | -1.5149 |
| 228744_at | CEP27 | centrosomal protein 27 kDa | -1.53605 |
| 229208_at | CEP27 | centrosomal protein 27 kDa | -1.51058 |
| 241836_x_at | CEP97 | centrosomal protein 97 kDa | 1.50275 |
| 207874_s_at | CFHR4 | complement factor H-related 4 | 1.74706 |
| 235117_at | CHAC2 | ChaC, cation transport regulator homolog 2 (*E. coli*) | -1.8177 |
| 220619_at | CHD7 | chromodomain helicase DNA binding protein 7 | 1.76809 |
| 1565951_s_at | CHML | choroideremia-like (Rab escort protein 2) | -1.91904 |
| 206079_at | CHML | choroideremia-like (Rab escort protein 2) | -1.64317 |
| 214596_at | CHRM3 | cholinergic receptor, muscarinic 3 | 2.54248 |
| 211587_x_at | CHRNA3 | cholinergic receptor, nicotinic, alpha 3 | 1.61917 |
| 221107_at | CHRNA9 | cholinergic receptor, nicotinic, alpha 9 | 1.56409 |
| 220026_at | CLCA4 | chloride channel regulator 4 | 2.16081 |
| 214598_at | CLDN8 | claudin 8 | 1.81271 |
| 219414_at | CLSTN2 | calsyntenin 2 | 1.84839 |
| 1552588_a_at | CNBD1 | cyclic nucleotide binding domain containing 1 | 1.55712 |
| 1552344_s_at | CNOT7 | CCR4-NOT transcription complex, subunit 7 | -1.82468 |
| 239989_at | CNTLN | centlein, centrosomal protein | 2.22761 |
| 227209_at | CNTN1 | Contactin 2 precursor (CNTN1) | 1.77739 |
| 229084_at | CNTN4 | contactin 4 | 2.67917 |
| 207195_at | CNTN6 | contactin 6 | 1.56557 |
| 205229_s_at | COCH | coagulation factor C homolog, cochlin (*Limulus polyphemus*) | -1.9015 |
| 205941_s_at | COL10A1 | collagen, type X, alpha 1 | 1.7013 |
| 37892_at | COL11A1 | collagen, type XI, alpha 1 | 2.34283 |
| 1556499_s_at | COL1A1 | collagen, type I, alpha 1 | 4.18573 |
| 202403_s_at | COL1A2 | collagen, type I, alpha 2 | 1.61064 |
| 229218_at | COL1A2 | collagen, type I, alpha 2 | 4.15668 |
| 1555253_at | COL25A1 | collagen, type XXV, alpha 1 | 3.31837 |
| 225293_at | COL27A1 | collagen, type XXVII, alpha 1 | 1.80939 |
| 211161_s_at | COL3A1 | collagen, type III, alpha 1 | 1.88084 |
| 215076_s_at | COL3A1 | collagen, type III, alpha 1 | 1.84665 |
| 232458_at | COL3A1 | MRNA 3' region for pro-alpha1(III) collagen | 2.19054 |
| 207420_at | COLEC10 | collectin sub-family member 10 (C-type lectin) | 1.54892 |
| 217645_at | COX16 | COX16 cytochrome c oxidase assembly homolog (*S. cerevisiae*) | -1.59605 |
| 227253_at | CP | ceruloplasmin (ferroxidase) | 1.66043 |
| 1552511_a_at | CPA6 | carboxypeptidase A6 | 2.12705 |
| 227721_at | CPAMD8 | C3 and PZP-like, alpha-2-macroglobulin domain containing 8 | -2.00772 |
| 1555250_a_at | CPEB3 | cytoplasmic polyadenylation element binding protein 3 | 1.57893 |
| 204920_at | CPS1 | carbamoyl-phosphate synthetase 1, mitochondrial | 1.95567 |
| 1552714_at | CREG2 | cellular repressor of E1A-stimulated genes 2 | 2.09357 |
| 237502_at | CRLS1 | Cardiolipin synthase 1 (CRLS1), transcript variant 2, mRNA | 1.62771 |
| 1555958_at | CRTAC1 | cartilage acidic protein 1 | 1.57641 |
| 1557143_at | CSMD2 | CUB and Sushi multiple domains 2 | 1.65198 |
| 1553080_at | CSN1S2A | casein alpha s2-like A | 1.73631 |
| 207030_s_at | CSRP2 | cysteine and glycine-rich protein 2 | 1.92858 |
| 1567912_s_at | CT45-4 /// CT45-6 /// LOC100133581 /// RP13-36C9.1 /// RP13-36C9.3 /// RP13-36C9.6 /// XX-FW88277B6.1 | cancer/testis antigen CT45-4 /// cancer/testis antigen CT45-6 /// hypothetical p | 5.90054 |
| 231568_at | CT47.7 /// CT47.8 /// RP6-166C19.1 /// RP6-166C19.10 /// RP6-166C19.11 /// RP6-166C19.2 /// RP6-166C19.3 /// RP6-166C19.4 /// RP6-166C19.5 /// RP6-166C19.6 /// RP6-166C19.9 | cancer/testis CT47 family, member 7 /// cancer/testis CT47 family, member 8 /// | 1.71304 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 213597_s_at | CTDSPL | CTD (carboxy-terminal domain, RNA polymerase II, polypeptide A) small phosphatas | 1.93739 |
| 209617_s_at | CTNND2 | catenin (cadherin-associated protein), delta 2 (neural plakophilin-related arm-r | 1.50335 |
| 203917_at | CXADR | coxsackie virus and adenovirus receptor | 2.66153 |
| 231389_at | CXorf41 | chromosome X open reading frame 41 | 1.97677 |
| 1553466_at | CXorf59 | chromosome X open reading frame 59 | 2.19023 |
| 235991_at | CYB5RL | cytochrome b5 reductase-like | −1.53055 |
| 216809_at | CYLC1 | cylicin, basic protein of sperm head cytoskeleton 1 | 1.90782 |
| 207780_at | CYLC2 | cylicin, basic protein of sperm head cytoskeleton 2 | 1.65232 |
| 240863_at | CYP19A1 | cytochrome P450, family 19, subfamily A, polypeptide 1 | 2.21129 |
| 214235_at | CYP3A5 | cytochrome P450, family 3, subfamily A, polypeptide 5 | 1.80203 |
| 205939_at | CYP3A7 | cytochrome P450, family 3, subfamily A, polypeptide 7 | 1.70992 |
| 205472_s_at | DACH1 | dachshund homolog 1 (*Drosophila*) | 1.65928 |
| 239738_at | DACH2 | dachshund homolog 2 (*Drosophila*) | 1.51034 |
| 1562772_a_at | DAND5 | DAN domain family, member 5 | 1.73689 |
| 238757_at | DBF4B | DBF4 homolog B (*S. cerevisiae*) | −1.67188 |
| 238508_at | DBF4B | DBF4 homolog B (*S. cerevisiae*) | −1.81109 |
| 205369_x_at | DBT | dihydrolipoamide branched chain transacylase E2 | 1.72887 |
| 213865_at | DCBLD2 | discoidin, CUB and LCCL domain containing 2 | 1.55339 |
| 205399_at | DCLK1 | doublecortin-like kinase 1 | 1.62886 |
| 215303_at | DCLK1 | doublecortin-like kinase 1 | 3.56201 |
| 201893_x_at | DCN | decorin | 1.94418 |
| 227561_at | DDR2 | discoidin domain receptor tyrosine kinase 2 | 1.53865 |
| 223662_x_at | DDX59 | DEAD (Asp-Glu-Ala-Asp) box polypeptide 59 | 1.55041 |
| 1553002_at | DEFB105A /// DEFB105B | defensin, beta 105A /// defensin, beta 105B | 1.94929 |
| 1552411_at | DEFB106A /// DEFB106B | defensin, beta 106A /// defensin, beta 106B | 1.9024 |
| 1563450_at | DEFB107A /// DEFB107B | defensin, beta 107A /// defensin, beta 107B | 3.12379 |
| 1562167_a_at | DEFB122 | defensin, beta 122 (pseudogene) | 1.58206 |
| 207356_at | DEFB4 | defensin, beta 4 | 1.95828 |
| 238917_s_at | DENND5B | DENN/MADD domain containing 5B | −1.87705 |
| 234071_at | DEPDC6 | DEP domain containing 6 | 1.54924 |
| 216947_at | DES | desmin | 4.20247 |
| 1553524_at | DGKB | diacylglycerol kinase, beta 90 kDa | 2.81068 |
| 203699_s_at | DIO2 | deiodinase, iodothyronine, type II | 1.61583 |
| 1557633_at | DKFZp434K191 | POM121 membrane glycoprotein-like 1 pseudogene | 1.87034 |
| 1569476_at | DKFZP434L187 | CDNA clone IMAGE: 5022014 | 3.78072 |
| 206819_at | DKFZP434P211 | POM121 membrane glycoprotein-like 1 pseudogene | 2.57115 |
| 222253_s_at | DKFZP434P211 | POM121 membrane glycoprotein-like 1 pseudogene | 5.5328 |
| 216877_at | DKFZp686O1327 | EST clone 251800 mariner transposon Hsmar1 sequence | 2.46877 |
| 224199_at | DKK2 | dickkopf homolog 2 (*Xenopus laevis*) | 1.52116 |
| 242631_x_at | DLC1 | deleted in liver cancer 1 | 1.70843 |
| 233056_x_at | DLGAP4 | discs, large (*Drosophila*) homolog-associated protein 4 | 1.52268 |
| 207147_at | DLX2 | distal-less homeobox 2 | 2.38281 |
| 239309_at | DLX6 | distal-less homeobox 6 | 4.54905 |
| 220493_at | DMRT1 | doublesex and mab-3 related transcription factor 1 | 2.29697 |
| 237804_at | DNAH11 | Axonemal dynein heavy chain (DNAH11), partial | 1.71964 |
| 1560416_at | DNAH11 | dynein, axonemal, heavy chain 11 | 2.87499 |
| 220725_x_at | DNAH3 | Dynein, axonemal, heavy chain 3 (DNAH3), mRNA | 1.58728 |
| 1552675_at | DNAJB7 | DnaJ (Hsp40) homolog, subfamily B, member 7 | 1.69507 |
| 1558501_at | DNM3 | dynamin 3 | 1.56409 |
| 214844_s_at | DOK5 | docking portein 5 | 2.18827 |
| 207789_s_at | DPP6 | dipeptidyl-peptidase 6 | 1.51336 |
| 231385_at | DPPA3 /// STELLAR | developmental pluripotency associated 3 /// germ and embryonic stem cell enriche | 2.12291 |
| 241199_x_at | DPPA4 | developmental pluripotency associated 4 | 4.80564 |
| 1557290_at | DPY19L2 /// DPY19L2P1 /// DPY19L2P2 /// DPY19L2P4 | dpy-19-like 2 (*C. elegans*) /// dpy-19-like 2 pseudogene 1 (*C. elegans*) /// dpy-1 | 1.62779 |
| 240218_at | DSCAM | Down syndrome cell adhesion molecule | 1.59287 |
| 1552708_a_at | DUSP19 | dual specificity phosphatase 19 | 2.25968 |
| 204014_at | DUSP4 | dual specificity phosphatase 4 | 1.67536 |
| 1569843_at | DYNC1I1 | dynein, cytoplasmic 1, intermediate chain 1 | 1.78891 |
| 1565149_at | DYNC2H1 | dynein, cytoplasmic 2, heavy chain 1 | 2.12554 |
| 204271_s_at | EDNRB | endothelin receptor type B | 1.68002 |
| 1558300_at | EFCAB5 | EF-hand calcium binding domain 5 | 2.24756 |
| 233814_at | EFNA5 | Receptor tyrosine kinase ligand LERK-7 precursor (EPLG7) | 1.57917 |
| 219454_at | EGFL6 | EGF-like-domain, multiple 6 | 1.63159 |
| 1565483_at | EGFR | epidermal growth factor receptor (erythroblastic leukemia viral (v-erb-b) oncoge | 1.75454 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 219850_s_at | EHF | ets homologous factor | 2.15949 |
| 232360_at | EHF | ets homologous factor | 2.97474 |
| 208427_s_at | ELAVL2 | ELAV (embryonic lethal, abnormal vision, *Drosophila*)-like 2 (Hu antigen B) | 1.52696 |
| 228260_at | ELAVL2 | ELAV (embryonic lethal, abnormal vision, *Drosophila*)-like 2 (Hu antigen B) | 4.26399 |
| 227612_at | ELAVL3 | ELAV (embryonic lethal, abnormal vision, *Drosophila*)-like 3 (Hu antigen C) | 6.80428 |
| 238073_at | ELAVL4 | ELAV (embryonic lethal, abnormal vision, *Drosophila*)-like 4 (Hu antigen D) | 1.54026 |
| 229581_at | ELFN1 | extracellular leucine-rich repeat and fibronectin type III domain containing 1 | 1.84175 |
| 1565254_s_at | ELL | elongation factor RNA polymerase II | 2.51255 |
| 1557836_at | ELMOD2 | ELMO/CED-12 domain containing 2 (ELMOD2), mRNA | 1.86018 |
| 219134_at | ELTD1 | EGF, latrophilin and seven transmembrane domain containing 1 | 2.15765 |
| 219436_s_at | EMCN | endomucin | 1.94422 |
| 1553672_at | ENAH | enabled homolog (*Drosophila*) | 1.64531 |
| 205066_s_at | ENPP1 | ectonucleotide pyrophosphatase/phosphodiesterase 1 | 1.63382 |
| 205065_at | ENPP1 | ectonucleotide pyrophosphatase/phosphodiesterase 1 | 1.52899 |
| 229292_at | EPB41L5 | erythrocyte membrane protein band 4.1 like 5 | -1.50762 |
| 206070_s_at | EPHA3 | EPH receptor A3 | 2.33775 |
| 211164_at | EPHA3 | EPH receptor A3 | 4.39517 |
| 216837_at | EPHA5 | EPH receptor A5 | 3.21486 |
| 229288_at | EPHA7 | EPH receptor A7 | 1.56981 |
| 216999_at | EPOR | erythropoietin receptor | 2.17646 |
| 202454_s_at | ERBB3 | v-erb-b2 erythroblastic leukemia viral oncogene homolog 3 (avian) | 1.58154 |
| 206794_at | ERBB4 | v-erb-a erythroblastic leukemia viral oncogene homolog 4 (avian) | 1.84155 |
| 233498_at | ERBB4 | v-erb-a erythroblastic leukemia viral oncogene homolog 4 (avian) | 1.68382 |
| 214053_at | ERBB4 | v-erb-a erythroblastic leukemia viral oncogene homolog 4 (avian) | 3.22256 |
| 216440_at | ERC1 | RAB6 interacting protein 2, mRNA (cDNA clone IMAGE: 4343516) | 2.35068 |
| 1569583_at | EREG | epiregulin | 1.55022 |
| 213365_at | ERI2 | exoribonuclease 2 | -1.60968 |
| 1564473_at | ESCO2 | Clone 305-4G mRNA sequence | 1.51202 |
| 235588_at | ESCO2 | establishment of cohesion 1 homolog 2 (*S. cerevisiae*) | 2.61641 |
| 209966_x_at | ESRRG | estrogen-related receptor gamma | 1.74023 |
| 224454_at | ETNK1 | ethanolamine kinase 1 | 1.50058 |
| 206501_x_at | ETV1 | ets variant 1 | 1.64042 |
| 230102_at | ETV5 | Ets-related protein | 1.68286 |
| 243277_x_at | EVI1 | ecotropic viral integration site 1 | 2.35623 |
| 208298_at | EVI5 | ecotropic viral integration site 5 | 2.18273 |
| 207327_at | EYA4 | eyes absent homolog 4 (*Drosophila*) | 2.48321 |
| 1569592_a_at | F11 | coagulation factor XI | 2.291 |
| 220575_at | FAM106A | family with sequence similarity 106, member A | 1.54075 |
| 209074_s_at | FAM107A | family with sequence similarity 107, member A | 1.63185 |
| 1557129_a_at | FAM111B | family with sequence similarity 111, member B | 2.02161 |
| 212979_s_at | FAM115A | family with sequence similarity 115, member A | 1.61927 |
| 1555944_at | FAM120A | family with sequence similarity 120A | -1.5885 |
| 1552323_s_at | FAM122C | family with sequence similarity 122C | -1.54021 |
| 1553720_a_at | FAM123A | family with sequence similarity 123A | 1.51994 |
| 235465_at | FAM123A | family with sequence similarity 123A | 1.86652 |
| 230496_at | FAM123A | family with sequence similarity 123A | 2.50999 |
| 231396_s_at | FAM126A | family with sequence similarity 126, member A | -1.50922 |
| 223625_at | FAM126A | family with sequence similarity 126, member A | -1.81004 |
| 239481_at | FAM133A | family with sequence similarity 133, member A | 4.33493 |
| 1569025_s_at | FAM13A1 | family with sequence similarity 13, member A1 | 1.57074 |
| 222291_at | FAM149A | family with sequence similarity 149, member A | 2.00081 |
| 214825_at | FAM155A | family with sequence similarity 155, member A | 1.68899 |
| 230869_at | FAM155A | family with sequence similarity 155, member A | 4.25508 |
| 242687_at | FAM160A1 | family with sequence similarity 160, member A1 | 1.63033 |
| 213304_at | FAM179B | family with sequence similarity 179, member B | -1.60915 |
| 230539_at | FAM182A | family with sequence similarity 182, member A | 1.57619 |
| 216053_x_at | FAM182A | CDNA FLJ38374 fis, clone FEBRA2002552 | 1.70561 |
| 222205_x_at | FAM182B /// RP13-401N8.2 | family with sequence similarity 182, member B /// hypothetical gene supported by | 2.46888 |
| 234945_at | FAM54A | family with sequence similarity 54, member A | 2.36602 |
| 234331_s_at | FAM84A | family with sequence similarity 84, member A | 1.85031 |
| 1555538_s_at | FAM9B | family with sequence similarity 9, member B | 1.61504 |
| 1568889_at | FANCD2 | Fanconi anemia, complementation group D2 | 1.62037 |
| 1568891_x_at | FANCD2 | Fanconi anemia, complementation group D2 | 2.51522 |
| 239246_at | FARP1 | CDEP | 1.90491 |
| 201579_at | FAT1 | FAT tumor suppressor homolog 1 (*Drosophila*) | 2.29159 |
| 1558964_at | FAT3 | FAT tumor suppressor homolog 3 (*Drosophila*) | 1.55077 |
| 1560490_at | FAT3 | FAT tumor suppressor homolog 3 (*Drosophila*) | 1.79133 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 236029_at | FAT3 | FAT tumor suppressor homolog 3 (*Drosophila*) | 4.17669 |
| 233087_at | FBXL17 | F-box and leucine-rich repeat protein 17 | 1.83402 |
| 218875_s_at | FBXO5 | F-box protein 5 | −1.6348 |
| 224402_s_at | FCRL4 | Fc receptor-like 4 | 1.66601 |
| 224403_at | FCRL4 | Fc receptor-like 4 | 3.64968 |
| 1555136_at | FGD6 | FYVE, RhoGEF and PH domain containing 6 | 2.22566 |
| 214589_at | FGF12 | fibroblast growth factor 12 | 1.87587 |
| 231523_at | FGF14 | fibroblast growth factor 14 | 2.00116 |
| 214284_s_at | FGF18 | Fibroblast growth factor 18, mRNA (cDNA clone MGC: 10529 IMAGE: 3948893) | 1.54076 |
| 220394_at | FGF20 | fibroblast growth factor 20 | 1.85663 |
| 210311_at | FGF5 | fibroblast growth factor 5 | 1.59913 |
| 205782_at | FGF7 | fibroblast growth factor 7 (keratinocyte growth factor) | 1.67479 |
| 239710_at | FIGN | fidgetin | 4.1857 |
| 238964_at | FIGN | fidgetin | 2.65603 |
| 1556325_at | FILIP1 | filamin A interacting protein 1 | 2.16122 |
| 1570515_a_at | FILIP1 | filamin A interacting protein 1 | 1.86592 |
| 223667_at | FKBP7 | FK506 binding protein 7 | 1.51179 |
| 220828_s_at | FLJ11292 | hypothetical protein FLJ11292 | 1.81486 |
| 215187_at | FLJ11292 | hypothetical protein FLJ11292 | 2.15766 |
| 1564160_at | FLJ16686 | FLJ16686 protein | 1.79597 |
| 234830_at | FLJ20518 | similar to FSHD region gene 2 protein | 2.17839 |
| 221172_at | FLJ21075 | hypothetical protein FLJ21075 | 1.7343 |
| 233604_at | FLJ22763 | hypothetical gene supported by AK026416 | 2.69416 |
| 217016_x_at | FLJ23172 /// TMEM212 | hypothetical LOC389177 /// transmembrane protein 212 | 1.7451 |
| 1553614_a_at | FLJ25694 | hypothetical protein FLJ25694 | 1.723 |
| 241953_at | FLJ25694 /// KRTAP21-1 | hypothetical protein FLJ25694 /// keratin associated protein 21-1 | 1.67966 |
| 1557155_a_at | FLJ30375 | CDNA clone IMAGE: 5301781 | 2.6058 |
| 241440_at | FLJ30375 | hypothetical gene supported by AK054937 | 2.70383 |
| 236739_at | FLJ30594 | CDNA FLJ34044 fis, clone FCBBF2007080 | 3.41974 |
| 1553775_at | FLJ31715 | hypothetical protein FLJ31715 | −1.57858 |
| 1553354_a_at | FLJ31958 | hypothetical protein FLJ31958 | 1.71642 |
| 230047_at | FLJ32810 | hypothetical protein FLJ32810 | 1.76353 |
| 1553472_at | FLJ32955 | hypothetical protein FLJ32955 | 2.65054 |
| 1569378_at | FLJ33297 | CDNA FLJ33297 fis, clone BNGH42001406 | 1.76909 |
| 1553335_x_at | FLJ34047 | hypothetical protein FLJ34047 | 1.59989 |
| 1559277_at | FLJ35700 | hypothetical protein FLJ35700 | 1.66616 |
| 1557206_at | FLJ35848 | hypothetical protein FLJ35848 | 2.97097 |
| 1566480_x_at | FLJ35848 | Hypothetical protein FLJ35848, mRNA (cDNA clone IMAGE: 5402642) | 2.19166 |
| 1557895_at | FLJ35934 | FLJ35934 protein | 2.05515 |
| 1561171_a_at | FLJ36131 /// LOC100131452 /// LOC100132025 /// LOC100132566 /// LOC100132727 /// LOC729272 | hypothetical protein FLJ36131 /// hypothetical protein LOC100131452 /// transmem | 1.78937 |
| 1560790_at | FLJ36144 | hypothetical protein FLJ36144 | 2.06719 |
| 1556558_s_at | FLJ36665 | hypothetical protein FLJ36665 | −1.73079 |
| 231527_at | FLJ36840 | CDNA FLJ36840 fis, clone ASTRO2011461 | 1.66566 |
| 1558579_at | FLJ37786 | hypothetical LOC642691 | 2.45337 |
| 242683_at | FLJ38028 | hypothetical gene supported by AK095347 | 1.51579 |
| 242546_at | FLJ39632 | hypothetical LOC642477 | 2.20629 |
| 239010_at | FLJ39632 | CDNA clone IMAGE: 5270501 | 2.23008 |
| 231882_at | FLJ39632 /// LOC100131139 | hypothetical LOC642477 /// similar to double homeobox A | 2.09022 |
| 1566665_at | FLJ40176 | hypothetical LOC121951 | 1.68357 |
| 1568698_at | FLJ43080 | hypothetical protein LOC642987 | 2.07737 |
| 1565786_x_at | FLJ45482 | hypothetical LOC645566 | 1.60292 |
| 240259_at | FLRT2 | CDNA FLJ51243 complete cds, highly similar to Leucine-rich repeat transmembrane | 2.20213 |
| 219250_s_at | FLRT3 | fibronectin leucine rich transmembrane protein 3 | 1.59215 |
| 1559244_at | FMN2 | formin 2 | 2.22149 |
| 223618_at | FMN2 | formin 2 | 1.85606 |
| 231231_at | FMNL3 | KIAA2014 protein | 2.66876 |
| 226930_at | FNDC1 | fibronectin type III domain containing 1 | 1.78354 |
| 217483_at | FOLH1 | folate hydrolase (prostate-specific membrane antigen) 1 | 2.41619 |
| 217487_x_at | FOLH1 | folate hydrolase (prostate-specific membrane antigen) 1 | 4.54562 |
| 40284_at | FOXA2 | forkhead box A2 | 3.21218 |
| 1553613_s_at | FOXC1 | forkhead box C1 | 1.8881 |
| 206018_at | FOXG1 | forkhead box G1 | 1.85819 |
| 235201_at | FOXP2 | forkhead box P2 | 2.75837 |
| 1555352_at | FOXP2 | forkhead box P2 | 1.7166 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
| --- | --- | --- | --- |
| 230964_at | FREM2 | FRAS1 related extracellular matrix protein 2 | 4.03728 |
| 243689_s_at | FRG1B | Hypothetical protein LOC283788, mRNA (cDNA clone MGC: 23868 IMAGE: 4297267) | 2.17705 |
| 234949_at | FRG1B | Hypothetical protein LOC283788, mRNA (cDNA clone MGC: 23868 IMAGE: 4297267) | 2.27959 |
| 207178_s_at | FRK | fyn-related kinase | 1.87638 |
| 1570207_at | FRRS1 | ferric-chelate reductase 1 | 2.89483 |
| 1562625_at | FRYL | FRY-like | 1.99342 |
| 244419_at | FRZB | Fritz | 1.54036 |
| 230904_at | FSD1L | fibronectin type III and SPRY domain containing 1-like | −1.99072 |
| 223985_at | FSD1L | fibronectin type III and SPRY domain containing 1-like | 1.83509 |
| 207345_at | FST | follistatin | 2.76648 |
| 203705_s_at | FZD7 | frizzled homolog 7 (Drosophila) | 1.55517 |
| 1553024_at | G30 | protein LG30-like | 2.51805 |
| 222187_x_at | G3BP1 | GTPase activating protein (SH3 domain) binding protein 1 | 1.62305 |
| 206952_at | G6PC | glucose-6-phosphatase, catalytic subunit | 2.12833 |
| 238569_at | GABBR1 | GABA-BR1a (hGB1a) receptor | −1.61754 |
| 209990_s_at | GABBR2 | gamma-aminobutyric acid (GABA) B receptor, 2 | 1.59875 |
| 233437_at | GABRA4 | gamma-aminobutyric acid (GABA) A receptor, alpha 4 | 3.25934 |
| 207010_at | GABRB1 | gamma-aminobutyric acid (GABA) A receptor, beta 1 | 2.42007 |
| 242344_at | GABRB2 | gamma-aminobutyric acid (GABA) A receptor, beta 2 | 5.10676 |
| 1557122_s_at | GABRB2 | gamma-aminobutyric acid (GABA) A receptor, beta 2 | 8.54122 |
| 229724_at | GABRB3 | gamma-aminobutyric acid (GABA) A receptor, beta 3 | 1.55943 |
| 1563533_at | GADL1 | glutamate decarboxylase-like 1 | 4.0883 |
| 208283_at | GAGE1 | G antigen 1 | 2.39924 |
| 207739_s_at | GAGE1 /// GAGE12F /// GAGE12G /// GAGE12I /// GAGE12J /// GAGE2A /// GAGE2B /// GAGE2C /// GAGE2D /// GAGE2E /// GAGE3 /// GAGE4 /// GAGE5 /// GAGE6 /// GAGE7 /// GAGE8 | G antigen 1 /// G antigen 12F /// G antigen 12G /// G antigen 12I /// G antigen | 2.7548 |
| 237183_at | GALNT5 | CDNA FLJ75131 complete cds, highly similar to Homo sapiens UDP-N-acetyl-alpha-D- | 1.57858 |
| 240390_at | GALNT5 | UDP-N-acetyl-alpha-D-galactosamine: polypeptide N-acetylgalactosaminyltransferase | 4.19183 |
| 236361_at | GALNTL2 | UDP-N-acetyl-alpha-D-galactosamine: polypeptide N-acetylgalactosaminyltransferase | 1.9112 |
| 220124_at | GAN | gigaxonin | 1.78227 |
| 204471_at | GAP43 | growth associated protein 43 | 1.67109 |
| 219954_s_at | GBA3 | glucosidase, beta, acid 3 (cytosolic) | 1.56599 |
| 230788_at | GCNT2 | glucosaminyl (N-acetyl) transferase 2, I-branching enzyme (I blood group) | −1.71043 |
| 236548_at | GIPC2 | GIPC PDZ domain containing family, member 2 | 2.02931 |
| 230258_at | GLIS3 | GLIS family zinc finger 3 | 2.8996 |
| 244680_at | GLRB | glycine receptor, beta | 1.90493 |
| 235371_at | GLT8D4 | glycosyltransferase 8 domain containing 4 | 1.5501 |
| 1554712_a_at | GLYATL2 | glycine-N-acyltransferase-like 2 | 2.06041 |
| 204763_s_at | GNAO1 | guanine nucleotide binding protein (G protein), alpha activating activity polype | 2.09098 |
| 229274_at | GNAS | Adenyl cyclase mRNA | −1.62372 |
| 207166_at | GNGT1 | guanine nucleotide binding protein (G protein), gamma transducing activity polyp | 1.92988 |
| 204324_s_at | GOLIM4 | golgi integral membrane protein 4 | 1.65786 |
| 1555199_at | GOSR1 | golgi SNAP receptor complex member 1 | 3.06916 |
| 1553879_a_at | GOT1L1 | glutamic-oxaloacetic transaminase 1-like 1 | 1.59882 |
| 1553878_at | GOT1L1 | glutamic-oxaloacetic transaminase 1-like 1 | 1.95653 |
| 215554_at | GPLD1 | glycosylphosphatidylinositol specific phospholipase D1 | 1.54336 |
| 236024_at | GPM6A | glycoprotein M6A | 2.04441 |
| 212950_at | GPR116 | G protein-coupled receptor 116 | 1.52524 |
| 212951_at | GPR116 | G protein-coupled receptor 116 | 1.57258 |
| 1555122_at | GPR125 | G protein-coupled receptor 125 | 2.42496 |
| 233887_at | GPR126 | G protein-coupled receptor 126 | 1.58837 |
| 1553025_at | GPR126 | G protein-coupled receptor 126 | 1.68374 |
| 209631_s_at | GPR37 | G protein-coupled receptor 37 (endothelin receptor type B-like) | 1.56859 |
| 219898_at | GPR85 | G protein-coupled receptor 85 | 2.09828 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 238049_at | GRAMD3 | GRAM domain containing 3 | 2.61185 |
| 206204_at | GRB14 | growth factor receptor-bound protein 14 | 2.23024 |
| 235504_at | GREM2 | gremlin 2, cysteine knot superfamily, homolog (*Xenopus laevis*) | 1.50319 |
| 219388_at | GRHL2 | grainyhead-like 2 (*Drosophila*) | 2.33499 |
| 205358_at | GRIA2 | glutamate receptor, ionotropic, AMPA 2 | 2.02789 |
| 206730_at | GRIA3 | glutamate receptor, ionotrophic, AMPA 3 | 2.12652 |
| 213845_at | GRIK2 | glutamate receptor, ionotrophic, kainate 2 | 1.74884 |
| 205814_at | GRM3 | glutamate receptor, metabotropic 3 | 2.30621 |
| 207235_s_at | GRM5 | glutamate receptor, metabotropic 5 | 2.95593 |
| 207548_at | GRM7 | glutamate receptor, metabotropic 7 | 1.64049 |
| 216992_s_at | GRM8 | glutamate receptor, metabotropic 8 | 1.54515 |
| 235387_at | GSTCD | glutathione S-transferase, C-terminal domain containing | −1.51561 |
| 242656_at | GTF2H1 | General transcription factor IIH, polypeptide 1, 62 kDa (GTF2H1), transcript vari | −1.65352 |
| 204237_at | GULP1 | GULP, engulfment adaptor PTB domain containing 1 | 1.726 |
| 204235_s_at | GULP1 | GULP, engulfment adaptor PTB domain containing 1 | 1.67838 |
| 215695_s_at | GYG2 | glycogenin 2 | 1.67125 |
| 1559520_at | GYPA | Glycophorin A | 3.86167 |
| 205523_at | HAPLN1 | hyaluronan and proteoglycan link protein 1 | 1.50177 |
| 230895_at | HAPLN1 | hyaluronan and proteoglycan link protein 1 | 2.33681 |
| 232848_at | hCG_1795283 | hCG1818123 | 1.60873 |
| 232239_at | hCG_2024094 | hCG2024094 | −1.88082 |
| 216229_x_at | HCG2P7 | HLA complex group 2 pseudogene 7 | 1.77053 |
| 1556351_at | HCN1 | hyperpolarization activated cyclic nucleotide-gated potassium channel 1 | 2.3437 |
| 232414_at | HEATR1 | HEAT repeat containing 1 | 1.52452 |
| 210331_at | HECW1 | HECT, C2 and WW domain containing E3 ubiquitin protein ligase 1 | 1.90413 |
| 233075_at | HERC2P7 | hect domain and RLD 2 pseudogene 7 | 1.58465 |
| 1555318_at | HIF3A | hypoxia inducible factor 3, alpha subunit | 2.41676 |
| 216548_x_at | HMG4L | high-mobility group (nonhistone chromosomal) protein 4-like | 1.68308 |
| 228772_at | HNMT | histamine N-methyltransferase | −1.93357 |
| 217353_at | HNRNPA1 /// HNRNPA1L2 /// HNRPA1L-2 /// HNRPA1P5 /// LOC100128836 /// LOC120364 /// LOC391670 /// LOC402112 /// LOC440125 /// LOC642817 /// LOC643033 /// LOC644037 /// LOC645001 /// LOC728170 /// LOC728643 /// LOC728732 /// LOC729102 /// LOC729366 /// LOC730246 | heterogeneous nuclear ribonucleoprotein A1 /// heterogeneous nuclear ribonucleop | 1.6011 |
| 227566_at | HNT | neurotrimin | 2.73516 |
| 213793_s_at | HOMER1 | homer homolog 1 (*Drosophila*) | 1.91311 |
| 1566140_at | HOPX | HOP homeobox | 1.73184 |
| 218959_at | HOXC10 | homeobox C10 | 1.72818 |
| 206858_s_at | HOXC4 /// HOXC6 | homeobox C4 /// homeobox C6 | 2.37146 |
| 229400_at | HOXD10 | homeobox D10 | 2.16969 |
| 219985_at | HS3ST3A1 | heparan sulfate (glucosamine) 3-O-sulfotransferase 3A1 | 1.65808 |
| 232276_at | HS6ST3 | heparan sulfate 6-O-sulfotransferase 3 | 2.29584 |
| 206639_x_at | HTN1 | histatin 1 | 1.56385 |
| 206786_at | HTN3 | histatin 3 | 2.99589 |
| 207577_at | HTR4 | 5-hydroxytryptamine (serotonin) receptor 4 | 1.55186 |
| 211740_at | ICA1 | islet cell autoantigen 1, 69 kDa | 2.1923 |
| 213450_s_at | ICOSLG | inducible T-cell co-stimulator ligand | −1.56491 |
| 209291_at | ID4 | inhibitor of DNA binding 4, dominant negative helix-loop-helix protein | 2.00627 |
| 236478_at | IFNAR1 | Interferon (alpha, beta and omega) receptor 1, mRNA (cDNA clone IMAGE: 4391580) | −1.50715 |
| 209540_at | IGF1 | insulin-like growth factor 1 (somatomedin C) | 2.21842 |
| 211959_at | IGFBP5 | insulin-like growth factor binding protein 5 | 1.8742 |
| 214973_x_at | IGHD | immunoglobulin heavy constant delta | −1.81338 |
| 220567_at | IKZF2 | IKAROS family zinc finger 2 (Helios) | 1.53299 |
| 205992_s_at | IL15 | interleukin 15 | −1.73897 |
| 220663_at | IL1RAPL1 | interleukin 1 receptor accessory protein-like 1 | 2.89062 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 222698_s_at | IMPACT | Impact homolog (mouse) | −1.54815 |
| 222250_s_at | INTS7 | integrator complex subunit 7 | −1.53873 |
| 228946_at | INTU | inturned planar cell polarity effector homolog (*Drosophila*) | 1.66051 |
| 1557770_at | IPO11 | importin 11 | 2.19277 |
| 241834_at | IPW | imprinted in Prader-Willi syndrome (non-protein coding) | 2.05282 |
| 229538_s_at | IQGAP3 | IQ motif containing GTPase activating protein 3 | 2.32378 |
| 1553949_at | IQSEC3 | IQ motif and Sec7 domain 3 | 1.82434 |
| 242694_at | IQSEC3 /// LOC100134209 /// LOC731035 | IQ motif and Sec7 domain 3 /// similar to IQ motif and Sec7 domain-containing pr | 2.81166 |
| 1568924_a_at | IQUB | IQ motif and ubiquitin domain containing | 2.23724 |
| 206104_at | ISL1 | ISL LIM homeobox 1 | 2.04554 |
| 242982_x_at | ITGB8 | integrin, beta 8 | 1.72645 |
| 1557080_s_at | ITGBL1 | integrin, beta-like 1 (with EGF-like repeat domains) | 1.58327 |
| 214927_at | ITGBL1 | integrin, beta-like 1 (with EGF-like repeat domains) | 2.53432 |
| 242788_at | JMJD2D | jumonji domain containing 2D | 1.7149 |
| 216763_at | KANK1 | KN motif and ankyrin repeat domains 1, mRNA (cDNA clone MGC: 43128 IMAGE: 5261060) | 1.90238 |
| 229125_at | KANK4 | KN motif and ankyrin repeat domains 4 | 2.24666 |
| 1555673_at | KAP2.1B /// KRTAP2-4 /// LOC644350 /// LOC728285 /// LOC728934 /// LOC730755 | keratin associated protein 2.1B /// keratin associated protein 2-4 /// hypotheti | 1.99107 |
| 208123_at | KCNB2 | potassium voltage-gated channel, Shab-related subfamily, member 2 | 2.26862 |
| 1555074_a_at | KCNH5 | potassium voltage-gated channel, subfamily H (eag-related), member 5 | 2.34582 |
| 240591_at | KCNIP4 | CDNA FLJ59677 complete cds, highly similar to Kv channel-interacting protein 4 | 1.77751 |
| 210179_at | KCNJ13 | potassium inwardly-rectifying channel, subfamily J, member 13 | 1.61478 |
| 219564_at | KCNJ16 | potassium inwardly-rectifying channel, subfamily J, member 16 | 2.4536 |
| 208404_x_at | KCNJ5 | potassium inwardly-rectifying channel, subfamily J, member 5 | 1.52838 |
| 244455_at | KCNT2 | potassium channel, subfamily T, member 2 | 1.96504 |
| 222664_at | KCTD15 | potassium channel tetramerisation domain containing 15 | −1.52793 |
| 222668_at | KCTD15 | potassium channel tetramerisation domain containing 15 | −1.53961 |
| 209781_s_at | KHDRBS3 | KH domain containing, RNA binding, signal transduction associated 3 | 1.64262 |
| 207161_at | KIAA0087 | KIAA0087 | 1.89736 |
| 227231_at | KIAA1211 | KIAA1211 protein | 1.60476 |
| 232762_at | KIAA1217 | KIAA1217 | 1.727 |
| 235956_at | KIAA1377 | KIAA1377 | 1.59988 |
| 233977_at | KIAA1772 | KIAA1772 | 1.50426 |
| 236518_at | KIAA1984 | KIAA1984 | −1.58518 |
| 244427_at | KIF23 | Mitotic kinesin-like protein-1 (MKLP-1 gene) | 2.12055 |
| 220652_at | KIF24 | kinesin family member 24 | 1.59148 |
| 234307_s_at | KIF26A | kinesin family member 26A | −1.73607 |
| 220657_at | KLHL11 | kelch-like 11 (*Drosophila*) | −1.60971 |
| 210634_at | KLHL20 | kelch-like 20 (*Drosophila*) | −1.58643 |
| 1553873_at | KLHL34 | kelch-like 34 (*Drosophila*) | 1.61075 |
| 211138_s_at | KMO | kynurenine 3-monooxygenase (kynurenine 3-hydroxylase) | −1.69994 |
| 205306_x_at | KMO | kynurenine 3-monooxygenase (kynurenine 3-hydroxylase) | −1.72294 |
| 243998_at | KRT222P | keratin 222 pseudogene | 1.64083 |
| 210662_at | KYNU | kynureninase (L-kynurenine hydrolase) | −2.0753 |
| 1552490_at | LACE1 | lactation elevated 1 | 1.753 |
| 215516_at | LAMB4 | laminin, beta 4 | 2.22608 |
| 229953_x_at | LCA5 | Leber congenital amaurosis 5 | 1.5775 |
| 213371_at | LDB3 | LIM domain binding 3 | 4.85498 |
| 207409_at | LECT2 | leukocyte cell-derived chemotaxin 2 | 3.74939 |
| 207092_at | LEP | leptin | 1.65443 |
| 236761_at | LHFPL3 | lipoma HMGIC fusion partner-like 3 | 1.57304 |
| 206140_at | LHX2 | LIM homeobox 2 | 3.42338 |
| 225571_at | LIFR | leukemia inhibitory factor receptor alpha | 2.72636 |
| 212328_at | LIMCH1 | LIM and calponin homology domains 1 | 1.8332 |
| 212327_at | LIMCH1 | LIM and calponin homology domains 1 | 2.30917 |
| 212325_at | LIMCH1 | LIM and calponin homology domains 1 | 1.61665 |
| 232457_at | LIMCH1 | LIM and calponin homology domains 1, mRNA (cDNA clone MGC: 16598 IMAGE: 4110496) | 1.61154 |
| 219823_at | LIN28 | lin-28 homolog (*C. elegans*) | 1.63702 |
| 229349_at | LIN28B | lin-28 homolog B (*C. elegans*) | 2.03446 |
| 241957_x_at | LIN7B | lin-7 homolog B (*C. elegans*) | −1.54121 |
| 219181_at | LIPG | lipase, endothelial | 1.55778 |
| 242178_at | LIPI | lipase, member I | 1.97767 |
| 216543_at | LOC100093698 | unknown transcript | 1.53623 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 217655_at | LOC100127972 | hypothetical LOC100127972 | −1.67943 |
| 224095_at | LOC100128175 | similar to PRO2591 | 1.71793 |
| 207478_at | LOC100128329 | similar to PRO2958 | 1.77096 |
| 229999_at | LOC100128416 | Full length insert cDNA clone ZE12A08 | −1.51964 |
| 215590_x_at | LOC100128640 | PREDICTED: *Homo sapiens* hypothetical protein LOC100128640 (LOC100128640), mRNA | 1.71347 |
| 240395_at | LOC100128727 | hypothetical LOC100128727 | 1.50691 |
| 244723_at | LOC100129488 | hypothetical protein LOC100129488 | 4.89676 |
| 244518_at | LOC100130452 | similar to hCG1777700 | 1.67252 |
| 1560425_s_at | LOC100130868 | hypothetical protein LOC100130868 | 1.784 |
| 215301_at | LOC100130958 | hypothetical protein LOC100130958 | 2.02489 |
| 1565814_at | LOC100131040 /// TRIM36 | hypothetical protein LOC100131040 /// tripartite motif-containing 36 | 1.71106 |
| 211341_at | LOC100131317 /// POU4F1 | similar to hCG1781072 /// POU class 4 homeobox 1 | 1.57041 |
| 237711_at | LOC100131980 /// ZNF705G | similar to zinc finger protein 705A /// zinc finger protein 705G-like | 1.78011 |
| 1561170_at | LOC100132025 | transmembrane domain-containing protein ENSP00000320207-like | 2.28603 |
| 236181_at | LOC100132181 | PREDICTED: *Homo sapiens* hypothetical protein LOC100132181 (LOC100132181), mRNA | 2.60614 |
| 243336_at | LOC100132726 | hypothetical protein LOC100132726 | −1.55162 |
| 1558640_a_at | LOC100132788 | MRNA (fetal brain cDNA e2_2g) | 3.6619 |
| 241821_at | LOC100132894 | hypothetical protein LOC100132894 | 3.24026 |
| 227631_at | LOC100133283 | PREDICTED: *Homo sapiens* hypothetical protein LOC100133283 (LOC100133283), mRNA | 1.58351 |
| 224110_at | LOC100133319 | PRO1804 | 1.87425 |
| 1562974_at | LOC100133899 | hypothetical protein LOC100133899 | 1.8921 |
| 1556704_s_at | LOC100133920 /// LOC286297 | hypothetical protein LOC100133920 /// hypothetical protein LOC286297 | 2.36676 |
| 1557617_at | LOC100189589 | hypothetical LOC100189589 | 2.06679 |
| 229994_at | LOC100190890 | MRNA; cDNA DKFZp686J23256 (from clone DKFZp686J23256) | 2.00185 |
| 234493_at | LOC116437 | hypothetical protein LOC116437 | 1.59059 |
| 242469_at | LOC120376 | Uncharacterized protein LOC120376 (LOC120376), mRNA | 1.77817 |
| 1555988_a_at | LOC126536 | hypothetical protein LOC126536 | 2.167 |
| 229178_at | LOC145786 | hypothetical protein LOC145786 | 1.58445 |
| 229073_at | LOC145786 | CDNA FLJ13221 fis, clone NT2RP4002075 | 3.33323 |
| 232450_at | LOC149351 | hypothetical protein LOC149351 | 1.85318 |
| 1561343_a_at | LOC150005 | hypothetical protein LOC150005 | 1.86593 |
| 239965_at | LOC151878 | hypothetical protein LOC151878 | 2.92204 |
| 215978_x_at | LOC152719 | hypothetical protein LOC152719 | 1.56227 |
| 239691_at | LOC196415 | hypothetical protein LOC196415 | 1.53729 |
| 232370_at | LOC254057 | hypothetical protein LOC254057 | 1.6305 |
| 1562501_at | LOC255177 | hypothetical protein LOC255177 | 1.66618 |
| 1562527_at | LOC283027 | hypothetical protein LOC283027 | 5.38799 |
| 1563854_s_at | LOC283045 | hypothetical protein LOC283045 | 1.50235 |
| 1558195_at | LOC283404 | hypothetical protein LOC283404 | 2.28078 |
| 1556425_a_at | LOC284219 | hypothetical protein LOC284219 | 2.26468 |
| 214162_at | LOC284244 | hypothetical protein LOC284244 | 3.07805 |
| 1563009_at | LOC284930 | *Homo sapiens*, clone IMAGE: 5538478, mRNA | 1.86884 |
| 1557267_s_at | LOC284952 | hypothetical protein LOC284952 | 1.61866 |
| 1557570_a_at | LOC285084 | hypothetical protein LOC285084 | 2.38931 |
| 1558601_at | LOC285194 | hypothetical LOC285194 | 1.54813 |
| 1556528_at | LOC285326 | hypothetical protein LOC285326 | 1.57263 |
| 1561096_at | LOC285419 | hypothetical protein LOC285419 | 1.77787 |
| 1557107_at | LOC286002 | hypothetical protein LOC286002 | 1.88346 |
| 1556573_s_at | LOC286178 | hypothetical protein LOC286178 | 1.76489 |
| 1556421_at | LOC286189 | hypothetical protein LOC286189 | 2.18301 |
| 240545_at | LOC286382 | hypothetical protein LOC286382 | 1.91794 |
| 1557717_at | LOC338862 | hypothetical protein LOC338862 | 3.97958 |
| 1557534_at | LOC339862 | hypothetical protein LOC339862 | 1.51746 |
| 1560823_at | LOC340017 | hypothetical protein LOC340017 | 2.06515 |
| 1563589_at | LOC340184 | hypothetical protein LOC340184 | 1.9 |
| 1557664_at | LOC340239 | PREDICTED: *Homo sapiens* hypothetical protein LOC340239, transcript variant 2 (LO | 1.67247 |
| 1559002_at | LOC340544 | hypothetical protein LOC340544 | −1.5369 |
| 235606_at | LOC344595 | hypothetical LOC344595 | 5.65601 |
| 1563022_at | LOC347475 | UPF0625 coiled-coil domain-containing protein ENSP00000359845 | 2.7715 |
| 1558423_at | LOC349114 | *Homo sapiens*, clone IMAGE: 4385460, mRNA | 1.6894 |
| 233879_at | LOC374491 | TPTE and PTEN homologous inositol lipid phosphatase pseudogene | 2.23513 |
| 1558982_at | LOC375010 | hypothetical LOC375010 | 2.62407 |
| 1558425_x_at | LOC388312 /// | hypothetical LOC388312 /// hypothetical LOC728417 /// | 1.50876 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
|  | LOC728417 /// LOC729737 /// LOC730235 | hypothetical LOC729737 /// |  |
| 1560773_at | LOC388458 | hypothetical gene supported by BC040718 | 1.99159 |
| 1560119_at | LOC389634 | hypothetical LOC389634 | 1.56826 |
| 226582_at | LOC400043 | hypothetical gene supported by BC009385 | 1.76427 |
| 1561414_at | LOC401497 | similar to PRO2738 | 2.43388 |
| 1561997_at | LOC440061 | PREDICTED: *Homo sapiens* misc_RNA (LOC440061), miscRNA | 1.61784 |
| 240268_at | LOC440117 | hypothetical gene supported by BC037858 | 1.82436 |
| 214984_at | LOC440345 | hypothetical protein LOC440345 | 4.24873 |
| 244766_at | LOC440354 /// LOC595101 /// LOC641298 /// LOC728423 /// LOC729513 /// SMG1 | PI-3-kinase-related kinase SMG-1 pseudogene /// PI-3-kinase-related kinase SMG-1 | 1.64874 |
| 216193_at | LOC440366 | hect domain and RLD 2 pseudogene | 1.81363 |
| 1562558_at | LOC440704 | hypothetical gene supported by BC042042 | 2.40362 |
| 224426_s_at | LOC440888 | ARP3 actin-related protein 3 homolog B pseudogene | 3.36427 |
| 224424_x_at | LOC440888 | ARP3 actin-related protein 3 homolog B pseudogene | 2.83853 |
| 224425_x_at | LOC440888 | ARP3 actin-related protein 3 homolog B pseudogene | 3.33132 |
| 229095_s_at | LOC440895 | LIM and senescent cell antigen-like domains 3-like | 2.24538 |
| 222207_x_at | LOC441258 | CDNA: FLJ20949 fis, clone ADSE01902 | 1.70745 |
| 220771_at | LOC51152 | melanoma antigen | 2.14963 |
| 220893_at | LOC57399 | uncharacterized gastric protein ZA52P | 1.76081 |
| 1559459_at | LOC613266 | hypothetical LOC613266 | -2.71264 |
| 1561098_at | LOC641365 | hypothetical protein LOC641365 | 1.59224 |
| 1562223_at | LOC642426 | hypothetical LOC642426 | 2.36874 |
| 1554996_at | LOC643955 /// ZNF479 /// ZNF727 | zinc finger protein 479 pseudogene /// zinc finger protein 479 /// zinc finger p | 3.79321 |
| 215625_at | LOC644450 | hypothetical protein LOC644450 | 1.56502 |
| 1566145_s_at | LOC644450 | hypothetical protein LOC644450 | 2.02346 |
| 227976_at | LOC644538 | hypothetical protein LOC644538 | 1.58277 |
| 230902_at | LOC645323 | CDNA clone IMAGE: 5260726 | 2.44976 |
| 238850_at | LOC645323 | hypothetical LOC645323 | 2.41121 |
| 1561760_s_at | LOC645513 | CDNA clone IMAGE: 5276804 | -1.54359 |
| 1564200_at | LOC646324 | hypothetical LOC646324 | 1.94425 |
| 1568933_at | LOC646627 | phospholipase inhibitor | 1.90895 |
| 215467_x_at | LOC647070 | hypothetical LOC647070 | 1.69676 |
| 1561492_at | LOC647107 | hypothetical protein LOC647107 | 4.0125 |
| 232696_at | LOC648556 | uncharacterized gastric protein ZA43P | 2.36077 |
| 217998_at | LOC652993 /// PHLDA1 | hypothetical LOC652993 /// pleckstrin homology-like domain, family A, member 1 | 1.57414 |
| 1557094_at | LOC653110 | hypothetical LOC653110 | 5.12803 |
| 243124_at | LOC653390 | RRN3 RNA polymerase I transcription factor homolog (*S. cerevisiae*) pseudogene | -1.5339 |
| 216469_at | LOC727867 /// LOC729501 /// LOC729863 /// ZNF834 | similar to PRED65 /// zinc finger protein ENSP00000344568-like /// similar to PR | 1.70529 |
| 1559322_at | LOC727916 | hypothetical protein LOC727916 | 1.58056 |
| 1564856_s_at | LOC727924 /// OR4N4 | hypothetical LOC727924 /// olfactory receptor, family 4, subfamily N, member 4 | 2.1379 |
| 1558828_s_at | LOC728264 | CDNA FLJ36638 fis, clone TRACH2018950 | 1.50367 |
| 231434_at | LOC728460 | similar to FLJ32921 protein | 2.51418 |
| 1559276_at | LOC728606 | hypothetical LOC728606 | 1.59845 |
| 234562_x_at | LOC728678 | PREDICTED: *Homo sapiens* misc_RNA (LOC728678), miscRNA | 2.04162 |
| 1566465_at | LOC728987 | MRNA; cDNA DKFZp686I1934 (from clone DKFZp686I1934) | 2.74786 |
| 214375_at | LOC729222 /// PPFIBP1 | similar to mKIAA1230 protein /// PTPRF interacting protein, binding protein 1 (1 | 3.23314 |
| 220167_s_at | LOC729355 /// TP53TG3 | similar to TP53TG3 protein /// TP53 target 3 | 2.68644 |
| 1563637_at | LOC729652 | hypothetical protein LOC729652 | 1.57589 |
| 237899_at | LOC729994 | hypothetical LOC729994 | -1.50022 |
| 233249_at | LOC730200 | PREDICTED: *Homo sapiens* hypothetical LOC730200 (LOC730200), mRNA | 3.67813 |
| 237312_at | LOC731477 | hypothetical protein LOC731477 | 1.62866 |
| 1570009_at | LOC732096 | similar to hCG2040240 | 4.14937 |
| 1563528_at | LOC91149 | hypothetical protein LOC91149 | 1.62561 |
| 1557523_at | LOC92270 | V-type proton ATPase subunit S1-like protein | 2.32742 |
| 234861_at | LOC93463 | hypothetical protein LOC93463 | 1.82869 |
| 220244_at | LOH3CR2A | loss of heterozygosity, 3, chromosomal region 2, gene A | 2.47424 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 235977_at | LONRF2 | LON peptidase N-terminal domain and ring finger 2 | 2.03367 |
| 206960_at | LPAR4 | lysophosphatidic acid receptor 4 | 4.08642 |
| 209866_s_at | LPHN3 | latrophilin 3 | 3.07024 |
| 230644_at | LRFN5 | leucine rich repeat and fibronectin type III domain containing 5 | 2.28648 |
| 230863_at | LRP2 | low density lipoprotein-related protein 2 | 2.0802 |
| 1562939_at | LRRC16A | leucine rich repeat containing 16A | 1.74525 |
| 216149_at | LRRC37B2 | leucine rich repeat containing 37, member B2 | 2.36761 |
| 232226_at | LRRC4C | leucine rich repeat containing 4C | 2.77481 |
| 1556427_s_at | LRRN4CL | LRRN4 C-terminal like | 1.55275 |
| 206144_at | MAGI1 | membrane associated guanylate kinase, WW and PDZ domain containing 1 | 1.70898 |
| 225465_at | MAGI1 | membrane associated guanylate kinase, WW and PDZ domain containing 1 | 1.58332 |
| 226084_at | MAP1B | microtubule-associated protein 1B | 2.91601 |
| 1562440_at | MAP3K13 | Leucine zipper bearing kinase | 1.84582 |
| 1565131_x_at | MAP3K2 | mitogen-activated protein kinase kinase kinase 2 | 1.69787 |
| 1552928_s_at | MAP3K7IP3 | mitogen-activated protein kinase kinase kinase 7 interacting protein 3 | −1.70651 |
| 235066_at | MAP4 | microtubule-associated protein 4 | 1.89346 |
| 235141_at | MARVELD2 | MARVEL domain containing 2 | 1.74329 |
| 233634_at | MARVELD3 | MARVEL domain containing 3 | 1.65824 |
| 205018_s_at | MBNL2 | muscleblind-like 2 (*Drosophila*) | −1.60512 |
| 1554604_at | MBTPS2 | membrane-bound transcription factor peptidase, site 2 | 1.51324 |
| 214884_at | MCF2 | DBL mRNA for DBL proto-oncogene splicing variant 1 | 1.97103 |
| 1559427_at | MCF2L | KIAA0362 gene | 1.55068 |
| 229797_at | MCOLN3 | mucolipin 3 | −2.39333 |
| 212732_at | MEG3 | maternally expressed 3 (non-protein coding) | 1.61766 |
| 235077_at | MEG3 | maternally expressed 3 (non-protein coding) | 2.45959 |
| 207480_s_at | MEIS2 | Meis homeobox 2 | 1.83267 |
| 214077_x_at | MEIS3P1 | Meis homeobox 3 pseudogene 1 | 1.90099 |
| 211424_x_at | METTL7A | methyltransferase like 7A | 2.40031 |
| 240814_at | MGC39584 | hypothetical gene supported by BC029568 | 1.77085 |
| 238481_at | MGP | matrix Gla protein | 1.57297 |
| 203637_s_at | MID1 | midline 1 (Opitz/BBB syndrome) | 2.07411 |
| 1552572_a_at | MIPOL1 | mirror-image polydactyly 1 | 1.96747 |
| 239468_at | MKX | mohawk homeobox | 2.02738 |
| 238257_at | MLLT10 | Zinc finger/leucine zipper protein (AF10) | 1.6337 |
| 1569998_at | MMD2 | monocyte to macrophage differentiation-associated 2 | 1.60681 |
| 207012_at | MMP16 | matrix metallopeptidase 16 (membrane-inserted) | 1.87224 |
| 208166_at | MMP16 | matrix metallopeptidase 16 (membrane-inserted) | 2.55402 |
| 204575_s_at | MMP19 | matrix metallopeptidase 19 | −1.70549 |
| 220541_at | MMP26 | matrix metallopeptidase 26 | 1.7046 |
| 221636_s_at | MOSC2 | MOCO sulphurase C-terminal domain containing 2 | −1.522 |
| 215692_s_at | MPPED2 | metallophosphoesterase domain containing 2 | 2.9265 |
| 205395_s_at | MRE11A | MRE11 meiotic recombination 11 homolog A (*S. cerevisiae*) | −1.60992 |
| 220790_s_at | MS4A5 | membrane-spanning 4-domains, subfamily A, member 5 | 1.51834 |
| 228473_at | MSX1 | CDNA FLJ75656 complete cds, highly similar to *Homo sapiens* msh homeo box homolog | 1.71357 |
| 205932_s_at | MSX1 | msh homeobox 1 | 2.16058 |
| 210319_x_at | MSX2 | msh homeobox 2 | 1.60287 |
| 242996_at | MTRF1 | mitochondrial translational release factor 1 | −1.77601 |
| 205675_at | MTTP | microsomal triglyceride transfer protein | 1.62218 |
| 227241_at | MUC15 | mucin 15, cell surface associated | 1.84206 |
| 216188_at | MYCNOS | v-myc myelocytomatosis viral related oncogene, neuroblastoma derived (avian) opp | 1.93694 |
| 1568926_x_at | MYLK3 | myosin light chain kinase 3 | 2.03024 |
| 1568925_at | MYLK3 | myosin light chain kinase 3 | 1.89636 |
| 1561503_at | MYLK4 | myosin light chain kinase family, member 4 | 1.51904 |
| 237510_at | MYNN | Myoneurin, mRNA (cDNA clone IMAGE: 4721583) | 2.07478 |
| 244350_at | MYO10 | myosin X | 2.7656 |
| 1554026_a_at | MYO10 | myosin X | 2.16462 |
| 1570141_at | MYO5B | myosin VB | 2.21328 |
| 211103_at | MYO7A | myosin VIIA | −1.64785 |
| 216660_at | MYO7B | myosin VIIB | 1.54433 |
| 1554507_at | NAALAD2 | N-acetylated alpha-linked acidic dipeptidase 2 | 1.87347 |
| 233815_at | NAALAD2 | N-acetylated alpha-linked acidic dipeptidase 2 | 1.93112 |
| 228608_at | NALCN | sodium leak channel, non-selective | 1.69469 |
| 242880_at | NALCN | sodium leak channel, non-selective | 1.75222 |
| 220184_at | NANOG | Nanog homeobox | 2.40254 |
| 242639_at | NARG2 | NMDA receptor regulated 2 | 1.98876 |
| 236141_at | NBLA00301 | Nbla00301 | 1.84851 |
| 237917_at | NBPF8 | neuroblastoma breakpoint family, member 8 | −1.8445 |
| 1563728_at | NCRNA00032 | non-protein coding RNA 32 | 1.54507 |
| 1559292_s_at | NCRNA00032 | Clone IMAGE: 2275835 C9orf14 mRNA, partial sequence; alternatively spliced | 2.20902 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 231491_at | NCRNA00113 | non-protein coding RNA 113 | 2.20943 |
| 1569882_at | NCRNA00119 | non-protein coding RNA 119 | 1.50636 |
| 220429_at | NDST3 | N-deacetylase/N-sulfotransferase (heparan glucosaminyl) 3 | 2.41867 |
| 229461_x_at | NEGR1 | neuronal growth regulator 1 | 1.53956 |
| 204641_at | NEK2 | NIMA (never in mitosis gene a)-related kinase 2 | 1.82542 |
| 206089_at | NELL1 | NEL-like 1 (chicken) | 1.9916 |
| 213438_at | NFASC | neurofascin homolog (chicken) | 1.51334 |
| 214799_at | NFASC | neurofascin homolog (chicken) | 1.74207 |
| 236471_at | NFE2L3 | nuclear factor (erythroid-derived 2)-like 3 | −1.94665 |
| 213033_s_at | NFIB | nuclear factor I/B | 1.58491 |
| 233304_at | NFIB | HMGIC/NFIB fusion protein (HMGIC/NFIB) | 1.71392 |
| 209289_at | NFIB | nuclear factor I/B | 2.33009 |
| 209290_s_at | NFIB | nuclear factor I/B | 3.26376 |
| 213032_at | NFIB | nuclear factor I/B | 3.91895 |
| 230291_s_at | NFIB | HMGIC/NFIB fusion protein (HMGIC/NFIB) | 2.58971 |
| 1555141_a_at | NHEDC1 | Na+/H+ exchanger domain containing 1 | 2.54405 |
| 1553633_s_at | NHEDC1 | Na+/H+ exchanger domain containing 1 | 2.24905 |
| 1564746_at | NHEDC2 | Na+/H+ exchanger domain containing 2 | 1.5816 |
| 215228_at | NHLH2 | nescient helix loop helix 2 | 1.86841 |
| 1554601_at | NKAIN2 | Na+/K+ transporting ATPase interacting 2 | 1.76903 |
| 211024_s_at | NKX2-1 | NK2 homeobox 1 | 1.7883 |
| 205893_at | NLGN1 | neuroligin 1 | 2.23077 |
| 221933_at | NLGN4X | neuroligin 4, X-linked | 1.7674 |
| 234762_x_at | NLN | CDNA FLJ39097 fis, clone NTONG2000977, highly similar to Neurolysin, mitochondri | 1.62853 |
| 1552712_a_at | NMNAT2 | nicotinamide nucleotide adenylyltransferase 2 | 1.52782 |
| 206045_s_at | NOL4 | nucleolar protein 4 | 2.539 |
| 1560974_s_at | NOS1 | nitric oxide synthase 1 (neuronal) | 1.5825 |
| 232158_x_at | NPAL1 | NIPA-like domain containing 1 | 1.9677 |
| 220128_s_at | NPAL2 | NIPA-like domain containing 2 | −1.5032 |
| 220316_at | NPAS3 | neuronal PAS domain protein 3 | 1.69165 |
| 229281_at | NPAS3 | neuronal PAS domain protein 3 | 1.8588 |
| 230412_at | NPAS3 | neuronal PAS domain protein 3 | 2.2537 |
| 211585_at | NPAT | nuclear protein, ataxia-telangiectasia locus | 1.94524 |
| 238844_s_at | NPHP1 | nephronophthisis 1 (juvenile) | 2.41213 |
| 225911_at | NPNT | nephronectin | 1.90656 |
| 219789_at | NPR3 | natriuretic peptide receptor C/guanylate cyclase C (atrionatriuretic peptide rec | 1.73795 |
| 207443_at | NR2E1 | nuclear receptor subfamily 2, group E, member 1 | 1.87607 |
| 209119_x_at | NR2F2 | nuclear receptor subfamily 2, group F, member 2 | 2.02969 |
| 215073_s_at | NR2F2 | nuclear receptor subfamily 2, group F, member 2 | 1.96135 |
| 209121_x_at | NR2F2 | nuclear receptor subfamily 2, group F, member 2 | 1.7412 |
| 208241_at | NRG1 | neuregulin 1 | 2.08161 |
| 208062_s_at | NRG2 | neuregulin 2 | 1.63978 |
| 206879_s_at | NRG2 | neuregulin 2 | 1.72088 |
| 232771_at | NRK | Nik related kinase | 1.88843 |
| 209914_s_at | NRXN1 | neurexin 1 | 1.67775 |
| 228547_at | NRXN1 | neurexin 1 | 1.66176 |
| 209915_s_at | NRXN1 | neurexin 1 | 1.53885 |
| 229649_at | NRXN3 | neurexin 3 | 2.45512 |
| 229463_at | NTRK2 | neurotrophic tyrosine kinase, receptor, type 2 | 1.50597 |
| 207152_at | NTRK2 | neurotrophic tyrosine kinase, receptor, type 2 | 2.00944 |
| 215311_at | NTRK3 | neurotrophic tyrosine kinase, receptor, type 3 | 1.65674 |
| 215025_at | NTRK3 | neurotrophic tyrosine kinase, receptor, type 3 | 1.75126 |
| 1562775_at | NUDT12 | nudix (nucleoside diphosphate linked moiety X)-type motif 12 | 2.25655 |
| 219347_at | NUDT15 | nudix (nucleoside diphosphate linked moiety X)-type motif 15 | −1.51719 |
| 239748_x_at | OCIAD1 | OCIA domain containing 1 | 1.50742 |
| 231867_at | ODZ2 | odz, odd Oz/ten-m homolog 2 (Drosophila) | 3.26427 |
| 1554524_a_at | OLFM3 | olfactomedin 3 | 1.97192 |
| 207093_s_at | OMG | oligodendrocyte myelin glycoprotein | −1.90409 |
| 239911_at | ONECUT2 | one cut homeobox 2 | 1.56079 |
| 214111_at | OPCML | opioid binding protein/cell adhesion molecule-like | 3.06809 |
| 1567657_at | OR2H1 | olfactory receptor, family 2, subfamily H, member 1 | 1.5335 |
| 1567656_at | OR2H1 | Olfactory receptor (6MI-16 gene), exon E variant 2 | 1.67337 |
| 1567246_at | OR5H1 | olfactory receptor, family 5, subfamily H, member 1 | 2.39135 |
| 1567247_at | OR5H1 | olfactory receptor, family 5, subfamily H, member 1 | 2.43277 |
| 243531_at | ORAOV1 | oral cancer overexpressed 1 | −1.53352 |
| 211213_at | ORC5L | origin recognition complex, subunit 5-like (yeast) | 1.73358 |
| 1553931_at | OSTCL | oligosaccharyltransferase complex subunit-like | 2.34808 |
| 1555251_a_at | OTOF | otoferlin | −1.90077 |
| 238994_at | OTUD7B | OTU domain containing 7B | 1.54049 |
| 206048_at | OVOL2 | ovo-like 2 (Drosophila) | 3.2046 |
| 238409_x_at | OXR1 | oxidation resistance 1 | 2.67129 |
| 243335_at | P4HA1 | prolyl 4-hydroxylase, alpha polypeptide I | 1.7653 |
| 220403_s_at | P53AIP1 | p53-regulated apoptosis-inducing protein 1 | 1.58587 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 220402_at | P53AIP1 | p53-regulated apoptosis-inducing protein 1 | 2.96255 |
| 242912_at | P704P | prostate-specific P704P | 3.72956 |
| 1560770_at | PABPC1 | Poly(A) binding protein, cytoplasmic 1, mRNA (cDNA clone MGC: 12727 IMAGE: 4123269 | 1.63652 |
| 238865_at | PABPC4L | poly(A) binding protein, cytoplasmic 4-like | 2.10195 |
| 214607_at | PAK3 | p21 protein (Cdc42/Rac)-activated kinase 3 | 2.88671 |
| 210721_s_at | PAK7 | p21 protein (Cdc42/Rac)-activated kinase 7 | 1.74992 |
| 228128_x_at | PAPPA | pregnancy-associated plasma protein A, pappalysin 1 | 2.13807 |
| 1559400_s_at | PAPPA | pregnancy-associated plasma protein A, pappalysin 1 | 1.93398 |
| 224940_s_at | PAPPA | pregnancy-associated plasma protein A, pappalysin 1 | 4.39116 |
| 205834_s_at | PART1 | prostate androgen-regulated transcript 1 | 1.8141 |
| 210292_s_at | PCDH11X /// PCDH11Y | protocadherin 11 X-linked /// protocadherin 11 Y-linked | 2.55484 |
| 205656_at | PCDH17 | protocadherin 17 | 1.50888 |
| 227289_at | PCDH17 | protocadherin 17 | 2.04806 |
| 225975_at | PCDH18 | protocadherin 18 | 2.30113 |
| 232054_at | PCDH20 | protocadherin 20 | 1.59426 |
| 210273_at | PCDH7 | protocadherin 7 | 1.72605 |
| 208205_at | PCDHA9 | protocadherin alpha 9 | 1.54772 |
| 232415_at | PCDHB13 | protocadherin beta 13 | 1.76909 |
| 231726_at | PCDHB14 | protocadherin beta 14 | 1.62133 |
| 232099_at | PCDHB16 | protocadherin beta 16 | 2.13788 |
| 223927_at | PCDHB9 | protocadherin beta 9 | 1.7009 |
| 234515_at | PCGEM1 | prostate-specific transcript 1 (non-protein coding) | 1.50251 |
| 210650_s_at | PCLO | piccolo (presynaptic cytomatrix protein) | 1.69469 |
| 242662_at | PCSK6 | PACE4A-II | 2.30596 |
| 233547_x_at | PDE1A | phosphodiesterase 1A, calmodulin-dependent | 1.80161 |
| 231213_at | PDE1A | phosphodiesterase 1A, calmodulin-dependent | 1.75945 |
| 233549_at | PDE1A | phosphodiesterase 1A, calmodulin-dependent | 1.69446 |
| 208396_s_at | PDE1A | phosphodiesterase 1A, calmodulin-dependent | 2.26838 |
| 215575_at | PDE4DIP | phosphodiesterase 4D interacting protein | 1.79302 |
| 231065_at | PDE6D | P17 protein | −1.55018 |
| 1554828_at | PDGFRA | platelet-derived growth factor receptor, alpha polypeptide | 1.53439 |
| 232288_at | PDXDC1 /// PDXDC2 | pyridoxal-dependent decarboxylase domain containing 1 /// pyridoxal-dependent de | 1.65294 |
| 238957_at | PDXDC2 | MRNA; cDNA DKFZp761H1120 (from clone DKFZp761H1120) | 2.03644 |
| 212092_at | PEG10 | paternally expressed 10 | 1.60907 |
| 230068_s_at | PEG3 | KIAA0287 gene | 1.82316 |
| 209243_s_at | PEG3 /// ZIM2 | paternally expressed 3 /// zinc finger, imprinted 2 | 2.16162 |
| 219642_s_at | PEX5L | peroxisomal biogenesis factor 5-like | 1.54143 |
| 222019_at | PFDN6 | prefoldin subunit 6 | −1.51654 |
| 240883_at | PFKFB1 | 6-phosphofructo-2-kinase/fructose-2,6-bisphosphatase (EC 2.7.1.105, EC 3.1.3.46) | 1.5229 |
| 244321_at | PGAP1 | post-GPI attachment to proteins 1 | 1.62493 |
| 215179_x_at | PGF | Placenta growth factor 2 (PIGF-2) | 1.53586 |
| 1554560_at | PGM5 | phosphoglucomutase 5 | 4.77525 |
| 1560431_at | PGM5P1 | phosphoglucomutase 5 pseudogene 1 | 1.50207 |
| 234405_s_at | PHAX | phosphorylated adaptor for RNA export | −1.66337 |
| 1556369_a_at | PHKG2 | phosphorylase kinase, gamma 2 (testis) | −1.66594 |
| 210919_at | PHLPP | PH domain and leucine rich repeat protein phosphatase | 2.708 |
| 217097_s_at | PHTF2 | putative homeodomain transcription factor 2 | 1.54839 |
| 237866_at | PID1 | phosphotyrosine interaction domain containing 1 | 1.52656 |
| 1558292_s_at | PIGW | phosphatidylinositol glycan anchor biosynthesis, class W | −1.79257 |
| 220041_at | PIGZ | phosphatidylinositol glycan anchor biosynthesis, class Z | −1.75754 |
| 215129_at | PIK3C2G | phosphoinositide-3-kinase, class 2, gamma polypeptide | 1.96389 |
| 214868_at | PIWIL1 | piwi-like 1 (Drosophila) | 2.16549 |
| 1563465_at | PKD1L1 | polycystic kidney disease 1 like 1 | 2.06488 |
| 203895_at | PLCB4 | phospholipase C, beta 4 | 1.68346 |
| 203896_s_at | PLCB4 | phospholipase C, beta 4 | 2.41741 |
| 240033_at | PLG | plasminogen | 1.56995 |
| 207374_at | PLSCR2 | phospholipid scramblase 2 | 1.56409 |
| 224421_x_at | PMCHL1 | pro-melanin-concentrating hormone-like 1 | 2.02666 |
| 224418_x_at | PMCHL1 | pro-melanin-concentrating hormone-like 1 | 1.90155 |
| 224419_x_at | PMCHL1 | pro-melanin-concentrating hormone-like 1 | 2.04898 |
| 224422_x_at | PMCHL2 | pro-melanin-concentrating hormone-like 2 | 1.91294 |
| 206826_at | PMP2 | peripheral myelin protein 2 | 2.22591 |
| 219926_at | POPDC3 | popeye domain containing 3 | 1.64053 |
| 1555778_a_at | POSTN | periostin, osteoblast specific factor | 1.55784 |
| 210809_s_at | POSTN | periostin, osteoblast specific factor | 1.68545 |
| 1569675_at | POU2AF1 | POU class 2 associating factor 1, mRNA (cDNA clone MGC: 45211 IMAGE: 5554134) | 2.48784 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 207109_at | POU2F3 | POU class 2 homeobox 3 | 1.72743 |
| 207084_at | POU3F2 | POU class 3 homeobox 2 | 1.51578 |
| 219195_at | PPARGC1A | peroxisome proliferator-activated receptor gamma, coactivator 1 alpha | 2.39587 |
| 232073_at | PPFIA2 | protein tyrosine phosphatase, receptor type, f polypeptide (PTPRF), interacting | 1.76444 |
| 204517_at | PPIC | peptidylprolyl isomerase C (cyclophilin C) | 2.51701 |
| 236142_at | PPIH | U-snRNP-associated cyclophilin (USA-CyP) | −1.72474 |
| 223999_at | PPIL2 | peptidylprolyl isomerase (cyclophilin)-like 2 | 1.50516 |
| 1555462_at | PPP1R1C | protein phosphatase 1, regulatory (inhibitor) subunit 1C | 2.33566 |
| 240187_at | PPP1R3C | protein phosphatase 1, regulatory (inhibitor) subunit 3C | 1.52454 |
| 202886_s_at | PPP2R1B | protein phosphatase 2 (formerly 2A), regulatory subunit A, beta isoform | −1.54317 |
| 220673_s_at | PPP4R4 | protein phosphatase 4, regulatory subunit 4 | 1.97256 |
| 230311_s_at | PRDM6 | PR domain containing 6 | 1.62777 |
| 238441_at | PRKAA2 | protein kinase, AMP-activated, alpha 2 catalytic subunit | 1.64369 |
| 227892_at | PRKAA2 | protein kinase, AMP-activated, alpha 2 catalytic subunit | 1.67124 |
| 1554910_at | PRKD3 | protein kinase D3 | −1.6967 |
| 220696_at | PRO0478 | PRO0478 protein | 2.36786 |
| 220883_at | PRO2012 | hypothetical protein PRO2012 | 1.781 |
| 208004_at | PROL1 | proline rich, lacrimal 1 | 2.63065 |
| 228656_at | PROX1 | prospero homeobox 1 | 1.83495 |
| 242119_at | PROX1 | Homeodomain protein (Prox 1) | 1.93805 |
| 229376_at | PROX1 | prospero homeobox 1 | 2.24415 |
| 1552455_at | PRUNE2 | prune homolog 2 (Drosophila) | 2.21968 |
| 210195_s_at | PSG1 | pregnancy specific beta-1-glycoprotein 1 | 2.30034 |
| 222796_at | PTCD1 | pentatricopeptide repeat domain 1 | 1.61999 |
| 209816_at | PTCH1 | patched homolog 1 (Drosophila) | 1.75809 |
| 1552848_a_at | PTCHD1 | patched domain containing 1 | 1.75618 |
| 228825_at | PTGR1 | prostaglandin reductase 1 | 2.7707 |
| 210355_at | PTHLH | parathyroid hormone-like hormone | 1.52732 |
| 1555324_at | PTK7 | PTK7 protein tyrosine kinase 7 | 2.09835 |
| 209465_x_at | PTN | pleiotrophin | 1.77916 |
| 211737_x_at | PTN | pleiotrophin | 1.62249 |
| 208011_at | PTPN22 | protein tyrosine phosphatase, non-receptor type 22 (lymphoid) | 1.55539 |
| 213362_at | PTPRD | protein tyrosine phosphatase, receptor type, D | 1.55396 |
| 214043_at | PTPRD | protein tyrosine phosphatase, receptor type, D | 4.76051 |
| 204944_at | PTPRG | protein tyrosine phosphatase, receptor type, G | 2.03281 |
| 235634_at | PURG | purine-rich element binding protein G | 2.04289 |
| 215517_at | PYGO1 | pygopus homolog 1 (Drosophila) | 1.83752 |
| 239570_at | RAB1A | GTP-binding protein (RAB1A) mRNA, 3' untranslated region | −1.61026 |
| 241977_s_at | RAB3C | RAB3C, member RAS oncogene family (RAB3C), mRNA | 1.93934 |
| 224200_s_at | RAD18 | RAD18 homolog (S. cerevisiae) | −1.56083 |
| 223417_at | RAD18 | RAD18 homolog (S. cerevisiae) | −1.61243 |
| 234662_at | RAD21L1 | RAD21-like 1 (S. pombe) | 2.08749 |
| 204146_at | RAD51AP1 | RAD51 associated protein 1 | −1.97583 |
| 206591_at | RAG1 | recombination activating gene 1 | 2.08266 |
| 242712_x_at | RANBP2 /// RGPD1 /// RGPD2 /// RGPD3 /// RGPD4 /// RGPD5 /// RGPD6 /// RGPD7 /// RGPD8 | RAN binding protein 2 /// RANBP2-like and GRIP domain containing 1 /// RANBP2-li | 1.6504 |
| 217201_at | RASAL2 | RAS protein activator like 2 | 1.84564 |
| 1557432_at | RASAL2 | RAS protein activator like 2 | 2.14711 |
| 217194_at | RASAL2 | RAS protein activator like 2 | 3.48961 |
| 1553986_at | RASEF | RAS and EF-hand domain containing | 1.63337 |
| 1553185_at | RASEF | RAS and EF-hand domain containing | 1.64601 |
| 1553186_x_at | RASEF | RAS and EF-hand domain containing | 1.848 |
| 235638_at | RASSF6 | Ras association (RalGDS/AF-6) domain family member 6 | 2.07978 |
| 225846_at | RBM35A | RNA binding motif protein 35A | 1.61178 |
| 219121_s_at | RBM35A | RNA binding motif protein 35A | 1.76238 |
| 242516_x_at | RBM46 | RNA binding motif protein 46 | 3.82539 |
| 1560322_at | RBMS3 | RNA binding motif, single stranded interacting protein | 1.60171 |
| 238447_at | RBMS3 | RNA binding motif, single stranded interacting protein | 4.85901 |
| 209487_at | RBPMS | RNA binding protein with multiple splicing | 2.17673 |
| 232359_at | RDH11 | Vesicle soluble NSF attachment protein receptor (VT11) | 1.86356 |
| 212398_at | RDX | radixin | 1.899 |
| 1561720_at | RECQL5 | RecQ protein-like 5 | 3.42158 |
| 205923_at | RELN | reelin | 1.58794 |
| 220276_at | RERGL | RERG/RAS-like | 1.7491 |
| 203225_s_at | RFK | riboflavin kinase | −1.66609 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 223673_at | RFX4 | regulatory factor X, 4 (influences HLA class II expression) | 2.13206 |
| 1556354_s_at | RGL3 | ral guanine nucleotide dissociation stimulator-like 3 | 1.56724 |
| 1568752_s_at | RGS13 | regulator of G-protein signaling 13 | 2.03693 |
| 209071_s_at | RGS5 | regulator of G-protein signaling 5 | 1.55719 |
| 237719_x_at | RGS7BP | regulator of G-protein signaling 7 binding protein | 2.97708 |
| 233409_at | RHBDL3 | rhomboid, veinlet-like 3 (*Drosophila*) | 1.6217 |
| 238906_s_at | RHOJ | ras homolog gene family, member J | 1.71684 |
| 1552922_at | RIMS1 | regulating synaptic membrane exocytosis 1 | 1.58145 |
| 235153_at | RNF183 | ring finger protein 183 | 1.59993 |
| 210931_at | RNF6 | ring finger protein (C3H2C3 type) 6 | 1.9021 |
| 226709_at | ROBO2 | roundabout, axon guidance receptor, homolog 2 (*Drosophila*) | 1.71534 |
| 226766_at | ROBO2 | roundabout, axon guidance receptor, homolog 2 (*Drosophila*) | 1.66383 |
| 240425_x_at | ROBO2 | Roundabout 2 (robo2) | 2.35616 |
| 242385_at | RORB | RAR-related orphan receptor B | 4.22051 |
| 1555990_at | RP1-127L4.6 | hypothetical protein LOC150297 | 2.08107 |
| 1556222_at | RP11-291L22.2 | similar to cell division cycle 10 | 1.74943 |
| 235700_at | RP13-36C9.6 | cancer/testis antigen CT45-5 | 1.55319 |
| 204666_s_at | RP5-1000E10.4 | suppressor of IKK epsilon | 1.58185 |
| 235294_at | RP5-1000E10.4 | suppressor of IKK epsilon | -1.58872 |
| 230661_at | RPESP | RPE-spondin (RPESP), mRNA | 1.54079 |
| 238375_at | RPL22 | Full open reading frame cDNA clone RZPDo834F116D for gene RPL22, ribosomal prote | 6.19279 |
| 238370_x_at | RPL22 | Full open reading frame cDNA clone RZPDo834F116D for gene RPL22, ribosomal prote | 5.65484 |
| 215249_at | RPL35A | ribosomal protein L35a | -1.53549 |
| 213459_at | RPL37A | ribosomal protein L37a | -1.577 |
| 220738_s_at | RPS6KA6 | ribosomal protein S6 kinase, 90 kDa, polypeptide 6 | 1.81745 |
| 228186_s_at | RSPO3 | R-spondin 3 homolog (*Xenopus laevis*) | 2.10349 |
| 1553277_at | RTTN | rotatin | 1.55066 |
| 215321_at | RUNDC3B | RUN domain containing 3B | 2.53893 |
| 205528_s_at | RUNX1T1 | runt-related transcription factor 1; translocated to, 1 (cyclin D-related) | 2.02137 |
| 205529_s_at | RUNX1T1 | runt-related transcription factor 1; translocated to, 1 (cyclin D-related) | 3.23118 |
| 239150_at | S100A1L | Protein S100-A1-like | 1.67335 |
| 229273_at | SALL1 | sal-like 1 (*Drosophila*) | 2.31825 |
| 1553411_s_at | SALL3 | sal-like 3 (*Drosophila*) | 1.64155 |
| 232847_at | SALL3 | sal-like 3 (*Drosophila*) | 2.0568 |
| 1569443_at | SAMD5 | sterile alpha motif domain containing 5 | 1.50746 |
| 228653_at | SAMD5 | sterile alpha motif domain containing 5 | 1.52142 |
| 1559882_at | SAMHD1 | Full length insert cDNA clone YP80A10 | 1.63358 |
| 1569599_at | SAMSN1 | SAMSN1 variant b (SAMSN1) mRNA, complete cds; alternatively spliced | 1.67178 |
| 211423_s_at | SC5DL | sterol-C5-desaturase (ERG3 delta-5-desaturase homolog, S. cerevisiae)-like | -1.78404 |
| 206667_s_at | SCAMP1 | secretory carrier membrane protein 1 | 3.99037 |
| 206021_at | SCAND2 | SCAN domain containing 2 pseudogene | 1.76903 |
| 220232_at | SCD5 | stearoyl-CoA desaturase 5 | 2.02692 |
| 1554921_a_at | SCEL | sciellin | 1.64729 |
| 206884_s_at | SCEL | sciellin | 1.98342 |
| 59705_at | SCLY | selenocysteine lyase | -1.63837 |
| 210853_at | SCN11A | sodium channel, voltage-gated, type XI, alpha subunit | 2.60254 |
| 1555246_a_at | SCN1A | sodium channel, voltage-gated, type I, alpha subunit | 2.29049 |
| 210383_at | SCN1A | sodium channel, voltage-gated, type I, alpha subunit | 3.19642 |
| 229057_at | SCN2A | sodium channel, voltage-gated, type II, alpha subunit | 1.98264 |
| 212157_at | SDC2 | syndecan 2 | 1.50872 |
| 229522_at | SDR42E1 | short chain dehydrogenase/reductase family 42E, member 1 | -1.52939 |
| 206941_x_at | SEMA3E | sema domain, immunoglobulin domain (Ig), short basic domain, secreted, (semaphor | 2.31714 |
| 226492_at | SEMA6D | sema domain, transmembrane domain (TM), and cytoplasmic domain, (semaphorin) 6D | 1.52645 |
| 239889_at | SERP2 | Stress-associated endoplasmic reticulum protein family member 2, mRNA (cDNA clon | 1.64374 |
| 211361_s_at | SERPINB13 | serpin peptidase inhibitor, clade B (ovalbumin), member 13 | 1.54593 |
| 217272_s_at | SERPINB13 | serpin peptidase inhibitor, clade B (ovalbumin), member 13 | 2.91352 |
| 240709_at | SEZ6L | seizure related 6 homolog (mouse)-like | 1.86136 |
| 233753_at | SFRS15 | splicing factor, arginine/serine-rich 15 | -1.58165 |
| 237485_at | SFRS3 | Pre-mRNA splicing factor SRp20, 5′UTR region | 1.63657 |
| 230730_at | SGCD | sarcoglycan, delta (35 kDa dystrophin-associated glycoprotein) | 1.56939 |
| 228602_at | SGCD | sarcoglycan, delta (35 kDa dystrophin-associated glycoprotein) | 2.64714 |
| 231938_at | SGOL1 | Shugoshin-like 1 (S. pombe), mRNA (cDNA clone IMAGE: 3861301) | 1.93941 |
| 225162_at | SH3D19 | SH3 domain containing 19 | 1.6843 |
| 211565_at | SH3GL3 | SH3-domain GRB2-like 3 | 6.2489 |
| 213307_at | SHANK2 | SH3 and multiple ankyrin repeat domains 2 | 2.22882 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 235238_at | SHC4 | SHC (Src homology 2 domain containing) family, member 4 | 2.48968 |
| 207570_at | SHOX | short stature homeobox | 3.56283 |
| 208443_x_at | SHOX2 | short stature homeobox 2 | 1.65982 |
| 210135_s_at | SHOX2 | short stature homeobox 2 | 4.81277 |
| 1554354_at | SIAE | sialic acid acetylesterase | 1.6335 |
| 215856_at | SIGLEC15 | sialic acid binding Ig-like lectin 15 | 1.59259 |
| 228347_at | SIX1 | SIX homeobox 1 | 1.60659 |
| 206634_at | SIX3 | SIX homeobox 3 | 2.19671 |
| 206675_s_at | SKIL | SKI-like oncogene | −1.59872 |
| 237106_at | SLC11A2 | NRAMP2 | 1.57374 |
| 220502_s_at | SLC13A1 | solute carrier family 13 (sodium/sulfate symporters), member 1 | 2.41997 |
| 211349_at | SLC15A1 | solute carrier family 15 (oligopeptide transporter), member 1 | 1.63562 |
| 205317_s_at | SLC15A2 | solute carrier family 15 (H+/peptide transporter), member 2 | −1.94245 |
| 205234_at | SLC16A4 | solute carrier family 16, member 4 (monocarboxylic acid transporter 5) | −1.66979 |
| 220551_at | SLC17A6 | solute carrier family 17 (sodium-dependent inorganic phosphate cotransporter), m | 2.40381 |
| 232232_s_at | SLC22A16 | solute carrier family 22 (organic cation/carnitine transporter), member 16 | −2.99841 |
| 234561_at | SLC2A13 | solute carrier family 2 (facilitated glucose transporter), member 13 | 1.52225 |
| 239596_at | SLC30A7 | solute carrier family 30 (zinc transporter), member 7 | 1.91435 |
| 220796_x_at | SLC35E1 | solute carrier family 35, member E1 | 1.67755 |
| 228060_at | SLC35F1 | solute carrier family 35, member F1 | 2.29249 |
| 220786_s_at | SLC38A4 | solute carrier family 38, member 4 | 1.67855 |
| 1553126_a_at | SLC39A12 | solute carrier family 39 (zinc transporter), member 12 | 1.66587 |
| 228945_s_at | SLC39A8 | MRNA, 3'UTR, up-regulated by BCG-CWS | 1.67744 |
| 210739_x_at | SLC4A4 | solute carrier family 4, sodium bicarbonate cotransporter, member 4 | 1.6053 |
| 211494_s_at | SLC4A4 | solute carrier family 4, sodium bicarbonate cotransporter, member 4 | 2.49002 |
| 231424_at | SLC5A12 | solute carrier family 5 (sodium/glucose cotransporter), member 12 | 3.26263 |
| 1554724_at | SLC6A11 | solute carrier family 6 (neurotransmitter transporter, GABA), member 11 | 1.51255 |
| 1556641_at | SLC7A14 | solute carrier family 7 (cationic amino acid transporter, y+ system), member 14 | 1.50049 |
| 216604_s_at | SLC7A8 | solute carrier family 7 (cationic amino acid transporter, y+ system), member 8 | 1.76482 |
| 1552745_at | SLCO6A1 | solute carrier organic anion transporter family, member 6A1 | 1.63132 |
| 236734_at | SLITRK1 | SLIT and NTRK-like family, member 1 | 1.73464 |
| 232481_s_at | SLITRK6 | SLIT and NTRK-like family, member 6 | 1.9486 |
| 215599_at | SMA4 | glucuronidase, beta pseudogene | 1.96895 |
| 207441_at | SMR3B | submaxillary gland androgen regulated protein 3B | 1.78909 |
| 1556629_a_at | SNAP25 | HUMSNAP25B(F) | 2.68011 |
| 219511_s_at | SNCAIP | synuclein, alpha interacting protein | 1.66212 |
| 237834_at | SNCAIP | synuclein, alpha interacting protein | 1.86709 |
| 232547_at | SNIP | SNAP25-interacting protein | 3.23498 |
| 202691_at | SNRPD1 | small nuclear ribonucleoprotein D1 polypeptide 16 kDa | −1.70602 |
| 216850_at | SNRPN | small nuclear ribonucleoprotein polypeptide N | 1.74192 |
| 1559545_at | SNRPN | small nuclear ribonucleoprotein polypeptide N | 2.24102 |
| 240204_at | SNRPN | small nuclear ribonucleoprotein polypeptide N | 2.35762 |
| 220487_at | SNTG2 | syntrophin, gamma 2 | −1.61256 |
| 218705_s_at | SNX24 | sorting nexin 24 | −1.55845 |
| 239739_at | SNX24 | sorting nexin 24 | 1.99704 |
| 241987_x_at | SNX31 | sorting nexin 31 | 3.63912 |
| 223666_at | SNX5 | sorting nexin 5 | −1.61478 |
| 1563906_at | SOBP | sine oculis binding protein homolog (Drosophila) | 1.59114 |
| 209648_x_at | SOCS5 | suppressor of cytokine signaling 5 | −1.52633 |
| 1558815_at | SORBS2 | sorbin and SH3 domain containing 2 | 2.73073 |
| 204914_s_at | SOX11 | SRY (sex determining region Y)-box 11 | 2.70367 |
| 204913_s_at | SOX11 | SRY (sex determining region Y)-box 11 | 4.13442 |
| 223865_at | SOX6 | SRY (sex determining region Y)-box 6 | 1.87491 |
| 1570486_at | SOX6 | SRY (sex determining region Y)-box 6 | 1.85225 |
| 202936_s_at | SOX9 | SRY (sex determining region Y)-box 9 | 1.53496 |
| 202935_s_at | SOX9 | SRY (sex determining region Y)-box 9 | 3.35729 |
| 231178_at | SPATA4 | spermatogenesis associated 4 | 1.61457 |
| 209891_at | SPC25 | SPC25, NDC80 kinetochore complex component, homolog (S. cerevisiae) | 1.75386 |
| 206318_at | SPINLW1 | serine peptidase inhibitor-like, with Kunitz and WAP domains 1 (eppin) | 1.7884 |
| 235342_at | SPOCK3 | sparc/osteonectin, cwcv and kazal-like domains proteoglycan (testican) 3 | 2.41614 |
| 220456_at | SPTLC3 | serine palmitoyltransferase, long chain base subunit 3 | 2.15437 |
| 241961_at | SRD5A2L2 | steroid 5 alpha-reductase 2-like 2 | 3.63908 |
| 241734_at | SRFBP1 | serum response factor binding protein 1 | −1.55343 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 1554473_at | SRGAP1 | SLIT-ROBO Rho GTPase activating protein 1 | 2.85701 |
| 228628_at | SRGAP2P1 | SLIT-ROBO Rho GTPase activating protein 2 pseudogene 1 | 2.17844 |
| 214597_at | SSTR2 | somatostatin receptor 2 | 1.79921 |
| 215885_at | SSX2 | synovial sarcoma, X breakpoint 2 | 1.80412 |
| 208586_s_at | SSX4 /// SSX4B | synovial sarcoma, X breakpoint 4 /// synovial sarcoma, X breakpoint 4B | 1.7382 |
| 206835_at | STATH | statherin | 1.86909 |
| 204595_s_at | STC1 | stanniocalcin 1 | 1.67438 |
| 204597_x_at | STC1 | stanniocalcin 1 | 3.94696 |
| 202695_s_at | STK17A | serine/threonine kinase 17a | −1.53066 |
| 223883_s_at | STK31 | serine/threonine kinase 31 | 1.59045 |
| 231969_at | STOX2 | storkhead box 2 | 3.87778 |
| 223245_at | STRBP | spermatid perinuclear RNA binding protein | −1.59889 |
| 235180_at | STYX | serine/threonine/tyrosine interacting protein | −1.63483 |
| 212354_at | SULF1 | sulfatase 1 | 1.9771 |
| 222940_at | SULT1E1 | sulfotransferase family 1E, estrogen-preferring, member 1 | 1.76639 |
| 213247_at | SVEP1 | sushi, von Willebrand factor type A, EGF and pentraxin domain containing 1 | 1.77875 |
| 1553129_at | SVEP1 | sushi, von Willebrand factor type A, EGF and pentraxin domain containing 1 | 1.98786 |
| 216917_s_at | SYCP1 | synaptonemal complex protein 1 | 2.71601 |
| 206740_x_at | SYCP1 | synaptonemal complex protein 1 | 2.55636 |
| 215350_at | SYNE1 | spectrin repeat containing, nuclear envelope 1 | 1.84406 |
| 202796_at | SYNPO | synaptopodin | −1.54553 |
| 225720_at | SYNPO2 | synaptopodin 2 | 2.47627 |
| 229053_at | SYT17 | CDNA FLJ56448 complete cds, highly similar to Homo sapiens synaptotagmin XVII (S | −2.12139 |
| 202287_s_at | TACSTD2 | tumor-associated calcium signal transducer 2 | 2.08528 |
| 242318_at | TAPT1 | Transmembrane anterior posterior transformation 1 (TAPT1), mRNA | 1.65116 |
| 214413_at | TAT | Tyrosine aminotransferase | 1.56842 |
| 221858_at | TBC1D12 | TBC1 domain family, member 12 | −1.89833 |
| 1563272_at | TBC1D8B | TBC1 domain family, member 8B (with GRAM domain) | 1.60724 |
| 233633_at | TBL1XR1 | Transducin (beta)-like 1X-linked receptor 1, mRNA (cDNA clone IMAGE: 4754868) | 2.06728 |
| 225544_at | TBX3 | T-box 3 | 2.58503 |
| 240715_at | TBX5 | T-box 5 | 3.04595 |
| 1561254_at | tcag7.1188 | hypothetical LOC340340 | 1.89091 |
| 1562664_at | tcag7.929 | hypothetical protein LOC286009 | 1.65909 |
| 202823_at | TCEB1 | transcription elongation factor B (SIII), polypeptide 1 (15 kDa, elongin C) | −1.5985 |
| 206286_s_at | TDGF1 /// TDGF3 | teratocarcinoma-derived growth factor 1 /// teratocarcinoma-derived growth facto | 1.64616 |
| 214600_at | TEAD1 | TEA domain family member 1 (SV40 transcriptional enhancer factor) | 1.68001 |
| 204653_at | TFAP2A | transcription factor AP-2 beta (activating enhancer binding protein 2 alpha) | 1.80715 |
| 214451_at | TFAP2B | transcription factor AP-2 beta (activating enhancer binding protein 2 beta) | 2.80351 |
| 233987_at | TFAP2D | transcription factor AP-2 delta (activating enhancer binding protein 2 delta) | 1.66515 |
| 1566931_at | TFB2M | Transcription factor B2, mitochondrial, mRNA (cDNA clone IMAGE: 5311413) | 1.53869 |
| 1566932_x_at | TFB2M | Transcription factor B2, mitochondrial, mRNA (cDNA clone IMAGE: 5311413) | 1.53363 |
| 215447_at | TFPI | Tissue factor pathway inhibitor (lipoprotein-associated coagulation inhibitor), | 4.00815 |
| 228121_at | TGFB2 | transforming growth factor, beta 2 | 2.06407 |
| 235653_s_at | THAP6 | THAP domain containing 6 | −1.78358 |
| 203083_at | THBS2 | thrombospondin 2 | 1.79394 |
| 204776_at | THBS4 | thrombospondin 4 | −1.51372 |
| 219044_at | THNSL2 | threonine synthase-like 2 (S. cerevisiae) | −1.81461 |
| 222835_at | THSD4 | thrombospondin, type I, domain containing 4 | 4.52581 |
| 230008_at | THSD7A | thrombospondin, type I, domain containing 7A | 1.71666 |
| 214920_at | THSD7A | thrombospondin, type I, domain containing 7A | 1.86908 |
| 210800_at | TIMM8A | translocase of inner mitochondrial membrane 8 homolog A (yeast) | 3.55929 |
| 202011_at | TJP1 | tight junction protein 1 (zona occludens 1) | 2.15499 |
| 1555071_at | TLL1 | tolloid-like 1 | 1.86768 |
| 215008_at | TLL2 | tolloid-like 2 | 3.33235 |
| 230061_at | TM4SF18 | MRNA; cDNA DKFZp313N1532 (from clone DKFZp313N1532) | 1.61636 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 220639_at | TM4SF20 | transmembrane 4 L six family member 20 | 1.53906 |
| 228610_at | TM9SF3 | CDNA FLJ90343 fis, clone NT2RP2002824, highly similar to Transmembrane 9 superfa | 1.79254 |
| 1564591_a_at | TMC1 | transmembrane channel-like 1 | 1.87321 |
| 1553636_at | TMCO5A | transmembrane and coiled-coil domains 5A | 1.91589 |
| 1554866_at | TMEM135 | transmembrane protein 135 | 1.70254 |
| 238497_at | TMEM136 | transmembrane protein 136 | 1.66054 |
| 239593_at | TMEM213 | transmembrane protein 213 | 1.53796 |
| 209655_s_at | TMEM47 | transmembrane protein 47 | 1.52814 |
| 204807_at | TMEM5 | transmembrane protein 5 | −1.53392 |
| 1569377_at | TMEM67 | transmembrane protein 67 | 2.34523 |
| 1563646_a_at | TMEM67 | transmembrane protein 67 | 2.05536 |
| 226483_at | TMEM68 | transmembrane protein 68 | −1.58264 |
| 213024_at | TMF1 | TATA element modulatory factor 1 | −1.513 |
| 220431_at | TMPRSS11E /// TMPRSS11E2 | transmembrane protease, serine 11E /// transmembrane protease, serine 11E2 | 1.56517 |
| 1555707_at | TNAP | TRAFs and NIK-associated protein | 2.65475 |
| 216005_at | TNC | Tenascin | 2.11502 |
| 216042_at | TNFRSF25 | tumor necrosis factor receptor superfamily, member 25 | −1.54437 |
| 1557278_s_at | TNPO1 | Transportin 1, mRNA (cDNA clone MGC: 17116 IMAGE: 4178989) | 1.686 |
| 232750_at | TNS1 | Tensin 1, mRNA (cDNA clone IMAGE: 4546443) | 2.98094 |
| 237469_at | TOP2A | Topoisomerase (DNA) II alpha 170 kDa, mRNA (cDNA clone IMAGE: 4101949) | 1.75261 |
| 220205_at | TPTE | transmembrane phosphatase with tensin homology | 2.99568 |
| 1556876_s_at | TPTEps1 | TPTE pseudogene 1 | 3.4786 |
| 244334_at | TRAM1L1 | translocation associated membrane protein 1-like 1 | 1.80692 |
| 1552791_a_at | TRDN | triadin | 1.71337 |
| 222754_at | TRNT1 | tRNA nucleotidyl transferase, CCA-adding, 1 | −1.57097 |
| 210814_at | TRPC3 | transient receptor potential cation channel, subfamily C, member 3 | 2.29944 |
| 234407_s_at | TRPC7 | transient receptor potential cation channel, subfamily C, member 7 | 2.14569 |
| 206479_at | TRPM1 | transient receptor potential cation channel, subfamily M, member 1 | 1.86699 |
| 240386_at | TRPM1 | *Homo sapiens*, clone IMAGE: 4332660, mRNA | 1.91651 |
| 216452_at | TRPM3 | transient receptor potential cation channel, subfamily M, member 3 | 1.64176 |
| 233022_at | TRPM3 | transient receptor potential cation channel, subfamily M, member 3 | 2.69873 |
| 203824_at | TSPAN8 | tetraspanin 8 | 1.91188 |
| 215146_s_at | TTC28 | tetratricopeptide repeat domain 28 | 1.58487 |
| 1556666_a_at | TTC6 | tetratricopeptide repeat domain 6 | 3.47481 |
| 240369_at | TTC7A | Tetratricopeptide repeat domain 7A, mRNA (cDNA clone IMAGE: 5113102) | −1.55993 |
| 242771_at | TTN | Titin | −1.82217 |
| 210614_at | TTPA | tocopherol (alpha) transfer protein | 1.58646 |
| 230891_at | TUBE1 | Tubulin, epsilon 1, mRNA (cDNA clone MGC: 33949 IMAGE: 5298159) | 2.16675 |
| 239742_at | TULP4 | Full length insert cDNA clone YU79H10 | 1.85499 |
| 213943_at | TWIST1 | twist homolog 1 (*Drosophila*) | 4.94261 |
| 220869_at | UBA6 | ubiquitin-like modifier activating enzyme 6 | 1.7396 |
| 1569262_x_at | UBE2CBP | ubiquitin-conjugating enzyme E2C binding protein | 2.10912 |
| 233327_at | UBE2CBP | ubiquitin-conjugating enzyme E2C binding protein | 2.67633 |
| 234163_at | UBE3A | E6-AP isoform-III | 2.16744 |
| 234166_at | UBE3A | E6-AP isoform-III | 1.65174 |
| 1555834_at | UCHL1 | Protein gene product (PGP) 9.5 | 1.73702 |
| 221304_at | UGT1A10 /// UGT1A6 /// UGT1A7 /// UGT1A8 | UDP glucuronosyltransferase 1 family, polypeptide A10 /// UDP glucuronosyltransf | 2.06331 |
| 221305_s_at | UGT1A6 /// UGT1A8 /// UGT1A9 | UDP glucuronosyltransferase 1 family, polypeptide A6 /// UDP glucuronosyltransfe | 2.18416 |
| 211682_x_at | UGT2B28 | UDP glucuronosyltransferase 2 family, polypeptide B28 | 2.56318 |
| 226899_at | UNC5B | unc-5 homolog B (*C. elegans*) | 2.95198 |
| 214640_at | UNC93A | unc-93 homolog A (*C. elegans*) | 1.66307 |
| 214382_at | UNC93A | unc-93 homolog A (*C. elegans*) | 1.71701 |
| 1560320_a_at | UNQ2963 | hypothetical protein LOC283314 | −1.53983 |
| 221173_at | USH1C | Usher syndrome 1C (autosomal recessive, severe) | 1.52879 |
| 207706_at | USH2A | Usher syndrome 2A (autosomal recessive, mild) | 1.87956 |
| 232621_at | USP48 | ubiquitin specific peptidase 48 | 1.77813 |
| 1555065_x_at | USP6 | ubiquitin specific peptidase 6 (Tre-2 oncogene) | 1.77628 |
| 227399_at | VGLL3 | vestigial like 3 (*Drosophila*) | 1.72088 |
| 220327_at | VGLL3 | vestigial like 3 (*Drosophila*) | 1.88289 |
| 203844_at | VHL | von Hippel-Lindau tumor suppressor | 1.64109 |
| 203106_s_at | VPS41 | vacuolar protein sorting 41 homolog (*S. cerevisiae*) | −1.70572 |
| 1561200_at | VWA3B | von Willebrand factor A domain containing 3B | 1.90857 |
| 1552430_at | WDR17 | WD repeat domain 17 | 2.05322 |
| 219538_at | WDR5B | WD repeat domain 5B | −1.61334 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 242162_at | WDR69 | WD repeat domain 69 | 1.51724 |
| 220769_s_at | WDR78 | WD repeat domain 78 | 2.25954 |
| 206954_at | WIT1 | Wilms tumor upstream neighbor 1 | 2.72357 |
| 213425_at | WNT5A | wingless-type MMTV integration site family, member 5A | 1.52031 |
| 205990_s_at | WNT5A | wingless-type MMTV integration site family, member 5A | 2.06024 |
| 206067_s_at | WT1 | Wilms tumor 1 | 1.72928 |
| 237656_at | WWC2 | CDNA FLJ51450 complete cds, highly similar to Claudin-22 | 1.97362 |
| 207598_x_at | XRCC2 | X-ray repair complementing defective repair in Chinese hamster cells 2 | 1.69611 |
| 214776_x_at | XYLB | xyluolkinase homolog (*H. influenzae*) | 1.87664 |
| 1569683_at | XYLB | xyluolkinase homolog (*H. influenzae*) | 1.60808 |
| 224895_at | YAP1 | Yes-associated protein 1, 65 kDa | 2.12127 |
| 206169_x_at | ZC3H7B | zinc finger CCCH-type containing 7B | 1.55615 |
| 216844_at | ZC3H7B | zinc finger CCCH-type containing 7B | 2.3575 |
| 1553781_at | ZC3HAV1L | zinc finger CCCH-type, antiviral 1-like | 2.0001 |
| 219917_at | ZCCHC4 | zinc finger, CCHC domain containing 4 | −1.52373 |
| 231946_at | ZFHX2 | zinc finger homeobox 2 | 1.53322 |
| 241700_at | ZFHX4 | zinc finger homeobox 4 | 1.74443 |
| 222237_s_at | ZFP112 | zinc finger protein 112 homolog (mouse) | −1.55145 |
| 211773_s_at | ZKSCAN3 | zinc finger with KRAB and SCAN domains 3 | −1.52752 |
| 1552947_x_at | ZNF114 | zinc finger protein 114 | 1.90546 |
| 1552946_at | ZNF114 | zinc finger protein 114 | 2.52625 |
| 207402_at | ZNF132 | zinc finger protein 132 | −1.58945 |
| 1558184_s_at | ZNF17 | zinc finger protein 17 | −1.56615 |
| 1568644_at | ZNF208 | zinc finger protein 208 | 2.29695 |
| 1568646_x_at | ZNF208 | zinc finger protein 208 | 3.20902 |
| 243456_at | ZNF214 | zinc finger protein 214 | 1.83302 |
| 1557322_at | ZNF230 | zinc finger protein 230 | −1.76902 |
| 1559449_a_at | ZNF254 | CDNA FLJ58216 complete cds, highly similar to Zinc finger protein 539 | −2.34406 |
| 215048_at | ZNF280B | zinc finger protein 280B | 1.52294 |
| 236328_at | ZNF285A | zinc finger protein 285A | −1.73084 |
| 216710_x_at | ZNF287 | zinc finger protein 287 | 1.92695 |
| 227680_at | ZNF326 | zinc finger protein 326 | −1.60787 |
| 224276_at | ZNF33A | zinc finger protein 33A | 1.76911 |
| 1562743_at | ZNF33B | Zinc finger protein 33B (ZNF33B), mRNA | 1.50959 |
| 233169_at | ZNF350 | zinc finger protein 350 | −1.54751 |
| 214761_at | ZNF423 | zinc finger protein 423 | 1.68652 |
| 219848_s_at | ZNF432 | zinc finger protein 432 | −1.52766 |
| 205928_at | ZNF443 | zinc finger protein 443 | −1.58322 |
| 226575_at | ZNF462 | zinc finger protein 462 | 2.79327 |
| 244007_at | ZNF462 | zinc finger protein 462 | 2.05007 |
| 1555368_x_at | ZNF479 | zinc finger protein 479 | 3.58093 |
| 1555367_at | ZNF479 | zinc finger protein 479 | 3.75576 |
| 1559988_at | ZNF483 | zinc finger protein 483 | 2.28434 |
| 1557616_at | ZNF496 | zinc finger protein 496 | −1.53565 |
| 226676_at | ZNF521 | zinc finger protein 521 | 2.55441 |
| 226592_at | ZNF618 | zinc finger protein 618 | 1.51197 |
| 232272_at | ZNF624 | zinc finger protein 624 | −1.60359 |
| 1553247_a_at | ZNF709 | zinc finger protein 709 | −1.6001 |
| 1560201_at | ZNF713 | zinc finger protein 713 | 1.5002 |
| 1553885_x_at | ZNF99 | zinc finger protein 99 | 1.66616 |
| 228330_at | ZUFSP | zinc finger with UFM1-specific peptidase domain | −1.55835 |
| 1564685_a_at | — | — | 1.83044 |
| 1566896_at | — | — | 1.81016 |
| 238137_at | — | — | 1.61463 |
| 1562201_x_at | — | — | 1.69439 |
| 241648_at | — | — | −1.52957 |
| 236996_at | — | — | −1.54814 |
| 1567706_at | — | — | 1.9772 |
| 239082_at | — | — | 1.62335 |
| 241235_at | — | — | −1.5976 |
| 244767_at | — | — | −1.56631 |
| 233424_at | — | — | 1.90728 |
| 243655_x_at | — | — | 1.52941 |
| 236395_at | — | — | −1.5143 |
| 239903_at | — | — | 1.61809 |
| 1566645_at | — | — | 1.5476 |
| 1562341_at | — | — | 1.52441 |
| 242952_at | — | — | 1.55967 |
| 1559807_at | — | — | 1.70594 |
| 238155_at | — | — | −1.5566 |
| 1566550_at | — | — | 1.54738 |
| 242797_x_at | — | — | −1.86201 |
| 242170_at | — | — | −1.89134 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 1570098_at | — | — | 1.82945 |
| 1559524_at | — | — | -1.71546 |
| 239606_at | — | — | -1.53539 |
| 1566544_at | — | — | 1.61104 |
| 242133_s_at | — | — | 1.56343 |
| 1556760_a_at | — | — | 2.00828 |
| 1563461_at | — | — | 1.53995 |
| 1570645_at | — | — | 1.55841 |
| 240730_at | — | — | 1.61181 |
| 236602_at | — | — | 1.52722 |
| 242122_at | — | — | -1.50641 |
| 1559410_at | — | — | 1.7089 |
| 234100_at | — | — | -1.52272 |
| 239856_at | — | — | -2.23215 |
| 229243_at | — | — | -1.73048 |
| 231465_at | — | — | 1.62758 |
| 1562208_a_at | — | — | 1.87064 |
| 1561149_at | — | — | 1.52562 |
| 240642_at | — | — | -1.71584 |
| 1557658_at | — | — | -1.61047 |
| 230503_at | — | — | 1.60016 |
| 242494_at | — | — | 1.6192 |
| 1561956_at | — | — | 1.59298 |
| 242495_at | — | — | 1.57521 |
| 222320_at | — | — | 1.61706 |
| 237886_at | — | — | 1.53331 |
| 1565788_at | — | — | 1.65726 |
| 240133_x_at | — | — | 1.88894 |
| 242074_at | — | — | -1.54665 |
| 215029_at | — | — | -1.61964 |
| 1568785_a_at | — | — | 1.52688 |
| 243381_at | — | — | 1.63013 |
| 216173_at | — | — | 1.57894 |
| 240688_at | — | — | 1.52689 |
| 243584_at | — | — | 1.76235 |
| 231136_at | — | — | 1.50646 |
| 1569833_at | — | — | 1.60643 |
| 230168_at | — | — | -1.93736 |
| 1564744_at | — | — | 1.63372 |
| 1562010_x_at | — | — | 1.50535 |
| 228734_at | — | — | -1.67929 |
| 1560717_at | — | — | 1.67536 |
| 243356_at | — | — | 1.72703 |
| 1562935_at | — | — | 1.5956 |
| 240973_s_at | — | — | -1.53876 |
| 207471_at | — | — | 1.75431 |
| 222246_at | — | — | 1.84054 |
| 237102_at | — | — | 1.73952 |
| 220871_at | — | — | 1.80151 |
| 228643_at | — | — | -1.6237 |
| 233180_at | — | — | 2.25381 |
| 1559709_at | — | — | 1.69535 |
| 242296_x_at | — | — | 1.56148 |
| 1562456_at | — | — | 1.66178 |
| 1556518_at | — | — | 1.537 |
| 233579_at | — | — | 2.32946 |
| 1563531_at | — | — | 1.91261 |
| 216757_at | — | — | 1.75028 |
| 234612_at | — | — | 1.54801 |
| 1562835_at | — | — | 1.7128 |
| 234224_at | — | — | 1.5186 |
| 242115_at | — | — | 1.5505 |
| 1569527_at | — | — | -1.54022 |
| 238415_at | — | — | 1.53194 |
| 226231_at | — | — | -1.79439 |
| 240506_at | — | — | 1.60003 |
| 240469_at | — | — | 1.62514 |
| 1557885_at | — | — | 1.52753 |
| 237356_at | — | — | 1.93218 |
| 242202_at | — | — | 1.57335 |
| 236778_at | — | — | 1.60299 |
| 240355_at | — | — | -1.66821 |
| 242142_at | — | — | 1.80096 |
| 236038_at | — | — | 2.10931 |
| 1557434_at | — | — | 1.53917 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 227051_at | — | — | −1.88686 |
| 1567304_at | — | — | 1.60926 |
| 239819_at | — | — | 1.56334 |
| 1563054_at | — | — | 1.71697 |
| 1557921_s_at | — | — | 1.68215 |
| 242321_at | — | — | 2.20104 |
| 1561135_at | — | — | 1.73638 |
| 1566787_at | — | — | 1.59838 |
| 239649_at | — | — | 1.65668 |
| 214645_at | — | — | 1.55285 |
| 232459_at | — | — | 1.82556 |
| 243236_at | — | — | −1.70988 |
| 1560094_at | — | — | −1.68062 |
| 237628_at | — | — | 1.51201 |
| 244551_at | — | — | −1.66189 |
| 243345_at | — | — | −1.65084 |
| 240442_at | — | — | 1.66955 |
| 1560372_at | — | — | 2.10286 |
| 1566504_at | — | — | 1.56292 |
| 239986_at | — | — | 1.53033 |
| 1561319_at | — | — | 1.62652 |
| 234560_at | — | — | 1.68465 |
| 1560258_a_at | — | — | 1.50646 |
| 239863_at | — | — | −1.97398 |
| 234064_at | — | — | 2.03588 |
| 238718_at | — | — | 1.68987 |
| 244016_at | — | — | 1.80815 |
| 217038_at | — | — | 2.36071 |
| 236659_x_at | — | — | 1.57533 |
| 1566772_at | — | — | 1.61228 |
| 1566809_a_at | — | — | 1.79265 |
| 244333_at | — | — | 1.65689 |
| 230294_at | — | — | −1.55001 |
| 1564479_a_at | — | — | 1.72664 |
| 215864_at | — | — | 2.03128 |
| 1563477_at | — | — | 2.05179 |
| 1570213_at | — | — | 1.98433 |
| 217137_x_at | — | — | 2.033 |
| 237912_at | — | — | 1.82582 |
| 241220_at | — | — | 1.54608 |
| 242166_at | — | — | 1.56101 |
| 237134_at | — | — | 1.84799 |
| 238372_s_at | — | — | 2.37201 |
| 239536_at | — | — | −1.66473 |
| 227857_at | — | — | 1.56563 |
| 1559664_at | — | — | 1.60616 |
| 240267_at | — | — | 1.51777 |
| 1564391_at | — | — | 1.97908 |
| 236161_at | — | — | 1.64402 |
| 233786_at | — | — | 1.81531 |
| 1567611_at | — | — | −1.50961 |
| 222298_at | — | — | 1.58123 |
| 232805_at | — | — | 1.59909 |
| 236678_at | — | — | 1.8314 |
| 241057_x_at | — | — | 1.56362 |
| 1556239_a_at | — | — | −1.7364 |
| 1558719_s_at | — | — | −1.86612 |
| 240658_at | — | — | 1.58761 |
| 242564_at | — | — | −1.77191 |
| 241100_at | — | — | 1.89642 |
| 236219_at | — | — | −1.78149 |
| 240245_at | — | — | 1.74041 |
| 1561328_at | — | — | 1.62167 |
| 237231_at | — | — | −1.50546 |
| 1558869_at | — | — | 1.75081 |
| 1554043_a_at | — | — | −1.65188 |
| 241030_at | — | — | 1.89393 |
| 233306_at | — | — | 1.8777 |
| 1565874_at | — | — | 1.63558 |
| 230874_at | — | — | −2.06833 |
| 1569661_at | — | — | 1.59665 |
| 237742_at | — | — | 1.61044 |
| 227985_at | — | — | −1.82784 |
| 1566867_at | — | — | 1.94122 |
| 1564773_x_at | — | — | 1.54988 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 1562053_at | — | — | −2.06402 |
| 235188_at | — | — | 1.84682 |
| 1557512_at | — | — | −1.627 |
| 242007_at | — | — | −1.69897 |
| 243455_at | — | — | 1.61965 |
| 239868_at | — | — | 1.5129 |
| 1561417_x_at | — | — | 1.60574 |
| 219367_s_at | — | — | 1.53187 |
| 236394_at | — | — | 1.76477 |
| 1561134_at | — | — | 1.54734 |
| 242468_at | — | — | 1.97864 |
| 1566994_at | — | — | 2.10394 |
| 210679_x_at | — | — | 1.5028 |
| 243636_s_at | — | — | 1.69661 |
| 234588_at | — | — | 1.61426 |
| 1566995_at | — | — | 2.12757 |
| 1566096_x_at | — | — | 2.08387 |
| 233187_s_at | — | — | −1.54128 |
| 227745_at | — | — | −1.73547 |
| 1557443_s_at | — | — | 1.60801 |
| 1561161_at | — | — | 1.81185 |
| 240997_at | — | — | 1.65329 |
| 1561689_at | — | — | 1.65238 |
| 241163_at | — | — | 1.59299 |
| 234248_at | — | — | 1.55099 |
| 1562065_at | — | — | 1.74757 |
| 239437_at | — | — | −1.80734 |
| 1569208_a_at | — | — | 1.93479 |
| 1559737_at | — | — | 1.72324 |
| 240016_at | — | — | 1.58788 |
| 235666_at | — | — | 1.57665 |
| 210914_at | — | — | 1.51724 |
| 233445_at | — | — | 1.81438 |
| 1565825_at | — | — | 1.56204 |
| 238203_at | — | — | 1.70123 |
| 1562327_at | — | — | 1.59003 |
| 1570316_at | — | — | 1.78431 |
| 242303_at | — | — | 1.7273 |
| 1563001_at | — | — | 1.56578 |
| 1562864_at | — | — | 1.54738 |
| 222168_at | — | — | 1.97664 |
| 1562091_at | — | — | 1.51347 |
| 1566424_at | — | — | 1.63682 |
| 232962_x_at | — | — | 1.69709 |
| 235831_at | — | — | 1.70453 |
| 233861_at | — | — | 2.22299 |
| 215278_at | — | — | 1.71066 |
| 242599_at | — | — | 1.62169 |
| 1565879_at | — | — | 1.86352 |
| 241002_at | — | — | 1.69313 |
| 241142_at | — | — | −1.67262 |
| 232800_at | — | — | 2.29403 |
| 242505_at | — | — | 1.57494 |
| 1558714_at | — | — | 1.9751 |
| 243014_at | — | — | 1.58464 |
| 240101_at | — | — | −1.75992 |
| 232541_at | — | — | 1.55706 |
| 241665_x_at | — | — | 1.7135 |
| 240468_at | — | — | 1.92795 |
| 215405_at | — | — | 1.98124 |
| 240800_x_at | — | — | 1.60351 |
| 221120_at | — | — | 1.53838 |
| 237332_at | — | — | 1.5951 |
| 1563036_at | — | — | 1.63532 |
| 1557659_a_at | — | — | −2.08984 |
| 233293_at | — | — | 1.51923 |
| 242811_x_at | — | — | 1.70854 |
| 1554439_at | — | — | 1.69729 |
| 1560453_at | — | — | 1.82015 |
| 1569779_at | — | — | 1.61263 |
| 237525_at | — | — | 1.51511 |
| 240989_at | — | — | 1.61747 |
| 234606_at | — | — | 1.54255 |
| 234692_at | — | — | 1.61537 |
| 216756_at | — | — | 1.65304 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 241637_at | — | — | 2.17642 |
| 1556656_at | — | — | 1.68075 |
| 235017_s_at | — | — | 1.7341 |
| 233130_at | — | — | 1.82787 |
| 233779_x_at | — | — | 1.51862 |
| 237355_at | — | — | 1.54889 |
| 232850_at | — | — | 1.55839 |
| 230020_at | — | — | −1.8275 |
| 243454_at | — | — | 2.15818 |
| 237573_at | — | — | 1.82449 |
| 234036_x_at | — | — | 1.82885 |
| 243666_at | — | — | 2.20715 |
| 1568736_s_at | — | — | 1.83385 |
| 215539_at | — | — | 1.57174 |
| 1556504_at | — | — | 1.51528 |
| 221144_at | — | — | 1.6864 |
| 239459_s_at | — | — | 2.16772 |
| 1552975_x_at | — | — | 1.63565 |
| 1562727_at | — | — | 1.87879 |
| 233450_at | — | — | 1.82759 |
| 241303_x_at | — | — | 1.51058 |
| 236617_at | — | — | 2.04757 |
| 1562473_at | — | — | 1.52865 |
| 1556650_at | — | — | 1.53931 |
| 238395_at | — | — | 1.84075 |
| 234597_at | — | — | 2.57012 |
| 240046_at | — | — | 1.75115 |
| 237526_at | — | — | 1.57771 |
| 237492_at | — | — | 1.70165 |
| 1563351_at | — | — | 1.57794 |
| 227140_at | — | — | 2.59379 |
| 216187_x_at | — | — | 1.58094 |
| 236187_s_at | — | — | 1.71841 |
| 228842_at | — | — | −1.51876 |
| 234532_at | — | — | 1.84698 |
| 234219_at | — | — | 1.83545 |
| 242189_at | — | — | 1.58063 |
| 241203_at | — | — | 1.57795 |
| 240580_at | — | — | 1.77583 |
| 1565576_at | — | — | 1.51264 |
| 242755_at | — | — | 2.01686 |
| 1568648_a_at | — | — | 1.98415 |
| 1562718_at | — | — | 1.64374 |
| 239017_at | — | — | 1.54796 |
| 1563427_at | — | — | 1.62296 |
| 242857_at | — | — | −1.7551 |
| 1557758_at | — | — | 1.8066 |
| 1559086_at | — | — | 1.85777 |
| 241758_at | — | — | 1.67733 |
| 236564_at | — | — | −1.68533 |
| 233721_x_at | — | — | 1.86315 |
| 202015_x_at | — | — | 1.99169 |
| 240640_at | — | — | 1.51291 |
| 1557861_at | — | — | 1.75142 |
| 240858_at | — | — | 1.54478 |
| 1559695_a_at | — | — | 1.82202 |
| 244891_x_at | — | — | 1.6181 |
| 240297_at | — | — | 1.62096 |
| 1558444_at | — | — | 2.92859 |
| 1570482_at | — | — | 2.57201 |
| 1563055_at | — | — | 1.58052 |
| 1567303_at | — | — | 1.9115 |
| 231037_at | — | — | 1.77578 |
| 1564690_at | — | — | 3.09408 |
| 1561129_at | — | — | 1.5641 |
| 244045_at | — | — | 2.06161 |
| 1560352_at | — | — | 1.84388 |
| 241130_at | — | — | 1.58428 |
| 232268_at | — | — | 1.57907 |
| 1566768_at | — | — | 1.84415 |
| 241173_at | — | — | 1.86436 |
| 1562760_at | — | — | 1.72579 |
| 1562588_at | — | — | 1.94416 |
| 1566763_at | — | — | 2.04467 |
| 1569740_at | — | — | 1.64645 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 240290_at | — | — | 1.67943 |
| 237496_at | — | — | 2.06865 |
| 1567379_at | — | — | 1.62299 |
| 244125_at | — | — | 2.57599 |
| 235445_at | — | — | 1.91795 |
| 1555174_at | — | — | 1.58019 |
| 216643_at | — | — | 1.89215 |
| 1569983_at | — | — | 2.39576 |
| 1560429_at | — | — | 2.04382 |
| 1563386_at | — | — | 1.76382 |
| 244511_at | — | — | 1.62772 |
| 1570350_at | — | — | 1.61993 |
| 241487_at | — | — | 1.66578 |
| 1567913_at | — | — | 5.71757 |
| 1562686_at | — | — | 1.74144 |
| 1565860_at | — | — | 2.96918 |
| 244510_at | — | — | 2.46633 |
| 237622_at | — | — | −2.61939 |
| 1557780_at | — | — | 1.71847 |
| 239520_at | — | — | 1.53506 |
| 243034_at | — | — | 1.5628 |
| 238571_at | — | — | 1.80516 |
| 232113_at | — | — | 2.22875 |
| 242641_at | — | — | 1.61615 |
| 234579_at | — | — | 1.55619 |
| 1566842_at | — | — | 1.75893 |
| 215587_x_at | — | — | 1.53373 |
| 236740_at | — | — | 1.8285 |
| 224549_x_at | — | — | 1.68422 |
| 233276_at | — | — | 1.62961 |
| 1561256_at | — | — | 1.92386 |
| 1566094_at | — | — | 2.44114 |
| 224234_at | — | — | 1.5266 |
| 244098_at | — | — | 1.6926 |
| 234428_at | — | — | 2.25705 |
| 1562720_at | — | — | 1.91297 |
| 243147_x_at | — | — | 1.67593 |
| 1569344_a_at | — | — | 2.19681 |
| 235560_at | — | — | 1.6268 |
| 228504_at | — | — | 1.72391 |
| 1556985_at | — | — | 1.79627 |
| 215628_x_at | — | — | 1.56039 |
| 1562086_at | — | — | 1.57298 |
| 222372_at | — | — | 1.84973 |
| 1566582_x_at | — | — | 1.79715 |
| 233958_at | — | — | 1.55915 |
| 243008_at | — | — | 1.64372 |
| 1553275_s_at | — | — | 1.89002 |
| 243322_at | — | — | 1.65429 |
| 234825_at | — | — | 1.73469 |
| 244609_at | — | — | 1.85048 |
| 215615_x_at | — | — | 1.53488 |
| 1561528_at | — | — | 1.55697 |
| 241852_at | — | — | 1.60268 |
| 1558489_at | — | — | 2.34982 |
| 239672_at | — | — | 1.66417 |
| 1560087_a_at | — | — | 1.92031 |
| 1556904_at | — | — | 2.30213 |
| 244724_at | — | — | 1.60549 |
| 241310_at | — | — | 2.15657 |
| 241655_at | — | — | 1.54091 |
| 234625_at | — | — | 1.58324 |
| 231616_at | — | — | 2.13008 |
| 236697_at | — | — | 1.5915 |
| 235642_at | — | — | 1.70455 |
| 241897_at | — | — | 2.12195 |
| 236670_s_at | — | — | 2.10982 |
| 240578_at | — | — | 1.61716 |
| 1562235_s_at | — | — | 1.55351 |
| 1562687_x_at | — | — | 1.8282 |
| 1556805_at | — | — | 2.61186 |
| 237727_at | — | — | 1.66554 |
| 215284_at | — | — | 2.05102 |
| 228740_at | — | — | 1.82664 |
| 244769_at | — | — | 1.95537 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 227484_at | — | — | 1.51603 |
| 233755_at | — | — | 1.86698 |
| 227126_at | — | — | 2.10379 |
| 224429_x_at | — | — | 1.56535 |
| 1556796_at | — | — | 2.47359 |
| 221146_at | — | — | 1.70639 |
| 233265_at | — | — | 1.84813 |
| 234494_x_at | — | — | 1.7031 |
| 1556206_at | — | — | 1.82973 |
| 244384_at | — | — | 1.92957 |
| 236466_at | — | — | 1.7519 |
| 238536_at | — | — | 1.76454 |
| 1561591_at | — | — | 1.63671 |
| 232808_at | — | — | 1.87054 |
| 1563052_at | — | — | 3.05615 |
| 1556813_at | — | — | 1.66613 |
| 233402_at | — | — | 1.53209 |
| 238847_at | — | — | 2.49299 |
| 237483_at | — | — | 2.00055 |
| 234753_x_at | — | — | 1.87523 |
| 220820_at | — | — | 1.58991 |
| 1562332_at | — | — | 1.92188 |
| 1562905_at | — | — | 1.56404 |
| 1561217_at | — | — | 1.75568 |
| 1561121_at | — | — | 1.52528 |
| 243762_at | — | — | 1.60241 |
| 236650_at | — | — | 1.89552 |
| 230577_at | — | — | 1.71798 |
| 1569753_at | — | — | 2.20368 |
| 233224_at | — | — | −1.51535 |
| 241479_at | — | — | 1.90387 |
| 1569491_at | — | — | 1.79905 |
| 237832_at | — | — | 2.86311 |
| 235733_at | — | — | 1.90522 |
| 1568803_at | — | — | 1.66131 |
| 237491_at | — | — | 2.70143 |
| 216151_at | — | — | 1.59221 |
| 1556352_at | — | — | 1.73928 |
| 229490_s_at | — | — | 2.20922 |
| 1570596_at | — | — | 1.65322 |
| 237600_at | — | — | 1.64121 |
| 211374_x_at | — | — | 1.57283 |
| 216110_x_at | — | — | 1.66876 |
| 240152_at | — | — | 2.07123 |
| 240949_x_at | — | — | 2.6364 |
| 1566968_at | — | — | 1.8345 |
| 216524_x_at | — | — | 1.52057 |
| 242188_at | — | — | 1.67993 |
| 1560690_at | — | — | 1.50865 |
| 240060_at | — | — | 1.50178 |
| 237946_at | — | — | 2.74367 |
| 220837_at | — | — | 1.76967 |
| 229330_at | — | — | −1.52841 |
| 1566666_at | — | — | 2.15745 |
| 240474_x_at | — | — | 1.54025 |
| 237903_at | — | — | 1.68116 |
| 1564567_at | — | — | 2.86081 |
| 227010_at | — | — | −1.54551 |
| 1562507_at | — | — | 2.46383 |
| 1562544_at | — | — | 1.83332 |
| 1560891_a_at | — | — | 1.60154 |
| 233714_at | — | — | 2.13082 |
| 244259_s_at | — | — | 1.69439 |
| 243279_at | — | — | 2.03405 |
| 234755_x_at | — | — | 1.52681 |
| 241639_at | — | — | 2.0758 |
| 234667_at | — | — | 1.61766 |
| 216625_at | — | — | 1.54839 |
| 244156_at | — | — | 2.63578 |
| 1556683_x_at | — | — | 1.50421 |
| 230785_at | — | — | 1.50472 |
| 232495_x_at | — | — | 1.50721 |
| 238361_s_at | — | — | 2.25068 |
| 217619_x_at | — | — | 1.54826 |
| 1560111_at | — | — | 1.80542 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 236184_at | — | — | 2.09878 |
| 235629_at | — | — | 1.52947 |
| 242236_at | — | — | 2.6709 |
| 217579_x_at | — | — | 1.6302 |
| 233240_at | — | — | 1.58366 |
| 222296_at | — | — | 1.66123 |
| 232592_at | — | — | 1.67559 |
| 237998_at | — | — | 1.95045 |
| 242559_at | — | — | 1.73911 |
| 243240_at | — | — | 1.812 |
| 241253_at | — | — | 1.53832 |
| 241069_at | — | — | 2.1882 |
| 238310_at | — | — | 1.68293 |
| 1564798_at | — | — | 1.74183 |
| 217524_x_at | — | — | 1.55266 |
| 240427_at | — | — | 2.39407 |
| 217713_x_at | — | — | 1.65536 |
| 240450_at | — | — | 2.21304 |
| 237893_at | — | — | 2.06445 |
| 241132_at | — | — | 2.13802 |
| 237267_at | — | — | 1.89267 |
| 1564236_at | — | — | 1.69733 |
| 1558473_at | — | — | 1.83005 |
| 1557519_at | — | — | −1.89371 |
| 1569231_x_at | — | — | 1.6864 |
| 241008_at | — | — | 1.54943 |
| 1561445_at | — | — | 1.55856 |
| 234571_at | — | — | 1.73178 |
| 234083_at | — | — | 2.037 |
| 241656_at | — | — | 1.55124 |
| 1563012_x_at | — | — | 1.50488 |
| 1560476_at | — | — | 2.17694 |
| 1561564_at | — | — | 2.75205 |
| 233118_at | — | — | 1.79787 |
| 233702_x_at | — | — | 1.54804 |
| 1563091_at | — | — | 1.67395 |
| 1559450_at | — | — | 1.77421 |
| 244793_at | — | — | 1.85576 |
| 233622_x_at | — | — | 1.51571 |
| 241223_x_at | — | — | 1.69464 |
| 239604_at | — | — | 2.18244 |
| 216158_at | — | — | 1.80396 |
| 1556817_a_at | — | — | 2.10569 |
| 1570099_at | — | — | 1.50845 |
| 1561692_at | — | — | 2.64312 |
| 242795_at | — | — | 3.20031 |
| 1559375_s_at | — | — | 1.57452 |
| 1569794_at | — | — | 1.79312 |
| 1562933_at | — | — | 1.7812 |
| 1561305_at | — | — | 1.51196 |
| 233502_at | — | — | 3.43598 |
| 244588_at | — | — | 1.86108 |
| 240783_at | — | — | 2.8921 |
| 235739_at | — | — | 1.88882 |
| 233273_at | — | — | 2.07697 |
| 1565873_at | — | — | 1.75922 |
| 242881_x_at | — | — | 2.91173 |
| 1563568_at | — | — | 1.89445 |
| 1569755_at | — | — | 1.86666 |
| 242391_at | — | — | 2.54095 |
| 1565637_at | — | — | 2.44504 |
| 241657_at | — | — | 1.65304 |
| 232957_x_at | — | — | 2.28244 |
| 233683_at | — | — | 2.15259 |
| 237065_s_at | — | — | −2.23415 |
| 1566597_at | — | — | 2.38873 |
| 239849_at | — | — | 2.49616 |
| 1564358_at | — | — | 3.57914 |
| 233152_x_at | — | — | 1.5398 |
| 243473_at | — | — | 1.8121 |
| 216094_at | — | — | 2.20104 |
| 1568589_at | — | — | 2.83131 |
| 1555925_at | — | — | 3.50923 |
| 243572_at | — | — | 1.7936 |
| 241186_at | — | — | 2.07335 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 239340_at | — | — | 3.10534 |
| 243192_at | — | — | 1.79294 |
| 1569230_at | — | — | 1.89893 |
| 215062_at | — | — | 1.66817 |
| 1561187_at | — | — | 1.53178 |
| 243763_x_at | — | — | 2.00712 |
| 1563329_s_at | — | — | 1.93939 |
| 238826_x_at | — | — | 1.63927 |
| 238298_at | — | — | 1.92448 |
| 205772_s_at | — | — | 1.92683 |
| 231482_at | — | — | 1.9948 |
| 242605_at | — | — | 1.68979 |
| 1565565_at | — | — | 1.67957 |
| 1562945_at | — | — | 1.51982 |
| 1556392_a_at | — | — | 1.8825 |
| 243929_at | — | — | 2.32352 |
| 1561509_at | — | — | 1.59259 |
| 1555601_at | — | — | 1.81067 |
| 232324_x_at | — | — | 1.53814 |
| 238184_at | — | — | 1.50493 |
| 1567008_at | — | — | 2.21042 |
| 243706_at | — | — | 1.82234 |
| 239514_at | — | — | 2.26505 |
| 234433_at | — | — | 2.20167 |
| 240067_at | — | — | 1.94901 |
| 1562263_at | — | — | 1.83224 |
| 237850_at | — | — | 1.60944 |
| 222299_x_at | — | — | 1.80516 |
| 1557215_at | — | — | 1.82993 |
| 239985_at | — | — | 1.67697 |
| 243877_at | — | — | 1.65948 |
| 1569656_at | — | — | 1.83943 |
| 239344_at | — | — | 1.53249 |
| 1561631_at | — | — | 1.67024 |
| 237365_at | — | — | 1.70238 |
| 243936_x_at | — | — | 2.23539 |
| 216337_at | — | — | 1.56682 |
| 1570423_at | — | — | 2.37274 |
| 1558672_at | — | — | 1.65888 |
| 1564580_at | — | — | 2.5145 |
| 1562923_at | — | — | 1.52114 |
| 237951_at | — | — | 1.6943 |
| 242890_at | — | — | 1.88508 |
| 234805_at | — | — | 1.76687 |
| 239311_at | — | — | 1.55589 |
| 1565861_at | — | — | 2.3658 |
| 1562409_s_at | — | — | 1.52328 |
| 230130_at | — | — | 2.07003 |
| 232833_at | — | — | 1.55799 |
| 244507_at | — | — | 3.42912 |
| 1561268_at | — | — | 1.54475 |
| 1563331_at | — | — | 2.23231 |
| 224254_x_at | — | — | 1.81892 |
| 1561346_at | — | — | 1.63069 |
| 240485_at | — | — | 1.61434 |
| 238751_at | — | — | 2.35739 |
| 1561478_at | — | — | 1.56036 |
| 239706_x_at | — | — | 2.03617 |
| 240877_x_at | — | — | 1.5753 |
| 232925_at | — | — | 1.58004 |
| 1558497_a_at | — | — | 2.17382 |
| 1555014_x_at | — | — | 1.87282 |
| 216101_at | — | — | 1.99447 |
| 240077_at | — | — | 1.51092 |
| 234550_at | — | — | 2.01775 |
| 242845_at | — | — | 1.60469 |
| 1561778_at | — | — | 2.41702 |
| 242401_x_at | — | — | 1.60265 |
| 1566695_at | — | — | 1.57644 |
| 1561123_at | — | — | 2.74835 |
| 1556491_at | — | — | 2.07615 |
| 233626_at | — | — | 1.68482 |
| 1562166_at | — | — | 1.63935 |
| 242483_at | — | — | 1.556 |
| 230746_s_at | — | — | 3.65236 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 1561437_at | — | — | 1.69604 |
| 238512_at | — | — | 2.14172 |
| 237486_at | — | — | 1.64718 |
| 215768_at | — | — | 2.61093 |
| 1561112_at | — | — | 2.307 |
| 243566_at | — | — | 1.54828 |
| 242733_at | — | — | 2.42057 |
| 242171_at | — | — | 1.8335 |
| 239962_at | — | — | 1.94384 |
| 1568931_at | — | — | 1.68134 |
| 239066_at | — | — | 1.90013 |
| 1558226_a_at | — | — | 2.12499 |
| 241549_at | — | — | 1.54525 |
| 1561962_at | — | — | 2.00865 |
| 1567009_at | — | — | 2.33801 |
| 238354_x_at | — | — | 2.18921 |
| 240670_at | — | — | 2.07815 |
| 220729_at | — | — | 2.066 |
| 1563414_at | — | — | 1.68084 |
| 1562491_at | — | — | 1.85416 |
| 1566805_at | — | — | 2.49158 |
| 1564819_at | — | — | 1.84755 |
| 1566848_x_at | — | — | 1.63636 |
| 244503_at | — | — | 2.28069 |
| 244736_at | — | — | 1.63528 |
| 232795_at | — | — | 1.88485 |
| 235938_at | — | — | 2.53577 |
| AFFX-M27830_3_at | — | — | 3.11913 |
| 233365_at | — | — | 2.76277 |
| 234282_at | — | — | 2.01659 |
| 241667_x_at | — | — | 1.7844 |
| 243211_at | — | — | 1.95149 |
| 1557029_at | — | — | 1.88354 |
| 1564878_at | — | — | 1.97934 |
| 242419_at | — | — | 1.54601 |
| 1560049_at | — | — | 3.57066 |
| 243401_at | — | — | 2.22064 |
| 1561012_at | — | — | 3.09703 |
| 1564451_at | — | — | 2.88901 |
| 1563077_at | — | — | 2.08269 |
| 244637_at | — | — | 1.83073 |
| 243694_at | — | — | 1.56713 |
| 237422_at | — | — | 1.60881 |
| 1557348_at | — | — | 3.30543 |
| 1564097_at | — | — | 2.32219 |
| 240157_at | — | — | 1.80217 |
| 241222_at | — | — | 1.72407 |
| 216104_at | — | — | 1.72674 |
| 1570506_at | — | — | 2.29335 |
| 1561418_at | — | — | 2.52035 |
| 1561658_at | — | — | 2.77763 |
| 243035_at | — | — | 1.77962 |
| 234179_at | — | — | 4.17162 |
| 1560760_s_at | — | — | 3.16782 |
| 231040_at | — | — | 1.98115 |
| 241387_at | — | — | 2.26199 |
| 1559724_at | — | — | 1.82952 |
| 232793_at | — | — | 2.69051 |
| 216007_at | — | — | 1.91365 |
| 238414_at | — | — | 1.93724 |
| 1562464_at | — | — | 2.31276 |
| 232582_at | — | — | 1.64746 |
| 244867_at | — | — | 2.06707 |
| 234652_at | — | — | 1.61083 |
| 236256_at | — | — | 1.97291 |
| 232723_at | — | — | 2.09444 |
| 233043_at | — | — | 2.7178 |
| 234593_at | — | — | 1.86662 |
| 233606_at | — | — | 3.32752 |
| 233668_at | — | — | 2.29868 |
| 1558019_at | — | — | 1.76057 |
| 233593_at | — | — | 1.64392 |
| 1561777_at | — | — | 2.12493 |
| 241536_at | — | — | 2.91919 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 236962_at | — | — | 1.50896 |
| 1564654_at | — | — | 1.58649 |
| 244821_at | — | — | 2.35422 |
| 231597_x_at | — | — | 3.28195 |
| 1564807_at | — | — | 2.09646 |
| 1562137_at | — | — | 1.80249 |
| 243781_at | — | — | 1.69708 |
| 244762_at | — | — | 2.22632 |
| 236276_at | — | — | 2.00169 |
| 238408_at | — | — | 2.44824 |
| 1560189_at | — | — | 1.70373 |
| 1561703_at | — | — | 3.73005 |
| 233427_x_at | — | — | 1.53672 |
| 233828_at | — | — | 1.6531 |
| 234509_at | — | — | 2.11383 |
| 238411_x_at | — | — | 3.42466 |
| 244211_at | — | — | 1.94329 |
| 221174_at | — | — | 2.05834 |
| 1570125_at | — | — | 2.23673 |
| 233257_at | — | — | 2.01104 |
| 233406_at | — | — | 2.43719 |
| 1562351_at | — | — | 1.79422 |
| 237353_at | — | — | 2.53975 |
| 233053_at | — | — | 2.26447 |
| 243424_at | — | — | 2.31946 |
| 237962_x_at | — | — | 2.49202 |
| 1562613_at | — | — | 2.67097 |
| 1566846_at | — | — | 2.74769 |
| 231239_at | — | — | 1.81363 |
| 1562311_at | — | — | 1.52118 |
| 216496_s_at | — | — | 1.69818 |
| 1562853_x_at | — | — | 1.6179 |
| 215801_at | — | — | 2.67753 |
| 1569809_at | — | — | 1.54798 |
| 1566469_at | — | — | 2.73721 |
| 1569858_at | — | — | 2.28984 |
| 1563561_at | — | — | 1.95979 |
| 1562828_at | — | — | 1.91629 |
| 1559434_at | — | — | 2.23908 |
| 240738_at | — | — | 1.68702 |
| 1555498_at | — | — | 1.8321 |
| 1561309_x_at | — | — | 1.5393 |
| 1566658_at | — | — | 1.88495 |
| 243828_at | — | — | 1.87947 |
| 239887_at | — | — | 1.96566 |
| 231315_at | — | — | 2.14126 |
| 1556834_at | — | — | 5.45617 |
| 230959_at | — | — | 3.63868 |
| 237361_at | — | — | 1.89401 |
| 241769_at | — | — | 2.05931 |
| 244112_x_at | — | — | 3.84372 |
| 1566633_at | — | — | 1.96728 |
| 216414_at | — | — | 1.87759 |
| 231598_x_at | — | — | 4.5426 |
| 237557_at | — | — | 2.78756 |
| 1566969_at | — | — | 1.76339 |
| 241654_at | — | — | 2.02175 |
| 240522_at | — | — | 1.83066 |
| 1562420_at | — | — | 2.41252 |
| 234827_at | — | — | 1.91205 |
| 216214_at | — | — | 2.46673 |
| 231546_at | — | — | 1.98214 |
| 1562820_at | — | — | 1.67996 |
| 233744_at | — | — | 1.99092 |
| 243902_at | — | — | 2.50007 |
| 234531_at | — | — | 2.08946 |
| 1561453_at | — | — | 1.68606 |
| 237207_at | — | — | 2.79429 |
| 216595_at | — | — | 3.77726 |
| 1568611_at | — | — | 2.16277 |
| 1566716_at | — | — | 1.92697 |
| 240502_at | — | — | 3.31561 |
| 238178_at | — | — | 1.87863 |
| 1562076_at | — | — | 2.40574 |
| 234581_at | — | — | 1.71821 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 239993_at | — | — | 1.6141 |
| 1561087_at | — | — | 2.91713 |
| 239303_at | — | — | 1.83918 |
| 240788_at | — | — | 1.76033 |
| 234578_at | — | — | 1.93338 |
| 241633_x_at | — | — | 1.98454 |
| 241509_at | — | — | 1.88307 |
| 1566938_at | — | — | 1.62844 |
| 241636_x_at | — | — | 2.81114 |
| 1562169_at | — | — | 2.81005 |
| 242715_at | — | — | 3.98461 |
| 1568872_at | — | — | 1.7538 |
| 1556021_at | — | — | 2.6888 |
| 241254_at | — | — | 2.0837 |
| 1564083_at | — | — | 2.39374 |
| 1564547_x_at | — | — | 2.68196 |
| 237149_at | — | — | 1.70862 |
| 233658_at | — | — | 1.82247 |
| 228732_at | — | — | 1.55938 |
| 1561450_at | — | — | 1.70802 |
| 234104_at | — | — | 1.61476 |
| 1563190_at | — | — | 2.07844 |
| 241870_at | — | — | 1.85956 |
| 233448_s_at | — | — | 2.276 |
| 1561351_at | — | — | 2.00141 |
| 239970_at | — | — | 3.00339 |
| 1559149_at | — | — | 1.90107 |
| 1569944_at | — | — | 2.22129 |
| 216745_x_at | — | — | 1.747 |
| 1561199_at | — | — | 3.48145 |
| 241583_x_at | — | — | 1.90832 |
| 234228_at | — | — | 1.73472 |
| 241287_x_at | — | — | 1.75873 |
| 233853_at | — | — | 1.55509 |
| 1566970_at | — | — | 2.31372 |
| 224546_at | — | — | 2.91364 |
| 1570191_at | — | — | 2.76356 |
| 215810_x_at | — | — | 1.56175 |
| 231284_at | — | — | 1.94763 |
| 239025_at | — | — | 1.66351 |
| 1566748_at | — | — | 2.34934 |
| 1569577_x_at | — | — | 1.81271 |
| 1562083_at | — | — | 3.40841 |
| 234279_at | — | — | 1.75062 |
| 236576_at | — | — | 1.78665 |
| 1562677_at | — | — | 1.8276 |
| 1560131_at | — | — | 2.6117 |
| 216858_x_at | — | — | 1.5146 |
| 1556622_s_at | — | — | 2.38938 |
| 244258_at | — | — | 2.02288 |
| 1566426_at | — | — | 2.34526 |
| 1555365_x_at | — | — | 2.6206 |
| 1561938_at | — | — | 2.13371 |
| 1560745_at | — | — | 1.79518 |
| 234558_at | — | — | 1.82691 |
| 216764_at | — | — | 1.78566 |
| 1570155_at | — | — | 2.22005 |
| 1561411_at | — | — | 1.51791 |
| 1564070_s_at | — | — | 1.64228 |
| 233449_at | — | — | 1.76305 |
| 216286_at | — | — | 2.06666 |
| 240431_at | — | — | 1.86816 |
| 244613_at | — | — | 1.93862 |
| 241628_at | — | — | 2.01118 |
| 1564134_at | — | — | 2.32579 |
| 1555187_at | — | — | 1.52436 |
| 1566863_at | — | — | 4.56348 |
| 237898_at | — | — | 1.51413 |
| 1563138_at | — | — | 1.72121 |
| 238358_x_at | — | — | 3.14686 |
| 243533_x_at | — | — | 2.2352 |
| 1558170_at | — | — | 2.47388 |
| 1564107_at | — | — | 2.4479 |
| 234773_x_at | — | — | 1.85715 |
| 1556936_at | — | — | 2.0032 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 1561143_at | — | — | 1.53123 |
| 242420_at | — | — | 2.36834 |
| 222325_at | — | — | 3.02684 |
| 1568878_at | — | — | 2.17186 |
| 220874_at | — | — | 2.17222 |
| 222300_at | — | — | 2.40438 |
| 243262_at | — | — | 1.86741 |
| 1570176_at | — | — | 2.79226 |
| 1562111_at | — | — | 5.11742 |
| 1555364_at | — | — | 2.73119 |
| 244668_at | — | — | 2.52855 |
| 233875_at | — | — | 2.9792 |
| 239959_x_at | — | — | 1.60572 |
| 215634_at | — | — | 2.33921 |
| 233908_x_at | — | — | 3.48141 |
| 237458_at | — | — | 1.59163 |
| 1560775_at | — | — | 2.48169 |
| 239095_at | — | — | 2.26387 |
| 241044_x_at | — | — | 2.11189 |
| 228731_at | — | — | 1.87164 |
| 1559360_at | — | — | 2.73146 |
| 233529_at | — | — | 1.63141 |
| 238410_x_at | — | — | 2.90964 |
| 234087_at | — | — | 1.80534 |
| 241061_at | — | — | 2.21281 |
| 230859_at | — | — | 2.68677 |
| 237675_at | — | — | 1.54439 |
| 234723_x_at | — | — | 1.90196 |
| 1561364_at | — | — | 3.40486 |
| 1561953_at | — | — | 2.39151 |
| 215849_x_at | — | — | 1.72743 |
| 1566887_x_at | — | — | 2.41216 |
| 1560517_s_at | — | — | 2.16789 |
| 220851_at | — | — | 2.14141 |
| 238392_at | — | — | 1.84284 |
| 1566609_at | — | — | 2.48679 |
| 1564610_at | — | — | 1.98581 |
| 215811_at | — | — | 2.30524 |
| 1563396_x_at | — | — | 1.65546 |
| 241584_at | — | — | 1.90797 |
| 228679_at | — | — | 2.37001 |
| 241119_at | — | — | 2.46146 |
| 237933_at | — | — | 2.58393 |
| 1570624_at | — | — | 1.7321 |
| 242500_at | — | — | 3.04026 |
| 216575_at | — | — | 4.14875 |
| 1566637_at | — | — | 2.58398 |
| 1566967_at | — | — | 2.61969 |
| 236389_x_at | — | — | 1.73264 |
| 1563941_at | — | — | 3.17348 |
| 244480_at | — | — | 3.52279 |
| 233372_at | — | — | 1.65994 |
| 1563115_at | — | — | 2.22091 |
| 1562642_at | — | — | 3.39927 |
| 1561473_at | — | — | 2.4745 |
| 238362_at | — | — | 3.29508 |
| 1564767_at | — | — | 2.62248 |
| 241200_x_at | — | — | 1.72239 |
| 242532_at | — | — | 4.03908 |
| 238297_at | — | — | 2.10442 |
| 1570300_at | — | — | 2.38986 |
| 1562678_at | — | — | 2.4369 |
| 237700_at | — | — | 2.31864 |
| 1561212_at | — | — | 2.10873 |
| 240208_at | — | — | 1.73797 |
| 238755_at | — | — | 2.35516 |
| 241883_x_at | — | — | 1.67224 |
| 243183_at | — | — | 2.87008 |
| 1559780_at | — | — | 1.80843 |
| 237454_at | — | — | 1.84902 |
| 233133_at | — | — | 1.86437 |
| 237608_at | — | — | 1.67052 |
| 215643_at | — | — | 3.20534 |
| 237399_at | — | — | 2.50183 |
| 1560144_at | — | — | 2.65265 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 220859_at | — | — | 2.28617 |
| 237049_at | — | — | 1.59226 |
| 216463_at | — | — | 2.33052 |
| 1555373_at | — | — | 2.40199 |
| 1561657_at | — | — | 1.67151 |
| 240921_at | — | — | 1.93703 |
| 1569409_x_at | — | — | 1.62694 |
| 237552_at | — | — | 2.25696 |
| 238390_at | — | — | 3.49633 |
| 220878_at | — | — | 2.63943 |
| 244420_at | — | — | 2.17474 |
| 1561895_at | — | — | 2.59003 |
| 233373_at | — | — | 2.31025 |
| 232712_at | — | — | 3.31619 |
| 244282_at | — | — | 1.64142 |
| 215473_at | — | — | 1.73547 |
| 238274_at | — | — | 1.71931 |
| 243041_s_at | — | — | 3.902 |
| 215448_at | — | — | 5.09122 |
| 241542_at | — | — | 2.64253 |
| 237480_at | — | — | 1.97714 |
| 242769_at | — | — | 2.65101 |
| 240956_at | — | — | 2.82294 |
| 242840_at | — | — | 1.81443 |
| 1558048_x_at | — | — | 4.43301 |
| 241094_at | — | — | 1.94022 |
| 241945_at | — | — | 1.75756 |
| 1561242_at | — | — | 3.36844 |
| 216319_at | — | — | 2.21853 |
| 1569927_at | — | — | 2.86702 |
| 234096_at | — | — | 1.89863 |
| 242645_at | — | — | 2.01823 |
| 234653_at | — | — | 1.92005 |
| 1557778_at | — | — | 1.77943 |
| 1563494_at | — | — | 1.61383 |
| 215962_at | — | — | 3.60791 |
| 242652_at | — | — | 1.9361 |
| 1561795_at | — | — | 1.78961 |
| 1566498_at | — | — | 2.74467 |
| 1563963_at | — | — | 2.14216 |
| 238386_x_at | — | — | 1.99773 |
| 232817_at | — | — | 2.19406 |
| 1569759_at | — | — | 2.46257 |
| 244885_at | — | — | 1.90316 |
| 242310_at | — | — | 1.91359 |
| 1569596_at | — | — | 3.39789 |
| 241183_at | — | — | 2.94372 |
| 230791_at | — | — | 3.79676 |
| 1570268_at | — | — | 2.16933 |
| 1557832_at | — | — | 2.09744 |
| 1570177_at | — | — | 2.4673 |
| 234655_at | — | — | 1.89067 |
| 1561065_at | — | — | 1.64279 |
| 1562480_at | — | — | 3.83981 |
| 1557644_at | — | — | 2.59969 |
| 234690_at | — | — | 1.69061 |
| 216518_at | — | — | 1.90215 |
| 234794_at | — | — | 2.89785 |
| 240186_at | — | — | 3.29381 |
| 240714_at | — | — | 2.18363 |
| 217132_at | — | — | 1.72792 |
| 1561881_at | — | — | 2.35965 |
| 1562992_at | — | — | 2.46132 |
| 1568794_at | — | — | 2.94005 |
| 1568936_a_at | — | — | 2.0225 |
| 1557665_at | — | — | 2.99179 |
| 233944_at | — | — | 4.72023 |
| 240160_x_at | — | — | 1.65013 |
| 231212_x_at | — | — | 2.89146 |
| 243756_at | — | — | 2.11775 |
| 232944_at | — | — | 2.10953 |
| 243177_at | — | — | 3.23332 |
| 243442_x_at | — | — | 1.9452 |
| 243897_at | — | — | 1.82779 |
| 240825_at | — | — | 2.47627 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 1569664_at | — | — | 4.45065 |
| 228936_at | — | — | 2.51633 |
| 1562353_x_at | — | — | 1.69798 |
| 224237_at | — | — | 2.90306 |
| 244169_x_at | — | — | 3.29173 |
| 241632_x_at | — | — | 1.59752 |
| 228934_x_at | — | — | 2.47447 |
| 220877_at | — | — | 2.67012 |
| 228218_at | — | — | 2.19026 |
| 1561340_at | — | — | 1.59817 |
| 240988_x_at | — | — | 3.81074 |
| 234270_at | — | — | 2.29525 |
| 1570246_at | — | — | 2.06463 |
| 240904_at | — | — | 2.72454 |
| 238368_at | — | — | 4.76547 |
| 240364_at | — | — | 2.02402 |
| 233209_at | — | — | 2.54469 |
| 215290_at | — | — | 3.33519 |
| 233035_at | — | — | 1.72582 |
| 1562997_a_at | — | — | 2.34547 |
| 229823_at | — | — | 1.67524 |
| 244866_at | — | — | 2.04538 |
| 1563546_at | — | — | 6.23891 |
| 233906_at | — | — | 3.09354 |
| 242266_x_at | — | — | 2.86831 |
| 243466_at | — | — | 2.07149 |
| 1570623_at | — | — | 2.34232 |
| 243632_at | — | — | 2.62996 |
| 240864_at | — | — | 3.79135 |
| 1569539_at | — | — | 5.27322 |
| 243489_at | — | — | 6.03255 |
| 207744_at | — | — | 2.86433 |
| 237684_at | — | — | 2.31226 |
| 1570054_at | — | — | 1.9518 |
| 1557025_a_at | — | — | 3.49339 |
| 1566115_at | — | — | 2.72849 |
| 1561069_at | — | — | 3.10071 |
| 1564840_at | — | — | 2.47198 |
| 215976_at | — | — | 2.16509 |
| 1563660_at | — | — | 4.23944 |
| 216290_x_at | — | — | 1.90371 |
| 233401_at | — | — | 4.47535 |
| 233653_at | — | — | 1.6959 |
| 234015_at | — | — | 2.59514 |
| 1563026_at | — | — | 2.232 |
| 210893_at | — | — | 2.14379 |
| 1563316_at | — | — | 4.10042 |
| 1554225_a_at | — | — | 3.18715 |
| 1562071_at | — | — | 1.73705 |
| 1561754_at | — | — | 5.09305 |
| 232453_at | — | — | 2.65615 |
| 243273_at | — | — | 2.91387 |
| 244300_at | — | — | 1.81931 |
| 238381_x_at | — | — | 1.85034 |
| 1561713_at | — | — | 3.415 |
| 234213_at | — | — | 1.5293 |
| 231494_at | — | — | 4.23233 |
| 1560025_at | — | — | 3.35764 |
| 217617_at | — | — | 2.45438 |
| 1570152_at | — | — | 2.42411 |
| 235079_at | — | — | 2.25401 |
| 1564841_at | — | — | 3.20049 |
| 237871_x_at | — | — | 3.55396 |
| 236881_at | — | — | 1.86195 |
| 233932_at | — | — | 3.68719 |
| 234137_s_at | — | — | 2.30775 |
| 1568660_a_at | — | — | 3.72993 |
| 222339_x_at | — | — | 2.47329 |
| 1563033_x_at | — | — | 6.31222 |
| 1559814_at | — | — | 2.7905 |
| 1556794_at | — | — | 2.98574 |
| 1560002_at | — | — | 1.93616 |
| 1561879_at | — | — | 2.39371 |
| 237596_at | — | — | 3.34796 |
| 1561513_at | — | — | 1.8622 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 241673_x_at | — | — | 2.80804 |
| 1561767_at | — | — | 2.33844 |
| 228827_at | — | — | 4.64642 |
| 1563332_at | — | — | 1.95777 |
| 1562800_at | — | — | 2.06622 |
| 237530_at | — | — | 2.59509 |
| 244412_at | — | — | 2.89052 |
| 232538_at | — | — | 3.79966 |
| 1561543_at | — | — | 5.85562 |
| 1555926_a_at | — | — | 3.01372 |
| 238407_at | — | — | 2.73065 |
| 240112_at | — | — | 2.66998 |
| 1556989_at | — | — | 2.84888 |
| 241506_at | — | — | 2.4216 |
| 1563038_at | — | — | 2.87832 |
| 237983_at | — | — | 3.01582 |
| 1563187_at | — | — | 3.70922 |
| 1559697_a_at | — | — | 3.36172 |
| 1557762_at | — | — | 5.09552 |
| 1564631_at | — | — | 2.34427 |
| 239984_at | — | — | 2.4818 |
| 1556935_at | — | — | 4.49148 |
| 233793_at | — | — | 3.15092 |
| 1561902_at | — | — | 3.08744 |
| 232935_at | — | — | 2.11436 |
| 244051_at | — | — | 1.55456 |
| 1562797_at | — | — | 3.02768 |
| 1563032_at | — | — | 6.99365 |
| 242232_at | — | — | 3.47935 |
| 1563189_at | — | — | 4.43695 |
| 228502_at | — | — | 3.37897 |
| 222288_at | — | — | 6.71681 |
| 1556983_a_at | — | — | 3.92804 |
| 1558496_at | — | — | 5.84122 |
| 1566600_at | — | — | 1.99013 |
| 1557645_at | — | — | 2.36718 |
| 231227_at | — | — | 1.90383 |
| 238384_x_at | — | — | 3.07283 |
| 240331_at | — | — | 6.60003 |
| 1569818_at | — | — | 2.5437 |
| 1562084_at | — | — | 4.88308 |
| 238103_at | — | — | 2.96539 |
| 1561448_at | — | — | 2.80876 |
| 240992_at | — | — | 1.70856 |
| 1568812_at | — | — | 2.82372 |
| 1562276_at | — | — | 4.36824 |
| 1564964_at | — | — | 5.68325 |
| 233330_s_at | — | — | 4.92758 |
| 233282_at | — | — | 3.53402 |
| 233331_at | — | — | 2.99413 |
| 241649_at | — | — | 1.98701 |
| 1568711_a_at | — | — | 1.88935 |
| 215736_at | — | — | 3.18179 |
| 1553498_at | — | — | 3.65853 |
| 1559696_at | — | — | 7.00732 |
| 241569_at | — | — | 2.15149 |
| 241770_x_at | — | — | 2.35449 |
| 238956_at | — | — | 1.77345 |
| 234105_at | — | — | 2.45775 |
| 241026_at | — | — | 2.03428 |
| 1560533_at | — | — | 1.83344 |
| 1559336_at | — | — | 3.17434 |
| 238852_at | — | — | 1.85111 |
| 244626_at | — | — | 3.61861 |
| 231687_at | — | — | 2.06469 |
| 243974_at | — | — | 2.23029 |
| 1561642_at | — | — | 2.17232 |
| 233611_at | — | — | 2.79902 |
| 1569545_at | — | — | 2.96746 |
| 1569853_at | — | — | 2.34808 |
| 217569_x_at | — | — | 2.20119 |
| 244216_at | — | — | 3.52052 |
| 234057_at | — | — | 3.12494 |
| 216406_at | — | — | 3.25332 |
| 241676_x_at | — | — | 3.07696 |

TABLE 8-continued

Table 8- Significant genes between TIA1 and TIA2 (FDR ≤ 0.05, absolute fold change ≥ 1.5, TIA1 vs TIA2)

| AFFY ID | Gene Symbol | Gene Title | Fold Change |
|---|---|---|---|
| 234906_at | — | — | 2.94251 |
| 1563881_at | — | — | 2.97996 |
| 237937_x_at | — | — | 7.10043 |
| 1561856_at | — | — | 8.77012 |
| 1561529_at | — | — | 1.93256 |
| 230064_at | — | — | 2.99589 |
| 1564676_a_at | — | — | 3.7315 |
| 1562755_at | — | — | 4.87812 |
| 235494_at | — | — | 2.65509 |
| 1568871_at | — | — | 1.71949 |
| 1562873_at | — | — | 1.93511 |
| 1561214_at | — | — | 4.07318 |
| 242718_at | — | — | 2.56091 |
| 1562811_at | — | — | 2.21403 |
| 241457_at | — | — | 2.64311 |
| 1564851_at | — | — | 2.15494 |
| 217085_at | — | — | 2.04989 |
| 241566_at | — | — | 4.90225 |
| 1562916_at | — | — | 4.01294 |
| 1564306_at | — | — | 3.50683 |
| 243398_at | — | — | 4.93521 |
| 241247_at | — | — | 2.40905 |
| 1561213_at | — | — | 2.01136 |
| 1569810_at | — | — | 3.1075 |
| 1566622_at | — | — | 3.07274 |
| 241312_at | — | — | 3.10323 |
| 241567_at | — | — | 2.31223 |
| 1560905_at | — | — | 5.46696 |
| 1560086_at | — | — | 3.09926 |
| 1556263_s_at | — | — | 2.85076 |
| 244612_at | — | — | 5.78514 |
| 1560296_at | — | — | 3.17524 |
| 231503_at | — | — | 3.63922 |
| 222342_at | — | — | 2.8616 |
| 1566638_at | — | — | 1.90699 |
| 1561926_at | — | — | 3.80796 |
| 1563087_at | — | — | 2.42998 |
| 234601_x_at | — | — | 1.68879 |
| 216728_at | — | — | 3.90174 |
| 1562610_at | — | — | 1.96876 |
| 234502_at | — | — | 3.82276 |
| 242198_at | — | — | 2.81983 |
| 234235_at | — | — | 5.71387 |
| 241675_s_at | — | — | 6.66189 |
| 1555263_at | — | — | 2.30475 |
| 1566862_at | — | — | 3.92941 |
| 207731_at | — | — | 7.5127 |
| 231074_at | — | — | 5.19962 |
| 237233_at | — | — | 4.19082 |
| 233279_at | — | — | 2.601 |
| 237479_at | — | — | 6.74027 |
| 242802_x_at | — | — | 4.62183 |
| 234800_at | — | — | 1.88126 |
| 231091_x_at | — | — | 3.87591 |
| 241674_s_at | — | — | 6.55087 |

TABLE 9

TIA subtype specific genes: pathways

| Ingenuity Canonical Pathways | p-value | # Molecules | Molecules |
|---|---|---|---|
| Axonal Guidance Signaling | 2.48E−03 | 32 | LRRC4C, BDNF, ARHGEF7, UNC5B, PGF, IGF1, SDC2, SRGAP1, EFNA5, ROBO2, SEMA3E, EPHA7, ADAM2, SHANK2, PTCH1, PIK3C2G, EPHA3, BMP5, ADAM18, GNAS, PLCB4, ADAM30, NTRK2, PAK3, ADAM12, NTRK3, SEMA6D, GNAO1, EPHA5, PAK7, WNT5A, FZD7 |

TABLE 9-continued

TIA subtype specific genes: pathways

| Ingenuity Canonical Pathways | p-value | # Molecules | Molecules |
|---|---|---|---|
| Hepatic Fibrosis/ Hepatic Stellate Cell Activation | 1.51E−02 | 13 | LEP, EDNRB, IGFBP5, PGF, COL1A2, COL1A1, IGF1, PDGFRA, TGFB2, IFNAR1, AGTR1, COL3A1, EGFR |
| Human Embryonic Stem Cell Pluripotency | 1.34E−02 | 13 | BDNF, TDGF1, PIK3C2G, BMP5, GNAS, BMPR1B, NANOG, NTRK2, NTRK3, PDGFRA, TGFB2, FZD7, WNT5A |
| Neuropathic Pain Signaling In Dorsal Horn Neurons | 9.78E−03 | 11 | GRM5, GRM7, PLCB4, NTRK2, GPR37, BDNF, GRM8, GRM3, PIK3C2G, GRIA2, GRIA3 |
| Bladder Cancer Signaling | 5.08E−03 | 11 | FGF18, MMP26, MMP16, FGF14, FGF12, FGF20, FGF7, PGF, EGFR, MMP19, FGF5 |
| Amyotrophic Lateral Sclerosis Signaling | 2.02E−02 | 10 | NOS1, CACNA1E, IGF1, HECW1, PIK3C2G, GRIA2, CACNA1C, GRIK2, PGF, GRIA3 |
| Glutamate Receptor Signaling | 2.74E−03 | 9 | GRM5, GRM7, SLC17A6, GRM8, GRM3, GRIA2, GRIK2, HOMER1, GRIA3 |
| GABA Receptor Signaling | 2.23E−03 | 8 | SLC6A11, GABBR2, GABRB3, GABRA4, GABRB1, GABBR1, MYO5B, GABRB2 |
| Agrin Interactions at Neuromuscular Junction | 2.35E−02 | 8 | NRG2, PAK3, ARHGEF7, ERBB4, NRG1, PAK7, ERBB3, EGFR |
| Maturity Onset Diabetes of Young (MODY) Signaling | 2.46E−02 | 4 | CACNA1E, ALDOB, FOXA2, CACNA1C |

REFERENCES

1. Johnston S C, Nguyen-Huynh M N, Schwarz M E et al. National Stroke Association guidelines for the management of transient ischemic attacks. Ann Neurol. 2006; 60:301-313
2. Rothwell P M, Buchan A, Johnston S C. Recent advances in management of transient ischaemic attacks and minor ischaemic strokes. Lancet Neurol. 2006; 5:323-331
3. Easton J D, Saver J L, Albers G W et al. Definition and Evaluation of Transient Ischemic Attack A Scientific Statement for Healthcare Professionals From the American Heart Association/American Stroke Association Stroke Council; Council on Cardiovascular Surgery and Anesthesia; Council on Cardiovascular Radiology and Intervention; Council on Cardiovascular Nursing; and the Interdisciplinary Council on Peripheral Vascular Disease The American Academy of Neurology affirms the value of this statement as an educational tool for neurologists. Stroke. 2009; 40:2276-2293
4. Josephson S A, Sidney S, Pham T N et al. Higher ABCD2 score predicts patients most likely to have true transient ischemic attack. Stroke. 2008; 39:3096-3098
5. Zhan X, Ander B P, Jickling G et al. Brief focal cerebral ischemia that simulates transient ischemic attacks in humans regulates gene expression in rat peripheral blood. J Cereb Blood Flow Metab. 2010; 30:110-118
6. Zhan X, Kim C, Sharp F R. Very brief focal ischemia simulating transient ischemic attacks (TIAs) can injure brain and induce Hsp70 protein. Brain Res. 2008; 1234: 183-197
7. Arenillas J F, Alvarez-Sabin J, Molina C A et al. C-reactive protein predicts further ischemic events in first-ever transient ischemic attack or stroke patients with intracranial large-artery occlusive disease. Stroke. 2003; 34:2463-2468
8. Elneihoum A M, Falke P, Axelsson L et al. Leukocyte activation detected by increased plasma levels of inflammatory mediators in patients with ischemic cerebrovascular diseases. Stroke. 1996; 27:1734-1738
9. Ross A M, Hum P, Perrin N et al. Evidence of the peripheral inflammatory response in patients with transient ischemic attack. J Stroke Cerebrovasc Dis. 2007; 16:203-207
10. Castillo J, Alvarez-Sabin J, Martinez-Vila E et al Inflammation markers and prediction of post-stroke vascular disease recurrence: the MITICO study. J Neurol. 2009; 256:217-224
11. Nambi V, Hoogeveen R C, Chambless L et al. Lipoprotein-associated phospholipase A2 and high-sensitivity C-reactive protein improve the stratification of ischemic stroke risk in the Atherosclerosis Risk in Communities (ARIC) study. Stroke. 2009; 40:376-381
12. Cucchiara B L, Messe S R, Sansing L et al. Lipoprotein-associated phospholipase A2 and C-reactive protein for risk-stratification of patients with TIA. Stroke. 2009; 40:2332-2336
13. Rothwell P M, Howard S C, Power D A et al. Fibrinogen concentration and risk of ischemic stroke and acute coronary events in 5113 patients with transient ischemic attack and minor ischemic stroke. Stroke. 2004; 35:2300-2305
14. Woodward M, Lowe G D, Campbell D J et al. Associations of inflammatory and hemostatic variables with the risk of recurrent stroke. Stroke. 2005; 36:2143-2147
15. Kang D W, Yoo S H, Chun S et al. Inflammatory and hemostatic biomarkers associated with early recurrent ischemic lesions in acute ischemic stroke. Stroke. 2009; 40:1653-1658
16. Moore D F, Li H, Jeffries N et al. Using peripheral blood mononuclear cells to determine a gene expression profile of acute ischemic stroke: a pilot investigation. Circulation. 2005; 111:212-221
17. Tang Y, Xu H, Du X et al. Gene expression in blood changes rapidly in neutrophils and monocytes after ischemic stroke in humans: a microarray study. J Cereb Blood Flow Metab. 2006; 26:1089-1102
18. Xu H, Tang Y, Liu D Z et al. Gene expression in peripheral blood differs after cardioembolic compared with large-vessel atherosclerotic stroke: biomarkers for the etiology of ischemic stroke. J Cereb Blood Flow Metab. 2008; 28:1320-1328

19. Giles M F, Rothwell P M. Systematic review and pooled analysis of published and unpublished validations of the ABCD and ABCD2 transient ischemic attack risk scores. Stroke. 2010; 41:667-673
20. Cucchiara B L, Messe S R, Sansing L et al. D-dimer, magnetic resonance imaging diffusion-weighted imaging, and ABCD2 score for transient ischemic attack risk stratification. *J Stroke Cerebrovasc Dis.* 2009; 18:367-373
21. Andersohn F, Waring M, Garbe E. Risk of ischemic stroke in patients with Crohn's disease: A population-based nested case-control study. *Inflamm Bowel Dis.* 2009
22. Freilinger T, Riedel E, Holtmannspotter M et al. Ischemic stroke and peripheral arterial thromboembolism in a patient with Crohn's disease: a case presentation. *J Neurol Sci.* 2008; 266:177-179
23. Karacostas D, Mavromatis J, Artemis K, Milonas I. Hemorrhagic cerebral infarct and ulcerative colitis. A case report. *Funct Neurol.* 1991; 6:181-184
24. Schneiderman J H, Sharpe J A, Sutton D M. Cerebral and retinal vascular complications of inflammatory bowel disease. *Ann Neurol.* 1979; 5:331-337
25. Beck J D, Offenbacher S. Systemic effects of periodontitis: epidemiology of periodontal disease and cardiovascular disease. *J Periodontol.* 2005; 76:2089-2100
26. Beck J, Garcia R, Heiss G et al. Periodontal disease and cardiovascular disease. *J Periodontol.* 1996; 67:1123-1137
27. Elter J R, Offenbacher S, Toole J F, Beck J D. Relationship of periodontal disease and edentulism to stroke/TIA. *J Dent Res.* 2003; 82:998-1001
28. Grau A J, Becher H, Ziegler C M et al. Periodontal disease as a risk factor for ischemic stroke. *Stroke.* 2004; 35:496-501
29. Grau A J. Infection, inflammation, and cerebrovascular ischemia. Neurology. 1997; 49:S47-51
30. Dourado D F, Fernandes P A, Ramos M J. Mammalian cytosolic glutathione transferases. *Curr Protein Pept Sci.* 2008; 9:325-337

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. A microarray comprising a set of nucleic acids, wherein each nucleic acid in the set specifically hybridizes to a different target gene, and wherein the set of nucleic acids hybridize to target genes comprising ATG9B, DIP2C, DKFZP434B061, EDAR, FAM55D, FLJ30375, GSTM1, GUSBL2, IGFBP5, LTBR, SCN2A, SMURF2, and ZNF512B, wherein the microarray is attached to 100 or fewer nucleic acids, and comprises a planar surface, and wherein the nucleic acids are coupled to the planar surface of the solid support in different, known locations.

2. The microarray of claim 1, further comprising a plurality of nucleic acids that hybridize to a plurality of the genes selected from the group consisting of SNIP, BXDC5, FAT3, LECT2, THSD4, CCDC144C, OVOL2, SPTLC3, CLEC4E, GLYATL1, RBMS3, SPIB, DKFZP434L187, GADL1, SHOX, TBX5, UNC5B, PGM5, TIMP2, ELL2, CXADR, and RNF141.

3. The microarray of claim 1, further comprising a plurality of nucleic acids that hybridize to a plurality of the genes selected from the group consisting of RPL22, SNIP, SH3GL3, MCTP1, FAT3, SPTLC3, RBMS3, SNRPN, and TIMP2.

4. The microarray of claim 1, further comprising a plurality of nucleic acids that hybridize to a plurality of the genes selected from the group consisting of FGD4, F5, ABCA1, LOC100290882, LTB4R, UBXN2B, CKLF, CLEC4E, PHTF1, ENTPD1, OSBPL1A, RRAGD, CPEB2, CKLF, BST1, and CKLF.

5. The solid support microarray of claim 1, further comprising a plurality of nucleic acids that hybridize to a plurality of the genes selected from the group consisting of ZNF608, FCHO2, ST3GAL6, ABCA1, THBD, AMN1, QKI, KIAA0319, MCTP1, VNN3, UBR5, FAR2, RBM25, CHMP1B, LAMP2, VAPA, IFRD1, HNRNPH2, REM2, and GAB1.

6. The microarray of claim 1, further comprising a plurality of nucleic acids that hybridize to a plurality of the genes selected from the group consisting of THSD4, SNRPN, ASTN2, SNIP, FAT3, TIMM8A, CCDC144C, ANKRD28, TBX5, PGM5, SCD5, FCRL4, SHOX, CCRL1, LECT2, PTPRD, CCDC144A, LDB3, LOC729222, RBMS3, P704P, GYPA, PRTG, GABRB2, HNRNPUL2, ELAVL2, SPTLC3, FOXA2, DLX6, ALDOAP2, and F1135934.

7. The solid support microarray of claim 1, further comprising a plurality of nucleic acids that hybridize to a plurality of the genes selected from the group consisting of RPL22, LOC100129488, LOC283027, LOC344595, THSD4, FAT3, and P704P.

8. The solid support microarray of claim 1, further comprising a plurality of nucleic acids that hybridize to a plurality of the genes selected from the group consisting of SNIP, BXDC5, FAT3, LECT2, THSD4, CCDC144C, OVOL2, SPTLC3, CLEC4E, GLYATL1, RBMS3, SPIB, DKFZP434L187, GADL1, SHOX, TBX5, UNC5B, PGM5, TIMP2, ELL2, CXADR, RNF141, RPL22, SH3GL3, MCTP1, SNRPN, FGD4, F5, ABCA1, LOC100290882, LTB4R, UBXN2B, CKLF, PHTF1, ENTPD1, OSBPL1A, RRAGD, CPEB2, CKLF, BST1, ZNF608, FCHO2, ST3GAL6, THBD, AMN1, QKI, KIAA0319, MCTP1, VNN3, UBR5, FAR2, RBM25, CHMP1B, LAMP2, VAPA, IFRD1, HNRNPH2, REM2, GAB1, ASTN2, TIMM8A, ANKRD28, SCD5, FCRL4, CCRL1, LECT2, PTPRD, CCDC144A, LDB3, PPFIBP1, P704P, GYPA, PRTG, GABRB2, HNRNPUL2, ELAVL2, FOXA2, DLX6, ALDOAP2, FLJ35934, LOC100129488, LOC283027, and LOC344595.

9. The solid support microarray of claim 1, further comprising a plurality of nucleic acids that hybridize to a plurality of the genes selected from the group consisting of EBF1, GRM5, TSKS, ENPP2, AP3S2, LRRC37A3, C16orf68, LOC284751, IRF6, LHFP, BANK1, ARHGEF5, ZNF254, TFDP1, COL13A1, GSTK1, ADAMTSL4, P2RX5, LHFP, PIK3C2B, CHURC1, EXT2, HLA-DOA, OOEP, ZNF185, TMEM19, FCRL1, FLJ40125, ARHGEF12, CLEC18A, CD46, PTPN20A, PTPN20B, and C19orf28.

10. The microarray of claim 1, further comprising a plurality of nucleic acids that hybridize to a plurality of the genes selected from the group consisting of EBF1, F1131945, C16orf68, SLC20A1, DOPEY2, COL13A1, LHFP, LOC284751, GRM5, LOC100144603, MTBP, SHOX2, ARHGEF5, RNF7, CLASP2, GIPC2, RANBP10, CMBL, LOC100127980, CYTH3, PROCR, LOC146880, SLC6A19, ICAM4, C12orf42, ARHGEF12, PRSS35, NT5E, LOC100271832, LHFP, NT5E and AKR1C3.

11. The microarray of claim 1, further comprising a plurality of nucleic acids that hybridize to a plurality of the genes selected from the group consisting of CMTM1, COL13A1, SDC4, C6orf164, GPR176, BRUNOL6, SNORA68, MIF, SLC2A11, DUSP16, HIPK2, TTC7A, PPIE, GRLF1, MAP3K7IP1, LOC100129034, PER3, SMC1A, and LRRC43.

12. The microarray of claim 1, further comprising a plurality of nucleic acids that hybridize to a plurality of the genes selected from the group consisting of USP7, MAPRE2, CSNK1G2, SAFB2, PRKAR2A, PI4KB, CRTC1, HADHA, MAP1LC3B, KAT5, CDC2L1, CDC2L2, GTSE1, TCF25, CHP, LRRC40, LYPLA2, LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445, PEX16.

13. A microarray comprising a set of nucleic acids, wherein each nucleic acid in the set specifically hybridizes to a different target gene, and wherein the set of nucleic acids hybridize to target genes consisting of ATG9B, DIP2C, DKFZP434B061, EDAR, FAM55D, FLJ30375, GSTM1, GUSBL2, IGFBP5, LTBR, SCN2A, SMURF2, ZNF512B, SNIP, BXDC5, FAT3, LECT2, THSD4, CCDC144C, OVOL2, SPTLC3, CLEC4E, GLYATL1, RBMS3, SPIB, DKFZP434L187, GADL1, SHOX, TBX5, UNC5B, PGM5, TIMP2, ELL2, CXADR, RNF141, RPL22, SH3GL3, MCTP1, FAT3, SPTLC3, RBMS3, SNRPN, FGD4, F5, ABCA1, LOC100290882, LTB4R, UBXN2B, CLEC4E, PHTF1, ENTPD1, OSBPL1A, RRAGD, CPEB2, CKLF, BST1, ZNF608, FCHO2, ST3GAL6, ABCA1, THBD, AMN1, QKI, KIAA0319, MCTP1, VNN3, UBR5, FAR2, RBM25, CHMP1B, LAMP2, VAPA, IFRD1, HNRNPH2, REM2, GAB1, THSD4, SNRPN, ASTN2, FAT3, TIMM8A, ANKRD28, TBX5, PGM5, SCD5, FCRL4, SHOX, CCRL1, LECT2, PTPRD, CCDC144A, LDB3, PPFIBP1, RBMS3, P704P, GYPA, PRTG, GABRB2, HNRNPUL2, ELAVL2, SPTLC3, FOXA2, DLX6, ALDOAP2, FLJ35934, RPL22, LOC100129488, LOC283027, LOC344595, THSD4, FAT3, P704P, BXDC5, FAT3, LECT2, THSD4, OVOL2, SPTLC3, CLEC4E, GLYATL1, RBMS3, SPIB, DKFZP434L187, GADL1, SHOX, TBX5, UNC5B, PGM5, TIMP2, ELL2, CXADR, RNF141, RPL22, SH3GL3, MCTP1, SNRPN, FGD4, F5, ABCA1, LOC100290882, LTB4R, UBXN2B, PHTF1, ENTPD1, OSBPL1A, RRAGD, CPEB2, BST1, ZNF608, FCHO2, ST3GAL6, THBD, AMN1, QKI, KIAA0319, MCTP1, VNN3, UBR5, FAR2, RBM25, CHMP1B, LAMP2, VAPA, IFRD1, HNRNPH2, REM2, GAB1, ASTN2, TIMM8A, ANKRD28, SCD5, FCRL4, CCRL1, LECT2, PTPRD, CCDC144A, LDB3, P704P, GYPA, PRTG, HNRNPUL2, FOXA2, DLX6, ALDOAP2, FLJ35934, LOC100129488, LOC283027, LOC344595, EBF1, GRM5, TSKS, ENPP2, AP3S2, LRRC37A3, C16orf68, LOC284751, IRF6, LHFP, BANK1, ARHGEF5, ZNF254, TFDP1, COL13A1, GSTK1, ADAMTSL4, P2RX5, LHFP, PIK3C2B, CHURC1, EXT2, HLA-DOA, OOEP, ZNF185, TMEM19, FCRL1, FLJ40125, ARHGEF12, CLEC18A, CD46, PTPN20A, PTPN20B, C19orf28, EBF1, FLJ31945, C16orf68, SLC20A1, DOPEY2, COL13A1, LHFP, LOC284751, GRM5, LOC100144603, MTBP, SHOX2, ARHGEF5, RNF7, CLASP2, GIPC2, RANBP10, CMBL, LOC100127980, CYTH3, PROCR, LOC146880, SLC6A19, ICAM4, C12orf42, ARHGEF12, PRSS35, NT5E, LOC100271832, LHFP, NT5E, AKR1C3, CMTM1, COL13A1, SDC4, C6orf164, GPR176, BRUNOL6, SNORA68, MIF, SLC2A11, DUSP16, HIPK2, TTC7A, PPIE, GRLF1, MAP3K7IP1, LOC100129034, PER3, SMC1A, LRRC43, USP7, MAPRE2, CSNK1G2, SAFB2, PRKAR2A, PI4KB, CRTC1, HADHA, MAP1LC3B, KAT5, CDC2L1, CDC2L2, GTSE1, TCF25, CHP, LRRC40, LYPLA2, LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445 and PEX16, wherein the microarray comprises a planar surface, and wherein the nucleic acids are coupled to the planar surface of the microarray in different, known locations.

14. A kit comprising the microarray of claim 1.

15. The kit of claim 14, the kit further comprising buffers, salts and other reagents to facilitate amplification and/or detection reactions.

16. The microarray of claim 1, wherein the planar substrate is comprised of glass.

17. The microarray of claim 1, wherein the nucleic acids comprise one or more non-naturally occurring nucleotide analogs.

18. The microarray of claim 1, wherein the microarray is produced using mechanical synthesis methods or light directed synthesis methods.

19. The microarray of claim 1, wherein the microarray is produced using a combination of photolithographic methods and solid phase synthesis methods.

\* \* \* \* \*